US012435111B2

(12) United States Patent
Albertini et al.

(10) Patent No.: US 12,435,111 B2
(45) Date of Patent: Oct. 7, 2025

(54) MUTANT VSV ECTODOMAIN POLYPEPTIDE AND USES THEREOF

(71) Applicants: CENTRE NATIONAL DE LA RECHERCHE SCIENTIFIQUE (CNRS), Paris (FR); UNIVERSITE PARIS SACLAY, Gif sur Yvette (FR)

(72) Inventors: Aurélie Albertini, Gometz le Chatel (FR); Hélène Raux, Antony (FR); Yves Gaudin, Paris (FR); Franck Perez, Paris (FR)

(73) Assignees: CENTRE NATIONAL DE LA RECHERCHE SCIENTIFIQUE (CNRS), Paris (FR); UNIVERSITE PARIS SACLAY, Gif sur Yvette (FR)

( * ) Notice: Subject to any disclaimer, the term of this patent is extended or adjusted under 35 U.S.C. 154(b) by 1053 days.

(21) Appl. No.: 17/439,166

(22) PCT Filed: Mar. 16, 2020

(86) PCT No.: PCT/EP2020/057144
§ 371 (c)(1),
(2) Date: Sep. 14, 2021

(87) PCT Pub. No.: WO2020/187850
PCT Pub. Date: Sep. 24, 2020

(65) Prior Publication Data

US 2022/0162266 A1 May 26, 2022

(30) Foreign Application Priority Data

Mar. 15, 2019 (EP) .................................... 19305317

(51) Int. Cl.
*C07K 14/005* (2006.01)
*C12N 15/86* (2006.01)

(52) U.S. Cl.
CPC ............ *C07K 14/005* (2013.01); *C12N 15/86* (2013.01); *C12N 2760/20222* (2013.01); *C12N 2760/20243* (2013.01)

(58) Field of Classification Search
CPC .............................. C07K 14/005; C12N 15/86
See application file for complete search history.

(56) References Cited

U.S. PATENT DOCUMENTS 8,420,104 B2 * 4/2013 Charneau ............ C07K 14/005 435/5
2014/0086971 A1 3/2014 Hall et al.
2015/0320810 A1 * 11/2015 Conrad ................. A61K 45/06 435/236

FOREIGN PATENT DOCUMENTS

WO WO-2009016433 A2 2/2009
WO WO-2009085178 A1 7/2009
WO WO-2013182503 A1 12/2013
WO WO-2018050738 A1 * 3/2018 ......... A61K 39/0011
WO WO-2019057974 A1 3/2019

OTHER PUBLICATIONS

Jeetendra et al., 2003, The Membrane-Proximal Region of Vesicular Stomatitis Virus Glycoprotein G Ectodomain Is Critical for Fusion and Virus Infectivity, Journal of Virology, 77(23): 12807-12818.*
Rose et al., 1981, Nucleotide Sequences of the mRNA's Encoding the Vesicular Stomatitis Virus G and M Proteins Determined from cDNA Clones Containing the Complete Coding Regions, 39(2): 519-528.*
Gallione et al., 1983, Nucleotide Sequence of a cDNA Clone Encoding the Entire Glycoprotein from the New Jersey Serotype of Vesicular Stomatitis Virus, Journal of Virology, 46(1): 162-169.*
Albertini et al., *Molecular and Cellular Aspects of Rhabdovirus Entry,* 4 Viruses 117-139 (2012).
Amirache et al., Mystery solved: *VSV-G-LVs do not allow efficient gene transfer into unstimulated T cells, B cells, and HSCs because they lack the LDL receptor,* 123(9) Blood 1422-1424 (Feb. 27, 2014).
Ammayappan et al., *Characteristics of Onvolytic Vesicular Stomatitis Virus Displaying Tumor-Targeting Ligands,* 87(24) *Journal of Virology* 13543-13555 (Dec. 2013).
Barber, Glen N., *VSV-tumor selective replication and protein translation,* 24 Oncogene 7710-7719 (2005).
Bishnoi et al., *Oncotargeting by Vesicular Stomatitis Virus (VSV): Advances in Cancer Therapy,* 10 Viruses 1-20 (2018).
Carajas virus glycoprotein (G protein), Seq ID 11, XP002792485, 1 page (Apr. 2, 2009).
Carajas virus glycoprotein, Seq ID 55, XP002792483, 1 page (May 3, 2018).
Felt et al., *Recent advances in vesicular stomatitis virus-based oncolytic virotherapy: a 5-year update,* 98 Journal of General Virology 2895-2911 (2017).
Fernandez et al., *Genetically Engineered Vesicular Stomatitis Virus in Gene Therapy: Application for Treatment of Malignant Disease,* 76(2) Journal of Virology 895-904 (Jan. 2002).
Hastie et al., *Understanding and altering cell tropism of vesicular stomatitis virus,* 176(0) *Virus Research* 1-34 (Sep. 2013).

(Continued)

*Primary Examiner* — Amber D Steele
(74) *Attorney, Agent, or Firm* — Panitch Schwarze Belisario & Nadel LLP; Erin M. Dunston

(57) ABSTRACT

The present invention relates to a mutant polypeptide comprising the amino acid sequence of the ectodomain of glycoprotein G of a vesicular stomatitis virus (VSV) strain, wherein said ectodomain comprises the amino acid sequence as set forth in SEQ ID NO: 2 or a sequence having at least 50% of identity with the amino acid sequence as set forth in SEQ ID NO: 2, with at least one substitution of an amino acid residue selected from the group consisting of: a) any amino acid residue located from position 421 to position 429 and any amino acid residue located from position 17 to position 25 of SEQ ID NO:2; or b) any amino acid residue located from a position equivalent to position 421 to a position equivalent to position 429 of SEQ ID NO: 2 and any amino acid residue located from a position equivalent to position 17 to a position equivalent to position 25 of SEQ ID NO: 2, after optimal global alignment with SEQ ID NO:2.

19 Claims, 13 Drawing Sheets

Specification includes a Sequence Listing.

(56) References Cited

OTHER PUBLICATIONS

Nikolic et al., *Structural basis for the recognition of LDL-receptor family members by VSV glycoprotein,* 9(1029) Nature Communications 1-12 (2018).

Rodriguez et al., *Full-length genome analysis of natural isolates of vesicular stomatitis virus (Indiana 1 serotype) from North, Central and South America,* 83 Journal of General Virology 2475-2483 (2002).

Schnell et al., *The Minimal Conserved Transcription Stop-Start Signal Promotes Stable Expression of a Foreign Gene in Vesicular Stomatitis Virus,* 70(4) Journal of Virology 2318-2323 (Apr. 1996).

Sequence 2 from patent, WO2018050738, XP002792484, 1 page (Apr. 27, 2018).

Velazquez-Salinas et al., *Complete Genome Sequences of Two Vesicular Stomatitis Virus Isolates Collected in Mexico,* 5(37):e01006-17 American Society for Microbiology 1-2 (2017).

* cited by examiner

Optimal global alignment of VSV Indiana/Maraba strains amino acid sequences of ectodomain of glycoprotein G

Parameters:
Aligned_sequences: 2 => 1: Indiana (SEQ ID NO:2), 2: Maraba (SEQ ID NO:4)
Matrix: EBLOSUM62, Gap_penalty: 10.0, Extend_penalty: 0.5, End_gap_penalty: false, End_gap_open: 10.0
Results:
Length: 496
Identity: 391/496 (78.8%)
Similarity: 441/496 (88.9%)
Gaps: 1/496 (0.2%)
Score: 2227.0

```
                                          22
                                   17     |  25
Indiana        1 KFTIVFPHNQKGNWKNVPSNYHYCPSSSDLNWHNDLIGTAIQVKMPKSHK     50
                 ||||||||:|||||||||||.|||||||||.||||||.|.::.||:||||
Maraba         1 KFTIVFPHHQKGNWKNVPSTYHYCPSSSDQNWHNDLTGVSLHVKIPKSHK     50
                                   17        25

Indiana       51 AIQADGWMCHASKWVTTCDFRWYGPKYITQSIRSFTPSVEQCKESIEQTK    100
                 |||||||||||:|||||||||||||||||.||.|.:|::||||.||||||
Maraba        51 AIQADGWMCHAAKWVTTCDFRWYGPKYITHSIHSMSPTLEQCKTSIEQTK    100

Indiana      101 QGTWLNPGFPPQSCGYATVTDAEAVIVQVTPHHVLVDEYTGEWVDSQFIN    150
                 ||.|:||||||||||||||||||.|:||.||||||||||||||:|||.:.
Maraba       101 QGVWINPGFPPQSCGYATVTDAEVVVVQATPHHVLVDEYTGEWIDSQLVG    150

Indiana      151 GKCSNYICPTVHNSTTWHSDYKVKGLCDSNLISMDITFFSEDGELSSLGK    200
                 ||||..:|.||||||.||:|||:.|||:|||.|:||||||||||:.:|||
Maraba       151 GKCSKEVCQTVHNSTVWHADYKITGLCESNLASVDITFFSEDGQKTSLGK    200

Indiana      201 EGTGFRSNYFAYETGGKACKMQYCKHWGVRLPSGVWFEMADKDLFAAARF    250
                 ..||||||:||||:|.|||:||||..||:|||||||||:.|||||.||:.
Maraba       201 PNTGFRSNHFAYESGEKACRMQYCTQWGIRLPSGVWFELVDKDLFQAAKL    250

Indiana      251 PECPEGSSISAPSQTSVDVSLIQDVERILDYSLCQETWSKIRAGLPISPV    300
                 ||||.||||||||||||||||||||||||||||||||||||||.||:|||
Maraba       251 PECPRGSSISAPSQTSVDVSLIQDVERILDYSLCQETWSKIRAKLPVSPV    300

Indiana      301 DLSYLAPKNPGTGPAFTIINGTLKYFETRYIRVDIAAPILSRMVGMISGT    350
                 |||||||||||:|||||||||||||||||||||||:.||:..|||.:|||
Maraba       301 DLSYLAPKNPGSGPAFTIINGTLKYFETRYIRVDISNPIIPHMVGTMSGT    350

Indiana      351 TTERELWDDWAPYEDVEIGPNGVLRTSSGYKFPLYMIGHGMLDSDLHLSS    400
                 |||||||:||.|||||||||||||:|.:|:|||||||||||||||||.||
Maraba       351 TTERELWNDWYPYEDVEIGPNGVLKTPTGFKFPLYMIGHGMLDSDLHKSS    400
                                     421     429
Indiana      401 KAQVFEHPHIQDAASQLPDDESLFFGDTGLSKNPIELVEGWFSSWKSSIA    450
                 :||||||||.:||||||||||:||||||||||||:||||||||||||::|
Maraba       401 QAQVFEHPHAKDAASQLPDDETLFFGDTGLSKNPVELVEGWFSSWKSTLA    450
                                     421     429
Indiana      451 SFFFIIGLIIGLFLVLRVGIHLCIKLKHTKKRQIYTDIEMNRLGK-     495
                 |||.||||.:.|..::|:.:.:..|.|..|.::||.|:||:|||.
Maraba       451 SFFLIIGLGVALIFIIRIIVAIRYKYKGRKTQKIYNDVEMSRLGNK     496
                                      |
                                     422
```

FIGURE 3A

Optimal global alignment of VSV Indiana/Cocal strains amino acid sequences of ectodomain of glycoprotein G

```
Parameters:
Aligned_sequences: 2 => 1: Indiana (SEQ ID NO:2), 2: Cocal (SEQ ID NO:6)
Matrix: EBLOSUM62, Gap_penalty: 10.0, Extend_penalty: 0.5, End_gap_penalty:
false, End_gap_open: 10.0
Results:
Length: 495
Identity:     362/495 (73.1%)
Similarity:   429/495 (86.7%)
Gaps:           0/495 (0.0%)
Score: 2085.0
```

```
                                           22
                                      17    ↓  25
Indiana       1 KFTIVFPHNQKGNWKNVPSNYHYCPSSSDLNWHNDLIGTAIQVKMPKSHK    50
                ||:||||.:||||||||||:|||||||||.||||||:|..::|||||:||
Cocal         1 KFSIVFPQSQKGNWKNVPSSYHYCPSSSDQNWHNDLLGITMKVKMPKTHK    50
                                      17       25
Indiana      51 AIQADGWMCHASKWVTTCDFRWYGPKYITQSIRSFTPSVEQCKESIEQTK   100
                |||||||||||:||:||||||||||||||||.||.|..|:.|||||||:|||
Cocal        51 AIQADGWMCHAAKWITTCDFRWYGPKYITHSIHSIQPTSEQCKESIKQTK   100

Indiana     101 QGTWLNPGFPPQSCGYATVTDAEAVIVQVTPHHVLVDEYTGEWVDSQFIN   150
                ||||::||||||:||||||||:.||:||.|||||||||||||||:||||.|
Cocal       101 QGTWMSPGFPPQNCGYATVTDSVAVVVQATPHHVLVDEYTGEWIDSQFPN   150

Indiana     151 GKCSNYICPTVHNSTTWHSDYKVKGLCDSNLISMDITFFSEDGELSSLGK   200
                |||....|.||||||.|:||||.||||:.|:..:||||||||:..|:||
Cocal       151 GKCETEECETVHNSTVWYSDYKVTGLCDATLVDTEITFFSEDGKKESIGK   200

Indiana     201 EGTGFRSNYFAYETGGKACKMQYCKHWGVRLPSGVWFEMADKDLFAAARF   250
                ..||:|||||||.|.|.|||.||||.|||||||||||..|:|::|||:.
Cocal       201 PNTGYRSNYFAYEKGDKVCKMNYCKHAGVRLPSGVWFEFVDQDVYAAAKL   250

Indiana     251 PECPEGSSISAPSQTSVDVSLIQDVERILDYSLCQETWSKIRAGLPISPV   300
                ||||.|::||||:|||||||||.|||||||||||||||||||:..|:|||
Cocal       251 PECPVGATISAPTQTSVDVSLILDVERILDYSLCQETWSKIRSKQPVSPV   300

Indiana     301 DLSYLAPKNPGTGPAFTIINGTLKYFETRYIRVDIAAPILSRMVGMISGT   350
                ||||||||||||||||||||||||||||||||:||..||:|:|||.|||:
Cocal       301 DLSYLAPKNPGTGPAFTIINGTLKYFETRYIRIDIDNPIISKMVGKISGS   350

Indiana     351 TTERELWDDWAPYEDVEIGPNGVLRTSSGYKFPLYMIGHGMLDSDLHLSS   400
                .||||||.:|.|||.|||||||:|:|.:||||||:||||||||||||.:|
Cocal       351 QTERELWTEWFPYEGVEIGPNGILKTPTGYKFPLFMIGHGMLDSDLHKTS   400
                                         421     429
Indiana     401 KAQVFEHPHIQDAASQLPDDESLFFGDTGLSKNPIELVEGWFSSWKSSIA   450
                :|:||||||:.:|..|||::|:|||||||:||||:||:||||||||::.
Cocal       401 QAEVFEHPHLAEAPKQLPEEETLFFGDTGISKNPVELIEGWFSSWKSTVV   450
                                         421↑    429
Indiana     451 SFFFIIGLIIGLFLVLRVGIHLCIKLKHTKKRQIYTDIEMNRLGK   495
                :|||.||:.|.|::|.|:.|.:..:.:.::.::||.||||:|..|
Cocal       451 TFFFAIGVFILLYVVARIVIAVRYRYQGSNNKRIYNDIEMSRFRK   495
                                         ↑
                                        422
```

FIGURE 3B

Optimal global alignment of VSV Indiana/Morreton strains amino acid sequences of ectodomain of glycoprotein G

```
Parameters:
Aligned_sequences: 2 => 1: Indiana (SEQ ID NO:2), 2: Morreton (SEQ ID NO:8)
Matrix: EBLOSUM62, Gap_penalty: 10.0, Extend_penalty: 0.5, End_gap_penalty:
false, End_gap_open: 10.0
Results:
Length: 496
Identity:     428/496 (86.3%)
Similarity:   466/496 (94.0%)
Gaps:           1/496 (0.2%)
Score: 2385.0


                                            22
                                  17        ↓  25
Indiana        1 KFTIVFPHNQKGNWKNVPSNYHYCPSSSDLNWHNDLIGTAIQVKMPKSHK     50
                 ||||||||||||||||||:||.||||||||||||.||||::||||||||
Morreton       1 KFTIVFPHNQKGNWKNVPANYQYCPSSSDLNWHNGLIGTSLQVKMPKSHK     50
                                  17           25

Indiana       51 AIQADGWMCHASKWVTTCDFRWYGPKYITQSIRSFTPSVEQCKESIEQTK    100
                 |||||||||||:|||||||||||||||:|.||:|..|:|:||||||.|||
Morreton      51 AIQADGWMCHAAKWVTTCDFRWYGPKYVTHSIKSMIPTVDQCKESIAQTK    100

Indiana      101 QGTWLNPGFPPQSCGYATVTDAEAVIVQVTPHHVLVDEYTGEWVDSQFIN    150
                 |||||||||||||||||:|||||||||:.|||.|||||||||||||||..
Morreton     101 QGTWLNPGFPPQSCGYASVTDAEAVIVKATPHQVLVDEYTGEWVDSQFPT    150

Indiana      151 GKCSNYICPTVHNSTTWHSDYKVKGLCDSNLISMDITFFSEDGELSSLGK    200
                 |||:..|||||||||||||||||.||||:||||||||||||||:|:||||
Morreton     151 GKCNKDICPTVHNSTTWHSDYKVTGLCDANLISMDITFFSEDGKLTSLGK    200

Indiana      201 EGTGFRSNYFAYETGGKACKMQYCKHWGVRLPSGVWFEMADKDLFAAARF    250
                 |||||||||||||.|.|||:|||||||||||||||||||||||::..|:|
Morreton     201 EGTGFRSNYFAYENGDKACRMQYCKHWGVRLPSGVWFEMADKDIYNDAKF    250

Indiana      251 PECPEGSSISAPSQTSVDVSLIQDVERILDYSLCQETWSKIRAGLPISPV    300
                 |:|||||||:|||||||||||||||||||||||||||||||||.||||||
Morreton     251 PDCPEGSSIAAPSQTSVDVSLIQDVERILDYSLCQETWSKIRAHLPISPV    300

Indiana      301 DLSYLAPKNPGTGPAFTIINGTLKYFETRYIRVDIAAPILSRMVGMISGT    350
                 |||||:||||||||||||||||||||||||||||||.||:.:|.|:||||
Morreton     301 DLSYLSPKNPGTGPAFTIINGTLKYFETRYIRVDIAGPIIPQMRGVISGT    350

Indiana      351 TTERELWDDWAPYEDVEIGPNGVLRTSSGYKFPLYMIGHGMLDSDLHLSS    400
                 |||||||.||.|||||||||||||:|::|||||||||||||||||||:||
Morreton     351 TTERELWTDWYPYEDVEIGPNGVLKTATGYKFPLYMIGHGMLDSDLHISS    400
                                      421     429
Indiana      401 KAQVFEHPHIQDAASQLPDDESLFFGDTGLSKNPIELVEGWFSSWKSSIA    450
                 |||||||||||||||||||||:|||||||||||||||||||||.|||:||
Morreton     401 KAQVFEHPHIQDAASQLPDDETLFFGDTGLSKNPIELVEGWFSGWKSTIA    450
                                      421↑    429
Indiana      451 SFFFIIGLIIGLFLVLRVGIHLCIKLKHTKKR-QIYTDIEMNRLGK    495
                 ||||||||:|||:||||:||.||||.:..:|| :||||:|||||.:
Morreton     451 SFFFIIGLVIGLYLVLRIGIALCIKCRVQEKRPKIYTDVEMNRLDR    496
                                      422
```

FIGURE 3C

Optimal global alignment of VSV Indiana/Alagoa strains amino acid sequences of ectodomain of glycoprotein G

Parameters:
Aligned_sequences: 2 => 1: Indiana (SEQ ID NO:2), 2: Alagoa (SEQ ID NO:10)
Matrix: EBLOSUM62, Gap_penalty: 10.0, Extend_penalty: 0.5, End_gap_penalty: false, End_gap_open: 10.0

Results:
Length: 498
Identity: 322/498 (64.7%)
Similarity: 413/498 (82.9%)
Gaps: 7/498 ( 1.4%)
Score: 1916.5

```
                                 22
                             17       25
Indiana      1 KFTIVFPHNQKGNWKNVPSNYHYCPSSSDLNWHNDLIGTAIQVKMPKSHK    50
                 |||||||.:|||:||:||.||.|||||:|.|||.||:|..|:.||||.||
Alagoa       1 KFTIVFPQSQKGDWKDVPPNYRYCPSSADQNWHGDLLGVNIRAKMPKVHK    50
                             17       25

Indiana     51 AIQADGWMCHASKWVTTCDFRWYGPKYITQSIRSFTPSVEQCKESIEQTK   100
                 ||:||||||||:|||||||:|||||:|||.||.||.|:..||:|||:|||
Alagoa      51 AIKADGWMCHAAKWVTTCDYRWYGPQYITHSIHSFIPTKAQCEESIKQTK   100

Indiana    101 QGTWLNPGFPPQSCGYATVTDAEAVIVQVTPHHVLVDEYTGEWVDSQFIN   150
                 :|.|:||||||::||||:|:|||::|||.|.|.|::|||:|:|:||||..
Alagoa     101 EGVWINPGFPPKNCGYASVSDAESIIVQATAHSVMIDEYSGDWLDSQFPT   150

Indiana    151 GKCSNYICPTVHNSTTWHSDYKVKGLCDSNLISMDITFFSEDGELSSLGK   200
                 |:|:...|.|:||||.|::||:|.|||||.|:|.::||:||||.::|:|:
Alagoa     151 GRCTGSTCETIHNSTLWYADYQVTGLCDSALVSTEVTFYSEDGLMTSIGR   200

Indiana    201 EGTGFRSNYFAYETGGKACKMQYCKHWGVRLPSGVWFEMADKDLFAAARF   250
                 :.||:|||||.||.|..||:|:||.|.|:||||||||||.||:|..:.:.
Alagoa     201 QNTGYRSNYFPYEKGAAACRMKYCTHEGIRLPSGVWFEMVDKELLESVQM   250

Indiana    251 PECPEGSSISAPSQTSVDVSLIQDVERILDYSLCQETWSKIRAGLPISPV   300
                 ||||.|.:||||:|||||||||.||||:||||||||||||:.:|||||||
Alagoa     251 PECPAGLTISAPTQTSVDVSLILDVERMLDYSLCQETWSKVHSGLPISPV   300

Indiana    301 DLSYLAPKNPGTGPAFTIINGTLKYFETRYIRVDIAAPILSRMVGMISGT   350
                 ||.|:||||||.||||||:||||||||:|||:|:||..|:|.:|.|.:|||
Alagoa     301 DLGYIAPKNPGAGPAFTIVNGTLKYFDTRYLRIDIEGPVLKKMTGKVSGT   350

Indiana    351 TTERELWDDWAPYEDVEIGPNGVLRTSSGYKFPLYMIGHGMLDSDLHLSS   400
                 .|:||||.:|.||:|||||||||||:|..||||||||||||||:|||||..:|
Alagoa     351 PTKRELWTEWFPYDDVEIGPNGVLKTPEGYKFPLYMIGHGLLDSDLQKTS   400
                                       421     429
Indiana    401 KAQVFEHPHIQDAASQLPDDESLFFGDTGLSKNPIELVEGWFSSWKSSIA   450
                 :|:||.||.|.:|..:||||:|||||||:||||:|::||||||:|:||:.
Alagoa     401 QAEVFHHPQIAEAVQKLPDDETLFFGDTGISKNPVEVIEGWFSNWRSSVM   450
                                       421     429
Indiana    451  SFFFIIGLIIGLFLVLRVGIHLCIKLKH---TKKRQIYTDIEMNRLGK   495
                  :..|.|.|::...|::|    ||:..:|    .|:.:||.|:|||:|.:
Alagoa     451  AIVFAILLLVITVLMVR----LCVAFRHFCCQKRHKIYNDLEMNQLRR   494
                                        422
```

FIGURE 3D

Optimal global alignment of VSV Indiana/New Jersey strains amino acid sequences of ectodomain of glycoprotein G

Parameters:
Aligned_sequences: 2 => 1: Indiana (SEQ ID NO:2), 2: NewJersey (SEQ ID NO:12)
Matrix: EBLOSUM62, Gap_penalty: 10.0, Extend_penalty: 0.5, End_gap_penalty: false, End_gap_open: 10.0

Results:
Length: 504
Identity: 260/504 (51.6%)
Similarity: 338/504 (67.1%)
Gaps: 12/504 (2.4%)
Score: 1404.0

```
                                        22
                                17      ↓  25
Indiana        1 KFTIVFPHNQKGNWKNVPSNYHYCPSSSDLNWHNDLIGTAIQVKMPKSHK    50
                 |..||||.:..|:||.||..|:|||:|:|.|.|....|..:::.|||...
NewJersey      1 KIEIVFPQHTTGDWKRVPHEYNYCPTSADKNSHGTQTGIPVELTMPKGLT    50
                                17        25

Indiana       51 AIQADGWMCHASKWVTTCDFRWYGPKYITQSIRSFTPSVEQCKESIEQTK   100
                 ..|.||:|||::.|:||||||||||||||.||.:..|:..||.|:|:..|
NewJersey     51 THQVDGFMCHSALWMTTCDFRWYGPKYITHSIHNEEPTDYQCLEAIKAYK   100

Indiana      101 QGTWLNPGFPPQSCGYATVTDAEAVIVQVTPHHVLVDEYTGEWVDSQFIN   150
                 .|...|||||||||||.|||||||.||.||||.|.||||||||:|..||.
NewJersey    101 DGVSFNPGFPPQSCGYGTVTDAEAHIVTVTPHSVKVDEYTGEWIDPHFIG   150

Indiana      151 GKCSNYICPTVHNSTTWHSDYKVKGLCDSNLISMDITFFSEDGELSSLGK   200
                 |:|...||.||||||.|.:....:.:|......:..||||:..|::|:|.
NewJersey    151 GRCKGQICETVHNSTKWFTSSDGESVCSQLFTLVGGTFFSDSEEITSMGL   200

Indiana      201 EGTGFRSNYFAYETGGKACKMQYCKHWGVRLPSGVWFEMADKDLFAAAR-   249
                 ..||.|||||.|.:....|||.:|:..|.:|.:.:||::.|.||....|
NewJersey    201 PETGIRSNYFPYVSTEGICKMPFCRKPGYKLKNDLWFQITDPDLDKTVRD   250

Indiana      250 ---FPECPEGSSISAPSQTSVDVSLIQDVERILDYSLCQETWSKIRAGLP   296
                    ..:|...|||..|.:.:.|:|||.||||||||:|||.|||||.||.|
NewJersey    251 LPHIKDCDLSSSIVTPGEHATDISLISDVERILDYALCQNTWSKIEAGEP   300

Indiana      297 ISPVDLSYLAPKNPGTGPAFTIINGTLKYFETRYIRVDIAAPILSRMVGM   346
                 |:|||||||.|||||.||.||||||:|.||.::|:||::.:|::.||.|.
NewJersey    301 ITPVDLSYLGPKNPGAGPVFTIINGSLHYFMSKYLRVELESPVIPRMEGK   350

Indiana      347 ISGTTTERELWDDWAPYEDVEIGPNGVLRTSSGYKFPLYMIGHGMLDSDL   396
                 ::||...|:|||.|.|:.:||||||||||:|..|||||||::||.|.:|:|:
NewJersey    351 VAGTRIVRQLWDQWFPFGEVEIGPNGVLKTKQGYKFPLHIIGTGEVDNDI   400
                                              421      429
Indiana      397 HLSSKAQVFEHPHIQDAASQLPDD---ESLFFGDTGLSKNPIELVEGWFS   443
                 .:.....:.:||||||:.|.:.|..|   ||.|::||||:||||:||||||||
NewJersey    401 KMERIVKHWEHPHIEAAQTFLKKDDTEEVLYYGDTGVSKNPVELVEGWFS   450
                                             428↑      436
Indiana      444 SWKSSIASFF-FIIGLIIGLFLVLRVGIHLCIKLKHTKKRQIY-TDIEMN   491
                 .|:|||....  .|||.:|.:||:..:|:   ...|...|:|.||  :|:||.
NewJersey    451 GWRSSIMGVLAVIIGFVILIFLIRLIGV--LSSLFRQKRRPIYKSDVEMA   498
                                              429

Indiana      492 RLGK    495
                 ...
NewJersey    499 HFR-    501
```

FIGURE 3E

Optimal global alignment of VSV Indiana/Carajas strains amino acid sequences of ectodomain of glycoprotein G

Parameters:
Aligned_sequences: 2 => 1: Indiana (SEQ ID NO:2), 2: Carajas (SEQ ID NO:14)
Matrix: EBLOSUM62, Gap_penalty: 10.0, Extend_penalty: 0.5, End_gap_penalty: false, End_gap_open: 10.0

Results:
Length: 505
Identity: 285/505 (56.4%)
Similarity: 369/505 (73.1%)
Gaps: 13/505 (2.6%)
Score: 1622.0

```
                                          22
                               17         |        25
Indiana       1 KFTIVFPHNQKGNWKNVPSNYHYCPSSSDLNWHNDLIGTAIQVKMPKSHK     50
                |.||.||.:.||:|:.||..|:|||:|:|.|.|.|||...::::.|||.|
Carajas       1 KITISFPQSLKGDWRPVPKGYNYCPTSADKNLHGDLIDIGLRLRAPKSFK     50
                               17              25

Indiana      51 AIQADGWMCHASKWVTTCDFRWYGPKYITQSIRSFTPSVEQCKESIEQTK    100
                .|.||||||||::|:|||||||||||||||.||.||.||.:||||:|..|.
Carajas      51 GISADGWMCHAARWITTCDFRWYGPKYITHSIHSFRPSNDQCKEAIRLTN    100

Indiana     101 QGTWLNPGFPPQSCGYATVTDAEAVIVQVTPHHVLVDEYTGEWVDSQFIN    150
                :|.|:||||||||||||:|||:|:|:|.||.|.||||||:|.|:||||..
Carajas     101 EGNWINPGFPPQSCGYASVTDSESVVVTVTKHQVLVDEYSGSWIDSQFPG    150

Indiana     151 GKCSNYICPTVHNSTTWHSDYKVKGLCDSNLISMDITFFSEDGELSSLGK    200
                |.|::.||.||||||.||:|:.:..:||...::||...|:|.|:....||
Carajas     151 GSCTSPICDTVHNSTLWHADHTLDSICDQEFVAMDAVLFTESGKFEEFGK    200

Indiana     201 EGTGFRSNYFAYETGGKACKMQYCKHWGVRLPSGVWFEMADKDLFAAA--    248
                ..:|.|||||.||:....|:|.:||..|.:|||||||||:.|.:....|
Carajas     201 PNSGIRSNYFPYESLKDVCQMDFCKRKGFKLPSGVWFEIEDAEKSHKAQV    250

Indiana     249 --RFPECPEGSSISAPSQTSVDVSLIQDVERILDYSLCQETWSKIRAGLP    296
                  :...||.|:.||||:|.:.|::||.|||||||||||||.|||||:....
Carajas     251 ELKIKRCPHGAVISAPNQNAADINLIMDVERILDYSLCQATWSKIQNKEA    300

Indiana     297 ISPVDLSYLAPKNPGTGPAFTIINGTLKYFETRYIRVDIAAPILSRMVGM    346
                ::|:|:|||.|||||.|||||||||||||.||.|||||||||.|:...:.|.
Carajas     301 LTPIDISYLGPKNPGPGPAFTIINGTLHYFNTRYIRVDIAGPVTKEITGF    350

Indiana     347 ISGTTTERELWDDWAPYEDVEIGPNGVLRTSSGYKFPLYMIGHGMLDSDL    396
                :|||:|.|.|||.|.||.:..|||||:|:|:||||:||:|:|.|:||:|:
Carajas     351 VSGTSTSRVLWDQWFPYGENSIGPNGLLKTASGYKYPLFMVGTGVLDADI    400
                                                421       429
Indiana     397 HLSSKAQVFEHPHIQDAASQLPDDESLFFGDTGLSKNPIELVEGWFSSWK    446
                |...:|.|.||||.::|...:.||.||.:||||||:||||:|:||||||.|:
Carajas     401 HKLGEATVIEHPHAKEAQKVVDDSEVIFFGDTGVSKNPVEVVEGWFSGWR    450
                                                425       433
Indiana     447 SSIASFFFIIGLIIGLFLVLRVGIHL---CIKLKHTKKRQIY-TDIEMNR    492
                ||:.|.|.||.||:.|.|::|:.|.|    |:  :| |||.|| .|:||.|
Carajas     451 SSLMSIFGIILLIVCLVLIVRILIALKYCCV--RH-KKRTIYKEDLEMGR    497
                                            426
Indiana     493 LGK--     495
                :.:
Carajas     498 IPRRA     502
```

FIGURE 3F

SEQUENCE LISTING

```
<160> NUMBER OF SEQ ID NOS: 87

<210> SEQ ID NO 1
<211> LENGTH: 511
<212> TYPE: PRT
<213> ORGANISM: Vesicular stomatitis Indiana virus

<400> SEQUENCE: 1

Met Lys Cys Leu Leu Tyr Leu Ala Phe Leu Phe Ile Gly Val Asn Cys
1               5                   10                  15

Lys Phe Thr Ile Val Phe Pro His Asn Gln Lys Gly Asn Trp Lys Asn
            20                  25                  30

Val Pro Ser Asn Tyr His Tyr Cys Pro Ser Ser Ser Asp Leu Asn Trp
        35                  40                  45

His Asn Asp Leu Ile Gly Thr Ala Ile Gln Val Lys Met Pro Lys Ser
    50                  55                  60

His Lys Ala Ile Gln Ala Asp Gly Trp Met Cys His Ala Ser Lys Trp
65                  70                  75                  80

Val Thr Thr Cys Asp Phe Arg Trp Tyr Gly Pro Lys Tyr Ile Thr Gln
                85                  90                  95

Ser Ile Arg Ser Phe Thr Pro Ser Val Glu Gln Cys Lys Glu Ser Ile
            100                 105                 110

Glu Gln Thr Lys Gln Gly Thr Trp Leu Asn Pro Gly Phe Pro Pro Gln
        115                 120                 125

Ser Cys Gly Tyr Ala Thr Val Thr Asp Ala Glu Ala Val Ile Val Gln
    130                 135                 140
```

Val Thr Pro His His Val Leu Val Asp Glu Tyr Thr Gly Glu Trp Val
145 150 155 160

Asp Ser Gln Phe Ile Asn Gly Lys Cys Ser Asn Tyr Ile Cys Pro Thr
165 170 175

Val His Asn Ser Thr Thr Trp His Ser Asp Tyr Lys Val Lys Gly Leu
180 185 190

Cys Asp Ser Asn Leu Ile Ser Met Asp Ile Thr Phe Phe Ser Glu Asp
195 200 205

Gly Glu Leu Ser Ser Leu Gly Lys Glu Gly Thr Gly Phe Arg Ser Asn
210 215 220

Tyr Phe Ala Tyr Glu Thr Gly Gly Lys Ala Cys Lys Met Gln Tyr Cys
225 230 235 240

Lys His Trp Gly Val Arg Leu Pro Ser Gly Val Trp Phe Glu Met Ala
245 250 255

Asp Lys Asp Leu Phe Ala Ala Ala Arg Phe Pro Glu Cys Pro Glu Gly
260 265 270

Ser Ser Ile Ser Ala Pro Ser Gln Thr Ser Val Asp Val Ser Leu Ile
275 280 285

Gln Asp Val Glu Arg Ile Leu Asp Tyr Ser Leu Cys Gln Glu Thr Trp
290 295 300

Ser Lys Ile Arg Ala Gly Leu Pro Ile Ser Pro Val Asp Leu Ser Tyr
305 310 315 320

Leu Ala Pro Lys Asn Pro Gly Thr Gly Pro Ala Phe Thr Ile Ile Asn
325 330 335

Gly Thr Leu Lys Tyr Phe Glu Thr Arg Tyr Ile Arg Val Asp Ile Ala
340 345 350

Ala Pro Ile Leu Ser Arg Met Val Gly Met Ile Ser Gly Thr Thr Thr
355 360 365

Glu Arg Glu Leu Trp Asp Asp Trp Ala Pro Tyr Glu Asp Val Glu Ile
370 375 380

Gly Pro Asn Gly Val Leu Arg Thr Ser Ser Gly Tyr Lys Phe Pro Leu
385 390 395 400

Tyr Met Ile Gly His Gly Met Leu Asp Ser Asp Leu His Leu Ser Ser
405 410 415

Lys Ala Gln Val Phe Glu His Pro His Ile Gln Asp Ala Ala Ser Gln
420 425 430

Leu Pro Asp Asp Glu Ser Leu Phe Phe Gly Asp Thr Gly Leu Ser Lys
435 440 445

Asn Pro Ile Glu Leu Val Glu Gly Trp Phe Ser Ser Trp Lys Ser Ser
450 455 460

Ile Ala Ser Phe Phe Phe Ile Ile Gly Leu Ile Ile Gly Leu Phe Leu
465 470 475 480

Val Leu Arg Val Gly Ile His Leu Cys Ile Lys Leu Lys His Thr Lys
485 490 495

Lys Arg Gln Ile Tyr Thr Asp Ile Glu Met Asn Arg Leu Gly Lys
500 505 510

<210> SEQ ID NO 2
<211> LENGTH: 495
<212> TYPE: PRT
<213> ORGANISM: Vesicular stomatitis Indiana virus

```
<400> SEQUENCE: 2

Lys Phe Thr Ile Val Phe Pro His Asn Gln Lys Gly Asn Trp Lys Asn
1               5                   10                  15

Val Pro Ser Asn Tyr His Tyr Cys Pro Ser Ser Ser Asp Leu Asn Trp
            20                  25                  30

His Asn Asp Leu Ile Gly Thr Ala Ile Gln Val Lys Met Pro Lys Ser
        35                  40                  45

His Lys Ala Ile Gln Ala Asp Gly Trp Met Cys His Ala Ser Lys Trp
    50                  55                  60

Val Thr Thr Cys Asp Phe Arg Trp Tyr Gly Pro Lys Tyr Ile Thr Gln
65                  70                  75                  80

Ser Ile Arg Ser Phe Thr Pro Ser Val Glu Gln Cys Lys Glu Ser Ile
                85                  90                  95

Glu Gln Thr Lys Gln Gly Thr Trp Leu Asn Pro Gly Phe Pro Pro Gln
            100                 105                 110

Ser Cys Gly Tyr Ala Thr Val Thr Asp Ala Glu Ala Val Ile Val Gln
        115                 120                 125

Val Thr Pro His His Val Leu Val Asp Glu Tyr Thr Gly Glu Trp Val
    130                 135                 140

Asp Ser Gln Phe Ile Asn Gly Lys Cys Ser Asn Tyr Ile Cys Pro Thr
145                 150                 155                 160

Val His Asn Ser Thr Thr Trp His Ser Asp Tyr Lys Val Lys Gly Leu
                165                 170                 175

Cys Asp Ser Asn Leu Ile Ser Met Asp Ile Thr Phe Phe Ser Glu Asp
            180                 185                 190

Gly Glu Leu Ser Ser Leu Gly Lys Glu Gly Thr Gly Phe Arg Ser Asn
        195                 200                 205

Tyr Phe Ala Tyr Glu Thr Gly Gly Lys Ala Cys Lys Met Gln Tyr Cys
    210                 215                 220

Lys His Trp Gly Val Arg Leu Pro Ser Gly Val Trp Phe Glu Met Ala
225                 230                 235                 240

Asp Lys Asp Leu Phe Ala Ala Ala Arg Phe Pro Glu Cys Pro Glu Gly
                245                 250                 255

Ser Ser Ile Ser Ala Pro Ser Gln Thr Ser Val Asp Val Ser Leu Ile
            260                 265                 270

Gln Asp Val Glu Arg Ile Leu Asp Tyr Ser Leu Cys Gln Glu Thr Trp
        275                 280                 285

Ser Lys Ile Arg Ala Gly Leu Pro Ile Ser Pro Val Asp Leu Ser Tyr
    290                 295                 300

Leu Ala Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Val Asp Ile Ala
                325                 330                 335

Ala Pro Ile Leu Ser Arg Met Val Gly Met Ile Ser Gly Thr Thr Thr
            340                 345                 350

Glu Arg Glu Leu Trp Asp Asp Trp Ala Pro Tyr Glu Asp Val Glu Ile
        355                 360                 365

Gly Pro Asn Gly Val Leu Arg Thr Ser Ser Gly Tyr Lys Phe Pro Leu
    370                 375                 380

Tyr Met Ile Gly His Gly Met Leu Asp Ser Asp Leu His Leu Ser Ser
385                 390                 395                 400
```

```
Lys Ala Gln Val Phe Glu His Pro His Ile Gln Asp Ala Ala Ser Gln
                405                 410                 415

Leu Pro Asp Asp Glu Ser Leu Phe Phe Gly Asp Thr Gly Leu Ser Lys
            420                 425                 430

Asn Pro Ile Glu Leu Val Glu Gly Trp Phe Ser Ser Trp Lys Ser Ser
        435                 440                 445

Ile Ala Ser Phe Phe Phe Ile Ile Gly Leu Ile Ile Gly Leu Phe Leu
    450                 455                 460

Val Leu Arg Val Gly Ile His Leu Cys Ile Lys Leu Lys His Thr Lys
465                 470                 475                 480

Lys Arg Gln Ile Tyr Thr Asp Ile Glu Met Asn Arg Leu Gly Lys
                485                 490                 495


<210> SEQ ID NO 3
<211> LENGTH: 512
<212> TYPE: PRT
<213> ORGANISM: Vesicular stomatitis Maraba virus

<400> SEQUENCE: 3

Met Leu Arg Leu Phe Leu Phe Cys Phe Leu Ala Leu Gly Ala His Ser
1               5                   10                  15

Lys Phe Thr Ile Val Phe Pro His His Gln Lys Gly Asn Trp Lys Asn
            20                  25                  30

Val Pro Ser Thr Tyr His Tyr Cys Pro Ser Ser Ser Asp Gln Asn Trp
        35                  40                  45

His Asn Asp Leu Thr Gly Val Ser Leu His Val Lys Ile Pro Lys Ser
    50                  55                  60

His Lys Ala Ile Gln Ala Asp Gly Trp Met Cys His Ala Ala Lys Trp
65                  70                  75                  80

Val Thr Thr Cys Asp Phe Arg Trp Tyr Gly Pro Lys Tyr Ile Thr His
                85                  90                  95

Ser Ile His Ser Met Ser Pro Thr Leu Glu Gln Cys Lys Thr Ser Ile
            100                 105                 110

Glu Gln Thr Lys Gln Gly Val Trp Ile Asn Pro Gly Phe Pro Pro Gln
        115                 120                 125

Ser Cys Gly Tyr Ala Thr Val Thr Asp Ala Glu Val Val Val Val Gln
    130                 135                 140

Ala Thr Pro His His Val Leu Val Asp Glu Tyr Thr Gly Glu Trp Ile
145                 150                 155                 160

Asp Ser Gln Leu Val Gly Gly Lys Cys Ser Lys Glu Val Cys Gln Thr
                165                 170                 175

Val His Asn Ser Thr Val Trp His Ala Asp Tyr Lys Ile Thr Gly Leu
            180                 185                 190

Cys Glu Ser Asn Leu Ala Ser Val Asp Ile Thr Phe Phe Ser Glu Asp
        195                 200                 205

Gly Gln Lys Thr Ser Leu Gly Lys Pro Asn Thr Gly Phe Arg Ser Asn
    210                 215                 220

His Phe Ala Tyr Glu Ser Gly Glu Lys Ala Cys Arg Met Gln Tyr Cys
225                 230                 235                 240

Thr Gln Trp Gly Ile Arg Leu Pro Ser Gly Val Trp Phe Glu Leu Val
                245                 250                 255

Asp Lys Asp Leu Phe Gln Ala Ala Lys Leu Pro Glu Cys Pro Arg Gly
            260                 265                 270
```

Ser Ser Ile Ser Ala Pro Ser Gln Thr Ser Val Asp Val Ser Leu Ile
        275                 280                 285

Gln Asp Val Glu Arg Ile Leu Asp Tyr Ser Leu Cys Gln Glu Thr Trp
    290                 295                 300

Ser Lys Ile Arg Ala Lys Leu Pro Val Ser Pro Val Asp Leu Ser Tyr
305                 310                 315                 320

Leu Ala Pro Lys Asn Pro Gly Ser Gly Pro Ala Phe Thr Ile Ile Asn
                325                 330                 335

Gly Thr Leu Lys Tyr Phe Glu Thr Arg Tyr Ile Arg Val Asp Ile Ser
            340                 345                 350

Asn Pro Ile Ile Pro His Met Val Gly Thr Met Ser Gly Thr Thr Thr
        355                 360                 365

Glu Arg Glu Leu Trp Asn Asp Trp Tyr Pro Tyr Glu Asp Val Glu Ile
    370                 375                 380

Gly Pro Asn Gly Val Leu Lys Thr Pro Thr Gly Phe Lys Phe Pro Leu
385                 390                 395                 400

Tyr Met Ile Gly His Gly Met Leu Asp Ser Asp Leu His Lys Ser Ser
                405                 410                 415

Gln Ala Gln Val Phe Glu His Pro His Ala Lys Asp Ala Ala Ser Gln
            420                 425                 430

Leu Pro Asp Asp Glu Thr Leu Phe Phe Gly Asp Thr Gly Leu Ser Lys
        435                 440                 445

Asn Pro Val Glu Leu Val Glu Gly Trp Phe Ser Ser Trp Lys Ser Thr
    450                 455                 460

Leu Ala Ser Phe Phe Leu Ile Ile Gly Leu Gly Val Ala Leu Ile Phe
465                 470                 475                 480

Ile Ile Arg Ile Ile Val Ala Ile Arg Tyr Lys Tyr Lys Gly Arg Lys
                485                 490                 495

Thr Gln Lys Ile Tyr Asn Asp Val Glu Met Ser Arg Leu Gly Asn Lys
            500                 505                 510

<210> SEQ ID NO 4
<211> LENGTH: 496
<212> TYPE: PRT
<213> ORGANISM: Vesicular stomatitis Maraba virus

<400> SEQUENCE: 4

Lys Phe Thr Ile Val Phe Pro His His Gln Lys Gly Asn Trp Lys Asn
1               5                   10                  15

Val Pro Ser Thr Tyr His Tyr Cys Pro Ser Ser Ser Asp Gln Asn Trp
            20                  25                  30

His Asn Asp Leu Thr Gly Val Ser Leu His Val Lys Ile Pro Lys Ser
        35                  40                  45

His Lys Ala Ile Gln Ala Asp Gly Trp Met Cys His Ala Ala Lys Trp
    50                  55                  60

Val Thr Thr Cys Asp Phe Arg Trp Tyr Gly Pro Lys Tyr Ile Thr His
65                  70                  75                  80

Ser Ile His Ser Met Ser Pro Thr Leu Glu Gln Cys Lys Thr Ser Ile
                85                  90                  95

Glu Gln Thr Lys Gln Gly Val Trp Ile Asn Pro Gly Phe Pro Pro Gln
            100                 105                 110

Ser Cys Gly Tyr Ala Thr Val Thr Asp Ala Glu Val Val Val Val Gln
        115                 120                 125

```
Ala Thr Pro His His Val Leu Val Asp Glu Tyr Thr Gly Glu Trp Ile
    130                 135                 140

Asp Ser Gln Leu Val Gly Gly Lys Cys Ser Lys Glu Val Cys Gln Thr
145                 150                 155                 160

Val His Asn Ser Thr Val Trp His Ala Asp Tyr Lys Ile Thr Gly Leu
                165                 170                 175

Cys Glu Ser Asn Leu Ala Ser Val Asp Ile Thr Phe Phe Ser Glu Asp
            180                 185                 190

Gly Gln Lys Thr Ser Leu Gly Lys Pro Asn Thr Gly Phe Arg Ser Asn
        195                 200                 205

His Phe Ala Tyr Glu Ser Gly Glu Lys Ala Cys Arg Met Gln Tyr Cys
    210                 215                 220

Thr Gln Trp Gly Ile Arg Leu Pro Ser Gly Val Trp Phe Glu Leu Val
225                 230                 235                 240

Asp Lys Asp Leu Phe Gln Ala Ala Lys Leu Pro Glu Cys Pro Arg Gly
                245                 250                 255

Ser Ser Ile Ser Ala Pro Ser Gln Thr Ser Val Asp Val Ser Leu Ile
            260                 265                 270

Gln Asp Val Glu Arg Ile Leu Asp Tyr Ser Leu Cys Gln Glu Thr Trp
        275                 280                 285

Ser Lys Ile Arg Ala Lys Leu Pro Val Ser Pro Val Asp Leu Ser Tyr
    290                 295                 300

Leu Ala Pro Lys Asn Pro Gly Ser Gly Pro Ala Phe Thr Ile Ile Asn
305                 310                 315                 320

Gly Thr Leu Lys Tyr Phe Glu Thr Arg Tyr Ile Arg Val Asp Ile Ser
                325                 330                 335

Asn Pro Ile Ile Pro His Met Val Gly Thr Met Ser Gly Thr Thr Thr
            340                 345                 350

Glu Arg Glu Leu Trp Asn Asp Trp Tyr Pro Tyr Glu Asp Val Glu Ile
        355                 360                 365

Gly Pro Asn Gly Val Leu Lys Thr Pro Thr Gly Phe Lys Phe Pro Leu
    370                 375                 380

Tyr Met Ile Gly His Gly Met Leu Asp Ser Asp Leu His Lys Ser Ser
385                 390                 395                 400

Gln Ala Gln Val Phe Glu His Pro His Ala Lys Asp Ala Ala Ser Gln
                405                 410                 415

Leu Pro Asp Asp Glu Thr Leu Phe Phe Gly Asp Thr Gly Leu Ser Lys
            420                 425                 430

Asn Pro Val Glu Leu Val Glu Gly Trp Phe Ser Ser Trp Lys Ser Thr
        435                 440                 445

Leu Ala Ser Phe Phe Leu Ile Ile Gly Leu Gly Val Ala Leu Ile Phe
    450                 455                 460

Ile Ile Arg Ile Ile Val Ala Ile Arg Tyr Lys Tyr Lys Gly Arg Lys
465                 470                 475                 480

Thr Gln Lys Ile Tyr Asn Asp Val Glu Met Ser Arg Leu Gly Asn Lys
                485                 490                 495
```

<210> SEQ ID NO 5
<211> LENGTH: 512
<212> TYPE: PRT
<213> ORGANISM: Vesicular stomatitis Cocal virus

<400> SEQUENCE: 5

Met Asn Phe Leu Leu Leu Thr Phe Ile Val Leu Pro Leu Cys Ser His
1               5                   10                  15

Ala Lys Phe Ser Ile Val Phe Pro Gln Ser Gln Lys Gly Asn Trp Lys
            20                  25                  30

Asn Val Pro Ser Ser Tyr His Tyr Cys Pro Ser Ser Ser Asp Gln Asn
        35                  40                  45

Trp His Asn Asp Leu Leu Gly Ile Thr Met Lys Val Lys Met Pro Lys
    50                  55                  60

Thr His Lys Ala Ile Gln Ala Asp Gly Trp Met Cys His Ala Ala Lys
65                  70                  75                  80

Trp Ile Thr Thr Cys Asp Phe Arg Trp Tyr Gly Pro Lys Tyr Ile Thr
                85                  90                  95

His Ser Ile His Ser Ile Gln Pro Thr Ser Glu Gln Cys Lys Glu Ser
            100                 105                 110

Ile Lys Gln Thr Lys Gln Gly Thr Trp Met Ser Pro Gly Phe Pro Pro
        115                 120                 125

Gln Asn Cys Gly Tyr Ala Thr Val Thr Asp Ser Val Ala Val Val Val
    130                 135                 140

Gln Ala Thr Pro His His Val Leu Val Asp Glu Tyr Thr Gly Glu Trp
145                 150                 155                 160

Ile Asp Ser Gln Phe Pro Asn Gly Lys Cys Glu Thr Glu Glu Cys Glu
                165                 170                 175

Thr Val His Asn Ser Thr Val Trp Tyr Ser Asp Tyr Lys Val Thr Gly
            180                 185                 190

Leu Cys Asp Ala Thr Leu Val Asp Thr Glu Ile Thr Phe Phe Ser Glu
        195                 200                 205

Asp Gly Lys Lys Glu Ser Ile Gly Lys Pro Asn Thr Gly Tyr Arg Ser
    210                 215                 220

Asn Tyr Phe Ala Tyr Glu Lys Gly Asp Lys Val Cys Lys Met Asn Tyr
225                 230                 235                 240

Cys Lys His Ala Gly Val Arg Leu Pro Ser Gly Val Trp Phe Glu Phe
                245                 250                 255

Val Asp Gln Asp Val Tyr Ala Ala Ala Lys Leu Pro Glu Cys Pro Val
            260                 265                 270

Gly Ala Thr Ile Ser Ala Pro Thr Gln Thr Ser Val Asp Val Ser Leu
        275                 280                 285

Ile Leu Asp Val Glu Arg Ile Leu Asp Tyr Ser Leu Cys Gln Glu Thr
    290                 295                 300

Trp Ser Lys Ile Arg Ser Lys Gln Pro Val Ser Pro Val Asp Leu Ser
305                 310                 315                 320

Tyr Leu Ala Pro Lys Asn Pro Gly Thr Gly Pro Ala Phe Thr Ile Ile
                325                 330                 335

Asn Gly Thr Leu Lys Tyr Phe Glu Thr Arg Tyr Ile Arg Ile Asp Ile
            340                 345                 350

Asp Asn Pro Ile Ile Ser Lys Met Val Gly Lys Ile Ser Gly Ser Gln
        355                 360                 365

Thr Glu Arg Glu Leu Trp Thr Glu Trp Phe Pro Tyr Glu Gly Val Glu
    370                 375                 380

Ile Gly Pro Asn Gly Ile Leu Lys Thr Pro Thr Gly Tyr Lys Phe Pro
385                 390                 395                 400

```
Leu Phe Met Ile Gly His Gly Met Leu Asp Ser Asp Leu His Lys Thr
                405                 410                 415

Ser Gln Ala Glu Val Phe Glu His Pro His Leu Ala Glu Ala Pro Lys
            420                 425                 430

Gln Leu Pro Glu Glu Glu Thr Leu Phe Phe Gly Asp Thr Gly Ile Ser
        435                 440                 445

Lys Asn Pro Val Glu Leu Ile Glu Gly Trp Phe Ser Ser Trp Lys Ser
    450                 455                 460

Thr Val Val Thr Phe Phe Phe Ala Ile Gly Val Phe Ile Leu Leu Tyr
465                 470                 475                 480

Val Val Ala Arg Ile Val Ile Ala Val Arg Tyr Arg Tyr Gln Gly Ser
                485                 490                 495

Asn Asn Lys Arg Ile Tyr Asn Asp Ile Glu Met Ser Arg Phe Arg Lys
            500                 505                 510


<210> SEQ ID NO 6
<211> LENGTH: 495
<212> TYPE: PRT
<213> ORGANISM: Vesicular stomatitis Cocal virus

<400> SEQUENCE: 6

Lys Phe Ser Ile Val Phe Pro Gln Ser Gln Lys Gly Asn Trp Lys Asn
1               5                   10                  15

Val Pro Ser Ser Tyr His Tyr Cys Pro Ser Ser Ser Asp Gln Asn Trp
            20                  25                  30

His Asn Asp Leu Leu Gly Ile Thr Met Lys Val Lys Met Pro Lys Thr
        35                  40                  45

His Lys Ala Ile Gln Ala Asp Gly Trp Met Cys His Ala Ala Lys Trp
    50                  55                  60

Ile Thr Thr Cys Asp Phe Arg Trp Tyr Gly Pro Lys Tyr Ile Thr His
65                  70                  75                  80

Ser Ile His Ser Ile Gln Pro Thr Ser Glu Gln Cys Lys Glu Ser Ile
                85                  90                  95

Lys Gln Thr Lys Gln Gly Thr Trp Met Ser Pro Gly Phe Pro Pro Gln
            100                 105                 110

Asn Cys Gly Tyr Ala Thr Val Thr Asp Ser Val Ala Val Val Val Gln
        115                 120                 125

Ala Thr Pro His His Val Leu Val Asp Glu Tyr Thr Gly Glu Trp Ile
    130                 135                 140

Asp Ser Gln Phe Pro Asn Gly Lys Cys Glu Thr Glu Glu Cys Glu Thr
145                 150                 155                 160

Val His Asn Ser Thr Val Trp Tyr Ser Asp Tyr Lys Val Thr Gly Leu
                165                 170                 175

Cys Asp Ala Thr Leu Val Asp Thr Glu Ile Thr Phe Phe Ser Glu Asp
            180                 185                 190

Gly Lys Lys Glu Ser Ile Gly Lys Pro Asn Thr Gly Tyr Arg Ser Asn
        195                 200                 205

Tyr Phe Ala Tyr Glu Lys Gly Asp Lys Val Cys Lys Met Asn Tyr Cys
    210                 215                 220

Lys His Ala Gly Val Arg Leu Pro Ser Gly Val Trp Phe Glu Phe Val
225                 230                 235                 240

Asp Gln Asp Val Tyr Ala Ala Ala Lys Leu Pro Glu Cys Pro Val Gly
                245                 250                 255
```

```
Ala Thr Ile Ser Ala Pro Thr Gln Thr Ser Val Asp Val Ser Leu Ile
            260                 265                 270

Leu Asp Val Glu Arg Ile Leu Asp Tyr Ser Leu Cys Gln Glu Thr Trp
        275                 280                 285

Ser Lys Ile Arg Ser Lys Gln Pro Val Ser Pro Val Asp Leu Ser Tyr
    290                 295                 300

Leu Ala Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Ile Asp Ile Asp
                325                 330                 335

Asn Pro Ile Ile Ser Lys Met Val Gly Lys Ile Ser Gly Ser Gln Thr
            340                 345                 350

Glu Arg Glu Leu Trp Thr Glu Trp Phe Pro Tyr Glu Gly Val Glu Ile
        355                 360                 365

Gly Pro Asn Gly Ile Leu Lys Thr Pro Thr Gly Tyr Lys Phe Pro Leu
    370                 375                 380

Phe Met Ile Gly His Gly Met Leu Asp Ser Asp Leu His Lys Thr Ser
385                 390                 395                 400

Gln Ala Glu Val Phe Glu His Pro His Leu Ala Glu Ala Pro Lys Gln
                405                 410                 415

Leu Pro Glu Glu Glu Thr Leu Phe Phe Gly Asp Thr Gly Ile Ser Lys
            420                 425                 430

Asn Pro Val Glu Leu Ile Glu Gly Trp Phe Ser Ser Trp Lys Ser Thr
        435                 440                 445

Val Val Thr Phe Phe Phe Ala Ile Gly Val Phe Ile Leu Leu Tyr Val
    450                 455                 460

Val Ala Arg Ile Val Ile Ala Val Arg Tyr Arg Tyr Gln Gly Ser Asn
465                 470                 475                 480

Asn Lys Arg Ile Tyr Asn Asp Ile Glu Met Ser Arg Phe Arg Lys
                485                 490                 495


<210> SEQ ID NO 7
<211> LENGTH: 513
<212> TYPE: PRT
<213> ORGANISM: Vesicular stomatitis Morreton virus

<400> SEQUENCE: 7

Met Leu Val Leu Tyr Leu Leu Leu Ser Leu Leu Ala Leu Gly Ala Gln
1               5                   10                  15

Cys Lys Phe Thr Ile Val Phe Pro His Asn Gln Lys Gly Asn Trp Lys
            20                  25                  30

Asn Val Pro Ala Asn Tyr Gln Tyr Cys Pro Ser Ser Ser Asp Leu Asn
        35                  40                  45

Trp His Asn Gly Leu Ile Gly Thr Ser Leu Gln Val Lys Met Pro Lys
    50                  55                  60

Ser His Lys Ala Ile Gln Ala Asp Gly Trp Met Cys His Ala Ala Lys
65                  70                  75                  80

Trp Val Thr Thr Cys Asp Phe Arg Trp Tyr Gly Pro Lys Tyr Val Thr
                85                  90                  95

His Ser Ile Lys Ser Met Ile Pro Thr Val Asp Gln Cys Lys Glu Ser
            100                 105                 110

Ile Ala Gln Thr Lys Gln Gly Thr Trp Leu Asn Pro Gly Phe Pro Pro
        115                 120                 125
```

```
Gln Ser Cys Gly Tyr Ala Ser Val Thr Asp Ala Glu Ala Val Ile Val
    130                 135                 140

Lys Ala Thr Pro His Gln Val Leu Val Asp Glu Tyr Thr Gly Glu Trp
145                 150                 155                 160

Val Asp Ser Gln Phe Pro Thr Gly Lys Cys Asn Lys Asp Ile Cys Pro
                165                 170                 175

Thr Val His Asn Ser Thr Thr Trp His Ser Asp Tyr Lys Val Thr Gly
            180                 185                 190

Leu Cys Asp Ala Asn Leu Ile Ser Met Asp Ile Thr Phe Phe Ser Glu
        195                 200                 205

Asp Gly Lys Leu Thr Ser Leu Gly Lys Glu Gly Thr Gly Phe Arg Ser
    210                 215                 220

Asn Tyr Phe Ala Tyr Glu Asn Gly Asp Lys Ala Cys Arg Met Gln Tyr
225                 230                 235                 240

Cys Lys His Trp Gly Val Arg Leu Pro Ser Gly Val Trp Phe Glu Met
                245                 250                 255

Ala Asp Lys Asp Ile Tyr Asn Asp Ala Lys Phe Pro Asp Cys Pro Glu
            260                 265                 270

Gly Ser Ser Ile Ala Ala Pro Ser Gln Thr Ser Val Asp Val Ser Leu
        275                 280                 285

Ile Gln Asp Val Glu Arg Ile Leu Asp Tyr Ser Leu Cys Gln Glu Thr
    290                 295                 300

Trp Ser Lys Ile Arg Ala His Leu Pro Ile Ser Pro Val Asp Leu Ser
305                 310                 315                 320

Tyr Leu Ser Pro Lys Asn Pro Gly Thr Gly Pro Ala Phe Thr Ile Ile
                325                 330                 335

Asn Gly Thr Leu Lys Tyr Phe Glu Thr Arg Tyr Ile Arg Val Asp Ile
            340                 345                 350

Ala Gly Pro Ile Ile Pro Gln Met Arg Gly Val Ile Ser Gly Thr Thr
        355                 360                 365

Thr Glu Arg Glu Leu Trp Thr Asp Trp Tyr Pro Tyr Glu Asp Val Glu
    370                 375                 380

Ile Gly Pro Asn Gly Val Leu Lys Thr Ala Thr Gly Tyr Lys Phe Pro
385                 390                 395                 400

Leu Tyr Met Ile Gly His Gly Met Leu Asp Ser Asp Leu His Ile Ser
                405                 410                 415

Ser Lys Ala Gln Val Phe Glu His Pro His Ile Gln Asp Ala Ala Ser
            420                 425                 430

Gln Leu Pro Asp Asp Glu Thr Leu Phe Phe Gly Asp Thr Gly Leu Ser
        435                 440                 445

Lys Asn Pro Ile Glu Leu Val Glu Gly Trp Phe Ser Gly Trp Lys Ser
    450                 455                 460

Thr Ile Ala Ser Phe Phe Phe Ile Ile Gly Leu Val Ile Gly Leu Tyr
465                 470                 475                 480

Leu Val Leu Arg Ile Gly Ile Ala Leu Cys Ile Lys Cys Arg Val Gln
                485                 490                 495

Glu Lys Arg Pro Lys Ile Tyr Thr Asp Val Glu Met Asn Arg Leu Asp
            500                 505                 510

Arg
```

<210> SEQ ID NO 8
<211> LENGTH: 496
<212> TYPE: PRT

<213> ORGANISM: Vesicular stomatitis Morreton virus

<400> SEQUENCE: 8

```
Lys Phe Thr Ile Val Phe Pro His Asn Gln Lys Gly Asn Trp Lys Asn
1               5                   10                  15

Val Pro Ala Asn Tyr Gln Tyr Cys Pro Ser Ser Ser Asp Leu Asn Trp
            20                  25                  30

His Asn Gly Leu Ile Gly Thr Ser Leu Gln Val Lys Met Pro Lys Ser
        35                  40                  45

His Lys Ala Ile Gln Ala Asp Gly Trp Met Cys His Ala Ala Lys Trp
    50                  55                  60

Val Thr Thr Cys Asp Phe Arg Trp Tyr Gly Pro Lys Tyr Val Thr His
65                  70                  75                  80

Ser Ile Lys Ser Met Ile Pro Thr Val Asp Gln Cys Lys Glu Ser Ile
                85                  90                  95

Ala Gln Thr Lys Gln Gly Thr Trp Leu Asn Pro Gly Phe Pro Pro Gln
            100                 105                 110

Ser Cys Gly Tyr Ala Ser Val Thr Asp Ala Glu Ala Val Ile Val Lys
        115                 120                 125

Ala Thr Pro His Gln Val Leu Val Asp Glu Tyr Thr Gly Glu Trp Val
    130                 135                 140

Asp Ser Gln Phe Pro Thr Gly Lys Cys Asn Lys Asp Ile Cys Pro Thr
145                 150                 155                 160

Val His Asn Ser Thr Thr Trp His Ser Asp Tyr Lys Val Thr Gly Leu
                165                 170                 175

Cys Asp Ala Asn Leu Ile Ser Met Asp Ile Thr Phe Phe Ser Glu Asp
            180                 185                 190

Gly Lys Leu Thr Ser Leu Gly Lys Glu Gly Thr Gly Phe Arg Ser Asn
        195                 200                 205

Tyr Phe Ala Tyr Glu Asn Gly Asp Lys Ala Cys Arg Met Gln Tyr Cys
    210                 215                 220

Lys His Trp Gly Val Arg Leu Pro Ser Gly Val Trp Phe Glu Met Ala
225                 230                 235                 240

Asp Lys Asp Ile Tyr Asn Asp Ala Lys Phe Pro Asp Cys Pro Glu Gly
                245                 250                 255

Ser Ser Ile Ala Ala Pro Ser Gln Thr Ser Val Asp Val Ser Leu Ile
            260                 265                 270

Gln Asp Val Glu Arg Ile Leu Asp Tyr Ser Leu Cys Gln Glu Thr Trp
        275                 280                 285

Ser Lys Ile Arg Ala His Leu Pro Ile Ser Pro Val Asp Leu Ser Tyr
    290                 295                 300

Leu Ser Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Val Asp Ile Ala
                325                 330                 335

Gly Pro Ile Ile Pro Gln Met Arg Gly Val Ile Ser Gly Thr Thr Thr
            340                 345                 350

Glu Arg Glu Leu Trp Thr Asp Trp Tyr Pro Tyr Glu Asp Val Glu Ile
        355                 360                 365

Gly Pro Asn Gly Val Leu Lys Thr Ala Thr Gly Tyr Lys Phe Pro Leu
    370                 375                 380

Tyr Met Ile Gly His Gly Met Leu Asp Ser Asp Leu His Ile Ser Ser
385                 390                 395                 400
```

```
Lys Ala Gln Val Phe Glu His Pro His Ile Gln Asp Ala Ala Ser Gln
                405                 410                 415

Leu Pro Asp Asp Glu Thr Leu Phe Phe Gly Asp Thr Gly Leu Ser Lys
            420                 425                 430

Asn Pro Ile Glu Leu Val Glu Gly Trp Phe Ser Gly Trp Lys Ser Thr
        435                 440                 445

Ile Ala Ser Phe Phe Phe Ile Ile Gly Leu Val Ile Gly Leu Tyr Leu
    450                 455                 460

Val Leu Arg Ile Gly Ile Ala Leu Cys Ile Lys Cys Arg Val Gln Glu
465                 470                 475                 480

Lys Arg Pro Lys Ile Tyr Thr Asp Val Glu Met Asn Arg Leu Asp Arg
                485                 490                 495


<210> SEQ ID NO 9
<211> LENGTH: 511
<212> TYPE: PRT
<213> ORGANISM: Vesicular stomatitis Alagoa virus

<400> SEQUENCE: 9

Met Thr Pro Ala Phe Ile Leu Cys Met Leu Leu Ala Gly Ser Ser Trp
1               5                   10                  15

Ala Lys Phe Thr Ile Val Phe Pro Gln Ser Gln Lys Gly Asp Trp Lys
            20                  25                  30

Asp Val Pro Pro Asn Tyr Arg Tyr Cys Pro Ser Ser Ala Asp Gln Asn
        35                  40                  45

Trp His Gly Asp Leu Leu Gly Val Asn Ile Arg Ala Lys Met Pro Lys
    50                  55                  60

Val His Lys Ala Ile Lys Ala Asp Gly Trp Met Cys His Ala Ala Lys
65                  70                  75                  80

Trp Val Thr Thr Cys Asp Tyr Arg Trp Tyr Gly Pro Gln Tyr Ile Thr
                85                  90                  95

His Ser Ile His Ser Phe Ile Pro Thr Lys Ala Gln Cys Glu Glu Ser
            100                 105                 110

Ile Lys Gln Thr Lys Glu Gly Val Trp Ile Asn Pro Gly Phe Pro Pro
        115                 120                 125

Lys Asn Cys Gly Tyr Ala Ser Val Ser Asp Ala Glu Ser Ile Ile Val
    130                 135                 140

Gln Ala Thr Ala His Ser Val Met Ile Asp Glu Tyr Ser Gly Asp Trp
145                 150                 155                 160

Leu Asp Ser Gln Phe Pro Thr Gly Arg Cys Thr Gly Ser Thr Cys Glu
                165                 170                 175

Thr Ile His Asn Ser Thr Leu Trp Tyr Ala Asp Tyr Gln Val Thr Gly
            180                 185                 190

Leu Cys Asp Ser Ala Leu Val Ser Thr Glu Val Thr Phe Tyr Ser Glu
        195                 200                 205

Asp Gly Leu Met Thr Ser Ile Gly Arg Gln Asn Thr Gly Tyr Arg Ser
    210                 215                 220

Asn Tyr Phe Pro Tyr Glu Lys Gly Ala Ala Ala Cys Arg Met Lys Tyr
225                 230                 235                 240

Cys Thr His Glu Gly Ile Arg Leu Pro Ser Gly Val Trp Phe Glu Met
                245                 250                 255

Val Asp Lys Glu Leu Leu Glu Ser Val Gln Met Pro Glu Cys Pro Ala
            260                 265                 270

Gly Leu Thr Ile Ser Ala Pro Thr Gln Thr Ser Val Asp Val Ser Leu
        275                 280                 285
```

```
Ile Leu Asp Val Glu Arg Met Leu Asp Tyr Ser Leu Cys Gln Glu Thr
    290                 295                 300

Trp Ser Lys Val His Ser Gly Leu Pro Ile Ser Pro Val Asp Leu Gly
305                 310                 315                 320

Tyr Ile Ala Pro Lys Asn Pro Gly Ala Gly Pro Ala Phe Thr Ile Val
                325                 330                 335

Asn Gly Thr Leu Lys Tyr Phe Asp Thr Arg Tyr Leu Arg Ile Asp Ile
            340                 345                 350

Glu Gly Pro Val Leu Lys Lys Met Thr Gly Lys Val Ser Gly Thr Pro
        355                 360                 365

Thr Lys Arg Glu Leu Trp Thr Glu Trp Phe Pro Tyr Asp Asp Val Glu
    370                 375                 380

Ile Gly Pro Asn Gly Val Leu Lys Thr Pro Glu Gly Tyr Lys Phe Pro
385                 390                 395                 400

Leu Tyr Met Ile Gly His Gly Leu Leu Asp Ser Asp Leu Gln Lys Thr
                405                 410                 415

Ser Gln Ala Glu Val Phe His His Pro Gln Ile Ala Glu Ala Val Gln
            420                 425                 430

Lys Leu Pro Asp Asp Glu Thr Leu Phe Phe Gly Asp Thr Gly Ile Ser
        435                 440                 445

Lys Asn Pro Val Glu Val Ile Glu Gly Trp Phe Ser Asn Trp Arg Ser
    450                 455                 460

Ser Val Met Ala Ile Val Phe Ala Ile Leu Leu Leu Val Ile Thr Val
465                 470                 475                 480

Leu Met Val Arg Leu Cys Val Ala Phe Arg His Phe Cys Cys Gln Lys
                485                 490                 495

Arg His Lys Ile Tyr Asn Asp Leu Glu Met Asn Gln Leu Arg Arg
            500                 505                 510


<210> SEQ ID NO 10
<211> LENGTH: 494
<212> TYPE: PRT
<213> ORGANISM: Vesicular stomatitis Alagoa virus

<400> SEQUENCE: 10

Lys Phe Thr Ile Val Phe Pro Gln Ser Gln Lys Gly Asp Trp Lys Asp
1               5                   10                  15

Val Pro Pro Asn Tyr Arg Tyr Cys Pro Ser Ser Ala Asp Gln Asn Trp
            20                  25                  30

His Gly Asp Leu Leu Gly Val Asn Ile Arg Ala Lys Met Pro Lys Val
        35                  40                  45

His Lys Ala Ile Lys Ala Asp Gly Trp Met Cys His Ala Ala Lys Trp
    50                  55                  60

Val Thr Thr Cys Asp Tyr Arg Trp Tyr Gly Pro Gln Tyr Ile Thr His
65                  70                  75                  80

Ser Ile His Ser Phe Ile Pro Thr Lys Ala Gln Cys Glu Glu Ser Ile
                85                  90                  95

Lys Gln Thr Lys Glu Gly Val Trp Ile Asn Pro Gly Phe Pro Pro Lys
            100                 105                 110

Asn Cys Gly Tyr Ala Ser Val Ser Asp Ala Glu Ser Ile Ile Val Gln
        115                 120                 125

Ala Thr Ala His Ser Val Met Ile Asp Glu Tyr Ser Gly Asp Trp Leu
    130                 135                 140
```

```
Asp Ser Gln Phe Pro Thr Gly Arg Cys Thr Gly Ser Thr Cys Glu Thr
145                 150                 155                 160

Ile His Asn Ser Thr Leu Trp Tyr Ala Asp Tyr Gln Val Thr Gly Leu
                165                 170                 175

Cys Asp Ser Ala Leu Val Ser Thr Glu Val Thr Phe Tyr Ser Glu Asp
            180                 185                 190

Gly Leu Met Thr Ser Ile Gly Arg Gln Asn Thr Gly Tyr Arg Ser Asn
        195                 200                 205

Tyr Phe Pro Tyr Glu Lys Gly Ala Ala Ala Cys Arg Met Lys Tyr Cys
    210                 215                 220

Thr His Glu Gly Ile Arg Leu Pro Ser Gly Val Trp Phe Glu Met Val
225                 230                 235                 240

Asp Lys Glu Leu Leu Glu Ser Val Gln Met Pro Glu Cys Pro Ala Gly
                245                 250                 255

Leu Thr Ile Ser Ala Pro Thr Gln Thr Ser Val Asp Val Ser Leu Ile
            260                 265                 270

Leu Asp Val Glu Arg Met Leu Asp Tyr Ser Leu Cys Gln Glu Thr Trp
        275                 280                 285

Ser Lys Val His Ser Gly Leu Pro Ile Ser Pro Val Asp Leu Gly Tyr
    290                 295                 300

Ile Ala Pro Lys Asn Pro Gly Ala Gly Pro Ala Phe Thr Ile Val Asn
305                 310                 315                 320

Gly Thr Leu Lys Tyr Phe Asp Thr Arg Tyr Leu Arg Ile Asp Ile Glu
                325                 330                 335

Gly Pro Val Leu Lys Lys Met Thr Gly Lys Val Ser Gly Thr Pro Thr
            340                 345                 350

Lys Arg Glu Leu Trp Thr Glu Trp Phe Pro Tyr Asp Asp Val Glu Ile
        355                 360                 365

Gly Pro Asn Gly Val Leu Lys Thr Pro Glu Gly Tyr Lys Phe Pro Leu
    370                 375                 380

Tyr Met Ile Gly His Gly Leu Leu Asp Ser Asp Leu Gln Lys Thr Ser
385                 390                 395                 400

Gln Ala Glu Val Phe His His Pro Gln Ile Ala Glu Ala Val Gln Lys
                405                 410                 415

Leu Pro Asp Asp Glu Thr Leu Phe Phe Gly Asp Thr Gly Ile Ser Lys
            420                 425                 430

Asn Pro Val Glu Val Ile Glu Gly Trp Phe Ser Asn Trp Arg Ser Ser
        435                 440                 445

Val Met Ala Ile Val Phe Ala Ile Leu Leu Leu Val Ile Thr Val Leu
    450                 455                 460

Met Val Arg Leu Cys Val Ala Phe Arg His Phe Cys Cys Gln Lys Arg
465                 470                 475                 480

His Lys Ile Tyr Asn Asp Leu Glu Met Asn Gln Leu Arg Arg
                485                 490


<210> SEQ ID NO 11
<211> LENGTH: 517
<212> TYPE: PRT
<213> ORGANISM: Vesicular stomatitis New Jersey virus

<400> SEQUENCE: 11

Met Leu Ser Tyr Leu Ile Phe Ala Leu Val Val Ser Pro Ile Leu Gly
1               5                   10                  15
```

```
Lys Ile Glu Ile Val Phe Pro Gln His Thr Thr Gly Asp Trp Lys Arg
            20                  25                  30

Val Pro His Glu Tyr Asn Tyr Cys Pro Thr Ser Ala Asp Lys Asn Ser
        35                  40                  45

His Gly Thr Gln Thr Gly Ile Pro Val Glu Leu Thr Met Pro Lys Gly
    50                  55                  60

Leu Thr Thr His Gln Val Asp Gly Phe Met Cys His Ser Ala Leu Trp
65                  70                  75                  80

Met Thr Thr Cys Asp Phe Arg Trp Tyr Gly Pro Lys Tyr Ile Thr His
                85                  90                  95

Ser Ile His Asn Glu Glu Pro Thr Asp Tyr Gln Cys Leu Glu Ala Ile
            100                 105                 110

Lys Ala Tyr Lys Asp Gly Val Ser Phe Asn Pro Gly Phe Pro Pro Gln
        115                 120                 125

Ser Cys Gly Tyr Gly Thr Val Thr Asp Ala Glu Ala His Ile Val Thr
    130                 135                 140

Val Thr Pro His Ser Val Lys Val Asp Glu Tyr Thr Gly Glu Trp Ile
145                 150                 155                 160

Asp Pro His Phe Ile Gly Gly Arg Cys Lys Gly Gln Ile Cys Glu Thr
                165                 170                 175

Val His Asn Ser Thr Lys Trp Phe Thr Ser Ser Asp Gly Glu Ser Val
            180                 185                 190

Cys Ser Gln Leu Phe Thr Leu Val Gly Gly Thr Phe Phe Ser Asp Ser
        195                 200                 205

Glu Glu Ile Thr Ser Met Gly Leu Pro Glu Thr Gly Ile Arg Ser Asn
    210                 215                 220

Tyr Phe Pro Tyr Val Ser Thr Glu Gly Ile Cys Lys Met Pro Phe Cys
225                 230                 235                 240

Arg Lys Pro Gly Tyr Lys Leu Lys Asn Asp Leu Trp Phe Gln Ile Thr
                245                 250                 255

Asp Pro Asp Leu Asp Lys Thr Val Arg Asp Leu Pro His Ile Lys Asp
            260                 265                 270

Cys Asp Leu Ser Ser Ser Ile Val Thr Pro Gly Glu His Ala Thr Asp
        275                 280                 285

Ile Ser Leu Ile Ser Asp Val Glu Arg Ile Leu Asp Tyr Ala Leu Cys
    290                 295                 300

Gln Asn Thr Trp Ser Lys Ile Glu Ala Gly Glu Pro Ile Thr Pro Val
305                 310                 315                 320

Asp Leu Ser Tyr Leu Gly Pro Lys Asn Pro Gly Ala Gly Pro Val Phe
                325                 330                 335

Thr Ile Ile Asn Gly Ser Leu His Tyr Phe Met Ser Lys Tyr Leu Arg
            340                 345                 350

Val Glu Leu Glu Ser Pro Val Ile Pro Arg Met Glu Gly Lys Val Ala
        355                 360                 365

Gly Thr Arg Ile Val Arg Gln Leu Trp Asp Gln Trp Phe Pro Phe Gly
    370                 375                 380

Glu Val Glu Ile Gly Pro Asn Gly Val Leu Lys Thr Lys Gln Gly Tyr
385                 390                 395                 400

Lys Phe Pro Leu His Ile Ile Gly Thr Gly Glu Val Asp Asn Asp Ile
                405                 410                 415

Lys Met Glu Arg Ile Val Lys His Trp Glu His Pro His Ile Glu Ala
            420                 425                 430
```

```
Ala Gln Thr Phe Leu Lys Lys Asp Asp Thr Glu Glu Val Leu Tyr Tyr
        435                 440                 445

Gly Asp Thr Gly Val Ser Lys Asn Pro Val Glu Leu Val Glu Gly Trp
    450                 455                 460

Phe Ser Gly Trp Arg Ser Ser Ile Met Gly Val Leu Ala Val Ile Ile
465                 470                 475                 480

Gly Phe Val Ile Leu Ile Phe Leu Ile Arg Leu Ile Gly Val Leu Ser
                485                 490                 495

Ser Leu Phe Arg Gln Lys Arg Arg Pro Ile Tyr Lys Ser Asp Val Glu
            500                 505                 510

Met Ala His Phe Arg
        515


<210> SEQ ID NO 12
<211> LENGTH: 501
<212> TYPE: PRT
<213> ORGANISM: Vesicular stomatitis New Jersey  virus

<400> SEQUENCE: 12

Lys Ile Glu Ile Val Phe Pro Gln His Thr Thr Gly Asp Trp Lys Arg
1               5                   10                  15

Val Pro His Glu Tyr Asn Tyr Cys Pro Thr Ser Ala Asp Lys Asn Ser
            20                  25                  30

His Gly Thr Gln Thr Gly Ile Pro Val Glu Leu Thr Met Pro Lys Gly
        35                  40                  45

Leu Thr Thr His Gln Val Asp Gly Phe Met Cys His Ser Ala Leu Trp
    50                  55                  60

Met Thr Thr Cys Asp Phe Arg Trp Tyr Gly Pro Lys Tyr Ile Thr His
65                  70                  75                  80

Ser Ile His Asn Glu Glu Pro Thr Asp Tyr Gln Cys Leu Glu Ala Ile
                85                  90                  95

Lys Ala Tyr Lys Asp Gly Val Ser Phe Asn Pro Gly Phe Pro Pro Gln
            100                 105                 110

Ser Cys Gly Tyr Gly Thr Val Thr Asp Ala Glu Ala His Ile Val Thr
        115                 120                 125

Val Thr Pro His Ser Val Lys Val Asp Glu Tyr Thr Gly Glu Trp Ile
    130                 135                 140

Asp Pro His Phe Ile Gly Gly Arg Cys Lys Gly Gln Ile Cys Glu Thr
145                 150                 155                 160

Val His Asn Ser Thr Lys Trp Phe Thr Ser Ser Asp Gly Glu Ser Val
                165                 170                 175

Cys Ser Gln Leu Phe Thr Leu Val Gly Gly Thr Phe Phe Ser Asp Ser
            180                 185                 190

Glu Glu Ile Thr Ser Met Gly Leu Pro Glu Thr Gly Ile Arg Ser Asn
        195                 200                 205

Tyr Phe Pro Tyr Val Ser Thr Glu Gly Ile Cys Lys Met Pro Phe Cys
    210                 215                 220

Arg Lys Pro Gly Tyr Lys Leu Lys Asn Asp Leu Trp Phe Gln Ile Thr
225                 230                 235                 240

Asp Pro Asp Leu Asp Lys Thr Val Arg Asp Leu Pro His Ile Lys Asp
                245                 250                 255

Cys Asp Leu Ser Ser Ser Ile Val Thr Pro Gly Glu His Ala Thr Asp
            260                 265                 270

Ile Ser Leu Ile Ser Asp Val Glu Arg Ile Leu Asp Tyr Ala Leu Cys
        275                 280                 285
```

Gln Asn Thr Trp Ser Lys Ile Glu Ala Gly Glu Pro Ile Thr Pro Val
290 295 300

Asp Leu Ser Tyr Leu Gly Pro Lys Asn Pro Gly Ala Gly Pro Val Phe
305 310 315 320

Thr Ile Ile Asn Gly Ser Leu His Tyr Phe Met Ser Lys Tyr Leu Arg
325 330 335

Val Glu Leu Glu Ser Pro Val Ile Pro Arg Met Glu Gly Lys Val Ala
340 345 350

Gly Thr Arg Ile Val Arg Gln Leu Trp Asp Gln Trp Phe Pro Phe Gly
355 360 365

Glu Val Glu Ile Gly Pro Asn Gly Val Leu Lys Thr Lys Gln Gly Tyr
370 375 380

Lys Phe Pro Leu His Ile Ile Gly Thr Gly Glu Val Asp Asn Asp Ile
385 390 395 400

Lys Met Glu Arg Ile Val Lys His Trp Glu His Pro His Ile Glu Ala
405 410 415

Ala Gln Thr Phe Leu Lys Lys Asp Asp Thr Glu Glu Val Leu Tyr Tyr
420 425 430

Gly Asp Thr Gly Val Ser Lys Asn Pro Val Glu Leu Val Glu Gly Trp
435 440 445

Phe Ser Gly Trp Arg Ser Ser Ile Met Gly Val Leu Ala Val Ile Ile
450 455 460

Gly Phe Val Ile Leu Ile Phe Leu Ile Arg Leu Ile Gly Val Leu Ser
465 470 475 480

Ser Leu Phe Arg Gln Lys Arg Arg Pro Ile Tyr Lys Ser Asp Val Glu
485 490 495

Met Ala His Phe Arg
500

<210> SEQ ID NO 13
<211> LENGTH: 523
<212> TYPE: PRT
<213> ORGANISM: Vesicular stomatitis Carajas virus

<400> SEQUENCE: 13

Met Lys Met Lys Met Val Ile Ala Gly Leu Ile Leu Cys Ile Gly Ile
1 5 10 15

Leu Pro Ala Ile Gly Lys Ile Thr Ile Ser Phe Pro Gln Ser Leu Lys
20 25 30

Gly Asp Trp Arg Pro Val Pro Lys Gly Tyr Asn Tyr Cys Pro Thr Ser
35 40 45

Ala Asp Lys Asn Leu His Gly Asp Leu Ile Asp Ile Gly Leu Arg Leu
50 55 60

Arg Ala Pro Lys Ser Phe Lys Gly Ile Ser Ala Asp Gly Trp Met Cys
65 70 75 80

His Ala Ala Arg Trp Ile Thr Thr Cys Asp Phe Arg Trp Tyr Gly Pro
85 90 95

Lys Tyr Ile Thr His Ser Ile His Ser Phe Arg Pro Ser Asn Asp Gln
100 105 110

Cys Lys Glu Ala Ile Arg Leu Thr Asn Glu Gly Asn Trp Ile Asn Pro
115 120 125

Gly Phe Pro Pro Gln Ser Cys Gly Tyr Ala Ser Val Thr Asp Ser Glu
130 135 140

```
Ser Val Val Val Thr Val Thr Lys His Gln Val Leu Val Asp Glu Tyr
145                 150                 155                 160

Ser Gly Ser Trp Ile Asp Ser Gln Phe Pro Gly Gly Ser Cys Thr Ser
                165                 170                 175

Pro Ile Cys Asp Thr Val His Asn Ser Thr Leu Trp His Ala Asp His
            180                 185                 190

Thr Leu Asp Ser Ile Cys Asp Gln Glu Phe Val Ala Met Asp Ala Val
        195                 200                 205

Leu Phe Thr Glu Ser Gly Lys Phe Glu Glu Phe Gly Lys Pro Asn Ser
    210                 215                 220

Gly Ile Arg Ser Asn Tyr Phe Pro Tyr Glu Ser Leu Lys Asp Val Cys
225                 230                 235                 240

Gln Met Asp Phe Cys Lys Arg Lys Gly Phe Lys Leu Pro Ser Gly Val
                245                 250                 255

Trp Phe Glu Ile Glu Asp Ala Glu Lys Ser His Lys Ala Gln Val Glu
            260                 265                 270

Leu Lys Ile Lys Arg Cys Pro His Gly Ala Val Ile Ser Ala Pro Asn
        275                 280                 285

Gln Asn Ala Ala Asp Ile Asn Leu Ile Met Asp Val Glu Arg Ile Leu
    290                 295                 300

Asp Tyr Ser Leu Cys Gln Ala Thr Trp Ser Lys Ile Gln Asn Lys Glu
305                 310                 315                 320

Ala Leu Thr Pro Ile Asp Ile Ser Tyr Leu Gly Pro Lys Asn Pro Gly
                325                 330                 335

Pro Gly Pro Ala Phe Thr Ile Ile Asn Gly Thr Leu His Tyr Phe Asn
            340                 345                 350

Thr Arg Tyr Ile Arg Val Asp Ile Ala Gly Pro Val Thr Lys Glu Ile
        355                 360                 365

Thr Gly Phe Val Ser Gly Thr Ser Thr Ser Arg Val Leu Trp Asp Gln
    370                 375                 380

Trp Phe Pro Tyr Gly Glu Asn Ser Ile Gly Pro Asn Gly Leu Leu Lys
385                 390                 395                 400

Thr Ala Ser Gly Tyr Lys Tyr Pro Leu Phe Met Val Gly Thr Gly Val
                405                 410                 415

Leu Asp Ala Asp Ile His Lys Leu Gly Glu Ala Thr Val Ile Glu His
            420                 425                 430

Pro His Ala Lys Glu Ala Gln Lys Val Val Asp Asp Ser Glu Val Ile
        435                 440                 445

Phe Phe Gly Asp Thr Gly Val Ser Lys Asn Pro Val Glu Val Val Glu
    450                 455                 460

Gly Trp Phe Ser Gly Trp Arg Ser Ser Leu Met Ser Ile Phe Gly Ile
465                 470                 475                 480

Ile Leu Leu Ile Val Cys Leu Val Leu Ile Val Arg Ile Leu Ile Ala
                485                 490                 495

Leu Lys Tyr Cys Cys Val Arg His Lys Lys Arg Thr Ile Tyr Lys Glu
            500                 505                 510

Asp Leu Glu Met Gly Arg Ile Pro Arg Arg Ala
        515                 520
```

<210> SEQ ID NO 14
<211> LENGTH: 502
<212> TYPE: PRT
<213> ORGANISM: Vesicular stomatitis Carajas virus

<400> SEQUENCE: 14

```
Lys Ile Thr Ile Ser Phe Pro Gln Ser Leu Lys Gly Asp Trp Arg Pro
1               5                   10                  15

Val Pro Lys Gly Tyr Asn Tyr Cys Pro Thr Ser Ala Asp Lys Asn Leu
            20                  25                  30

His Gly Asp Leu Ile Asp Ile Gly Leu Arg Leu Arg Ala Pro Lys Ser
        35                  40                  45

Phe Lys Gly Ile Ser Ala Asp Gly Trp Met Cys His Ala Ala Arg Trp
    50                  55                  60

Ile Thr Thr Cys Asp Phe Arg Trp Tyr Gly Pro Lys Tyr Ile Thr His
65                  70                  75                  80

Ser Ile His Ser Phe Arg Pro Ser Asn Asp Gln Cys Lys Glu Ala Ile
                85                  90                  95

Arg Leu Thr Asn Glu Gly Asn Trp Ile Asn Pro Gly Phe Pro Pro Gln
            100                 105                 110

Ser Cys Gly Tyr Ala Ser Val Thr Asp Ser Glu Ser Val Val Val Thr
        115                 120                 125

Val Thr Lys His Gln Val Leu Val Asp Glu Tyr Ser Gly Ser Trp Ile
    130                 135                 140

Asp Ser Gln Phe Pro Gly Gly Ser Cys Thr Ser Pro Ile Cys Asp Thr
145                 150                 155                 160

Val His Asn Ser Thr Leu Trp His Ala Asp His Thr Leu Asp Ser Ile
                165                 170                 175

Cys Asp Gln Glu Phe Val Ala Met Asp Ala Val Leu Phe Thr Glu Ser
            180                 185                 190

Gly Lys Phe Glu Glu Phe Gly Lys Pro Asn Ser Gly Ile Arg Ser Asn
        195                 200                 205

Tyr Phe Pro Tyr Glu Ser Leu Lys Asp Val Cys Gln Met Asp Phe Cys
    210                 215                 220

Lys Arg Lys Gly Phe Lys Leu Pro Ser Gly Val Trp Phe Glu Ile Glu
225                 230                 235                 240

Asp Ala Glu Lys Ser His Lys Ala Gln Val Glu Leu Lys Ile Lys Arg
                245                 250                 255

Cys Pro His Gly Ala Val Ile Ser Ala Pro Asn Gln Asn Ala Ala Asp
            260                 265                 270

Ile Asn Leu Ile Met Asp Val Glu Arg Ile Leu Asp Tyr Ser Leu Cys
        275                 280                 285

Gln Ala Thr Trp Ser Lys Ile Gln Asn Lys Glu Ala Leu Thr Pro Ile
    290                 295                 300

Asp Ile Ser Tyr Leu Gly Pro Lys Asn Pro Gly Pro Gly Pro Ala Phe
305                 310                 315                 320

Thr Ile Ile Asn Gly Thr Leu His Tyr Phe Asn Thr Arg Tyr Ile Arg
                325                 330                 335

Val Asp Ile Ala Gly Pro Val Thr Lys Glu Ile Thr Gly Phe Val Ser
            340                 345                 350

Gly Thr Ser Thr Ser Arg Val Leu Trp Asp Gln Trp Phe Pro Tyr Gly
        355                 360                 365

Glu Asn Ser Ile Gly Pro Asn Gly Leu Leu Lys Thr Ala Ser Gly Tyr
    370                 375                 380

Lys Tyr Pro Leu Phe Met Val Gly Thr Gly Val Leu Asp Ala Asp Ile
385                 390                 395                 400

His Lys Leu Gly Glu Ala Thr Val Ile Glu His Pro His Ala Lys Glu
                405                 410                 415
```

```
Ala Gln Lys Val Val Asp Asp Ser Glu Val Ile Phe Phe Gly Asp Thr
            420                 425                 430

Gly Val Ser Lys Asn Pro Val Glu Val Val Glu Gly Trp Phe Ser Gly
        435                 440                 445

Trp Arg Ser Ser Leu Met Ser Ile Phe Gly Ile Ile Leu Leu Ile Val
    450                 455                 460

Cys Leu Val Leu Ile Val Arg Ile Leu Ile Ala Leu Lys Tyr Cys Cys
465                 470                 475                 480

Val Arg His Lys Lys Arg Thr Ile Tyr Lys Glu Asp Leu Glu Met Gly
                485                 490                 495

Arg Ile Pro Arg Arg Ala
            500


<210> SEQ ID NO 15
<211> LENGTH: 9
<212> TYPE: PRT
<213> ORGANISM: Artificial sequence
<220> FEATURE:
<223> OTHER INFORMATION: Consensus positions 17-25
<220> FEATURE:
<221> NAME/KEY: MISC_FEATURE
<222> LOCATION: (3)..(3)
<223> OTHER INFORMATION: Xaa can be serine (S), histidine (H), lysine
      (K), proline (P), or alanine (A)
<220> FEATURE:
<221> NAME/KEY: MISC_FEATURE
<222> LOCATION: (4)..(4)
<223> OTHER INFORMATION: Xaa can be asparagine (N), glutamic acid (E),
      threonine (T), glycine (G), or serine (S)
<220> FEATURE:
<221> NAME/KEY: MISC_FEATURE
<222> LOCATION: (6)..(6)
<223> OTHER INFORMATION: Xaa can be histidine (H), asparagine (N),
      arginine (R), or glutamine (Q)

<400> SEQUENCE: 15

Val Pro Xaa Xaa Tyr Xaa Tyr Cys Pro
1               5


<210> SEQ ID NO 16
<211> LENGTH: 9
<212> TYPE: PRT
<213> ORGANISM: Artificial sequence
<220> FEATURE:
<223> OTHER INFORMATION: Consensus positions 421-429
<220> FEATURE:
<221> NAME/KEY: MISC_FEATURE
<222> LOCATION: (2)..(2)
<223> OTHER INFORMATION: Xaa can be serine (S), valine (V), or threonine
      (T)
<220> FEATURE:
<221> NAME/KEY: MISC_FEATURE
<222> LOCATION: (3)..(3)
<223> OTHER INFORMATION: Xaa can be serine (S), valine (V), or threonine
      (T)
<220> FEATURE:
<221> NAME/KEY: MISC_FEATURE
<222> LOCATION: (4)..(4)
<223> OTHER INFORMATION: Xaa can be phenylalanine (F) or tyrosine (Y)
<220> FEATURE:
<221> NAME/KEY: MISC_FEATURE
<222> LOCATION: (5)..(5)
<223> OTHER INFORMATION: Xaa can be phenylalanine (F) or tyrosine (Y)

<400> SEQUENCE: 16

Glu Xaa Xaa Xaa Xaa Gly Asp Thr Gly
1               5
```

<210> SEQ ID NO 17
<211> LENGTH: 495
<212> TYPE: PRT
<213> ORGANISM: Artificial sequence
<220> FEATURE:
<223> OTHER INFORMATION: Glycoprotein Vesicular stomatitis Indiana virus H22N

<400> SEQUENCE: 17

```
Lys Phe Thr Ile Val Phe Pro His Asn Gln Lys Gly Asn Trp Lys Asn
1               5                   10                  15

Val Pro Ser Asn Tyr Asn Tyr Cys Pro Ser Ser Ser Asp Leu Asn Trp
            20                  25                  30

His Asn Asp Leu Ile Gly Thr Ala Ile Gln Val Lys Met Pro Lys Ser
        35                  40                  45

His Lys Ala Ile Gln Ala Asp Gly Trp Met Cys His Ala Ser Lys Trp
    50                  55                  60

Val Thr Thr Cys Asp Phe Arg Trp Tyr Gly Pro Lys Tyr Ile Thr Gln
65                  70                  75                  80

Ser Ile Arg Ser Phe Thr Pro Ser Val Glu Gln Cys Lys Glu Ser Ile
                85                  90                  95

Glu Gln Thr Lys Gln Gly Thr Trp Leu Asn Pro Gly Phe Pro Pro Gln
            100                 105                 110

Ser Cys Gly Tyr Ala Thr Val Thr Asp Ala Glu Ala Val Ile Val Gln
        115                 120                 125

Val Thr Pro His His Val Leu Val Asp Glu Tyr Thr Gly Glu Trp Val
    130                 135                 140

Asp Ser Gln Phe Ile Asn Gly Lys Cys Ser Asn Tyr Ile Cys Pro Thr
145                 150                 155                 160

Val His Asn Ser Thr Thr Trp His Ser Asp Tyr Lys Val Lys Gly Leu
                165                 170                 175

Cys Asp Ser Asn Leu Ile Ser Met Asp Ile Thr Phe Phe Ser Glu Asp
            180                 185                 190

Gly Glu Leu Ser Ser Leu Gly Lys Glu Gly Thr Gly Phe Arg Ser Asn
        195                 200                 205

Tyr Phe Ala Tyr Glu Thr Gly Gly Lys Ala Cys Lys Met Gln Tyr Cys
    210                 215                 220

Lys His Trp Gly Val Arg Leu Pro Ser Gly Val Trp Phe Glu Met Ala
225                 230                 235                 240

Asp Lys Asp Leu Phe Ala Ala Ala Arg Phe Pro Glu Cys Pro Glu Gly
                245                 250                 255

Ser Ser Ile Ser Ala Pro Ser Gln Thr Ser Val Asp Val Ser Leu Ile
            260                 265                 270

Gln Asp Val Glu Arg Ile Leu Asp Tyr Ser Leu Cys Gln Glu Thr Trp
        275                 280                 285

Ser Lys Ile Arg Ala Gly Leu Pro Ile Ser Pro Val Asp Leu Ser Tyr
    290                 295                 300

Leu Ala Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Val Asp Ile Ala
                325                 330                 335

Ala Pro Ile Leu Ser Arg Met Val Gly Met Ile Ser Gly Thr Thr Thr
            340                 345                 350

Glu Arg Glu Leu Trp Asp Asp Trp Ala Pro Tyr Glu Asp Val Glu Ile
        355                 360                 365
```

```
Gly Pro Asn Gly Val Leu Arg Thr Ser Ser Gly Tyr Lys Phe Pro Leu
    370                 375                 380

Tyr Met Ile Gly His Gly Met Leu Asp Ser Asp Leu His Leu Ser Ser
385                 390                 395                 400

Lys Ala Gln Val Phe Glu His Pro His Ile Gln Asp Ala Ala Ser Gln
                405                 410                 415

Leu Pro Asp Asp Glu Ser Leu Phe Phe Gly Asp Thr Gly Leu Ser Lys
            420                 425                 430

Asn Pro Ile Glu Leu Val Glu Gly Trp Phe Ser Ser Trp Lys Ser Ser
        435                 440                 445

Ile Ala Ser Phe Phe Phe Ile Ile Gly Leu Ile Ile Gly Leu Phe Leu
    450                 455                 460

Val Leu Arg Val Gly Ile His Leu Cys Ile Lys Leu Lys His Thr Lys
465                 470                 475                 480

Lys Arg Gln Ile Tyr Thr Asp Ile Glu Met Asn Arg Leu Gly Lys
                485                 490                 495


<210> SEQ ID NO 18
<211> LENGTH: 495
<212> TYPE: PRT
<213> ORGANISM: Artificial sequence
<220> FEATURE:
<223> OTHER INFORMATION: Glycoprotein Vesicular stomatitis Indiana virus
      S422I

<400> SEQUENCE: 18

Lys Phe Thr Ile Val Phe Pro His Asn Gln Lys Gly Asn Trp Lys Asn
1               5                   10                  15

Val Pro Ser Asn Tyr His Tyr Cys Pro Ser Ser Ser Asp Leu Asn Trp
            20                  25                  30

His Asn Asp Leu Ile Gly Thr Ala Ile Gln Val Lys Met Pro Lys Ser
        35                  40                  45

His Lys Ala Ile Gln Ala Asp Gly Trp Met Cys His Ala Ser Lys Trp
    50                  55                  60

Val Thr Thr Cys Asp Phe Arg Trp Tyr Gly Pro Lys Tyr Ile Thr Gln
65                  70                  75                  80

Ser Ile Arg Ser Phe Thr Pro Ser Val Glu Gln Cys Lys Glu Ser Ile
                85                  90                  95

Glu Gln Thr Lys Gln Gly Thr Trp Leu Asn Pro Gly Phe Pro Pro Gln
            100                 105                 110

Ser Cys Gly Tyr Ala Thr Val Thr Asp Ala Glu Ala Val Ile Val Gln
        115                 120                 125

Val Thr Pro His His Val Leu Val Asp Glu Tyr Thr Gly Glu Trp Val
    130                 135                 140

Asp Ser Gln Phe Ile Asn Gly Lys Cys Ser Asn Tyr Ile Cys Pro Thr
145                 150                 155                 160

Val His Asn Ser Thr Thr Trp His Ser Asp Tyr Lys Val Lys Gly Leu
                165                 170                 175

Cys Asp Ser Asn Leu Ile Ser Met Asp Ile Thr Phe Phe Ser Glu Asp
            180                 185                 190

Gly Glu Leu Ser Ser Leu Gly Lys Glu Gly Thr Gly Phe Arg Ser Asn
        195                 200                 205

Tyr Phe Ala Tyr Glu Thr Gly Gly Lys Ala Cys Lys Met Gln Tyr Cys
    210                 215                 220

Lys His Trp Gly Val Arg Leu Pro Ser Gly Val Trp Phe Glu Met Ala
225                 230                 235                 240
```

```
Asp Lys Asp Leu Phe Ala Ala Ala Arg Phe Pro Glu Cys Pro Glu Gly
                245                 250                 255

Ser Ser Ile Ser Ala Pro Ser Gln Thr Ser Val Asp Val Ser Leu Ile
            260                 265                 270

Gln Asp Val Glu Arg Ile Leu Asp Tyr Ser Leu Cys Gln Glu Thr Trp
        275                 280                 285

Ser Lys Ile Arg Ala Gly Leu Pro Ile Ser Pro Val Asp Leu Ser Tyr
    290                 295                 300

Leu Ala Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Val Asp Ile Ala
                325                 330                 335

Ala Pro Ile Leu Ser Arg Met Val Gly Met Ile Ser Gly Thr Thr Thr
            340                 345                 350

Glu Arg Glu Leu Trp Asp Asp Trp Ala Pro Tyr Glu Asp Val Glu Ile
        355                 360                 365

Gly Pro Asn Gly Val Leu Arg Thr Ser Ser Gly Tyr Lys Phe Pro Leu
    370                 375                 380

Tyr Met Ile Gly His Gly Met Leu Asp Ser Asp Leu His Leu Ser Ser
385                 390                 395                 400

Lys Ala Gln Val Phe Glu His Pro His Ile Gln Asp Ala Ala Ser Gln
                405                 410                 415

Leu Pro Asp Asp Glu Ile Leu Phe Phe Gly Asp Thr Gly Leu Ser Lys
            420                 425                 430

Asn Pro Ile Glu Leu Val Glu Gly Trp Phe Ser Ser Trp Lys Ser Ser
        435                 440                 445

Ile Ala Ser Phe Phe Phe Ile Ile Gly Leu Ile Ile Gly Leu Phe Leu
    450                 455                 460

Val Leu Arg Val Gly Ile His Leu Cys Ile Lys Leu Lys His Thr Lys
465                 470                 475                 480

Lys Arg Gln Ile Tyr Thr Asp Ile Glu Met Asn Arg Leu Gly Lys
                485                 490                 495


<210> SEQ ID NO 19
<211> LENGTH: 495
<212> TYPE: PRT
<213> ORGANISM: Artificial sequence
<220> FEATURE:
<223> OTHER INFORMATION: Glycoprotein Vesicular stomatitis Indiana virus
      S422L

<400> SEQUENCE: 19

Lys Phe Thr Ile Val Phe Pro His Asn Gln Lys Gly Asn Trp Lys Asn
1               5                   10                  15

Val Pro Ser Asn Tyr His Tyr Cys Pro Ser Ser Ser Asp Leu Asn Trp
            20                  25                  30

His Asn Asp Leu Ile Gly Thr Ala Ile Gln Val Lys Met Pro Lys Ser
        35                  40                  45

His Lys Ala Ile Gln Ala Asp Gly Trp Met Cys His Ala Ser Lys Trp
    50                  55                  60

Val Thr Thr Cys Asp Phe Arg Trp Tyr Gly Pro Lys Tyr Ile Thr Gln
65                  70                  75                  80

Ser Ile Arg Ser Phe Thr Pro Ser Val Glu Gln Cys Lys Glu Ser Ile
                85                  90                  95
```

```
Glu Gln Thr Lys Gln Gly Thr Trp Leu Asn Pro Gly Phe Pro Pro Gln
            100                 105                 110

Ser Cys Gly Tyr Ala Thr Val Thr Asp Ala Glu Ala Val Ile Val Gln
        115                 120                 125

Val Thr Pro His His Val Leu Val Asp Glu Tyr Thr Gly Glu Trp Val
    130                 135                 140

Asp Ser Gln Phe Ile Asn Gly Lys Cys Ser Asn Tyr Ile Cys Pro Thr
145                 150                 155                 160

Val His Asn Ser Thr Thr Trp His Ser Asp Tyr Lys Val Lys Gly Leu
                165                 170                 175

Cys Asp Ser Asn Leu Ile Ser Met Asp Ile Thr Phe Phe Ser Glu Asp
            180                 185                 190

Gly Glu Leu Ser Ser Leu Gly Lys Glu Gly Thr Gly Phe Arg Ser Asn
        195                 200                 205

Tyr Phe Ala Tyr Glu Thr Gly Gly Lys Ala Cys Lys Met Gln Tyr Cys
    210                 215                 220

Lys His Trp Gly Val Arg Leu Pro Ser Gly Val Trp Phe Glu Met Ala
225                 230                 235                 240

Asp Lys Asp Leu Phe Ala Ala Ala Arg Phe Pro Glu Cys Pro Glu Gly
                245                 250                 255

Ser Ser Ile Ser Ala Pro Ser Gln Thr Ser Val Asp Val Ser Leu Ile
            260                 265                 270

Gln Asp Val Glu Arg Ile Leu Asp Tyr Ser Leu Cys Gln Glu Thr Trp
        275                 280                 285

Ser Lys Ile Arg Ala Gly Leu Pro Ile Ser Pro Val Asp Leu Ser Tyr
    290                 295                 300

Leu Ala Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Val Asp Ile Ala
                325                 330                 335

Ala Pro Ile Leu Ser Arg Met Val Gly Met Ile Ser Gly Thr Thr Thr
            340                 345                 350

Glu Arg Glu Leu Trp Asp Asp Trp Ala Pro Tyr Glu Asp Val Glu Ile
        355                 360                 365

Gly Pro Asn Gly Val Leu Arg Thr Ser Ser Gly Tyr Lys Phe Pro Leu
    370                 375                 380

Tyr Met Ile Gly His Gly Met Leu Asp Ser Asp Leu His Leu Ser Ser
385                 390                 395                 400

Lys Ala Gln Val Phe Glu His Pro His Ile Gln Asp Ala Ala Ser Gln
                405                 410                 415

Leu Pro Asp Asp Glu Leu Leu Phe Phe Gly Asp Thr Gly Leu Ser Lys
            420                 425                 430

Asn Pro Ile Glu Leu Val Glu Gly Trp Phe Ser Ser Trp Lys Ser Ser
        435                 440                 445

Ile Ala Ser Phe Phe Phe Ile Ile Gly Leu Ile Ile Gly Leu Phe Leu
    450                 455                 460

Val Leu Arg Val Gly Ile His Leu Cys Ile Lys Leu Lys His Thr Lys
465                 470                 475                 480

Lys Arg Gln Ile Tyr Thr Asp Ile Glu Met Asn Arg Leu Gly Lys
                485                 490                 495
```

<210> SEQ ID NO 20
<211> LENGTH: 494

```
<212> TYPE: PRT
<213> ORGANISM: Artificial sequence
<220> FEATURE:
<223> OTHER INFORMATION: Glycoprotein Vesicular stomatitis Indiana virus
      S422F

<400> SEQUENCE: 20

Lys Phe Thr Ile Val Phe Pro His Asn Gln Lys Gly Asn Trp Lys Asn
1               5                   10                  15

Val Pro Ser Asn Tyr His Tyr Cys Pro Ser Ser Ser Asp Leu Asn Trp
            20                  25                  30

His Asn Asp Leu Ile Gly Thr Ala Ile Gln Val Lys Met Pro Lys Ser
        35                  40                  45

His Lys Ala Ile Gln Ala Asp Gly Trp Met Cys His Ala Ser Lys Trp
    50                  55                  60

Val Thr Thr Cys Asp Phe Arg Trp Tyr Gly Pro Lys Tyr Ile Thr Gln
65                  70                  75                  80

Ser Ile Arg Ser Phe Thr Pro Ser Val Glu Gln Cys Lys Glu Ser Ile
                85                  90                  95

Glu Gln Thr Lys Gln Gly Thr Trp Leu Asn Pro Gly Phe Pro Pro Gln
            100                 105                 110

Ser Cys Gly Tyr Ala Thr Val Thr Asp Ala Glu Ala Val Ile Val Gln
        115                 120                 125

Val Thr Pro His His Val Leu Val Asp Glu Tyr Thr Gly Glu Trp Val
    130                 135                 140

Asp Ser Gln Phe Ile Asn Gly Lys Cys Ser Asn Tyr Ile Cys Pro Thr
145                 150                 155                 160

Val His Asn Ser Thr Thr Trp His Ser Asp Tyr Lys Val Lys Gly Leu
                165                 170                 175

Cys Asp Ser Asn Leu Ile Ser Met Asp Ile Thr Phe Phe Ser Glu Asp
            180                 185                 190

Gly Glu Leu Ser Ser Leu Gly Lys Glu Gly Thr Gly Phe Arg Ser Asn
        195                 200                 205

Tyr Phe Ala Tyr Glu Thr Gly Gly Lys Ala Cys Lys Met Gln Tyr Cys
    210                 215                 220

Lys His Trp Gly Val Arg Leu Pro Ser Gly Val Trp Phe Glu Met Ala
225                 230                 235                 240

Asp Lys Asp Leu Phe Ala Ala Ala Arg Phe Pro Glu Cys Pro Glu Gly
                245                 250                 255

Ser Ser Ile Ser Ala Pro Ser Gln Thr Ser Val Asp Val Ser Leu Ile
            260                 265                 270

Gln Asp Val Glu Arg Ile Leu Asp Tyr Ser Leu Cys Gln Glu Thr Trp
        275                 280                 285

Ser Lys Ile Arg Ala Gly Leu Pro Ile Ser Pro Val Asp Leu Ser Tyr
    290                 295                 300

Leu Ala Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Val Asp Ile Ala
                325                 330                 335

Ala Pro Ile Leu Ser Arg Met Val Gly Met Ile Ser Gly Thr Thr Thr
            340                 345                 350

Glu Arg Glu Leu Trp Asp Asp Trp Ala Pro Tyr Glu Asp Val Glu Ile
        355                 360                 365

Gly Pro Asn Gly Val Leu Arg Thr Ser Ser Gly Tyr Lys Phe Pro Leu
    370                 375                 380
```

Tyr Met Ile Gly His Gly Met Leu Asp Ser Asp Leu His Leu Ser Ser
385 390 395 400

Lys Ala Gln Val Phe Glu His Pro His Ile Gln Asp Ala Ala Ser Gln
405 410 415

Leu Pro Asp Asp Glu Phe Leu Phe Gly Asp Thr Gly Leu Ser Lys Asn
420 425 430

Pro Ile Glu Leu Val Glu Gly Trp Phe Ser Ser Trp Lys Ser Ser Ile
435 440 445

Ala Ser Phe Phe Phe Ile Ile Gly Leu Ile Ile Gly Leu Phe Leu Val
450 455 460

Leu Arg Val Gly Ile His Leu Cys Ile Lys Leu Lys His Thr Lys Lys
465 470 475 480

Arg Gln Ile Tyr Thr Asp Ile Glu Met Asn Arg Leu Gly Lys
485 490

<210> SEQ ID NO 21
<211> LENGTH: 495
<212> TYPE: PRT
<213> ORGANISM: Artificial sequence
<220> FEATURE:
<223> OTHER INFORMATION: Glycoprotein Vesicular stomatitis Indiana virus S422M

<400> SEQUENCE: 21

Lys Phe Thr Ile Val Phe Pro His Asn Gln Lys Gly Asn Trp Lys Asn
1 5 10 15

Val Pro Ser Asn Tyr His Tyr Cys Pro Ser Ser Ser Asp Leu Asn Trp
20 25 30

His Asn Asp Leu Ile Gly Thr Ala Ile Gln Val Lys Met Pro Lys Ser
35 40 45

His Lys Ala Ile Gln Ala Asp Gly Trp Met Cys His Ala Ser Lys Trp
50 55 60

Val Thr Thr Cys Asp Phe Arg Trp Tyr Gly Pro Lys Tyr Ile Thr Gln
65 70 75 80

Ser Ile Arg Ser Phe Thr Pro Ser Val Glu Gln Cys Lys Glu Ser Ile
85 90 95

Glu Gln Thr Lys Gln Gly Thr Trp Leu Asn Pro Gly Phe Pro Pro Gln
100 105 110

Ser Cys Gly Tyr Ala Thr Val Thr Asp Ala Glu Ala Val Ile Val Gln
115 120 125

Val Thr Pro His His Val Leu Val Asp Glu Tyr Thr Gly Glu Trp Val
130 135 140

Asp Ser Gln Phe Ile Asn Gly Lys Cys Ser Asn Tyr Ile Cys Pro Thr
145 150 155 160

Val His Asn Ser Thr Thr Trp His Ser Asp Tyr Lys Val Lys Gly Leu
165 170 175

Cys Asp Ser Asn Leu Ile Ser Met Asp Ile Thr Phe Phe Ser Glu Asp
180 185 190

Gly Glu Leu Ser Ser Leu Gly Lys Glu Gly Thr Gly Phe Arg Ser Asn
195 200 205

Tyr Phe Ala Tyr Glu Thr Gly Gly Lys Ala Cys Lys Met Gln Tyr Cys
210 215 220

Lys His Trp Gly Val Arg Leu Pro Ser Gly Val Trp Phe Glu Met Ala
225 230 235 240

Asp Lys Asp Leu Phe Ala Ala Ala Arg Phe Pro Glu Cys Pro Glu Gly
245 250 255

Ser Ser Ile Ser Ala Pro Ser Gln Thr Ser Val Asp Val Ser Leu Ile
260 265 270

Gln Asp Val Glu Arg Ile Leu Asp Tyr Ser Leu Cys Gln Glu Thr Trp
275 280 285

Ser Lys Ile Arg Ala Gly Leu Pro Ile Ser Pro Val Asp Leu Ser Tyr
290 295 300

Leu Ala Pro Lys Asn Pro Gly Thr Gly Pro Ala Phe Thr Ile Ile Asn
305 310 315 320

Gly Thr Leu Lys Tyr Phe Glu Thr Arg Tyr Ile Arg Val Asp Ile Ala
325 330 335

Ala Pro Ile Leu Ser Arg Met Val Gly Met Ile Ser Gly Thr Thr Thr
340 345 350

Glu Arg Glu Leu Trp Asp Asp Trp Ala Pro Tyr Glu Asp Val Glu Ile
355 360 365

Gly Pro Asn Gly Val Leu Arg Thr Ser Ser Gly Tyr Lys Phe Pro Leu
370 375 380

Tyr Met Ile Gly His Gly Met Leu Asp Ser Asp Leu His Leu Ser Ser
385 390 395 400

Lys Ala Gln Val Phe Glu His Pro His Ile Gln Asp Ala Ala Ser Gln
405 410 415

Leu Pro Asp Asp Glu Met Leu Phe Phe Gly Asp Thr Gly Leu Ser Lys
420 425 430

Asn Pro Ile Glu Leu Val Glu Gly Trp Phe Ser Ser Trp Lys Ser Ser
435 440 445

Ile Ala Ser Phe Phe Phe Ile Ile Gly Leu Ile Ile Gly Leu Phe Leu
450 455 460

Val Leu Arg Val Gly Ile His Leu Cys Ile Lys Leu Lys His Thr Lys
465 470 475 480

Lys Arg Gln Ile Tyr Thr Asp Ile Glu Met Asn Arg Leu Gly Lys
485 490 495

<210> SEQ ID NO 22
<211> LENGTH: 495
<212> TYPE: PRT
<213> ORGANISM: Artificial sequence
<220> FEATURE:
<223> OTHER INFORMATION: Glycoprotein Vesicular stomatitis Indiana virus S422V

<400> SEQUENCE: 22

Lys Phe Thr Ile Val Phe Pro His Asn Gln Lys Gly Asn Trp Lys Asn
1 5 10 15

Val Pro Ser Asn Tyr His Tyr Cys Pro Ser Ser Ser Asp Leu Asn Trp
20 25 30

His Asn Asp Leu Ile Gly Thr Ala Ile Gln Val Lys Met Pro Lys Ser
35 40 45

His Lys Ala Ile Gln Ala Asp Gly Trp Met Cys His Ala Ser Lys Trp
50 55 60

Val Thr Thr Cys Asp Phe Arg Trp Tyr Gly Pro Lys Tyr Ile Thr Gln
65 70 75 80

Ser Ile Arg Ser Phe Thr Pro Ser Val Glu Gln Cys Lys Glu Ser Ile
85 90 95

```
Glu Gln Thr Lys Gln Gly Thr Trp Leu Asn Pro Gly Phe Pro Pro Gln
            100                 105                 110

Ser Cys Gly Tyr Ala Thr Val Thr Asp Ala Glu Ala Val Ile Val Gln
        115                 120                 125

Val Thr Pro His His Val Leu Val Asp Glu Tyr Thr Gly Glu Trp Val
    130                 135                 140

Asp Ser Gln Phe Ile Asn Gly Lys Cys Ser Asn Tyr Ile Cys Pro Thr
145                 150                 155                 160

Val His Asn Ser Thr Thr Trp His Ser Asp Tyr Lys Val Lys Gly Leu
                165                 170                 175

Cys Asp Ser Asn Leu Ile Ser Met Asp Ile Thr Phe Phe Ser Glu Asp
            180                 185                 190

Gly Glu Leu Ser Ser Leu Gly Lys Glu Gly Thr Gly Phe Arg Ser Asn
        195                 200                 205

Tyr Phe Ala Tyr Glu Thr Gly Gly Lys Ala Cys Lys Met Gln Tyr Cys
    210                 215                 220

Lys His Trp Gly Val Arg Leu Pro Ser Gly Val Trp Phe Glu Met Ala
225                 230                 235                 240

Asp Lys Asp Leu Phe Ala Ala Ala Arg Phe Pro Glu Cys Pro Glu Gly
                245                 250                 255

Ser Ser Ile Ser Ala Pro Ser Gln Thr Ser Val Asp Val Ser Leu Ile
            260                 265                 270

Gln Asp Val Glu Arg Ile Leu Asp Tyr Ser Leu Cys Gln Glu Thr Trp
        275                 280                 285

Ser Lys Ile Arg Ala Gly Leu Pro Ile Ser Pro Val Asp Leu Ser Tyr
    290                 295                 300

Leu Ala Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Val Asp Ile Ala
                325                 330                 335

Ala Pro Ile Leu Ser Arg Met Val Gly Met Ile Ser Gly Thr Thr Thr
            340                 345                 350

Glu Arg Glu Leu Trp Asp Asp Trp Ala Pro Tyr Glu Asp Val Glu Ile
        355                 360                 365

Gly Pro Asn Gly Val Leu Arg Thr Ser Ser Gly Tyr Lys Phe Pro Leu
    370                 375                 380

Tyr Met Ile Gly His Gly Met Leu Asp Ser Asp Leu His Leu Ser Ser
385                 390                 395                 400

Lys Ala Gln Val Phe Glu His Pro His Ile Gln Asp Ala Ala Ser Gln
                405                 410                 415

Leu Pro Asp Asp Glu Val Leu Phe Phe Gly Asp Thr Gly Leu Ser Lys
            420                 425                 430

Asn Pro Ile Glu Leu Val Glu Gly Trp Phe Ser Ser Trp Lys Ser Ser
        435                 440                 445

Ile Ala Ser Phe Phe Phe Ile Ile Gly Leu Ile Ile Gly Leu Phe Leu
    450                 455                 460

Val Leu Arg Val Gly Ile His Leu Cys Ile Lys Leu Lys His Thr Lys
465                 470                 475                 480

Lys Arg Gln Ile Tyr Thr Asp Ile Glu Met Asn Arg Leu Gly Lys
                485                 490                 495
```

<210> SEQ ID NO 23
<211> LENGTH: 495

<212> TYPE: PRT
<213> ORGANISM: Artificial sequence
<220> FEATURE:
<223> OTHER INFORMATION: Glycoprotein Vesicular stomatitis Indiana virus
H22N S422I

<400> SEQUENCE: 23

```
Lys Phe Thr Ile Val Phe Pro His Asn Gln Lys Gly Asn Trp Lys Asn
1               5                   10                  15

Val Pro Ser Asn Tyr Asn Tyr Cys Pro Ser Ser Ser Asp Leu Asn Trp
            20                  25                  30

His Asn Asp Leu Ile Gly Thr Ala Ile Gln Val Lys Met Pro Lys Ser
        35                  40                  45

His Lys Ala Ile Gln Ala Asp Gly Trp Met Cys His Ala Ser Lys Trp
    50                  55                  60

Val Thr Thr Cys Asp Phe Arg Trp Tyr Gly Pro Lys Tyr Ile Thr Gln
65                  70                  75                  80

Ser Ile Arg Ser Phe Thr Pro Ser Val Glu Gln Cys Lys Glu Ser Ile
                85                  90                  95

Glu Gln Thr Lys Gln Gly Thr Trp Leu Asn Pro Gly Phe Pro Pro Gln
            100                 105                 110

Ser Cys Gly Tyr Ala Thr Val Thr Asp Ala Glu Ala Val Ile Val Gln
        115                 120                 125

Val Thr Pro His His Val Leu Val Asp Glu Tyr Thr Gly Glu Trp Val
    130                 135                 140

Asp Ser Gln Phe Ile Asn Gly Lys Cys Ser Asn Tyr Ile Cys Pro Thr
145                 150                 155                 160

Val His Asn Ser Thr Thr Trp His Ser Asp Tyr Lys Val Lys Gly Leu
                165                 170                 175

Cys Asp Ser Asn Leu Ile Ser Met Asp Ile Thr Phe Phe Ser Glu Asp
            180                 185                 190

Gly Glu Leu Ser Ser Leu Gly Lys Glu Gly Thr Gly Phe Arg Ser Asn
        195                 200                 205

Tyr Phe Ala Tyr Glu Thr Gly Gly Lys Ala Cys Lys Met Gln Tyr Cys
    210                 215                 220

Lys His Trp Gly Val Arg Leu Pro Ser Gly Val Trp Phe Glu Met Ala
225                 230                 235                 240

Asp Lys Asp Leu Phe Ala Ala Ala Arg Phe Pro Glu Cys Pro Glu Gly
                245                 250                 255

Ser Ser Ile Ser Ala Pro Ser Gln Thr Ser Val Asp Val Ser Leu Ile
            260                 265                 270

Gln Asp Val Glu Arg Ile Leu Asp Tyr Ser Leu Cys Gln Glu Thr Trp
        275                 280                 285

Ser Lys Ile Arg Ala Gly Leu Pro Ile Ser Pro Val Asp Leu Ser Tyr
    290                 295                 300

Leu Ala Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Val Asp Ile Ala
                325                 330                 335

Ala Pro Ile Leu Ser Arg Met Val Gly Met Ile Ser Gly Thr Thr Thr
            340                 345                 350

Glu Arg Glu Leu Trp Asp Asp Trp Ala Pro Tyr Glu Asp Val Glu Ile
        355                 360                 365

Gly Pro Asn Gly Val Leu Arg Thr Ser Ser Gly Tyr Lys Phe Pro Leu
    370                 375                 380
```

```
Tyr Met Ile Gly His Gly Met Leu Asp Ser Asp Leu His Leu Ser Ser
385                 390                 395                 400

Lys Ala Gln Val Phe Glu His Pro His Ile Gln Asp Ala Ala Ser Gln
                405                 410                 415

Leu Pro Asp Asp Glu Ile Leu Phe Phe Gly Asp Thr Gly Leu Ser Lys
            420                 425                 430

Asn Pro Ile Glu Leu Val Glu Gly Trp Phe Ser Ser Trp Lys Ser Ser
        435                 440                 445

Ile Ala Ser Phe Phe Phe Ile Ile Gly Leu Ile Ile Gly Leu Phe Leu
    450                 455                 460

Val Leu Arg Val Gly Ile His Leu Cys Ile Lys Leu Lys His Thr Lys
465                 470                 475                 480

Lys Arg Gln Ile Tyr Thr Asp Ile Glu Met Asn Arg Leu Gly Lys
                485                 490                 495


<210> SEQ ID NO 24
<211> LENGTH: 495
<212> TYPE: PRT
<213> ORGANISM: Artificial sequence
<220> FEATURE:
<223> OTHER INFORMATION: Glycoprotein Vesicular stomatitis Indiana virus
      H22N S422L

<400> SEQUENCE: 24

Lys Phe Thr Ile Val Phe Pro His Asn Gln Lys Gly Asn Trp Lys Asn
1               5                   10                  15

Val Pro Ser Asn Tyr Asn Tyr Cys Pro Ser Ser Ser Asp Leu Asn Trp
            20                  25                  30

His Asn Asp Leu Ile Gly Thr Ala Ile Gln Val Lys Met Pro Lys Ser
        35                  40                  45

His Lys Ala Ile Gln Ala Asp Gly Trp Met Cys His Ala Ser Lys Trp
    50                  55                  60

Val Thr Thr Cys Asp Phe Arg Trp Tyr Gly Pro Lys Tyr Ile Thr Gln
65                  70                  75                  80

Ser Ile Arg Ser Phe Thr Pro Ser Val Glu Gln Cys Lys Glu Ser Ile
                85                  90                  95

Glu Gln Thr Lys Gln Gly Thr Trp Leu Asn Pro Gly Phe Pro Pro Gln
            100                 105                 110

Ser Cys Gly Tyr Ala Thr Val Thr Asp Ala Glu Ala Val Ile Val Gln
        115                 120                 125

Val Thr Pro His His Val Leu Val Asp Glu Tyr Thr Gly Glu Trp Val
    130                 135                 140

Asp Ser Gln Phe Ile Asn Gly Lys Cys Ser Asn Tyr Ile Cys Pro Thr
145                 150                 155                 160

Val His Asn Ser Thr Thr Trp His Ser Asp Tyr Lys Val Lys Gly Leu
                165                 170                 175

Cys Asp Ser Asn Leu Ile Ser Met Asp Ile Thr Phe Phe Ser Glu Asp
            180                 185                 190

Gly Glu Leu Ser Ser Leu Gly Lys Glu Gly Thr Gly Phe Arg Ser Asn
        195                 200                 205

Tyr Phe Ala Tyr Glu Thr Gly Gly Lys Ala Cys Lys Met Gln Tyr Cys
    210                 215                 220

Lys His Trp Gly Val Arg Leu Pro Ser Gly Val Trp Phe Glu Met Ala
225                 230                 235                 240
```

```
Asp Lys Asp Leu Phe Ala Ala Ala Arg Phe Pro Glu Cys Pro Glu Gly
                245                 250                 255

Ser Ser Ile Ser Ala Pro Ser Gln Thr Ser Val Asp Val Ser Leu Ile
            260                 265                 270

Gln Asp Val Glu Arg Ile Leu Asp Tyr Ser Leu Cys Gln Glu Thr Trp
        275                 280                 285

Ser Lys Ile Arg Ala Gly Leu Pro Ile Ser Pro Val Asp Leu Ser Tyr
    290                 295                 300

Leu Ala Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Val Asp Ile Ala
                325                 330                 335

Ala Pro Ile Leu Ser Arg Met Val Gly Met Ile Ser Gly Thr Thr Thr
            340                 345                 350

Glu Arg Glu Leu Trp Asp Asp Trp Ala Pro Tyr Glu Asp Val Glu Ile
        355                 360                 365

Gly Pro Asn Gly Val Leu Arg Thr Ser Ser Gly Tyr Lys Phe Pro Leu
    370                 375                 380

Tyr Met Ile Gly His Gly Met Leu Asp Ser Asp Leu His Leu Ser Ser
385                 390                 395                 400

Lys Ala Gln Val Phe Glu His Pro His Ile Gln Asp Ala Ala Ser Gln
                405                 410                 415

Leu Pro Asp Asp Glu Leu Leu Phe Phe Gly Asp Thr Gly Leu Ser Lys
            420                 425                 430

Asn Pro Ile Glu Leu Val Glu Gly Trp Phe Ser Ser Trp Lys Ser Ser
        435                 440                 445

Ile Ala Ser Phe Phe Phe Ile Ile Gly Leu Ile Ile Gly Leu Phe Leu
    450                 455                 460

Val Leu Arg Val Gly Ile His Leu Cys Ile Lys Leu Lys His Thr Lys
465                 470                 475                 480

Lys Arg Gln Ile Tyr Thr Asp Ile Glu Met Asn Arg Leu Gly Lys
                485                 490                 495


<210> SEQ ID NO 25
<211> LENGTH: 494
<212> TYPE: PRT
<213> ORGANISM: Artificial sequence
<220> FEATURE:
<223> OTHER INFORMATION: Glycoprotein Vesicular stomatitis Indiana virus
      H22N S422F

<400> SEQUENCE: 25

Lys Phe Thr Ile Val Phe Pro His Asn Gln Lys Gly Asn Trp Lys Asn
1               5                   10                  15

Val Pro Ser Asn Tyr Asn Tyr Cys Pro Ser Ser Ser Asp Leu Asn Trp
            20                  25                  30

His Asn Asp Leu Ile Gly Thr Ala Ile Gln Val Lys Met Pro Lys Ser
        35                  40                  45

His Lys Ala Ile Gln Ala Asp Gly Trp Met Cys His Ala Ser Lys Trp
    50                  55                  60

Val Thr Thr Cys Asp Phe Arg Trp Tyr Gly Pro Lys Tyr Ile Thr Gln
65                  70                  75                  80

Ser Ile Arg Ser Phe Thr Pro Ser Val Glu Gln Cys Lys Glu Ser Ile
                85                  90                  95
```

```
Glu Gln Thr Lys Gln Gly Thr Trp Leu Asn Pro Gly Phe Pro Pro Gln
            100                 105                 110

Ser Cys Gly Tyr Ala Thr Val Thr Asp Ala Glu Ala Val Ile Val Gln
        115                 120                 125

Val Thr Pro His His Val Leu Val Asp Glu Tyr Thr Gly Glu Trp Val
    130                 135                 140

Asp Ser Gln Phe Ile Asn Gly Lys Cys Ser Asn Tyr Ile Cys Pro Thr
145                 150                 155                 160

Val His Asn Ser Thr Thr Trp His Ser Asp Tyr Lys Val Lys Gly Leu
                165                 170                 175

Cys Asp Ser Asn Leu Ile Ser Met Asp Ile Thr Phe Phe Ser Glu Asp
            180                 185                 190

Gly Glu Leu Ser Ser Leu Gly Lys Glu Gly Thr Gly Phe Arg Ser Asn
        195                 200                 205

Tyr Phe Ala Tyr Glu Thr Gly Gly Lys Ala Cys Lys Met Gln Tyr Cys
    210                 215                 220

Lys His Trp Gly Val Arg Leu Pro Ser Gly Val Trp Phe Glu Met Ala
225                 230                 235                 240

Asp Lys Asp Leu Phe Ala Ala Ala Arg Phe Pro Glu Cys Pro Glu Gly
                245                 250                 255

Ser Ser Ile Ser Ala Pro Ser Gln Thr Ser Val Asp Val Ser Leu Ile
            260                 265                 270

Gln Asp Val Glu Arg Ile Leu Asp Tyr Ser Leu Cys Gln Glu Thr Trp
        275                 280                 285

Ser Lys Ile Arg Ala Gly Leu Pro Ile Ser Pro Val Asp Leu Ser Tyr
    290                 295                 300

Leu Ala Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Val Asp Ile Ala
                325                 330                 335

Ala Pro Ile Leu Ser Arg Met Val Gly Met Ile Ser Gly Thr Thr Thr
            340                 345                 350

Glu Arg Glu Leu Trp Asp Asp Trp Ala Pro Tyr Glu Asp Val Glu Ile
        355                 360                 365

Gly Pro Asn Gly Val Leu Arg Thr Ser Ser Gly Tyr Lys Phe Pro Leu
    370                 375                 380

Tyr Met Ile Gly His Gly Met Leu Asp Ser Asp Leu His Leu Ser Ser
385                 390                 395                 400

Lys Ala Gln Val Phe Glu His Pro His Ile Gln Asp Ala Ala Ser Gln
                405                 410                 415

Leu Pro Asp Asp Glu Phe Leu Phe Gly Asp Thr Gly Leu Ser Lys Asn
            420                 425                 430

Pro Ile Glu Leu Val Glu Gly Trp Phe Ser Ser Trp Lys Ser Ser Ile
        435                 440                 445

Ala Ser Phe Phe Phe Ile Ile Gly Leu Ile Ile Gly Leu Phe Leu Val
    450                 455                 460

Leu Arg Val Gly Ile His Leu Cys Ile Lys Leu Lys His Thr Lys Lys
465                 470                 475                 480

Arg Gln Ile Tyr Thr Asp Ile Glu Met Asn Arg Leu Gly Lys
                485                 490
```

<210> SEQ ID NO 26
<211> LENGTH: 495

```
<212> TYPE: PRT
<213> ORGANISM: Artificial sequence
<220> FEATURE:
<223> OTHER INFORMATION: Glycoprotein Vesicular stomatitis Indiana virus
      H22N S422M

<400> SEQUENCE: 26

Lys Phe Thr Ile Val Phe Pro His Asn Gln Lys Gly Asn Trp Lys Asn
1               5                   10                  15

Val Pro Ser Asn Tyr Asn Tyr Cys Pro Ser Ser Ser Asp Leu Asn Trp
            20                  25                  30

His Asn Asp Leu Ile Gly Thr Ala Ile Gln Val Lys Met Pro Lys Ser
        35                  40                  45

His Lys Ala Ile Gln Ala Asp Gly Trp Met Cys His Ala Ser Lys Trp
    50                  55                  60

Val Thr Thr Cys Asp Phe Arg Trp Tyr Gly Pro Lys Tyr Ile Thr Gln
65                  70                  75                  80

Ser Ile Arg Ser Phe Thr Pro Ser Val Glu Gln Cys Lys Glu Ser Ile
                85                  90                  95

Glu Gln Thr Lys Gln Gly Thr Trp Leu Asn Pro Gly Phe Pro Pro Gln
            100                 105                 110

Ser Cys Gly Tyr Ala Thr Val Thr Asp Ala Glu Ala Val Ile Val Gln
        115                 120                 125

Val Thr Pro His His Val Leu Val Asp Glu Tyr Thr Gly Glu Trp Val
    130                 135                 140

Asp Ser Gln Phe Ile Asn Gly Lys Cys Ser Asn Tyr Ile Cys Pro Thr
145                 150                 155                 160

Val His Asn Ser Thr Thr Trp His Ser Asp Tyr Lys Val Lys Gly Leu
                165                 170                 175

Cys Asp Ser Asn Leu Ile Ser Met Asp Ile Thr Phe Phe Ser Glu Asp
            180                 185                 190

Gly Glu Leu Ser Ser Leu Gly Lys Glu Gly Thr Gly Phe Arg Ser Asn
        195                 200                 205

Tyr Phe Ala Tyr Glu Thr Gly Gly Lys Ala Cys Lys Met Gln Tyr Cys
    210                 215                 220

Lys His Trp Gly Val Arg Leu Pro Ser Gly Val Trp Phe Glu Met Ala
225                 230                 235                 240

Asp Lys Asp Leu Phe Ala Ala Ala Arg Phe Pro Glu Cys Pro Glu Gly
                245                 250                 255

Ser Ser Ile Ser Ala Pro Ser Gln Thr Ser Val Asp Val Ser Leu Ile
            260                 265                 270

Gln Asp Val Glu Arg Ile Leu Asp Tyr Ser Leu Cys Gln Glu Thr Trp
        275                 280                 285

Ser Lys Ile Arg Ala Gly Leu Pro Ile Ser Pro Val Asp Leu Ser Tyr
    290                 295                 300

Leu Ala Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Val Asp Ile Ala
                325                 330                 335

Ala Pro Ile Leu Ser Arg Met Val Gly Met Ile Ser Gly Thr Thr Thr
            340                 345                 350

Glu Arg Glu Leu Trp Asp Asp Trp Ala Pro Tyr Glu Asp Val Glu Ile
        355                 360                 365

Gly Pro Asn Gly Val Leu Arg Thr Ser Ser Gly Tyr Lys Phe Pro Leu
    370                 375                 380
```

Tyr Met Ile Gly His Gly Met Leu Asp Ser Asp Leu His Leu Ser Ser
385 390 395 400

Lys Ala Gln Val Phe Glu His Pro His Ile Gln Asp Ala Ala Ser Gln
405 410 415

Leu Pro Asp Asp Glu Met Leu Phe Phe Gly Asp Thr Gly Leu Ser Lys
420 425 430

Asn Pro Ile Glu Leu Val Glu Gly Trp Phe Ser Ser Trp Lys Ser Ser
435 440 445

Ile Ala Ser Phe Phe Phe Ile Ile Gly Leu Ile Ile Gly Leu Phe Leu
450 455 460

Val Leu Arg Val Gly Ile His Leu Cys Ile Lys Leu Lys His Thr Lys
465 470 475 480

Lys Arg Gln Ile Tyr Thr Asp Ile Glu Met Asn Arg Leu Gly Lys
485 490 495

<210> SEQ ID NO 27
<211> LENGTH: 495
<212> TYPE: PRT
<213> ORGANISM: Artificial sequence
<220> FEATURE:
<223> OTHER INFORMATION: Glycoprotein Vesicular stomatitis Indiana virus
H22N S422V

<400> SEQUENCE: 27

Lys Phe Thr Ile Val Phe Pro His Asn Gln Lys Gly Asn Trp Lys Asn
1 5 10 15

Val Pro Ser Asn Tyr Asn Tyr Cys Pro Ser Ser Ser Asp Leu Asn Trp
20 25 30

His Asn Asp Leu Ile Gly Thr Ala Ile Gln Val Lys Met Pro Lys Ser
35 40 45

His Lys Ala Ile Gln Ala Asp Gly Trp Met Cys His Ala Ser Lys Trp
50 55 60

Val Thr Thr Cys Asp Phe Arg Trp Tyr Gly Pro Lys Tyr Ile Thr Gln
65 70 75 80

Ser Ile Arg Ser Phe Thr Pro Ser Val Glu Gln Cys Lys Glu Ser Ile
85 90 95

Glu Gln Thr Lys Gln Gly Thr Trp Leu Asn Pro Gly Phe Pro Pro Gln
100 105 110

Ser Cys Gly Tyr Ala Thr Val Thr Asp Ala Glu Ala Val Ile Val Gln
115 120 125

Val Thr Pro His His Val Leu Val Asp Glu Tyr Thr Gly Glu Trp Val
130 135 140

Asp Ser Gln Phe Ile Asn Gly Lys Cys Ser Asn Tyr Ile Cys Pro Thr
145 150 155 160

Val His Asn Ser Thr Thr Trp His Ser Asp Tyr Lys Val Lys Gly Leu
165 170 175

Cys Asp Ser Asn Leu Ile Ser Met Asp Ile Thr Phe Phe Ser Glu Asp
180 185 190

Gly Glu Leu Ser Ser Leu Gly Lys Glu Gly Thr Gly Phe Arg Ser Asn
195 200 205

Tyr Phe Ala Tyr Glu Thr Gly Gly Lys Ala Cys Lys Met Gln Tyr Cys
210 215 220

Lys His Trp Gly Val Arg Leu Pro Ser Gly Val Trp Phe Glu Met Ala
225 230 235 240

```
Asp Lys Asp Leu Phe Ala Ala Ala Arg Phe Pro Glu Cys Pro Glu Gly
                245                 250                 255

Ser Ser Ile Ser Ala Pro Ser Gln Thr Ser Val Asp Val Ser Leu Ile
            260                 265                 270

Gln Asp Val Glu Arg Ile Leu Asp Tyr Ser Leu Cys Gln Glu Thr Trp
        275                 280                 285

Ser Lys Ile Arg Ala Gly Leu Pro Ile Ser Pro Val Asp Leu Ser Tyr
    290                 295                 300

Leu Ala Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Val Asp Ile Ala
                325                 330                 335

Ala Pro Ile Leu Ser Arg Met Val Gly Met Ile Ser Gly Thr Thr Thr
            340                 345                 350

Glu Arg Glu Leu Trp Asp Asp Trp Ala Pro Tyr Glu Asp Val Glu Ile
        355                 360                 365

Gly Pro Asn Gly Val Leu Arg Thr Ser Ser Gly Tyr Lys Phe Pro Leu
    370                 375                 380

Tyr Met Ile Gly His Gly Met Leu Asp Ser Asp Leu His Leu Ser Ser
385                 390                 395                 400

Lys Ala Gln Val Phe Glu His Pro His Ile Gln Asp Ala Ala Ser Gln
                405                 410                 415

Leu Pro Asp Asp Glu Val Leu Phe Phe Gly Asp Thr Gly Leu Ser Lys
            420                 425                 430

Asn Pro Ile Glu Leu Val Glu Gly Trp Phe Ser Ser Trp Lys Ser Ser
        435                 440                 445

Ile Ala Ser Phe Phe Phe Ile Ile Gly Leu Ile Ile Gly Leu Phe Leu
    450                 455                 460

Val Leu Arg Val Gly Ile His Leu Cys Ile Lys Leu Lys His Thr Lys
465                 470                 475                 480

Lys Arg Gln Ile Tyr Thr Asp Ile Glu Met Asn Arg Leu Gly Lys
                485                 490                 495
```

<210> SEQ ID NO 28
<211> LENGTH: 496
<212> TYPE: PRT
<213> ORGANISM: Artificial sequence
<220> FEATURE:
<223> OTHER INFORMATION: Glycoprotein Vesicular stomatitis Maraba virus H22N

<400> SEQUENCE: 28

```
Lys Phe Thr Ile Val Phe Pro His His Gln Lys Gly Asn Trp Lys Asn
1               5                   10                  15

Val Pro Ser Thr Tyr Asn Tyr Cys Pro Ser Ser Ser Asp Gln Asn Trp
            20                  25                  30

His Asn Asp Leu Thr Gly Val Ser Leu His Val Lys Ile Pro Lys Ser
        35                  40                  45

His Lys Ala Ile Gln Ala Asp Gly Trp Met Cys His Ala Ala Lys Trp
    50                  55                  60

Val Thr Thr Cys Asp Phe Arg Trp Tyr Gly Pro Lys Tyr Ile Thr His
65                  70                  75                  80

Ser Ile His Ser Met Ser Pro Thr Leu Glu Gln Cys Lys Thr Ser Ile
                85                  90                  95
```

```
Glu Gln Thr Lys Gln Gly Val Trp Ile Asn Pro Gly Phe Pro Pro Gln
            100                 105                 110

Ser Cys Gly Tyr Ala Thr Val Thr Asp Ala Glu Val Val Val Val Gln
        115                 120                 125

Ala Thr Pro His His Val Leu Val Asp Glu Tyr Thr Gly Glu Trp Ile
    130                 135                 140

Asp Ser Gln Leu Val Gly Gly Lys Cys Ser Lys Glu Val Cys Gln Thr
145                 150                 155                 160

Val His Asn Ser Thr Val Trp His Ala Asp Tyr Lys Ile Thr Gly Leu
                165                 170                 175

Cys Glu Ser Asn Leu Ala Ser Val Asp Ile Thr Phe Phe Ser Glu Asp
            180                 185                 190

Gly Gln Lys Thr Ser Leu Gly Lys Pro Asn Thr Gly Phe Arg Ser Asn
        195                 200                 205

His Phe Ala Tyr Glu Ser Gly Glu Lys Ala Cys Arg Met Gln Tyr Cys
    210                 215                 220

Thr Gln Trp Gly Ile Arg Leu Pro Ser Gly Val Trp Phe Glu Leu Val
225                 230                 235                 240

Asp Lys Asp Leu Phe Gln Ala Ala Lys Leu Pro Glu Cys Pro Arg Gly
                245                 250                 255

Ser Ser Ile Ser Ala Pro Ser Gln Thr Ser Val Asp Val Ser Leu Ile
            260                 265                 270

Gln Asp Val Glu Arg Ile Leu Asp Tyr Ser Leu Cys Gln Glu Thr Trp
        275                 280                 285

Ser Lys Ile Arg Ala Lys Leu Pro Val Ser Pro Val Asp Leu Ser Tyr
    290                 295                 300

Leu Ala Pro Lys Asn Pro Gly Ser Gly Pro Ala Phe Thr Ile Ile Asn
305                 310                 315                 320

Gly Thr Leu Lys Tyr Phe Glu Thr Arg Tyr Ile Arg Val Asp Ile Ser
                325                 330                 335

Asn Pro Ile Ile Pro His Met Val Gly Thr Met Ser Gly Thr Thr Thr
            340                 345                 350

Glu Arg Glu Leu Trp Asn Asp Trp Tyr Pro Tyr Glu Asp Val Glu Ile
        355                 360                 365

Gly Pro Asn Gly Val Leu Lys Thr Pro Thr Gly Phe Lys Phe Pro Leu
    370                 375                 380

Tyr Met Ile Gly His Gly Met Leu Asp Ser Asp Leu His Lys Ser Ser
385                 390                 395                 400

Gln Ala Gln Val Phe Glu His Pro His Ala Lys Asp Ala Ala Ser Gln
                405                 410                 415

Leu Pro Asp Asp Glu Thr Leu Phe Phe Gly Asp Thr Gly Leu Ser Lys
            420                 425                 430

Asn Pro Val Glu Leu Val Glu Gly Trp Phe Ser Ser Trp Lys Ser Thr
        435                 440                 445

Leu Ala Ser Phe Phe Leu Ile Ile Gly Leu Gly Val Ala Leu Ile Phe
    450                 455                 460

Ile Ile Arg Ile Ile Val Ala Ile Arg Tyr Lys Tyr Lys Gly Arg Lys
465                 470                 475                 480

Thr Gln Lys Ile Tyr Asn Asp Val Glu Met Ser Arg Leu Gly Asn Lys
                485                 490                 495
```

<210> SEQ ID NO 29
<211> LENGTH: 496

```
<212> TYPE: PRT
<213> ORGANISM: Artificial sequence
<220> FEATURE:
<223> OTHER INFORMATION: Glycoprotein Vesicular stomatitis Maraba virus
      T422I

<400> SEQUENCE: 29

Lys Phe Thr Ile Val Phe Pro His His Gln Lys Gly Asn Trp Lys Asn
1               5                   10                  15

Val Pro Ser Thr Tyr His Tyr Cys Pro Ser Ser Ser Asp Gln Asn Trp
            20                  25                  30

His Asn Asp Leu Thr Gly Val Ser Leu His Val Lys Ile Pro Lys Ser
        35                  40                  45

His Lys Ala Ile Gln Ala Asp Gly Trp Met Cys His Ala Ala Lys Trp
    50                  55                  60

Val Thr Thr Cys Asp Phe Arg Trp Tyr Gly Pro Lys Tyr Ile Thr His
65                  70                  75                  80

Ser Ile His Ser Met Ser Pro Thr Leu Glu Gln Cys Lys Thr Ser Ile
                85                  90                  95

Glu Gln Thr Lys Gln Gly Val Trp Ile Asn Pro Gly Phe Pro Pro Gln
            100                 105                 110

Ser Cys Gly Tyr Ala Thr Val Thr Asp Ala Glu Val Val Val Val Gln
        115                 120                 125

Ala Thr Pro His His Val Leu Val Asp Glu Tyr Thr Gly Glu Trp Ile
    130                 135                 140

Asp Ser Gln Leu Val Gly Gly Lys Cys Ser Lys Glu Val Cys Gln Thr
145                 150                 155                 160

Val His Asn Ser Thr Val Trp His Ala Asp Tyr Lys Ile Thr Gly Leu
                165                 170                 175

Cys Glu Ser Asn Leu Ala Ser Val Asp Ile Thr Phe Phe Ser Glu Asp
            180                 185                 190

Gly Gln Lys Thr Ser Leu Gly Lys Pro Asn Thr Gly Phe Arg Ser Asn
        195                 200                 205

His Phe Ala Tyr Glu Ser Gly Glu Lys Ala Cys Arg Met Gln Tyr Cys
    210                 215                 220

Thr Gln Trp Gly Ile Arg Leu Pro Ser Gly Val Trp Phe Glu Leu Val
225                 230                 235                 240

Asp Lys Asp Leu Phe Gln Ala Ala Lys Leu Pro Glu Cys Pro Arg Gly
                245                 250                 255

Ser Ser Ile Ser Ala Pro Ser Gln Thr Ser Val Asp Val Ser Leu Ile
            260                 265                 270

Gln Asp Val Glu Arg Ile Leu Asp Tyr Ser Leu Cys Gln Glu Thr Trp
        275                 280                 285

Ser Lys Ile Arg Ala Lys Leu Pro Val Ser Pro Val Asp Leu Ser Tyr
    290                 295                 300

Leu Ala Pro Lys Asn Pro Gly Ser Gly Pro Ala Phe Thr Ile Ile Asn
305                 310                 315                 320

Gly Thr Leu Lys Tyr Phe Glu Thr Arg Tyr Ile Arg Val Asp Ile Ser
                325                 330                 335

Asn Pro Ile Ile Pro His Met Val Gly Thr Met Ser Gly Thr Thr Thr
            340                 345                 350

Glu Arg Glu Leu Trp Asn Asp Trp Tyr Pro Tyr Glu Asp Val Glu Ile
        355                 360                 365

Gly Pro Asn Gly Val Leu Lys Thr Pro Thr Gly Phe Lys Phe Pro Leu
    370                 375                 380
```

```
Tyr Met Ile Gly His Gly Met Leu Asp Ser Asp Leu His Lys Ser Ser
385                 390                 395                 400

Gln Ala Gln Val Phe Glu His Pro His Ala Lys Asp Ala Ala Ser Gln
                405                 410                 415

Leu Pro Asp Asp Glu Ile Leu Phe Phe Gly Asp Thr Gly Leu Ser Lys
            420                 425                 430

Asn Pro Val Glu Leu Val Glu Gly Trp Phe Ser Ser Trp Lys Ser Thr
        435                 440                 445

Leu Ala Ser Phe Phe Leu Ile Ile Gly Leu Gly Val Ala Leu Ile Phe
    450                 455                 460

Ile Ile Arg Ile Ile Val Ala Ile Arg Tyr Lys Tyr Lys Gly Arg Lys
465                 470                 475                 480

Thr Gln Lys Ile Tyr Asn Asp Val Glu Met Ser Arg Leu Gly Asn Lys
                485                 490                 495


<210> SEQ ID NO 30
<211> LENGTH: 496
<212> TYPE: PRT
<213> ORGANISM: Artificial sequence
<220> FEATURE:
<223> OTHER INFORMATION: Glycoprotein Vesicular stomatitis Maraba virus
      T422L

<400> SEQUENCE: 30

Lys Phe Thr Ile Val Phe Pro His His Gln Lys Gly Asn Trp Lys Asn
1               5                   10                  15

Val Pro Ser Thr Tyr His Tyr Cys Pro Ser Ser Ser Asp Gln Asn Trp
            20                  25                  30

His Asn Asp Leu Thr Gly Val Ser Leu His Val Lys Ile Pro Lys Ser
        35                  40                  45

His Lys Ala Ile Gln Ala Asp Gly Trp Met Cys His Ala Ala Lys Trp
    50                  55                  60

Val Thr Thr Cys Asp Phe Arg Trp Tyr Gly Pro Lys Tyr Ile Thr His
65                  70                  75                  80

Ser Ile His Ser Met Ser Pro Thr Leu Glu Gln Cys Lys Thr Ser Ile
                85                  90                  95

Glu Gln Thr Lys Gln Gly Val Trp Ile Asn Pro Gly Phe Pro Pro Gln
            100                 105                 110

Ser Cys Gly Tyr Ala Thr Val Thr Asp Ala Glu Val Val Val Val Gln
        115                 120                 125

Ala Thr Pro His His Val Leu Val Asp Glu Tyr Thr Gly Glu Trp Ile
    130                 135                 140

Asp Ser Gln Leu Val Gly Gly Lys Cys Ser Lys Glu Val Cys Gln Thr
145                 150                 155                 160

Val His Asn Ser Thr Val Trp His Ala Asp Tyr Lys Ile Thr Gly Leu
                165                 170                 175

Cys Glu Ser Asn Leu Ala Ser Val Asp Ile Thr Phe Phe Ser Glu Asp
            180                 185                 190

Gly Gln Lys Thr Ser Leu Gly Lys Pro Asn Thr Gly Phe Arg Ser Asn
        195                 200                 205

His Phe Ala Tyr Glu Ser Gly Glu Lys Ala Cys Arg Met Gln Tyr Cys
    210                 215                 220

Thr Gln Trp Gly Ile Arg Leu Pro Ser Gly Val Trp Phe Glu Leu Val
225                 230                 235                 240
```

Asp Lys Asp Leu Phe Gln Ala Ala Lys Leu Pro Glu Cys Pro Arg Gly
245 250 255

Ser Ser Ile Ser Ala Pro Ser Gln Thr Ser Val Asp Val Ser Leu Ile
260 265 270

Gln Asp Val Glu Arg Ile Leu Asp Tyr Ser Leu Cys Gln Glu Thr Trp
275 280 285

Ser Lys Ile Arg Ala Lys Leu Pro Val Ser Pro Val Asp Leu Ser Tyr
290 295 300

Leu Ala Pro Lys Asn Pro Gly Ser Gly Pro Ala Phe Thr Ile Ile Asn
305 310 315 320

Gly Thr Leu Lys Tyr Phe Glu Thr Arg Tyr Ile Arg Val Asp Ile Ser
325 330 335

Asn Pro Ile Ile Pro His Met Val Gly Thr Met Ser Gly Thr Thr Thr
340 345 350

Glu Arg Glu Leu Trp Asn Asp Trp Tyr Pro Tyr Glu Asp Val Glu Ile
355 360 365

Gly Pro Asn Gly Val Leu Lys Thr Pro Thr Gly Phe Lys Phe Pro Leu
370 375 380

Tyr Met Ile Gly His Gly Met Leu Asp Ser Asp Leu His Lys Ser Ser
385 390 395 400

Gln Ala Gln Val Phe Glu His Pro His Ala Lys Asp Ala Ala Ser Gln
405 410 415

Leu Pro Asp Asp Glu Leu Leu Phe Phe Gly Asp Thr Gly Leu Ser Lys
420 425 430

Asn Pro Val Glu Leu Val Glu Gly Trp Phe Ser Ser Trp Lys Ser Thr
435 440 445

Leu Ala Ser Phe Phe Leu Ile Ile Gly Leu Gly Val Ala Leu Ile Phe
450 455 460

Ile Ile Arg Ile Ile Val Ala Ile Arg Tyr Lys Tyr Lys Gly Arg Lys
465 470 475 480

Thr Gln Lys Ile Tyr Asn Asp Val Glu Met Ser Arg Leu Gly Asn Lys
485 490 495

<210> SEQ ID NO 31
<211> LENGTH: 496
<212> TYPE: PRT
<213> ORGANISM: Artificial sequence
<220> FEATURE:
<223> OTHER INFORMATION: Glycoprotein Vesicular stomatitis Maraba virus T422F

<400> SEQUENCE: 31

Lys Phe Thr Ile Val Phe Pro His His Gln Lys Gly Asn Trp Lys Asn
1 5 10 15

Val Pro Ser Thr Tyr His Tyr Cys Pro Ser Ser Ser Asp Gln Asn Trp
20 25 30

His Asn Asp Leu Thr Gly Val Ser Leu His Val Lys Ile Pro Lys Ser
35 40 45

His Lys Ala Ile Gln Ala Asp Gly Trp Met Cys His Ala Ala Lys Trp
50 55 60

Val Thr Thr Cys Asp Phe Arg Trp Tyr Gly Pro Lys Tyr Ile Thr His
65 70 75 80

Ser Ile His Ser Met Ser Pro Thr Leu Glu Gln Cys Lys Thr Ser Ile
85 90 95

Glu Gln Thr Lys Gln Gly Val Trp Ile Asn Pro Gly Phe Pro Pro Gln
100 105 110

Ser Cys Gly Tyr Ala Thr Val Thr Asp Ala Glu Val Val Val Val Gln
115 120 125

Ala Thr Pro His His Val Leu Val Asp Glu Tyr Thr Gly Glu Trp Ile
130 135 140

Asp Ser Gln Leu Val Gly Gly Lys Cys Ser Lys Glu Val Cys Gln Thr
145 150 155 160

Val His Asn Ser Thr Val Trp His Ala Asp Tyr Lys Ile Thr Gly Leu
165 170 175

Cys Glu Ser Asn Leu Ala Ser Val Asp Ile Thr Phe Phe Ser Glu Asp
180 185 190

Gly Gln Lys Thr Ser Leu Gly Lys Pro Asn Thr Gly Phe Arg Ser Asn
195 200 205

His Phe Ala Tyr Glu Ser Gly Glu Lys Ala Cys Arg Met Gln Tyr Cys
210 215 220

Thr Gln Trp Gly Ile Arg Leu Pro Ser Gly Val Trp Phe Glu Leu Val
225 230 235 240

Asp Lys Asp Leu Phe Gln Ala Ala Lys Leu Pro Glu Cys Pro Arg Gly
245 250 255

Ser Ser Ile Ser Ala Pro Ser Gln Thr Ser Val Asp Val Ser Leu Ile
260 265 270

Gln Asp Val Glu Arg Ile Leu Asp Tyr Ser Leu Cys Gln Glu Thr Trp
275 280 285

Ser Lys Ile Arg Ala Lys Leu Pro Val Ser Pro Val Asp Leu Ser Tyr
290 295 300

Leu Ala Pro Lys Asn Pro Gly Ser Gly Pro Ala Phe Thr Ile Ile Asn
305 310 315 320

Gly Thr Leu Lys Tyr Phe Glu Thr Arg Tyr Ile Arg Val Asp Ile Ser
325 330 335

Asn Pro Ile Ile Pro His Met Val Gly Thr Met Ser Gly Thr Thr Thr
340 345 350

Glu Arg Glu Leu Trp Asn Asp Trp Tyr Pro Tyr Glu Asp Val Glu Ile
355 360 365

Gly Pro Asn Gly Val Leu Lys Thr Pro Thr Gly Phe Lys Phe Pro Leu
370 375 380

Tyr Met Ile Gly His Gly Met Leu Asp Ser Asp Leu His Lys Ser Ser
385 390 395 400

Gln Ala Gln Val Phe Glu His Pro His Ala Lys Asp Ala Ala Ser Gln
405 410 415

Leu Pro Asp Asp Glu Phe Leu Phe Phe Gly Asp Thr Gly Leu Ser Lys
420 425 430

Asn Pro Val Glu Leu Val Glu Gly Trp Phe Ser Ser Trp Lys Ser Thr
435 440 445

Leu Ala Ser Phe Phe Leu Ile Ile Gly Leu Gly Val Ala Leu Ile Phe
450 455 460

Ile Ile Arg Ile Ile Val Ala Ile Arg Tyr Lys Tyr Lys Gly Arg Lys
465 470 475 480

Thr Gln Lys Ile Tyr Asn Asp Val Glu Met Ser Arg Leu Gly Asn Lys
485 490 495

<210> SEQ ID NO 32
<211> LENGTH: 496

```
<212> TYPE: PRT
<213> ORGANISM: Artificial sequence
<220> FEATURE:
<223> OTHER INFORMATION: Glycoprotein Vesicular stomatitis Maraba virus
      T422M

<400> SEQUENCE: 32

Lys Phe Thr Ile Val Phe Pro His His Gln Lys Gly Asn Trp Lys Asn
1               5                   10                  15

Val Pro Ser Thr Tyr His Tyr Cys Pro Ser Ser Ser Asp Gln Asn Trp
            20                  25                  30

His Asn Asp Leu Thr Gly Val Ser Leu His Val Lys Ile Pro Lys Ser
        35                  40                  45

His Lys Ala Ile Gln Ala Asp Gly Trp Met Cys His Ala Ala Lys Trp
    50                  55                  60

Val Thr Thr Cys Asp Phe Arg Trp Tyr Gly Pro Lys Tyr Ile Thr His
65                  70                  75                  80

Ser Ile His Ser Met Ser Pro Thr Leu Glu Gln Cys Lys Thr Ser Ile
                85                  90                  95

Glu Gln Thr Lys Gln Gly Val Trp Ile Asn Pro Gly Phe Pro Pro Gln
            100                 105                 110

Ser Cys Gly Tyr Ala Thr Val Thr Asp Ala Glu Val Val Val Val Gln
        115                 120                 125

Ala Thr Pro His His Val Leu Val Asp Glu Tyr Thr Gly Glu Trp Ile
    130                 135                 140

Asp Ser Gln Leu Val Gly Gly Lys Cys Ser Lys Glu Val Cys Gln Thr
145                 150                 155                 160

Val His Asn Ser Thr Val Trp His Ala Asp Tyr Lys Ile Thr Gly Leu
                165                 170                 175

Cys Glu Ser Asn Leu Ala Ser Val Asp Ile Thr Phe Phe Ser Glu Asp
            180                 185                 190

Gly Gln Lys Thr Ser Leu Gly Lys Pro Asn Thr Gly Phe Arg Ser Asn
        195                 200                 205

His Phe Ala Tyr Glu Ser Gly Glu Lys Ala Cys Arg Met Gln Tyr Cys
    210                 215                 220

Thr Gln Trp Gly Ile Arg Leu Pro Ser Gly Val Trp Phe Glu Leu Val
225                 230                 235                 240

Asp Lys Asp Leu Phe Gln Ala Ala Lys Leu Pro Glu Cys Pro Arg Gly
                245                 250                 255

Ser Ser Ile Ser Ala Pro Ser Gln Thr Ser Val Asp Val Ser Leu Ile
            260                 265                 270

Gln Asp Val Glu Arg Ile Leu Asp Tyr Ser Leu Cys Gln Glu Thr Trp
        275                 280                 285

Ser Lys Ile Arg Ala Lys Leu Pro Val Ser Pro Val Asp Leu Ser Tyr
    290                 295                 300

Leu Ala Pro Lys Asn Pro Gly Ser Gly Pro Ala Phe Thr Ile Ile Asn
305                 310                 315                 320

Gly Thr Leu Lys Tyr Phe Glu Thr Arg Tyr Ile Arg Val Asp Ile Ser
                325                 330                 335

Asn Pro Ile Ile Pro His Met Val Gly Thr Met Ser Gly Thr Thr Thr
            340                 345                 350

Glu Arg Glu Leu Trp Asn Asp Trp Pro Tyr Glu Asp Val Glu Ile
        355                 360                 365

Gly Pro Asn Gly Val Leu Lys Thr Pro Thr Gly Phe Lys Phe Pro Leu
    370                 375                 380
```

Tyr Met Ile Gly His Gly Met Leu Asp Ser Asp Leu His Lys Ser Ser
385 390 395 400

Gln Ala Gln Val Phe Glu His Pro His Ala Lys Asp Ala Ala Ser Gln
405 410 415

Leu Pro Asp Asp Glu Met Leu Phe Phe Gly Asp Thr Gly Leu Ser Lys
420 425 430

Asn Pro Val Glu Leu Val Glu Gly Trp Phe Ser Ser Trp Lys Ser Thr
435 440 445

Leu Ala Ser Phe Phe Leu Ile Ile Gly Leu Gly Val Ala Leu Ile Phe
450 455 460

Ile Ile Arg Ile Ile Val Ala Ile Arg Tyr Lys Tyr Lys Gly Arg Lys
465 470 475 480

Thr Gln Lys Ile Tyr Asn Asp Val Glu Met Ser Arg Leu Gly Asn Lys
485 490 495

<210> SEQ ID NO 33
<211> LENGTH: 496
<212> TYPE: PRT
<213> ORGANISM: Artificial sequence
<220> FEATURE:
<223> OTHER INFORMATION: Glycoprotein Vesicular stomatitis Maraba virus T422V

<400> SEQUENCE: 33

Lys Phe Thr Ile Val Phe Pro His His Gln Lys Gly Asn Trp Lys Asn
1 5 10 15

Val Pro Ser Thr Tyr His Tyr Cys Pro Ser Ser Ser Asp Gln Asn Trp
20 25 30

His Asn Asp Leu Thr Gly Val Ser Leu His Val Lys Ile Pro Lys Ser
35 40 45

His Lys Ala Ile Gln Ala Asp Gly Trp Met Cys His Ala Ala Lys Trp
50 55 60

Val Thr Thr Cys Asp Phe Arg Trp Tyr Gly Pro Lys Tyr Ile Thr His
65 70 75 80

Ser Ile His Ser Met Ser Pro Thr Leu Glu Gln Cys Lys Thr Ser Ile
85 90 95

Glu Gln Thr Lys Gln Gly Val Trp Ile Asn Pro Gly Phe Pro Pro Gln
100 105 110

Ser Cys Gly Tyr Ala Thr Val Thr Asp Ala Glu Val Val Val Gln
115 120 125

Ala Thr Pro His His Val Leu Val Asp Glu Tyr Thr Gly Glu Trp Ile
130 135 140

Asp Ser Gln Leu Val Gly Gly Lys Cys Ser Lys Glu Val Cys Gln Thr
145 150 155 160

Val His Asn Ser Thr Val Trp His Ala Asp Tyr Lys Ile Thr Gly Leu
165 170 175

Cys Glu Ser Asn Leu Ala Ser Val Asp Ile Thr Phe Phe Ser Glu Asp
180 185 190

Gly Gln Lys Thr Ser Leu Gly Lys Pro Asn Thr Gly Phe Arg Ser Asn
195 200 205

His Phe Ala Tyr Glu Ser Gly Glu Lys Ala Cys Arg Met Gln Tyr Cys
210 215 220

Thr Gln Trp Gly Ile Arg Leu Pro Ser Gly Val Trp Phe Glu Leu Val
225 230 235 240

Asp Lys Asp Leu Phe Gln Ala Ala Lys Leu Pro Glu Cys Pro Arg Gly
245 250 255

Ser Ser Ile Ser Ala Pro Ser Gln Thr Ser Val Asp Val Ser Leu Ile
260 265 270

Gln Asp Val Glu Arg Ile Leu Asp Tyr Ser Leu Cys Gln Glu Thr Trp
275 280 285

Ser Lys Ile Arg Ala Lys Leu Pro Val Ser Pro Val Asp Leu Ser Tyr
290 295 300

Leu Ala Pro Lys Asn Pro Gly Ser Gly Pro Ala Phe Thr Ile Ile Asn
305 310 315 320

Gly Thr Leu Lys Tyr Phe Glu Thr Arg Tyr Ile Arg Val Asp Ile Ser
325 330 335

Asn Pro Ile Ile Pro His Met Val Gly Thr Met Ser Gly Thr Thr Thr
340 345 350

Glu Arg Glu Leu Trp Asn Asp Trp Tyr Pro Tyr Glu Asp Val Glu Ile
355 360 365

Gly Pro Asn Gly Val Leu Lys Thr Pro Thr Gly Phe Lys Phe Pro Leu
370 375 380

Tyr Met Ile Gly His Gly Met Leu Asp Ser Asp Leu His Lys Ser Ser
385 390 395 400

Gln Ala Gln Val Phe Glu His Pro His Ala Lys Asp Ala Ala Ser Gln
405 410 415

Leu Pro Asp Asp Glu Val Leu Phe Phe Gly Asp Thr Gly Leu Ser Lys
420 425 430

Asn Pro Val Glu Leu Val Glu Gly Trp Phe Ser Ser Trp Lys Ser Thr
435 440 445

Leu Ala Ser Phe Phe Leu Ile Ile Gly Leu Gly Val Ala Leu Ile Phe
450 455 460

Ile Ile Arg Ile Ile Val Ala Ile Arg Tyr Lys Tyr Lys Gly Arg Lys
465 470 475 480

Thr Gln Lys Ile Tyr Asn Asp Val Glu Met Ser Arg Leu Gly Asn Lys
485 490 495

<210> SEQ ID NO 34
<211> LENGTH: 496
<212> TYPE: PRT
<213> ORGANISM: Artificial sequence
<220> FEATURE:
<223> OTHER INFORMATION: Glycoprotein Vesicular stomatitis Maraba virus H22N T422I

<400> SEQUENCE: 34

Lys Phe Thr Ile Val Phe Pro His His Gln Lys Gly Asn Trp Lys Asn
1 5 10 15

Val Pro Ser Thr Tyr Asn Tyr Cys Pro Ser Ser Ser Asp Gln Asn Trp
20 25 30

His Asn Asp Leu Thr Gly Val Ser Leu His Val Lys Ile Pro Lys Ser
35 40 45

His Lys Ala Ile Gln Ala Asp Gly Trp Met Cys His Ala Ala Lys Trp
50 55 60

Val Thr Thr Cys Asp Phe Arg Trp Tyr Gly Pro Lys Tyr Ile Thr His
65 70 75 80

Ser Ile His Ser Met Ser Pro Thr Leu Glu Gln Cys Lys Thr Ser Ile
85 90 95

```
Glu Gln Thr Lys Gln Gly Val Trp Ile Asn Pro Gly Phe Pro Pro Gln
            100                 105                 110

Ser Cys Gly Tyr Ala Thr Val Thr Asp Ala Glu Val Val Val Val Gln
        115                 120                 125

Ala Thr Pro His His Val Leu Val Asp Glu Tyr Thr Gly Glu Trp Ile
    130                 135                 140

Asp Ser Gln Leu Val Gly Gly Lys Cys Ser Lys Glu Val Cys Gln Thr
145                 150                 155                 160

Val His Asn Ser Thr Val Trp His Ala Asp Tyr Lys Ile Thr Gly Leu
                165                 170                 175

Cys Glu Ser Asn Leu Ala Ser Val Asp Ile Thr Phe Phe Ser Glu Asp
            180                 185                 190

Gly Gln Lys Thr Ser Leu Gly Lys Pro Asn Thr Gly Phe Arg Ser Asn
        195                 200                 205

His Phe Ala Tyr Glu Ser Gly Glu Lys Ala Cys Arg Met Gln Tyr Cys
    210                 215                 220

Thr Gln Trp Gly Ile Arg Leu Pro Ser Gly Val Trp Phe Glu Leu Val
225                 230                 235                 240

Asp Lys Asp Leu Phe Gln Ala Ala Lys Leu Pro Glu Cys Pro Arg Gly
                245                 250                 255

Ser Ser Ile Ser Ala Pro Ser Gln Thr Ser Val Asp Val Ser Leu Ile
            260                 265                 270

Gln Asp Val Glu Arg Ile Leu Asp Tyr Ser Leu Cys Gln Glu Thr Trp
        275                 280                 285

Ser Lys Ile Arg Ala Lys Leu Pro Val Ser Pro Val Asp Leu Ser Tyr
    290                 295                 300

Leu Ala Pro Lys Asn Pro Gly Ser Gly Pro Ala Phe Thr Ile Ile Asn
305                 310                 315                 320

Gly Thr Leu Lys Tyr Phe Glu Thr Arg Tyr Ile Arg Val Asp Ile Ser
                325                 330                 335

Asn Pro Ile Ile Pro His Met Val Gly Thr Met Ser Gly Thr Thr Thr
            340                 345                 350

Glu Arg Glu Leu Trp Asn Asp Trp Tyr Pro Tyr Glu Asp Val Glu Ile
        355                 360                 365

Gly Pro Asn Gly Val Leu Lys Thr Pro Thr Gly Phe Lys Phe Pro Leu
    370                 375                 380

Tyr Met Ile Gly His Gly Met Leu Asp Ser Asp Leu His Lys Ser Ser
385                 390                 395                 400

Gln Ala Gln Val Phe Glu His Pro His Ala Lys Asp Ala Ala Ser Gln
                405                 410                 415

Leu Pro Asp Asp Glu Ile Leu Phe Phe Gly Asp Thr Gly Leu Ser Lys
            420                 425                 430

Asn Pro Val Glu Leu Val Glu Gly Trp Phe Ser Ser Trp Lys Ser Thr
        435                 440                 445

Leu Ala Ser Phe Phe Leu Ile Ile Gly Leu Gly Val Ala Leu Ile Phe
    450                 455                 460

Ile Ile Arg Ile Ile Val Ala Ile Arg Tyr Lys Tyr Lys Gly Arg Lys
465                 470                 475                 480

Thr Gln Lys Ile Tyr Asn Asp Val Glu Met Ser Arg Leu Gly Asn Lys
                485                 490                 495
```

<210> SEQ ID NO 35
<211> LENGTH: 496

```
<212> TYPE: PRT
<213> ORGANISM: Artificial sequence
<220> FEATURE:
<223> OTHER INFORMATION: Glycoprotein Vesicular stomatitis Maraba virus
      H22N T422L

<400> SEQUENCE: 35

Lys Phe Thr Ile Val Phe Pro His His Gln Lys Gly Asn Trp Lys Asn
1               5                   10                  15

Val Pro Ser Thr Tyr Asn Tyr Cys Pro Ser Ser Ser Asp Gln Asn Trp
            20                  25                  30

His Asn Asp Leu Thr Gly Val Ser Leu His Val Lys Ile Pro Lys Ser
        35                  40                  45

His Lys Ala Ile Gln Ala Asp Gly Trp Met Cys His Ala Ala Lys Trp
    50                  55                  60

Val Thr Thr Cys Asp Phe Arg Trp Tyr Gly Pro Lys Tyr Ile Thr His
65                  70                  75                  80

Ser Ile His Ser Met Ser Pro Thr Leu Glu Gln Cys Lys Thr Ser Ile
                85                  90                  95

Glu Gln Thr Lys Gln Gly Val Trp Ile Asn Pro Gly Phe Pro Pro Gln
            100                 105                 110

Ser Cys Gly Tyr Ala Thr Val Thr Asp Ala Glu Val Val Val Val Gln
        115                 120                 125

Ala Thr Pro His His Val Leu Val Asp Glu Tyr Thr Gly Glu Trp Ile
    130                 135                 140

Asp Ser Gln Leu Val Gly Gly Lys Cys Ser Lys Glu Val Cys Gln Thr
145                 150                 155                 160

Val His Asn Ser Thr Val Trp His Ala Asp Tyr Lys Ile Thr Gly Leu
                165                 170                 175

Cys Glu Ser Asn Leu Ala Ser Val Asp Ile Thr Phe Phe Ser Glu Asp
            180                 185                 190

Gly Gln Lys Thr Ser Leu Gly Lys Pro Asn Thr Gly Phe Arg Ser Asn
        195                 200                 205

His Phe Ala Tyr Glu Ser Gly Glu Lys Ala Cys Arg Met Gln Tyr Cys
    210                 215                 220

Thr Gln Trp Gly Ile Arg Leu Pro Ser Gly Val Trp Phe Glu Leu Val
225                 230                 235                 240

Asp Lys Asp Leu Phe Gln Ala Ala Lys Leu Pro Glu Cys Pro Arg Gly
                245                 250                 255

Ser Ser Ile Ser Ala Pro Ser Gln Thr Ser Val Asp Val Ser Leu Ile
            260                 265                 270

Gln Asp Val Glu Arg Ile Leu Asp Tyr Ser Leu Cys Gln Glu Thr Trp
        275                 280                 285

Ser Lys Ile Arg Ala Lys Leu Pro Val Ser Pro Val Asp Leu Ser Tyr
    290                 295                 300

Leu Ala Pro Lys Asn Pro Gly Ser Gly Pro Ala Phe Thr Ile Ile Asn
305                 310                 315                 320

Gly Thr Leu Lys Tyr Phe Glu Thr Arg Tyr Ile Arg Val Asp Ile Ser
                325                 330                 335

Asn Pro Ile Ile Pro His Met Val Gly Thr Met Ser Gly Thr Thr Thr
            340                 345                 350

Glu Arg Glu Leu Trp Asn Asp Trp Tyr Pro Tyr Glu Asp Val Glu Ile
        355                 360                 365

Gly Pro Asn Gly Val Leu Lys Thr Pro Thr Gly Phe Lys Phe Pro Leu
    370                 375                 380
```

```
Tyr Met Ile Gly His Gly Met Leu Asp Ser Asp Leu His Lys Ser Ser
385                 390                 395                 400

Gln Ala Gln Val Phe Glu His Pro His Ala Lys Asp Ala Ala Ser Gln
                405                 410                 415

Leu Pro Asp Asp Glu Leu Leu Phe Phe Gly Asp Thr Gly Leu Ser Lys
            420                 425                 430

Asn Pro Val Glu Leu Val Glu Gly Trp Phe Ser Ser Trp Lys Ser Thr
        435                 440                 445

Leu Ala Ser Phe Phe Leu Ile Ile Gly Leu Gly Val Ala Leu Ile Phe
    450                 455                 460

Ile Ile Arg Ile Ile Val Ala Ile Arg Tyr Lys Tyr Lys Gly Arg Lys
465                 470                 475                 480

Thr Gln Lys Ile Tyr Asn Asp Val Glu Met Ser Arg Leu Gly Asn Lys
                485                 490                 495


<210> SEQ ID NO 36
<211> LENGTH: 496
<212> TYPE: PRT
<213> ORGANISM: Artificial sequence
<220> FEATURE:
<223> OTHER INFORMATION: Glycoprotein Vesicular stomatitis Maraba virus
      H22N T422F

<400> SEQUENCE: 36

Lys Phe Thr Ile Val Phe Pro His His Gln Lys Gly Asn Trp Lys Asn
1               5                   10                  15

Val Pro Ser Thr Tyr Asn Tyr Cys Pro Ser Ser Ser Asp Gln Asn Trp
            20                  25                  30

His Asn Asp Leu Thr Gly Val Ser Leu His Val Lys Ile Pro Lys Ser
        35                  40                  45

His Lys Ala Ile Gln Ala Asp Gly Trp Met Cys His Ala Ala Lys Trp
    50                  55                  60

Val Thr Thr Cys Asp Phe Arg Trp Tyr Gly Pro Lys Tyr Ile Thr His
65                  70                  75                  80

Ser Ile His Ser Met Ser Pro Thr Leu Glu Gln Cys Lys Thr Ser Ile
                85                  90                  95

Glu Gln Thr Lys Gln Gly Val Trp Ile Asn Pro Gly Phe Pro Pro Gln
            100                 105                 110

Ser Cys Gly Tyr Ala Thr Val Thr Asp Ala Glu Val Val Val Gln
        115                 120                 125

Ala Thr Pro His His Val Leu Val Asp Glu Tyr Thr Gly Glu Trp Ile
    130                 135                 140

Asp Ser Gln Leu Val Gly Gly Lys Cys Ser Lys Glu Val Cys Gln Thr
145                 150                 155                 160

Val His Asn Ser Thr Val Trp His Ala Asp Tyr Lys Ile Thr Gly Leu
                165                 170                 175

Cys Glu Ser Asn Leu Ala Ser Val Asp Ile Thr Phe Phe Ser Glu Asp
            180                 185                 190

Gly Gln Lys Thr Ser Leu Gly Lys Pro Asn Thr Gly Phe Arg Ser Asn
        195                 200                 205

His Phe Ala Tyr Glu Ser Gly Glu Lys Ala Cys Arg Met Gln Tyr Cys
    210                 215                 220

Thr Gln Trp Gly Ile Arg Leu Pro Ser Gly Val Trp Phe Glu Leu Val
225                 230                 235                 240
```

Asp Lys Asp Leu Phe Gln Ala Ala Lys Leu Pro Glu Cys Pro Arg Gly
245 250 255

Ser Ser Ile Ser Ala Pro Ser Gln Thr Ser Val Asp Val Ser Leu Ile
260 265 270

Gln Asp Val Glu Arg Ile Leu Asp Tyr Ser Leu Cys Gln Glu Thr Trp
275 280 285

Ser Lys Ile Arg Ala Lys Leu Pro Val Ser Pro Val Asp Leu Ser Tyr
290 295 300

Leu Ala Pro Lys Asn Pro Gly Ser Gly Pro Ala Phe Thr Ile Ile Asn
305 310 315 320

Gly Thr Leu Lys Tyr Phe Glu Thr Arg Tyr Ile Arg Val Asp Ile Ser
325 330 335

Asn Pro Ile Ile Pro His Met Val Gly Thr Met Ser Gly Thr Thr Thr
340 345 350

Glu Arg Glu Leu Trp Asn Asp Trp Tyr Pro Tyr Glu Asp Val Glu Ile
355 360 365

Gly Pro Asn Gly Val Leu Lys Thr Pro Thr Gly Phe Lys Phe Pro Leu
370 375 380

Tyr Met Ile Gly His Gly Met Leu Asp Ser Asp Leu His Lys Ser Ser
385 390 395 400

Gln Ala Gln Val Phe Glu His Pro His Ala Lys Asp Ala Ala Ser Gln
405 410 415

Leu Pro Asp Asp Glu Phe Leu Phe Phe Gly Asp Thr Gly Leu Ser Lys
420 425 430

Asn Pro Val Glu Leu Val Glu Gly Trp Phe Ser Ser Trp Lys Ser Thr
435 440 445

Leu Ala Ser Phe Phe Leu Ile Ile Gly Leu Gly Val Ala Leu Ile Phe
450 455 460

Ile Ile Arg Ile Ile Val Ala Ile Arg Tyr Lys Tyr Lys Gly Arg Lys
465 470 475 480

Thr Gln Lys Ile Tyr Asn Asp Val Glu Met Ser Arg Leu Gly Asn Lys
485 490 495

<210> SEQ ID NO 37
<211> LENGTH: 496
<212> TYPE: PRT
<213> ORGANISM: Artificial sequence
<220> FEATURE:
<223> OTHER INFORMATION: Glycoprotein Vesicular stomatitis Maraba virus H22N T422M

<400> SEQUENCE: 37

Lys Phe Thr Ile Val Phe Pro His His Gln Lys Gly Asn Trp Lys Asn
1 5 10 15

Val Pro Ser Thr Tyr Asn Tyr Cys Pro Ser Ser Ser Asp Gln Asn Trp
20 25 30

His Asn Asp Leu Thr Gly Val Ser Leu His Val Lys Ile Pro Lys Ser
35 40 45

His Lys Ala Ile Gln Ala Asp Gly Trp Met Cys His Ala Ala Lys Trp
50 55 60

Val Thr Thr Cys Asp Phe Arg Trp Tyr Gly Pro Lys Tyr Ile Thr His
65 70 75 80

Ser Ile His Ser Met Ser Pro Thr Leu Glu Gln Cys Lys Thr Ser Ile
85 90 95

```
Glu Gln Thr Lys Gln Gly Val Trp Ile Asn Pro Gly Phe Pro Pro Gln
            100                 105                 110

Ser Cys Gly Tyr Ala Thr Val Thr Asp Ala Glu Val Val Val Val Gln
        115                 120                 125

Ala Thr Pro His His Val Leu Val Asp Glu Tyr Thr Gly Glu Trp Ile
    130                 135                 140

Asp Ser Gln Leu Val Gly Gly Lys Cys Ser Lys Glu Val Cys Gln Thr
145                 150                 155                 160

Val His Asn Ser Thr Val Trp His Ala Asp Tyr Lys Ile Thr Gly Leu
                165                 170                 175

Cys Glu Ser Asn Leu Ala Ser Val Asp Ile Thr Phe Phe Ser Glu Asp
            180                 185                 190

Gly Gln Lys Thr Ser Leu Gly Lys Pro Asn Thr Gly Phe Arg Ser Asn
        195                 200                 205

His Phe Ala Tyr Glu Ser Gly Glu Lys Ala Cys Arg Met Gln Tyr Cys
    210                 215                 220

Thr Gln Trp Gly Ile Arg Leu Pro Ser Gly Val Trp Phe Glu Leu Val
225                 230                 235                 240

Asp Lys Asp Leu Phe Gln Ala Ala Lys Leu Pro Glu Cys Pro Arg Gly
                245                 250                 255

Ser Ser Ile Ser Ala Pro Ser Gln Thr Ser Val Asp Val Ser Leu Ile
            260                 265                 270

Gln Asp Val Glu Arg Ile Leu Asp Tyr Ser Leu Cys Gln Glu Thr Trp
        275                 280                 285

Ser Lys Ile Arg Ala Lys Leu Pro Val Ser Pro Val Asp Leu Ser Tyr
    290                 295                 300

Leu Ala Pro Lys Asn Pro Gly Ser Gly Pro Ala Phe Thr Ile Ile Asn
305                 310                 315                 320

Gly Thr Leu Lys Tyr Phe Glu Thr Arg Tyr Ile Arg Val Asp Ile Ser
                325                 330                 335

Asn Pro Ile Ile Pro His Met Val Gly Thr Met Ser Gly Thr Thr Thr
            340                 345                 350

Glu Arg Glu Leu Trp Asn Asp Trp Tyr Pro Tyr Glu Asp Val Glu Ile
        355                 360                 365

Gly Pro Asn Gly Val Leu Lys Thr Pro Thr Gly Phe Lys Phe Pro Leu
    370                 375                 380

Tyr Met Ile Gly His Gly Met Leu Asp Ser Asp Leu His Lys Ser Ser
385                 390                 395                 400

Gln Ala Gln Val Phe Glu His Pro His Ala Lys Asp Ala Ala Ser Gln
                405                 410                 415

Leu Pro Asp Asp Glu Met Leu Phe Phe Gly Asp Thr Gly Leu Ser Lys
            420                 425                 430

Asn Pro Val Glu Leu Val Glu Gly Trp Phe Ser Ser Trp Lys Ser Thr
        435                 440                 445

Leu Ala Ser Phe Phe Leu Ile Ile Gly Leu Gly Val Ala Leu Ile Phe
    450                 455                 460

Ile Ile Arg Ile Ile Val Ala Ile Arg Tyr Lys Tyr Lys Gly Arg Lys
465                 470                 475                 480

Thr Gln Lys Ile Tyr Asn Asp Val Glu Met Ser Arg Leu Gly Asn Lys
                485                 490                 495
```

<210> SEQ ID NO 38
<211> LENGTH: 496

```
<212> TYPE: PRT
<213> ORGANISM: Artificial sequence
<220> FEATURE:
<223> OTHER INFORMATION: Glycoprotein Vesicular stomatitis Maraba virus
      H22N T422V

<400> SEQUENCE: 38

Lys Phe Thr Ile Val Phe Pro His His Gln Lys Gly Asn Trp Lys Asn
1               5                   10                  15

Val Pro Ser Thr Tyr Asn Tyr Cys Pro Ser Ser Ser Asp Gln Asn Trp
            20                  25                  30

His Asn Asp Leu Thr Gly Val Ser Leu His Val Lys Ile Pro Lys Ser
        35                  40                  45

His Lys Ala Ile Gln Ala Asp Gly Trp Met Cys His Ala Ala Lys Trp
    50                  55                  60

Val Thr Thr Cys Asp Phe Arg Trp Tyr Gly Pro Lys Tyr Ile Thr His
65                  70                  75                  80

Ser Ile His Ser Met Ser Pro Thr Leu Glu Gln Cys Lys Thr Ser Ile
                85                  90                  95

Glu Gln Thr Lys Gln Gly Val Trp Ile Asn Pro Gly Phe Pro Pro Gln
            100                 105                 110

Ser Cys Gly Tyr Ala Thr Val Thr Asp Ala Glu Val Val Val Val Gln
        115                 120                 125

Ala Thr Pro His His Val Leu Val Asp Glu Tyr Thr Gly Glu Trp Ile
    130                 135                 140

Asp Ser Gln Leu Val Gly Gly Lys Cys Ser Lys Glu Val Cys Gln Thr
145                 150                 155                 160

Val His Asn Ser Thr Val Trp His Ala Asp Tyr Lys Ile Thr Gly Leu
                165                 170                 175

Cys Glu Ser Asn Leu Ala Ser Val Asp Ile Thr Phe Phe Ser Glu Asp
            180                 185                 190

Gly Gln Lys Thr Ser Leu Gly Lys Pro Asn Thr Gly Phe Arg Ser Asn
        195                 200                 205

His Phe Ala Tyr Glu Ser Gly Glu Lys Ala Cys Arg Met Gln Tyr Cys
    210                 215                 220

Thr Gln Trp Gly Ile Arg Leu Pro Ser Gly Val Trp Phe Glu Leu Val
225                 230                 235                 240

Asp Lys Asp Leu Phe Gln Ala Ala Lys Leu Pro Glu Cys Pro Arg Gly
                245                 250                 255

Ser Ser Ile Ser Ala Pro Ser Gln Thr Ser Val Asp Val Ser Leu Ile
            260                 265                 270

Gln Asp Val Glu Arg Ile Leu Asp Tyr Ser Leu Cys Gln Glu Thr Trp
        275                 280                 285

Ser Lys Ile Arg Ala Lys Leu Pro Val Ser Pro Val Asp Leu Ser Tyr
    290                 295                 300

Leu Ala Pro Lys Asn Pro Gly Ser Gly Pro Ala Phe Thr Ile Ile Asn
305                 310                 315                 320

Gly Thr Leu Lys Tyr Phe Glu Thr Arg Tyr Ile Arg Val Asp Ile Ser
                325                 330                 335

Asn Pro Ile Ile Pro His Met Val Gly Thr Met Ser Gly Thr Thr Thr
            340                 345                 350

Glu Arg Glu Leu Trp Asn Asp Trp Tyr Pro Tyr Glu Asp Val Glu Ile
        355                 360                 365

Gly Pro Asn Gly Val Leu Lys Thr Pro Thr Gly Phe Lys Phe Pro Leu
    370                 375                 380
```

Tyr Met Ile Gly His Gly Met Leu Asp Ser Asp Leu His Lys Ser Ser
385 390 395 400

Gln Ala Gln Val Phe Glu His Pro His Ala Lys Asp Ala Ala Ser Gln
405 410 415

Leu Pro Asp Asp Glu Val Leu Phe Phe Gly Asp Thr Gly Leu Ser Lys
420 425 430

Asn Pro Val Glu Leu Val Glu Gly Trp Phe Ser Ser Trp Lys Ser Thr
435 440 445

Leu Ala Ser Phe Phe Leu Ile Ile Gly Leu Gly Val Ala Leu Ile Phe
450 455 460

Ile Ile Arg Ile Ile Val Ala Ile Arg Tyr Lys Tyr Lys Gly Arg Lys
465 470 475 480

Thr Gln Lys Ile Tyr Asn Asp Val Glu Met Ser Arg Leu Gly Asn Lys
485 490 495

<210> SEQ ID NO 39
<211> LENGTH: 495
<212> TYPE: PRT
<213> ORGANISM: Artificial sequence
<220> FEATURE:
<223> OTHER INFORMATION: Glycoprotein Vesicular stomatitis Cocal virus H22N

<400> SEQUENCE: 39

Lys Phe Ser Ile Val Phe Pro Gln Ser Gln Lys Gly Asn Trp Lys Asn
1 5 10 15

Val Pro Ser Ser Tyr Asn Tyr Cys Pro Ser Ser Ser Asp Gln Asn Trp
20 25 30

His Asn Asp Leu Leu Gly Ile Thr Met Lys Val Lys Met Pro Lys Thr
35 40 45

His Lys Ala Ile Gln Ala Asp Gly Trp Met Cys His Ala Ala Lys Trp
50 55 60

Ile Thr Thr Cys Asp Phe Arg Trp Tyr Gly Pro Lys Tyr Ile Thr His
65 70 75 80

Ser Ile His Ser Ile Gln Pro Thr Ser Glu Gln Cys Lys Glu Ser Ile
85 90 95

Lys Gln Thr Lys Gln Gly Thr Trp Met Ser Pro Gly Phe Pro Pro Gln
100 105 110

Asn Cys Gly Tyr Ala Thr Val Thr Asp Ser Val Ala Val Val Val Gln
115 120 125

Ala Thr Pro His His Val Leu Val Asp Glu Tyr Thr Gly Glu Trp Ile
130 135 140

Asp Ser Gln Phe Pro Asn Gly Lys Cys Glu Thr Glu Glu Cys Glu Thr
145 150 155 160

Val His Asn Ser Thr Val Trp Tyr Ser Asp Tyr Lys Val Thr Gly Leu
165 170 175

Cys Asp Ala Thr Leu Val Asp Thr Glu Ile Thr Phe Phe Ser Glu Asp
180 185 190

Gly Lys Lys Glu Ser Ile Gly Lys Pro Asn Thr Gly Tyr Arg Ser Asn
195 200 205

Tyr Phe Ala Tyr Glu Lys Gly Asp Lys Val Cys Lys Met Asn Tyr Cys
210 215 220

Lys His Ala Gly Val Arg Leu Pro Ser Gly Val Trp Phe Glu Phe Val
225 230 235 240

```
Asp Gln Asp Val Tyr Ala Ala Ala Lys Leu Pro Glu Cys Pro Val Gly
                245                 250                 255

Ala Thr Ile Ser Ala Pro Thr Gln Thr Ser Val Asp Val Ser Leu Ile
            260                 265                 270

Leu Asp Val Glu Arg Ile Leu Asp Tyr Ser Leu Cys Gln Glu Thr Trp
        275                 280                 285

Ser Lys Ile Arg Ser Lys Gln Pro Val Ser Pro Val Asp Leu Ser Tyr
    290                 295                 300

Leu Ala Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Ile Asp Ile Asp
                325                 330                 335

Asn Pro Ile Ile Ser Lys Met Val Gly Lys Ile Ser Gly Ser Gln Thr
            340                 345                 350

Glu Arg Glu Leu Trp Thr Glu Trp Phe Pro Tyr Glu Gly Val Glu Ile
        355                 360                 365

Gly Pro Asn Gly Ile Leu Lys Thr Pro Thr Gly Tyr Lys Phe Pro Leu
    370                 375                 380

Phe Met Ile Gly His Gly Met Leu Asp Ser Asp Leu His Lys Thr Ser
385                 390                 395                 400

Gln Ala Glu Val Phe Glu His Pro His Leu Ala Glu Ala Pro Lys Gln
                405                 410                 415

Leu Pro Glu Glu Glu Thr Leu Phe Phe Gly Asp Thr Gly Ile Ser Lys
            420                 425                 430

Asn Pro Val Glu Leu Ile Glu Gly Trp Phe Ser Ser Trp Lys Ser Thr
        435                 440                 445

Val Val Thr Phe Phe Phe Ala Ile Gly Val Phe Ile Leu Leu Tyr Val
    450                 455                 460

Val Ala Arg Ile Val Ile Ala Val Arg Tyr Arg Tyr Gln Gly Ser Asn
465                 470                 475                 480

Asn Lys Arg Ile Tyr Asn Asp Ile Glu Met Ser Arg Phe Arg Lys
                485                 490                 495


<210> SEQ ID NO 40
<211> LENGTH: 495
<212> TYPE: PRT
<213> ORGANISM: Artificial sequence
<220> FEATURE:
<223> OTHER INFORMATION: Glycoprotein Vesicular stomatitis Cocal virus
      T422I

<400> SEQUENCE: 40

Lys Phe Ser Ile Val Phe Pro Gln Ser Gln Lys Gly Asn Trp Lys Asn
1               5                   10                  15

Val Pro Ser Ser Tyr His Tyr Cys Pro Ser Ser Ser Asp Gln Asn Trp
            20                  25                  30

His Asn Asp Leu Leu Gly Ile Thr Met Lys Val Lys Met Pro Lys Thr
        35                  40                  45

His Lys Ala Ile Gln Ala Asp Gly Trp Met Cys His Ala Ala Lys Trp
    50                  55                  60

Ile Thr Thr Cys Asp Phe Arg Trp Tyr Gly Pro Lys Tyr Ile Thr His
65                  70                  75                  80

Ser Ile His Ser Ile Gln Pro Thr Ser Glu Gln Cys Lys Glu Ser Ile
                85                  90                  95
```

```
Lys Gln Thr Lys Gln Gly Thr Trp Met Ser Pro Gly Phe Pro Pro Gln
            100                 105                 110

Asn Cys Gly Tyr Ala Thr Val Thr Asp Ser Val Ala Val Val Val Gln
        115                 120                 125

Ala Thr Pro His His Val Leu Val Asp Glu Tyr Thr Gly Glu Trp Ile
    130                 135                 140

Asp Ser Gln Phe Pro Asn Gly Lys Cys Glu Thr Glu Glu Cys Glu Thr
145                 150                 155                 160

Val His Asn Ser Thr Val Trp Tyr Ser Asp Tyr Lys Val Thr Gly Leu
                165                 170                 175

Cys Asp Ala Thr Leu Val Asp Thr Glu Ile Thr Phe Phe Ser Glu Asp
            180                 185                 190

Gly Lys Lys Glu Ser Ile Gly Lys Pro Asn Thr Gly Tyr Arg Ser Asn
        195                 200                 205

Tyr Phe Ala Tyr Glu Lys Gly Asp Lys Val Cys Lys Met Asn Tyr Cys
    210                 215                 220

Lys His Ala Gly Val Arg Leu Pro Ser Gly Val Trp Phe Glu Phe Val
225                 230                 235                 240

Asp Gln Asp Val Tyr Ala Ala Ala Lys Leu Pro Glu Cys Pro Val Gly
                245                 250                 255

Ala Thr Ile Ser Ala Pro Thr Gln Thr Ser Val Asp Val Ser Leu Ile
            260                 265                 270

Leu Asp Val Glu Arg Ile Leu Asp Tyr Ser Leu Cys Gln Glu Thr Trp
        275                 280                 285

Ser Lys Ile Arg Ser Lys Gln Pro Val Ser Pro Val Asp Leu Ser Tyr
    290                 295                 300

Leu Ala Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Ile Asp Ile Asp
                325                 330                 335

Asn Pro Ile Ile Ser Lys Met Val Gly Lys Ile Ser Gly Ser Gln Thr
            340                 345                 350

Glu Arg Glu Leu Trp Thr Glu Trp Phe Pro Tyr Glu Gly Val Glu Ile
        355                 360                 365

Gly Pro Asn Gly Ile Leu Lys Thr Pro Thr Gly Tyr Lys Phe Pro Leu
    370                 375                 380

Phe Met Ile Gly His Gly Met Leu Asp Ser Asp Leu His Lys Thr Ser
385                 390                 395                 400

Gln Ala Glu Val Phe Glu His Pro His Leu Ala Glu Ala Pro Lys Gln
                405                 410                 415

Leu Pro Glu Glu Glu Ile Leu Phe Phe Gly Asp Thr Gly Ile Ser Lys
            420                 425                 430

Asn Pro Val Glu Leu Ile Glu Gly Trp Phe Ser Ser Trp Lys Ser Thr
        435                 440                 445

Val Val Thr Phe Phe Phe Ala Ile Gly Val Phe Ile Leu Leu Tyr Val
    450                 455                 460

Val Ala Arg Ile Val Ile Ala Val Arg Tyr Arg Tyr Gln Gly Ser Asn
465                 470                 475                 480

Asn Lys Arg Ile Tyr Asn Asp Ile Glu Met Ser Arg Phe Arg Lys
                485                 490                 495
```

<210> SEQ ID NO 41
<211> LENGTH: 495

```
<212> TYPE: PRT
<213> ORGANISM: Artificial sequence
<220> FEATURE:
<223> OTHER INFORMATION: Glycoprotein Vesicular stomatitis Cocal virus
      T422L

<400> SEQUENCE: 41

Lys Phe Ser Ile Val Phe Pro Gln Ser Gln Lys Gly Asn Trp Lys Asn
1               5                   10                  15

Val Pro Ser Ser Tyr His Tyr Cys Pro Ser Ser Ser Asp Gln Asn Trp
            20                  25                  30

His Asn Asp Leu Leu Gly Ile Thr Met Lys Val Lys Met Pro Lys Thr
        35                  40                  45

His Lys Ala Ile Gln Ala Asp Gly Trp Met Cys His Ala Ala Lys Trp
    50                  55                  60

Ile Thr Thr Cys Asp Phe Arg Trp Tyr Gly Pro Lys Tyr Ile Thr His
65                  70                  75                  80

Ser Ile His Ser Ile Gln Pro Thr Ser Glu Gln Cys Lys Glu Ser Ile
                85                  90                  95

Lys Gln Thr Lys Gln Gly Thr Trp Met Ser Pro Gly Phe Pro Pro Gln
            100                 105                 110

Asn Cys Gly Tyr Ala Thr Val Thr Asp Ser Val Ala Val Val Val Gln
        115                 120                 125

Ala Thr Pro His His Val Leu Val Asp Glu Tyr Thr Gly Glu Trp Ile
    130                 135                 140

Asp Ser Gln Phe Pro Asn Gly Lys Cys Glu Thr Glu Glu Cys Glu Thr
145                 150                 155                 160

Val His Asn Ser Thr Val Trp Tyr Ser Asp Tyr Lys Val Thr Gly Leu
                165                 170                 175

Cys Asp Ala Thr Leu Val Asp Thr Glu Ile Thr Phe Phe Ser Glu Asp
            180                 185                 190

Gly Lys Lys Glu Ser Ile Gly Lys Pro Asn Thr Gly Tyr Arg Ser Asn
        195                 200                 205

Tyr Phe Ala Tyr Glu Lys Gly Asp Lys Val Cys Lys Met Asn Tyr Cys
    210                 215                 220

Lys His Ala Gly Val Arg Leu Pro Ser Gly Val Trp Phe Glu Phe Val
225                 230                 235                 240

Asp Gln Asp Val Tyr Ala Ala Ala Lys Leu Pro Glu Cys Pro Val Gly
                245                 250                 255

Ala Thr Ile Ser Ala Pro Thr Gln Thr Ser Val Asp Val Ser Leu Ile
            260                 265                 270

Leu Asp Val Glu Arg Ile Leu Asp Tyr Ser Leu Cys Gln Glu Thr Trp
        275                 280                 285

Ser Lys Ile Arg Ser Lys Gln Pro Val Ser Pro Val Asp Leu Ser Tyr
    290                 295                 300

Leu Ala Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Ile Asp Ile Asp
                325                 330                 335

Asn Pro Ile Ile Ser Lys Met Val Gly Lys Ile Ser Gly Ser Gln Thr
            340                 345                 350

Glu Arg Glu Leu Trp Thr Glu Trp Phe Pro Tyr Glu Gly Val Glu Ile
        355                 360                 365

Gly Pro Asn Gly Ile Leu Lys Thr Pro Thr Gly Tyr Lys Phe Pro Leu
    370                 375                 380
```

Phe Met Ile Gly His Gly Met Leu Asp Ser Asp Leu His Lys Thr Ser
385 390 395 400

Gln Ala Glu Val Phe Glu His Pro His Leu Ala Glu Ala Pro Lys Gln
405 410 415

Leu Pro Glu Glu Glu Leu Leu Phe Phe Gly Asp Thr Gly Ile Ser Lys
420 425 430

Asn Pro Val Glu Leu Ile Glu Gly Trp Phe Ser Ser Trp Lys Ser Thr
435 440 445

Val Val Thr Phe Phe Phe Ala Ile Gly Val Phe Ile Leu Leu Tyr Val
450 455 460

Val Ala Arg Ile Val Ile Ala Val Arg Tyr Arg Tyr Gln Gly Ser Asn
465 470 475 480

Asn Lys Arg Ile Tyr Asn Asp Ile Glu Met Ser Arg Phe Arg Lys
485 490 495

<210> SEQ ID NO 42
<211> LENGTH: 495
<212> TYPE: PRT
<213> ORGANISM: Artificial sequence
<220> FEATURE:
<223> OTHER INFORMATION: Glycoprotein Vesicular stomatitis Cocal virus T422F

<400> SEQUENCE: 42

Lys Phe Ser Ile Val Phe Pro Gln Ser Gln Lys Gly Asn Trp Lys Asn
1 5 10 15

Val Pro Ser Ser Tyr His Tyr Cys Pro Ser Ser Ser Asp Gln Asn Trp
20 25 30

His Asn Asp Leu Leu Gly Ile Thr Met Lys Val Lys Met Pro Lys Thr
35 40 45

His Lys Ala Ile Gln Ala Asp Gly Trp Met Cys His Ala Ala Lys Trp
50 55 60

Ile Thr Thr Cys Asp Phe Arg Trp Tyr Gly Pro Lys Tyr Ile Thr His
65 70 75 80

Ser Ile His Ser Ile Gln Pro Thr Ser Glu Gln Cys Lys Glu Ser Ile
85 90 95

Lys Gln Thr Lys Gln Gly Thr Trp Met Ser Pro Gly Phe Pro Pro Gln
100 105 110

Asn Cys Gly Tyr Ala Thr Val Thr Asp Ser Val Ala Val Val Val Gln
115 120 125

Ala Thr Pro His His Val Leu Val Asp Glu Tyr Thr Gly Glu Trp Ile
130 135 140

Asp Ser Gln Phe Pro Asn Gly Lys Cys Glu Thr Glu Glu Cys Glu Thr
145 150 155 160

Val His Asn Ser Thr Val Trp Tyr Ser Asp Tyr Lys Val Thr Gly Leu
165 170 175

Cys Asp Ala Thr Leu Val Asp Thr Glu Ile Thr Phe Phe Ser Glu Asp
180 185 190

Gly Lys Lys Glu Ser Ile Gly Lys Pro Asn Thr Gly Tyr Arg Ser Asn
195 200 205

Tyr Phe Ala Tyr Glu Lys Gly Asp Lys Val Cys Lys Met Asn Tyr Cys
210 215 220

Lys His Ala Gly Val Arg Leu Pro Ser Gly Val Trp Phe Glu Phe Val
225 230 235 240

```
Asp Gln Asp Val Tyr Ala Ala Ala Lys Leu Pro Glu Cys Pro Val Gly
                245                 250                 255

Ala Thr Ile Ser Ala Pro Thr Gln Thr Ser Val Asp Val Ser Leu Ile
            260                 265                 270

Leu Asp Val Glu Arg Ile Leu Asp Tyr Ser Leu Cys Gln Glu Thr Trp
        275                 280                 285

Ser Lys Ile Arg Ser Lys Gln Pro Val Ser Pro Val Asp Leu Ser Tyr
    290                 295                 300

Leu Ala Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Ile Asp Ile Asp
                325                 330                 335

Asn Pro Ile Ile Ser Lys Met Val Gly Lys Ile Ser Gly Ser Gln Thr
            340                 345                 350

Glu Arg Glu Leu Trp Thr Glu Trp Phe Pro Tyr Glu Gly Val Glu Ile
        355                 360                 365

Gly Pro Asn Gly Ile Leu Lys Thr Pro Thr Gly Tyr Lys Phe Pro Leu
    370                 375                 380

Phe Met Ile Gly His Gly Met Leu Asp Ser Asp Leu His Lys Thr Ser
385                 390                 395                 400

Gln Ala Glu Val Phe Glu His Pro His Leu Ala Glu Ala Pro Lys Gln
                405                 410                 415

Leu Pro Glu Glu Glu Phe Leu Phe Phe Gly Asp Thr Gly Ile Ser Lys
            420                 425                 430

Asn Pro Val Glu Leu Ile Glu Gly Trp Phe Ser Ser Trp Lys Ser Thr
        435                 440                 445

Val Val Thr Phe Phe Phe Ala Ile Gly Val Phe Ile Leu Leu Tyr Val
    450                 455                 460

Val Ala Arg Ile Val Ile Ala Val Arg Tyr Arg Tyr Gln Gly Ser Asn
465                 470                 475                 480

Asn Lys Arg Ile Tyr Asn Asp Ile Glu Met Ser Arg Phe Arg Lys
                485                 490                 495


<210> SEQ ID NO 43
<211> LENGTH: 495
<212> TYPE: PRT
<213> ORGANISM: Artificial sequence
<220> FEATURE:
<223> OTHER INFORMATION: Glycoprotein Vesicular stomatitis Cocal virus
      T422M

<400> SEQUENCE: 43

Lys Phe Ser Ile Val Phe Pro Gln Ser Gln Lys Gly Asn Trp Lys Asn
1               5                   10                  15

Val Pro Ser Ser Tyr His Tyr Cys Pro Ser Ser Ser Asp Gln Asn Trp
            20                  25                  30

His Asn Asp Leu Leu Gly Ile Thr Met Lys Val Lys Met Pro Lys Thr
        35                  40                  45

His Lys Ala Ile Gln Ala Asp Gly Trp Met Cys His Ala Ala Lys Trp
    50                  55                  60

Ile Thr Thr Cys Asp Phe Arg Trp Tyr Gly Pro Lys Tyr Ile Thr His
65                  70                  75                  80

Ser Ile His Ser Ile Gln Pro Thr Ser Glu Gln Cys Lys Glu Ser Ile
                85                  90                  95
```

```
Lys Gln Thr Lys Gln Gly Thr Trp Met Ser Pro Gly Phe Pro Pro Gln
            100                 105                 110

Asn Cys Gly Tyr Ala Thr Val Thr Asp Ser Val Ala Val Val Val Gln
        115                 120                 125

Ala Thr Pro His His Val Leu Val Asp Glu Tyr Thr Gly Glu Trp Ile
    130                 135                 140

Asp Ser Gln Phe Pro Asn Gly Lys Cys Glu Thr Glu Glu Cys Glu Thr
145                 150                 155                 160

Val His Asn Ser Thr Val Trp Tyr Ser Asp Tyr Lys Val Thr Gly Leu
                165                 170                 175

Cys Asp Ala Thr Leu Val Asp Thr Glu Ile Thr Phe Phe Ser Glu Asp
            180                 185                 190

Gly Lys Lys Glu Ser Ile Gly Lys Pro Asn Thr Gly Tyr Arg Ser Asn
        195                 200                 205

Tyr Phe Ala Tyr Glu Lys Gly Asp Lys Val Cys Lys Met Asn Tyr Cys
    210                 215                 220

Lys His Ala Gly Val Arg Leu Pro Ser Gly Val Trp Phe Glu Phe Val
225                 230                 235                 240

Asp Gln Asp Val Tyr Ala Ala Ala Lys Leu Pro Glu Cys Pro Val Gly
                245                 250                 255

Ala Thr Ile Ser Ala Pro Thr Gln Thr Ser Val Asp Val Ser Leu Ile
            260                 265                 270

Leu Asp Val Glu Arg Ile Leu Asp Tyr Ser Leu Cys Gln Glu Thr Trp
        275                 280                 285

Ser Lys Ile Arg Ser Lys Gln Pro Val Ser Pro Val Asp Leu Ser Tyr
    290                 295                 300

Leu Ala Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Ile Asp Ile Asp
                325                 330                 335

Asn Pro Ile Ile Ser Lys Met Val Gly Lys Ile Ser Gly Ser Gln Thr
            340                 345                 350

Glu Arg Glu Leu Trp Thr Glu Trp Phe Pro Tyr Glu Gly Val Glu Ile
        355                 360                 365

Gly Pro Asn Gly Ile Leu Lys Thr Pro Thr Gly Tyr Lys Phe Pro Leu
    370                 375                 380

Phe Met Ile Gly His Gly Met Leu Asp Ser Asp Leu His Lys Thr Ser
385                 390                 395                 400

Gln Ala Glu Val Phe Glu His Pro His Leu Ala Glu Ala Pro Lys Gln
                405                 410                 415

Leu Pro Glu Glu Glu Met Leu Phe Phe Gly Asp Thr Gly Ile Ser Lys
            420                 425                 430

Asn Pro Val Glu Leu Ile Glu Gly Trp Phe Ser Ser Trp Lys Ser Thr
        435                 440                 445

Val Val Thr Phe Phe Phe Ala Ile Gly Val Phe Ile Leu Leu Tyr Val
    450                 455                 460

Val Ala Arg Ile Val Ile Ala Val Arg Tyr Arg Tyr Gln Gly Ser Asn
465                 470                 475                 480

Asn Lys Arg Ile Tyr Asn Asp Ile Glu Met Ser Arg Phe Arg Lys
                485                 490                 495
```

<210> SEQ ID NO 44
<211> LENGTH: 495

```
<212> TYPE: PRT
<213> ORGANISM: Artificial sequence
<220> FEATURE:
<223> OTHER INFORMATION: Glycoprotein Vesicular stomatitis Cocal virus
      T422V

<400> SEQUENCE: 44

Lys Phe Ser Ile Val Phe Pro Gln Ser Gln Lys Gly Asn Trp Lys Asn
1               5                   10                  15

Val Pro Ser Ser Tyr His Tyr Cys Pro Ser Ser Ser Asp Gln Asn Trp
            20                  25                  30

His Asn Asp Leu Leu Gly Ile Thr Met Lys Val Lys Met Pro Lys Thr
        35                  40                  45

His Lys Ala Ile Gln Ala Asp Gly Trp Met Cys His Ala Ala Lys Trp
    50                  55                  60

Ile Thr Thr Cys Asp Phe Arg Trp Tyr Gly Pro Lys Tyr Ile Thr His
65                  70                  75                  80

Ser Ile His Ser Ile Gln Pro Thr Ser Glu Gln Cys Lys Glu Ser Ile
                85                  90                  95

Lys Gln Thr Lys Gln Gly Thr Trp Met Ser Pro Gly Phe Pro Pro Gln
            100                 105                 110

Asn Cys Gly Tyr Ala Thr Val Thr Asp Ser Val Ala Val Val Val Gln
        115                 120                 125

Ala Thr Pro His His Val Leu Val Asp Glu Tyr Thr Gly Glu Trp Ile
    130                 135                 140

Asp Ser Gln Phe Pro Asn Gly Lys Cys Glu Thr Glu Glu Cys Glu Thr
145                 150                 155                 160

Val His Asn Ser Thr Val Trp Tyr Ser Asp Tyr Lys Val Thr Gly Leu
                165                 170                 175

Cys Asp Ala Thr Leu Val Asp Thr Glu Ile Thr Phe Phe Ser Glu Asp
            180                 185                 190

Gly Lys Lys Glu Ser Ile Gly Lys Pro Asn Thr Gly Tyr Arg Ser Asn
        195                 200                 205

Tyr Phe Ala Tyr Glu Lys Gly Asp Lys Val Cys Lys Met Asn Tyr Cys
    210                 215                 220

Lys His Ala Gly Val Arg Leu Pro Ser Gly Val Trp Phe Glu Phe Val
225                 230                 235                 240

Asp Gln Asp Val Tyr Ala Ala Ala Lys Leu Pro Glu Cys Pro Val Gly
                245                 250                 255

Ala Thr Ile Ser Ala Pro Thr Gln Thr Ser Val Asp Val Ser Leu Ile
            260                 265                 270

Leu Asp Val Glu Arg Ile Leu Asp Tyr Ser Leu Cys Gln Glu Thr Trp
        275                 280                 285

Ser Lys Ile Arg Ser Lys Gln Pro Val Ser Pro Val Asp Leu Ser Tyr
    290                 295                 300

Leu Ala Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Ile Asp Ile Asp
                325                 330                 335

Asn Pro Ile Ile Ser Lys Met Val Gly Lys Ile Ser Gly Ser Gln Thr
            340                 345                 350

Glu Arg Glu Leu Trp Thr Glu Trp Phe Pro Tyr Glu Gly Val Glu Ile
        355                 360                 365

Gly Pro Asn Gly Ile Leu Lys Thr Pro Thr Gly Tyr Lys Phe Pro Leu
    370                 375                 380
```

```
Phe Met Ile Gly His Gly Met Leu Asp Ser Asp Leu His Lys Thr Ser
385                 390                 395                 400

Gln Ala Glu Val Phe Glu His Pro His Leu Ala Glu Ala Pro Lys Gln
                405                 410                 415

Leu Pro Glu Glu Glu Val Leu Phe Phe Gly Asp Thr Gly Ile Ser Lys
            420                 425                 430

Asn Pro Val Glu Leu Ile Glu Gly Trp Phe Ser Ser Trp Lys Ser Thr
        435                 440                 445

Val Val Thr Phe Phe Phe Ala Ile Gly Val Phe Ile Leu Leu Tyr Val
    450                 455                 460

Val Ala Arg Ile Val Ile Ala Val Arg Tyr Arg Tyr Gln Gly Ser Asn
465                 470                 475                 480

Asn Lys Arg Ile Tyr Asn Asp Ile Glu Met Ser Arg Phe Arg Lys
                485                 490                 495


<210> SEQ ID NO 45
<211> LENGTH: 495
<212> TYPE: PRT
<213> ORGANISM: Artificial sequence
<220> FEATURE:
<223> OTHER INFORMATION: Glycoprotein Vesicular stomatitis Cocal virus
      H22N T422I

<400> SEQUENCE: 45

Lys Phe Ser Ile Val Phe Pro Gln Ser Gln Lys Gly Asn Trp Lys Asn
1               5                   10                  15

Val Pro Ser Ser Tyr Asn Tyr Cys Pro Ser Ser Ser Asp Gln Asn Trp
            20                  25                  30

His Asn Asp Leu Leu Gly Ile Thr Met Lys Val Lys Met Pro Lys Thr
        35                  40                  45

His Lys Ala Ile Gln Ala Asp Gly Trp Met Cys His Ala Ala Lys Trp
    50                  55                  60

Ile Thr Thr Cys Asp Phe Arg Trp Tyr Gly Pro Lys Tyr Ile Thr His
65                  70                  75                  80

Ser Ile His Ser Ile Gln Pro Thr Ser Glu Gln Cys Lys Glu Ser Ile
                85                  90                  95

Lys Gln Thr Lys Gln Gly Thr Trp Met Ser Pro Gly Phe Pro Pro Gln
            100                 105                 110

Asn Cys Gly Tyr Ala Thr Val Thr Asp Ser Val Ala Val Val Val Gln
        115                 120                 125

Ala Thr Pro His His Val Leu Val Asp Glu Tyr Thr Gly Glu Trp Ile
    130                 135                 140

Asp Ser Gln Phe Pro Asn Gly Lys Cys Glu Thr Glu Glu Cys Glu Thr
145                 150                 155                 160

Val His Asn Ser Thr Val Trp Tyr Ser Asp Tyr Lys Val Thr Gly Leu
                165                 170                 175

Cys Asp Ala Thr Leu Val Asp Thr Glu Ile Thr Phe Phe Ser Glu Asp
            180                 185                 190

Gly Lys Lys Glu Ser Ile Gly Lys Pro Asn Thr Gly Tyr Arg Ser Asn
        195                 200                 205

Tyr Phe Ala Tyr Glu Lys Gly Asp Lys Val Cys Lys Met Asn Tyr Cys
    210                 215                 220

Lys His Ala Gly Val Arg Leu Pro Ser Gly Val Trp Phe Glu Phe Val
225                 230                 235                 240
```

```
Asp Gln Asp Val Tyr Ala Ala Ala Lys Leu Pro Glu Cys Pro Val Gly
                245                 250                 255

Ala Thr Ile Ser Ala Pro Thr Gln Thr Ser Val Asp Val Ser Leu Ile
            260                 265                 270

Leu Asp Val Glu Arg Ile Leu Asp Tyr Ser Leu Cys Gln Glu Thr Trp
        275                 280                 285

Ser Lys Ile Arg Ser Lys Gln Pro Val Ser Pro Val Asp Leu Ser Tyr
    290                 295                 300

Leu Ala Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Ile Asp Ile Asp
                325                 330                 335

Asn Pro Ile Ile Ser Lys Met Val Gly Lys Ile Ser Gly Ser Gln Thr
            340                 345                 350

Glu Arg Glu Leu Trp Thr Glu Trp Phe Pro Tyr Glu Gly Val Glu Ile
        355                 360                 365

Gly Pro Asn Gly Ile Leu Lys Thr Pro Thr Gly Tyr Lys Phe Pro Leu
    370                 375                 380

Phe Met Ile Gly His Gly Met Leu Asp Ser Asp Leu His Lys Thr Ser
385                 390                 395                 400

Gln Ala Glu Val Phe Glu His Pro His Leu Ala Glu Ala Pro Lys Gln
                405                 410                 415

Leu Pro Glu Glu Glu Ile Leu Phe Phe Gly Asp Thr Gly Ile Ser Lys
            420                 425                 430

Asn Pro Val Glu Leu Ile Glu Gly Trp Phe Ser Ser Trp Lys Ser Thr
        435                 440                 445

Val Val Thr Phe Phe Phe Ala Ile Gly Val Phe Ile Leu Leu Tyr Val
    450                 455                 460

Val Ala Arg Ile Val Ile Ala Val Arg Tyr Arg Tyr Gln Gly Ser Asn
465                 470                 475                 480

Asn Lys Arg Ile Tyr Asn Asp Ile Glu Met Ser Arg Phe Arg Lys
                485                 490                 495


<210> SEQ ID NO 46
<211> LENGTH: 495
<212> TYPE: PRT
<213> ORGANISM: Artificial sequence
<220> FEATURE:
<223> OTHER INFORMATION: Glycoprotein Vesicular stomatitis Cocal virus
      H22N T422L

<400> SEQUENCE: 46

Lys Phe Ser Ile Val Phe Pro Gln Ser Gln Lys Gly Asn Trp Lys Asn
1               5                   10                  15

Val Pro Ser Ser Tyr Asn Tyr Cys Pro Ser Ser Ser Asp Gln Asn Trp
            20                  25                  30

His Asn Asp Leu Leu Gly Ile Thr Met Lys Val Lys Met Pro Lys Thr
        35                  40                  45

His Lys Ala Ile Gln Ala Asp Gly Trp Met Cys His Ala Ala Lys Trp
    50                  55                  60

Ile Thr Thr Cys Asp Phe Arg Trp Tyr Gly Pro Lys Tyr Ile Thr His
65                  70                  75                  80

Ser Ile His Ser Ile Gln Pro Thr Ser Glu Gln Cys Lys Glu Ser Ile
                85                  90                  95
```

```
Lys Gln Thr Lys Gln Gly Thr Trp Met Ser Pro Gly Phe Pro Pro Gln
            100                 105                 110

Asn Cys Gly Tyr Ala Thr Val Thr Asp Ser Val Ala Val Val Val Gln
        115                 120                 125

Ala Thr Pro His His Val Leu Val Asp Glu Tyr Thr Gly Glu Trp Ile
    130                 135                 140

Asp Ser Gln Phe Pro Asn Gly Lys Cys Glu Thr Glu Glu Cys Glu Thr
145                 150                 155                 160

Val His Asn Ser Thr Val Trp Tyr Ser Asp Tyr Lys Val Thr Gly Leu
                165                 170                 175

Cys Asp Ala Thr Leu Val Asp Thr Glu Ile Thr Phe Phe Ser Glu Asp
            180                 185                 190

Gly Lys Lys Glu Ser Ile Gly Lys Pro Asn Thr Gly Tyr Arg Ser Asn
        195                 200                 205

Tyr Phe Ala Tyr Glu Lys Gly Asp Lys Val Cys Lys Met Asn Tyr Cys
    210                 215                 220

Lys His Ala Gly Val Arg Leu Pro Ser Gly Val Trp Phe Glu Phe Val
225                 230                 235                 240

Asp Gln Asp Val Tyr Ala Ala Ala Lys Leu Pro Glu Cys Pro Val Gly
                245                 250                 255

Ala Thr Ile Ser Ala Pro Thr Gln Thr Ser Val Asp Val Ser Leu Ile
            260                 265                 270

Leu Asp Val Glu Arg Ile Leu Asp Tyr Ser Leu Cys Gln Glu Thr Trp
        275                 280                 285

Ser Lys Ile Arg Ser Lys Gln Pro Val Ser Pro Val Asp Leu Ser Tyr
    290                 295                 300

Leu Ala Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Ile Asp Ile Asp
                325                 330                 335

Asn Pro Ile Ile Ser Lys Met Val Gly Lys Ile Ser Gly Ser Gln Thr
            340                 345                 350

Glu Arg Glu Leu Trp Thr Glu Trp Phe Pro Tyr Glu Gly Val Glu Ile
        355                 360                 365

Gly Pro Asn Gly Ile Leu Lys Thr Pro Thr Gly Tyr Lys Phe Pro Leu
    370                 375                 380

Phe Met Ile Gly His Gly Met Leu Asp Ser Asp Leu His Lys Thr Ser
385                 390                 395                 400

Gln Ala Glu Val Phe Glu His Pro His Leu Ala Glu Ala Pro Lys Gln
                405                 410                 415

Leu Pro Glu Glu Glu Leu Leu Phe Phe Gly Asp Thr Gly Ile Ser Lys
            420                 425                 430

Asn Pro Val Glu Leu Ile Glu Gly Trp Phe Ser Ser Trp Lys Ser Thr
        435                 440                 445

Val Val Thr Phe Phe Phe Ala Ile Gly Val Phe Ile Leu Leu Tyr Val
    450                 455                 460

Val Ala Arg Ile Val Ile Ala Val Arg Tyr Arg Tyr Gln Gly Ser Asn
465                 470                 475                 480

Asn Lys Arg Ile Tyr Asn Asp Ile Glu Met Ser Arg Phe Arg Lys
                485                 490                 495
```

<210> SEQ ID NO 47
<211> LENGTH: 495

```
<212> TYPE: PRT
<213> ORGANISM: Artificial sequence
<220> FEATURE:
<223> OTHER INFORMATION: Glycoprotein Vesicular stomatitis Cocal virus
      H22N T422F

<400> SEQUENCE: 47

Lys Phe Ser Ile Val Phe Pro Gln Ser Gln Lys Gly Asn Trp Lys Asn
1               5                   10                  15

Val Pro Ser Ser Tyr Asn Tyr Cys Pro Ser Ser Ser Asp Gln Asn Trp
            20                  25                  30

His Asn Asp Leu Leu Gly Ile Thr Met Lys Val Lys Met Pro Lys Thr
        35                  40                  45

His Lys Ala Ile Gln Ala Asp Gly Trp Met Cys His Ala Ala Lys Trp
    50                  55                  60

Ile Thr Thr Cys Asp Phe Arg Trp Tyr Gly Pro Lys Tyr Ile Thr His
65                  70                  75                  80

Ser Ile His Ser Ile Gln Pro Thr Ser Glu Gln Cys Lys Glu Ser Ile
                85                  90                  95

Lys Gln Thr Lys Gln Gly Thr Trp Met Ser Pro Gly Phe Pro Pro Gln
            100                 105                 110

Asn Cys Gly Tyr Ala Thr Val Thr Asp Ser Val Ala Val Val Val Gln
        115                 120                 125

Ala Thr Pro His His Val Leu Val Asp Glu Tyr Thr Gly Glu Trp Ile
    130                 135                 140

Asp Ser Gln Phe Pro Asn Gly Lys Cys Glu Thr Glu Glu Cys Glu Thr
145                 150                 155                 160

Val His Asn Ser Thr Val Trp Tyr Ser Asp Tyr Lys Val Thr Gly Leu
                165                 170                 175

Cys Asp Ala Thr Leu Val Asp Thr Glu Ile Thr Phe Phe Ser Glu Asp
            180                 185                 190

Gly Lys Lys Glu Ser Ile Gly Lys Pro Asn Thr Gly Tyr Arg Ser Asn
        195                 200                 205

Tyr Phe Ala Tyr Glu Lys Gly Asp Lys Val Cys Lys Met Asn Tyr Cys
    210                 215                 220

Lys His Ala Gly Val Arg Leu Pro Ser Gly Val Trp Phe Glu Phe Val
225                 230                 235                 240

Asp Gln Asp Val Tyr Ala Ala Ala Lys Leu Pro Glu Cys Pro Val Gly
                245                 250                 255

Ala Thr Ile Ser Ala Pro Thr Gln Thr Ser Val Asp Val Ser Leu Ile
            260                 265                 270

Leu Asp Val Glu Arg Ile Leu Asp Tyr Ser Leu Cys Gln Glu Thr Trp
        275                 280                 285

Ser Lys Ile Arg Ser Lys Gln Pro Val Ser Pro Val Asp Leu Ser Tyr
    290                 295                 300

Leu Ala Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Ile Asp Ile Asp
                325                 330                 335

Asn Pro Ile Ile Ser Lys Met Val Gly Lys Ile Ser Gly Ser Gln Thr
            340                 345                 350

Glu Arg Glu Leu Trp Thr Glu Trp Phe Pro Tyr Glu Gly Val Glu Ile
        355                 360                 365

Gly Pro Asn Gly Ile Leu Lys Thr Pro Thr Gly Tyr Lys Phe Pro Leu
    370                 375                 380
```

Phe Met Ile Gly His Gly Met Leu Asp Ser Asp Leu His Lys Thr Ser
385 390 395 400

Gln Ala Glu Val Phe Glu His Pro His Leu Ala Glu Ala Pro Lys Gln
405 410 415

Leu Pro Glu Glu Glu Phe Leu Phe Phe Gly Asp Thr Gly Ile Ser Lys
420 425 430

Asn Pro Val Glu Leu Ile Glu Gly Trp Phe Ser Ser Trp Lys Ser Thr
435 440 445

Val Val Thr Phe Phe Phe Ala Ile Gly Val Phe Ile Leu Leu Tyr Val
450 455 460

Val Ala Arg Ile Val Ile Ala Val Arg Tyr Arg Tyr Gln Gly Ser Asn
465 470 475 480

Asn Lys Arg Ile Tyr Asn Asp Ile Glu Met Ser Arg Phe Arg Lys
485 490 495

<210> SEQ ID NO 48
<211> LENGTH: 495
<212> TYPE: PRT
<213> ORGANISM: Artificial sequence
<220> FEATURE:
<223> OTHER INFORMATION: Glycoprotein Vesicular stomatitis Cocal virus H22N T422M

<400> SEQUENCE: 48

Lys Phe Ser Ile Val Phe Pro Gln Ser Gln Lys Gly Asn Trp Lys Asn
1 5 10 15

Val Pro Ser Ser Tyr Asn Tyr Cys Pro Ser Ser Ser Asp Gln Asn Trp
20 25 30

His Asn Asp Leu Leu Gly Ile Thr Met Lys Val Lys Met Pro Lys Thr
35 40 45

His Lys Ala Ile Gln Ala Asp Gly Trp Met Cys His Ala Ala Lys Trp
50 55 60

Ile Thr Thr Cys Asp Phe Arg Trp Tyr Gly Pro Lys Tyr Ile Thr His
65 70 75 80

Ser Ile His Ser Ile Gln Pro Thr Ser Glu Gln Cys Lys Glu Ser Ile
85 90 95

Lys Gln Thr Lys Gln Gly Thr Trp Met Ser Pro Gly Phe Pro Pro Gln
100 105 110

Asn Cys Gly Tyr Ala Thr Val Thr Asp Ser Val Ala Val Val Val Gln
115 120 125

Ala Thr Pro His His Val Leu Val Asp Glu Tyr Thr Gly Glu Trp Ile
130 135 140

Asp Ser Gln Phe Pro Asn Gly Lys Cys Glu Thr Glu Glu Cys Glu Thr
145 150 155 160

Val His Asn Ser Thr Val Trp Tyr Ser Asp Tyr Lys Val Thr Gly Leu
165 170 175

Cys Asp Ala Thr Leu Val Asp Thr Glu Ile Thr Phe Phe Ser Glu Asp
180 185 190

Gly Lys Lys Glu Ser Ile Gly Lys Pro Asn Thr Gly Tyr Arg Ser Asn
195 200 205

Tyr Phe Ala Tyr Glu Lys Gly Asp Lys Val Cys Lys Met Asn Tyr Cys
210 215 220

Lys His Ala Gly Val Arg Leu Pro Ser Gly Val Trp Phe Glu Phe Val
225 230 235 240

```
Asp Gln Asp Val Tyr Ala Ala Ala Lys Leu Pro Glu Cys Pro Val Gly
                245                 250                 255

Ala Thr Ile Ser Ala Pro Thr Gln Thr Ser Val Asp Val Ser Leu Ile
            260                 265                 270

Leu Asp Val Glu Arg Ile Leu Asp Tyr Ser Leu Cys Gln Glu Thr Trp
        275                 280                 285

Ser Lys Ile Arg Ser Lys Gln Pro Val Ser Pro Val Asp Leu Ser Tyr
    290                 295                 300

Leu Ala Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Ile Asp Ile Asp
                325                 330                 335

Asn Pro Ile Ile Ser Lys Met Val Gly Lys Ile Ser Gly Ser Gln Thr
            340                 345                 350

Glu Arg Glu Leu Trp Thr Glu Trp Phe Pro Tyr Glu Gly Val Glu Ile
        355                 360                 365

Gly Pro Asn Gly Ile Leu Lys Thr Pro Thr Gly Tyr Lys Phe Pro Leu
    370                 375                 380

Phe Met Ile Gly His Gly Met Leu Asp Ser Asp Leu His Lys Thr Ser
385                 390                 395                 400

Gln Ala Glu Val Phe Glu His Pro His Leu Ala Glu Ala Pro Lys Gln
                405                 410                 415

Leu Pro Glu Glu Glu Met Leu Phe Phe Gly Asp Thr Gly Ile Ser Lys
            420                 425                 430

Asn Pro Val Glu Leu Ile Glu Gly Trp Phe Ser Ser Trp Lys Ser Thr
        435                 440                 445

Val Val Thr Phe Phe Phe Ala Ile Gly Val Phe Ile Leu Leu Tyr Val
    450                 455                 460

Val Ala Arg Ile Val Ile Ala Val Arg Tyr Arg Tyr Gln Gly Ser Asn
465                 470                 475                 480

Asn Lys Arg Ile Tyr Asn Asp Ile Glu Met Ser Arg Phe Arg Lys
                485                 490                 495


<210> SEQ ID NO 49
<211> LENGTH: 495
<212> TYPE: PRT
<213> ORGANISM: Artificial sequence
<220> FEATURE:
<223> OTHER INFORMATION: Glycoprotein Vesicular stomatitis Cocal virus
      H22N T422V

<400> SEQUENCE: 49

Lys Phe Ser Ile Val Phe Pro Gln Ser Gln Lys Gly Asn Trp Lys Asn
1               5                   10                  15

Val Pro Ser Ser Tyr Asn Tyr Cys Pro Ser Ser Ser Asp Gln Asn Trp
            20                  25                  30

His Asn Asp Leu Leu Gly Ile Thr Met Lys Val Lys Met Pro Lys Thr
        35                  40                  45

His Lys Ala Ile Gln Ala Asp Gly Trp Met Cys His Ala Ala Lys Trp
    50                  55                  60

Ile Thr Thr Cys Asp Phe Arg Trp Tyr Gly Pro Lys Tyr Ile Thr His
65                  70                  75                  80

Ser Ile His Ser Ile Gln Pro Thr Ser Glu Gln Cys Lys Glu Ser Ile
                85                  90                  95
```

```
Lys Gln Thr Lys Gln Gly Thr Trp Met Ser Pro Gly Phe Pro Pro Gln
            100                 105                 110

Asn Cys Gly Tyr Ala Thr Val Thr Asp Ser Val Ala Val Val Val Gln
        115                 120                 125

Ala Thr Pro His His Val Leu Val Asp Glu Tyr Thr Gly Glu Trp Ile
    130                 135                 140

Asp Ser Gln Phe Pro Asn Gly Lys Cys Glu Thr Glu Glu Cys Glu Thr
145                 150                 155                 160

Val His Asn Ser Thr Val Trp Tyr Ser Asp Tyr Lys Val Thr Gly Leu
                165                 170                 175

Cys Asp Ala Thr Leu Val Asp Thr Glu Ile Thr Phe Phe Ser Glu Asp
            180                 185                 190

Gly Lys Lys Glu Ser Ile Gly Lys Pro Asn Thr Gly Tyr Arg Ser Asn
        195                 200                 205

Tyr Phe Ala Tyr Glu Lys Gly Asp Lys Val Cys Lys Met Asn Tyr Cys
    210                 215                 220

Lys His Ala Gly Val Arg Leu Pro Ser Gly Val Trp Phe Glu Phe Val
225                 230                 235                 240

Asp Gln Asp Val Tyr Ala Ala Ala Lys Leu Pro Glu Cys Pro Val Gly
                245                 250                 255

Ala Thr Ile Ser Ala Pro Thr Gln Thr Ser Val Asp Val Ser Leu Ile
            260                 265                 270

Leu Asp Val Glu Arg Ile Leu Asp Tyr Ser Leu Cys Gln Glu Thr Trp
        275                 280                 285

Ser Lys Ile Arg Ser Lys Gln Pro Val Ser Pro Val Asp Leu Ser Tyr
    290                 295                 300

Leu Ala Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Ile Asp Ile Asp
                325                 330                 335

Asn Pro Ile Ile Ser Lys Met Val Gly Lys Ile Ser Gly Ser Gln Thr
            340                 345                 350

Glu Arg Glu Leu Trp Thr Glu Trp Phe Pro Tyr Glu Gly Val Glu Ile
        355                 360                 365

Gly Pro Asn Gly Ile Leu Lys Thr Pro Thr Gly Tyr Lys Phe Pro Leu
    370                 375                 380

Phe Met Ile Gly His Gly Met Leu Asp Ser Asp Leu His Lys Thr Ser
385                 390                 395                 400

Gln Ala Glu Val Phe Glu His Pro His Leu Ala Glu Ala Pro Lys Gln
                405                 410                 415

Leu Pro Glu Glu Glu Val Leu Phe Phe Gly Asp Thr Gly Ile Ser Lys
            420                 425                 430

Asn Pro Val Glu Leu Ile Glu Gly Trp Phe Ser Ser Trp Lys Ser Thr
        435                 440                 445

Val Val Thr Phe Phe Phe Ala Ile Gly Val Phe Ile Leu Leu Tyr Val
    450                 455                 460

Val Ala Arg Ile Val Ile Ala Val Arg Tyr Arg Tyr Gln Gly Ser Asn
465                 470                 475                 480

Asn Lys Arg Ile Tyr Asn Asp Ile Glu Met Ser Arg Phe Arg Lys
                485                 490                 495
```

<210> SEQ ID NO 50
<211> LENGTH: 496

```
<212> TYPE: PRT
<213> ORGANISM: Artificial sequence
<220> FEATURE:
<223> OTHER INFORMATION: Glycoprotein Vesicular stomatitis Morreton
      virus Q22N

<400> SEQUENCE: 50

Lys Phe Thr Ile Val Phe Pro His Asn Gln Lys Gly Asn Trp Lys Asn
1               5                   10                  15

Val Pro Ala Asn Tyr Asn Tyr Cys Pro Ser Ser Ser Asp Leu Asn Trp
            20                  25                  30

His Asn Gly Leu Ile Gly Thr Ser Leu Gln Val Lys Met Pro Lys Ser
        35                  40                  45

His Lys Ala Ile Gln Ala Asp Gly Trp Met Cys His Ala Ala Lys Trp
    50                  55                  60

Val Thr Thr Cys Asp Phe Arg Trp Tyr Gly Pro Lys Tyr Val Thr His
65                  70                  75                  80

Ser Ile Lys Ser Met Ile Pro Thr Val Asp Gln Cys Lys Glu Ser Ile
                85                  90                  95

Ala Gln Thr Lys Gln Gly Thr Trp Leu Asn Pro Gly Phe Pro Pro Gln
            100                 105                 110

Ser Cys Gly Tyr Ala Ser Val Thr Asp Ala Glu Ala Val Ile Val Lys
        115                 120                 125

Ala Thr Pro His Gln Val Leu Val Asp Glu Tyr Thr Gly Glu Trp Val
    130                 135                 140

Asp Ser Gln Phe Pro Thr Gly Lys Cys Asn Lys Asp Ile Cys Pro Thr
145                 150                 155                 160

Val His Asn Ser Thr Thr Trp His Ser Asp Tyr Lys Val Thr Gly Leu
                165                 170                 175

Cys Asp Ala Asn Leu Ile Ser Met Asp Ile Thr Phe Phe Ser Glu Asp
            180                 185                 190

Gly Lys Leu Thr Ser Leu Gly Lys Glu Gly Thr Gly Phe Arg Ser Asn
        195                 200                 205

Tyr Phe Ala Tyr Glu Asn Gly Asp Lys Ala Cys Arg Met Gln Tyr Cys
    210                 215                 220

Lys His Trp Gly Val Arg Leu Pro Ser Gly Val Trp Phe Glu Met Ala
225                 230                 235                 240

Asp Lys Asp Ile Tyr Asn Asp Ala Lys Phe Pro Asp Cys Pro Glu Gly
                245                 250                 255

Ser Ser Ile Ala Ala Pro Ser Gln Thr Ser Val Asp Val Ser Leu Ile
            260                 265                 270

Gln Asp Val Glu Arg Ile Leu Asp Tyr Ser Leu Cys Gln Glu Thr Trp
        275                 280                 285

Ser Lys Ile Arg Ala His Leu Pro Ile Ser Pro Val Asp Leu Ser Tyr
    290                 295                 300

Leu Ser Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Val Asp Ile Ala
                325                 330                 335

Gly Pro Ile Ile Pro Gln Met Arg Gly Val Ile Ser Gly Thr Thr Thr
            340                 345                 350

Glu Arg Glu Leu Trp Thr Asp Trp Pro Tyr Glu Asp Val Glu Ile
        355                 360                 365

Gly Pro Asn Gly Val Leu Lys Thr Ala Thr Gly Tyr Lys Phe Pro Leu
    370                 375                 380
```

Tyr Met Ile Gly His Gly Met Leu Asp Ser Asp Leu His Ile Ser Ser
385 390 395 400

Lys Ala Gln Val Phe Glu His Pro His Ile Gln Asp Ala Ala Ser Gln
405 410 415

Leu Pro Asp Asp Glu Thr Leu Phe Phe Gly Asp Thr Gly Leu Ser Lys
420 425 430

Asn Pro Ile Glu Leu Val Glu Gly Trp Phe Ser Gly Trp Lys Ser Thr
435 440 445

Ile Ala Ser Phe Phe Phe Ile Ile Gly Leu Val Ile Gly Leu Tyr Leu
450 455 460

Val Leu Arg Ile Gly Ile Ala Leu Cys Ile Lys Cys Arg Val Gln Glu
465 470 475 480

Lys Arg Pro Lys Ile Tyr Thr Asp Val Glu Met Asn Arg Leu Asp Arg
485 490 495

<210> SEQ ID NO 51
<211> LENGTH: 496
<212> TYPE: PRT
<213> ORGANISM: Artificial sequence
<220> FEATURE:
<223> OTHER INFORMATION: Glycoprotein Vesicular stomatitis Morreton virus T422I

<400> SEQUENCE: 51

Lys Phe Thr Ile Val Phe Pro His Asn Gln Lys Gly Asn Trp Lys Asn
1 5 10 15

Val Pro Ala Asn Tyr Gln Tyr Cys Pro Ser Ser Ser Asp Leu Asn Trp
20 25 30

His Asn Gly Leu Ile Gly Thr Ser Leu Gln Val Lys Met Pro Lys Ser
35 40 45

His Lys Ala Ile Gln Ala Asp Gly Trp Met Cys His Ala Ala Lys Trp
50 55 60

Val Thr Thr Cys Asp Phe Arg Trp Tyr Gly Pro Lys Tyr Val Thr His
65 70 75 80

Ser Ile Lys Ser Met Ile Pro Thr Val Asp Gln Cys Lys Glu Ser Ile
85 90 95

Ala Gln Thr Lys Gln Gly Thr Trp Leu Asn Pro Gly Phe Pro Pro Gln
100 105 110

Ser Cys Gly Tyr Ala Ser Val Thr Asp Ala Glu Ala Val Ile Val Lys
115 120 125

Ala Thr Pro His Gln Val Leu Val Asp Glu Tyr Thr Gly Glu Trp Val
130 135 140

Asp Ser Gln Phe Pro Thr Gly Lys Cys Asn Lys Asp Ile Cys Pro Thr
145 150 155 160

Val His Asn Ser Thr Thr Trp His Ser Asp Tyr Lys Val Thr Gly Leu
165 170 175

Cys Asp Ala Asn Leu Ile Ser Met Asp Ile Thr Phe Phe Ser Glu Asp
180 185 190

Gly Lys Leu Thr Ser Leu Gly Lys Glu Gly Thr Gly Phe Arg Ser Asn
195 200 205

Tyr Phe Ala Tyr Glu Asn Gly Asp Lys Ala Cys Arg Met Gln Tyr Cys
210 215 220

Lys His Trp Gly Val Arg Leu Pro Ser Gly Val Trp Phe Glu Met Ala
225 230 235 240

```
Asp Lys Asp Ile Tyr Asn Asp Ala Lys Phe Pro Asp Cys Pro Glu Gly
                245                 250                 255

Ser Ser Ile Ala Ala Pro Ser Gln Thr Ser Val Asp Val Ser Leu Ile
            260                 265                 270

Gln Asp Val Glu Arg Ile Leu Asp Tyr Ser Leu Cys Gln Glu Thr Trp
        275                 280                 285

Ser Lys Ile Arg Ala His Leu Pro Ile Ser Pro Val Asp Leu Ser Tyr
    290                 295                 300

Leu Ser Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Val Asp Ile Ala
                325                 330                 335

Gly Pro Ile Ile Pro Gln Met Arg Gly Val Ile Ser Gly Thr Thr Thr
            340                 345                 350

Glu Arg Glu Leu Trp Thr Asp Trp Tyr Pro Tyr Glu Asp Val Glu Ile
        355                 360                 365

Gly Pro Asn Gly Val Leu Lys Thr Ala Thr Gly Tyr Lys Phe Pro Leu
    370                 375                 380

Tyr Met Ile Gly His Gly Met Leu Asp Ser Asp Leu His Ile Ser Ser
385                 390                 395                 400

Lys Ala Gln Val Phe Glu His Pro His Ile Gln Asp Ala Ala Ser Gln
                405                 410                 415

Leu Pro Asp Asp Glu Ile Leu Phe Phe Gly Asp Thr Gly Leu Ser Lys
            420                 425                 430

Asn Pro Ile Glu Leu Val Glu Gly Trp Phe Ser Gly Trp Lys Ser Thr
        435                 440                 445

Ile Ala Ser Phe Phe Phe Ile Ile Gly Leu Val Ile Gly Leu Tyr Leu
    450                 455                 460

Val Leu Arg Ile Gly Ile Ala Leu Cys Ile Lys Cys Arg Val Gln Glu
465                 470                 475                 480

Lys Arg Pro Lys Ile Tyr Thr Asp Val Glu Met Asn Arg Leu Asp Arg
                485                 490                 495


<210> SEQ ID NO 52
<211> LENGTH: 496
<212> TYPE: PRT
<213> ORGANISM: Artificial sequence
<220> FEATURE:
<223> OTHER INFORMATION: Glycoprotein Vesicular stomatitis Morreton
      virus T422L

<400> SEQUENCE: 52

Lys Phe Thr Ile Val Phe Pro His Asn Gln Lys Gly Asn Trp Lys Asn
1               5                   10                  15

Val Pro Ala Asn Tyr Gln Tyr Cys Pro Ser Ser Ser Asp Leu Asn Trp
            20                  25                  30

His Asn Gly Leu Ile Gly Thr Ser Leu Gln Val Lys Met Pro Lys Ser
        35                  40                  45

His Lys Ala Ile Gln Ala Asp Gly Trp Met Cys His Ala Ala Lys Trp
    50                  55                  60

Val Thr Thr Cys Asp Phe Arg Trp Tyr Gly Pro Lys Tyr Val Thr His
65                  70                  75                  80

Ser Ile Lys Ser Met Ile Pro Thr Val Asp Gln Cys Lys Glu Ser Ile
                85                  90                  95
```

```
Ala Gln Thr Lys Gln Gly Thr Trp Leu Asn Pro Gly Phe Pro Pro Gln
            100                 105                 110

Ser Cys Gly Tyr Ala Ser Val Thr Asp Ala Glu Ala Val Ile Val Lys
        115                 120                 125

Ala Thr Pro His Gln Val Leu Val Asp Glu Tyr Thr Gly Glu Trp Val
    130                 135                 140

Asp Ser Gln Phe Pro Thr Gly Lys Cys Asn Lys Asp Ile Cys Pro Thr
145                 150                 155                 160

Val His Asn Ser Thr Thr Trp His Ser Asp Tyr Lys Val Thr Gly Leu
                165                 170                 175

Cys Asp Ala Asn Leu Ile Ser Met Asp Ile Thr Phe Phe Ser Glu Asp
            180                 185                 190

Gly Lys Leu Thr Ser Leu Gly Lys Glu Gly Thr Gly Phe Arg Ser Asn
        195                 200                 205

Tyr Phe Ala Tyr Glu Asn Gly Asp Lys Ala Cys Arg Met Gln Tyr Cys
    210                 215                 220

Lys His Trp Gly Val Arg Leu Pro Ser Gly Val Trp Phe Glu Met Ala
225                 230                 235                 240

Asp Lys Asp Ile Tyr Asn Asp Ala Lys Phe Pro Asp Cys Pro Glu Gly
                245                 250                 255

Ser Ser Ile Ala Ala Pro Ser Gln Thr Ser Val Asp Val Ser Leu Ile
            260                 265                 270

Gln Asp Val Glu Arg Ile Leu Asp Tyr Ser Leu Cys Gln Glu Thr Trp
        275                 280                 285

Ser Lys Ile Arg Ala His Leu Pro Ile Ser Pro Val Asp Leu Ser Tyr
    290                 295                 300

Leu Ser Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Val Asp Ile Ala
                325                 330                 335

Gly Pro Ile Ile Pro Gln Met Arg Gly Val Ile Ser Gly Thr Thr Thr
            340                 345                 350

Glu Arg Glu Leu Trp Thr Asp Trp Tyr Pro Tyr Glu Asp Val Glu Ile
        355                 360                 365

Gly Pro Asn Gly Val Leu Lys Thr Ala Thr Gly Tyr Lys Phe Pro Leu
    370                 375                 380

Tyr Met Ile Gly His Gly Met Leu Asp Ser Asp Leu His Ile Ser Ser
385                 390                 395                 400

Lys Ala Gln Val Phe Glu His Pro His Ile Gln Asp Ala Ala Ser Gln
                405                 410                 415

Leu Pro Asp Asp Glu Leu Leu Phe Phe Gly Asp Thr Gly Leu Ser Lys
            420                 425                 430

Asn Pro Ile Glu Leu Val Glu Gly Trp Phe Ser Gly Trp Lys Ser Thr
        435                 440                 445

Ile Ala Ser Phe Phe Phe Ile Ile Gly Leu Val Ile Gly Leu Tyr Leu
    450                 455                 460

Val Leu Arg Ile Gly Ile Ala Leu Cys Ile Lys Cys Arg Val Gln Glu
465                 470                 475                 480

Lys Arg Pro Lys Ile Tyr Thr Asp Val Glu Met Asn Arg Leu Asp Arg
                485                 490                 495
```

<210> SEQ ID NO 53
<211> LENGTH: 496

```
<212> TYPE: PRT
<213> ORGANISM: Artificial sequence
<220> FEATURE:
<223> OTHER INFORMATION: Glycoprotein Vesicular stomatitis Morreton
      virus T422F

<400> SEQUENCE: 53

Lys Phe Thr Ile Val Phe Pro His Asn Gln Lys Gly Asn Trp Lys Asn
1               5                   10                  15

Val Pro Ala Asn Tyr Gln Tyr Cys Pro Ser Ser Ser Asp Leu Asn Trp
            20                  25                  30

His Asn Gly Leu Ile Gly Thr Ser Leu Gln Val Lys Met Pro Lys Ser
        35                  40                  45

His Lys Ala Ile Gln Ala Asp Gly Trp Met Cys His Ala Ala Lys Trp
    50                  55                  60

Val Thr Thr Cys Asp Phe Arg Trp Tyr Gly Pro Lys Tyr Val Thr His
65                  70                  75                  80

Ser Ile Lys Ser Met Ile Pro Thr Val Asp Gln Cys Lys Glu Ser Ile
                85                  90                  95

Ala Gln Thr Lys Gln Gly Thr Trp Leu Asn Pro Gly Phe Pro Pro Gln
            100                 105                 110

Ser Cys Gly Tyr Ala Ser Val Thr Asp Ala Glu Ala Val Ile Val Lys
        115                 120                 125

Ala Thr Pro His Gln Val Leu Val Asp Glu Tyr Thr Gly Glu Trp Val
    130                 135                 140

Asp Ser Gln Phe Pro Thr Gly Lys Cys Asn Lys Asp Ile Cys Pro Thr
145                 150                 155                 160

Val His Asn Ser Thr Thr Trp His Ser Asp Tyr Lys Val Thr Gly Leu
                165                 170                 175

Cys Asp Ala Asn Leu Ile Ser Met Asp Ile Thr Phe Phe Ser Glu Asp
            180                 185                 190

Gly Lys Leu Thr Ser Leu Gly Lys Glu Gly Thr Gly Phe Arg Ser Asn
        195                 200                 205

Tyr Phe Ala Tyr Glu Asn Gly Asp Lys Ala Cys Arg Met Gln Tyr Cys
    210                 215                 220

Lys His Trp Gly Val Arg Leu Pro Ser Gly Val Trp Phe Glu Met Ala
225                 230                 235                 240

Asp Lys Asp Ile Tyr Asn Asp Ala Lys Phe Pro Asp Cys Pro Glu Gly
                245                 250                 255

Ser Ser Ile Ala Ala Pro Ser Gln Thr Ser Val Asp Val Ser Leu Ile
            260                 265                 270

Gln Asp Val Glu Arg Ile Leu Asp Tyr Ser Leu Cys Gln Glu Thr Trp
        275                 280                 285

Ser Lys Ile Arg Ala His Leu Pro Ile Ser Pro Val Asp Leu Ser Tyr
    290                 295                 300

Leu Ser Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Val Asp Ile Ala
                325                 330                 335

Gly Pro Ile Ile Pro Gln Met Arg Gly Val Ile Ser Gly Thr Thr Thr
            340                 345                 350

Glu Arg Glu Leu Trp Thr Asp Trp Pro Tyr Glu Asp Val Glu Ile
        355                 360                 365

Gly Pro Asn Gly Val Leu Lys Thr Ala Thr Gly Tyr Lys Phe Pro Leu
    370                 375                 380
```

Tyr Met Ile Gly His Gly Met Leu Asp Ser Asp Leu His Ile Ser Ser
385 390 395 400

Lys Ala Gln Val Phe Glu His Pro His Ile Gln Asp Ala Ala Ser Gln
405 410 415

Leu Pro Asp Asp Glu Phe Leu Phe Phe Gly Asp Thr Gly Leu Ser Lys
420 425 430

Asn Pro Ile Glu Leu Val Glu Gly Trp Phe Ser Gly Trp Lys Ser Thr
435 440 445

Ile Ala Ser Phe Phe Phe Ile Ile Gly Leu Val Ile Gly Leu Tyr Leu
450 455 460

Val Leu Arg Ile Gly Ile Ala Leu Cys Ile Lys Cys Arg Val Gln Glu
465 470 475 480

Lys Arg Pro Lys Ile Tyr Thr Asp Val Glu Met Asn Arg Leu Asp Arg
485 490 495

<210> SEQ ID NO 54
<211> LENGTH: 496
<212> TYPE: PRT
<213> ORGANISM: Artificial sequence
<220> FEATURE:
<223> OTHER INFORMATION: Glycoprotein Vesicular stomatitis Morreton virus T422M

<400> SEQUENCE: 54

Lys Phe Thr Ile Val Phe Pro His Asn Gln Lys Gly Asn Trp Lys Asn
1 5 10 15

Val Pro Ala Asn Tyr Gln Tyr Cys Pro Ser Ser Ser Asp Leu Asn Trp
20 25 30

His Asn Gly Leu Ile Gly Thr Ser Leu Gln Val Lys Met Pro Lys Ser
35 40 45

His Lys Ala Ile Gln Ala Asp Gly Trp Met Cys His Ala Ala Lys Trp
50 55 60

Val Thr Thr Cys Asp Phe Arg Trp Tyr Gly Pro Lys Tyr Val Thr His
65 70 75 80

Ser Ile Lys Ser Met Ile Pro Thr Val Asp Gln Cys Lys Glu Ser Ile
85 90 95

Ala Gln Thr Lys Gln Gly Thr Trp Leu Asn Pro Gly Phe Pro Pro Gln
100 105 110

Ser Cys Gly Tyr Ala Ser Val Thr Asp Ala Glu Ala Val Ile Val Lys
115 120 125

Ala Thr Pro His Gln Val Leu Val Asp Glu Tyr Thr Gly Glu Trp Val
130 135 140

Asp Ser Gln Phe Pro Thr Gly Lys Cys Asn Lys Asp Ile Cys Pro Thr
145 150 155 160

Val His Asn Ser Thr Thr Trp His Ser Asp Tyr Lys Val Thr Gly Leu
165 170 175

Cys Asp Ala Asn Leu Ile Ser Met Asp Ile Thr Phe Phe Ser Glu Asp
180 185 190

Gly Lys Leu Thr Ser Leu Gly Lys Glu Gly Thr Gly Phe Arg Ser Asn
195 200 205

Tyr Phe Ala Tyr Glu Asn Gly Asp Lys Ala Cys Arg Met Gln Tyr Cys
210 215 220

Lys His Trp Gly Val Arg Leu Pro Ser Gly Val Trp Phe Glu Met Ala
225 230 235 240

```
Asp Lys Asp Ile Tyr Asn Asp Ala Lys Phe Pro Asp Cys Pro Glu Gly
                245                 250                 255

Ser Ser Ile Ala Ala Pro Ser Gln Thr Ser Val Asp Val Ser Leu Ile
            260                 265                 270

Gln Asp Val Glu Arg Ile Leu Asp Tyr Ser Leu Cys Gln Glu Thr Trp
        275                 280                 285

Ser Lys Ile Arg Ala His Leu Pro Ile Ser Pro Val Asp Leu Ser Tyr
    290                 295                 300

Leu Ser Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Val Asp Ile Ala
                325                 330                 335

Gly Pro Ile Ile Pro Gln Met Arg Gly Val Ile Ser Gly Thr Thr Thr
            340                 345                 350

Glu Arg Glu Leu Trp Thr Asp Trp Tyr Pro Tyr Glu Asp Val Glu Ile
        355                 360                 365

Gly Pro Asn Gly Val Leu Lys Thr Ala Thr Gly Tyr Lys Phe Pro Leu
    370                 375                 380

Tyr Met Ile Gly His Gly Met Leu Asp Ser Asp Leu His Ile Ser Ser
385                 390                 395                 400

Lys Ala Gln Val Phe Glu His Pro His Ile Gln Asp Ala Ala Ser Gln
                405                 410                 415

Leu Pro Asp Asp Glu Met Leu Phe Phe Gly Asp Thr Gly Leu Ser Lys
            420                 425                 430

Asn Pro Ile Glu Leu Val Glu Gly Trp Phe Ser Gly Trp Lys Ser Thr
        435                 440                 445

Ile Ala Ser Phe Phe Phe Ile Ile Gly Leu Val Ile Gly Leu Tyr Leu
    450                 455                 460

Val Leu Arg Ile Gly Ile Ala Leu Cys Ile Lys Cys Arg Val Gln Glu
465                 470                 475                 480

Lys Arg Pro Lys Ile Tyr Thr Asp Val Glu Met Asn Arg Leu Asp Arg
                485                 490                 495


<210> SEQ ID NO 55
<211> LENGTH: 496
<212> TYPE: PRT
<213> ORGANISM: Artificial sequence
<220> FEATURE:
<223> OTHER INFORMATION: Glycoprotein Vesicular stomatitis Morreton
      virus T422V

<400> SEQUENCE: 55

Lys Phe Thr Ile Val Phe Pro His Asn Gln Lys Gly Asn Trp Lys Asn
1               5                   10                  15

Val Pro Ala Asn Tyr Gln Tyr Cys Pro Ser Ser Ser Asp Leu Asn Trp
            20                  25                  30

His Asn Gly Leu Ile Gly Thr Ser Leu Gln Val Lys Met Pro Lys Ser
        35                  40                  45

His Lys Ala Ile Gln Ala Asp Gly Trp Met Cys His Ala Ala Lys Trp
    50                  55                  60

Val Thr Thr Cys Asp Phe Arg Trp Tyr Gly Pro Lys Tyr Val Thr His
65                  70                  75                  80

Ser Ile Lys Ser Met Ile Pro Thr Val Asp Gln Cys Lys Glu Ser Ile
                85                  90                  95
```

```
Ala Gln Thr Lys Gln Gly Thr Trp Leu Asn Pro Gly Phe Pro Pro Gln
            100                 105                 110

Ser Cys Gly Tyr Ala Ser Val Thr Asp Ala Glu Ala Val Ile Val Lys
        115                 120                 125

Ala Thr Pro His Gln Val Leu Val Asp Glu Tyr Thr Gly Glu Trp Val
    130                 135                 140

Asp Ser Gln Phe Pro Thr Gly Lys Cys Asn Lys Asp Ile Cys Pro Thr
145                 150                 155                 160

Val His Asn Ser Thr Thr Trp His Ser Asp Tyr Lys Val Thr Gly Leu
                165                 170                 175

Cys Asp Ala Asn Leu Ile Ser Met Asp Ile Thr Phe Phe Ser Glu Asp
            180                 185                 190

Gly Lys Leu Thr Ser Leu Gly Lys Glu Gly Thr Gly Phe Arg Ser Asn
        195                 200                 205

Tyr Phe Ala Tyr Glu Asn Gly Asp Lys Ala Cys Arg Met Gln Tyr Cys
    210                 215                 220

Lys His Trp Gly Val Arg Leu Pro Ser Gly Val Trp Phe Glu Met Ala
225                 230                 235                 240

Asp Lys Asp Ile Tyr Asn Asp Ala Lys Phe Pro Asp Cys Pro Glu Gly
                245                 250                 255

Ser Ser Ile Ala Ala Pro Ser Gln Thr Ser Val Asp Val Ser Leu Ile
            260                 265                 270

Gln Asp Val Glu Arg Ile Leu Asp Tyr Ser Leu Cys Gln Glu Thr Trp
        275                 280                 285

Ser Lys Ile Arg Ala His Leu Pro Ile Ser Pro Val Asp Leu Ser Tyr
    290                 295                 300

Leu Ser Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Val Asp Ile Ala
                325                 330                 335

Gly Pro Ile Ile Pro Gln Met Arg Gly Val Ile Ser Gly Thr Thr Thr
            340                 345                 350

Glu Arg Glu Leu Trp Thr Asp Trp Tyr Pro Tyr Glu Asp Val Glu Ile
        355                 360                 365

Gly Pro Asn Gly Val Leu Lys Thr Ala Thr Gly Tyr Lys Phe Pro Leu
    370                 375                 380

Tyr Met Ile Gly His Gly Met Leu Asp Ser Asp Leu His Ile Ser Ser
385                 390                 395                 400

Lys Ala Gln Val Phe Glu His Pro His Ile Gln Asp Ala Ala Ser Gln
                405                 410                 415

Leu Pro Asp Asp Glu Val Leu Phe Phe Gly Asp Thr Gly Leu Ser Lys
            420                 425                 430

Asn Pro Ile Glu Leu Val Glu Gly Trp Phe Ser Gly Trp Lys Ser Thr
        435                 440                 445

Ile Ala Ser Phe Phe Phe Ile Ile Gly Leu Val Ile Gly Leu Tyr Leu
    450                 455                 460

Val Leu Arg Ile Gly Ile Ala Leu Cys Ile Lys Cys Arg Val Gln Glu
465                 470                 475                 480

Lys Arg Pro Lys Ile Tyr Thr Asp Val Glu Met Asn Arg Leu Asp Arg
                485                 490                 495
```

<210> SEQ ID NO 56
<211> LENGTH: 496

```
<212> TYPE: PRT
<213> ORGANISM: Artificial sequence
<220> FEATURE:
<223> OTHER INFORMATION: Glycoprotein Vesicular stomatitis Morreton
      virus Q22N T422I

<400> SEQUENCE: 56

Lys Phe Thr Ile Val Phe Pro His Asn Gln Lys Gly Asn Trp Lys Asn
1               5                   10                  15

Val Pro Ala Asn Tyr Asn Tyr Cys Pro Ser Ser Ser Asp Leu Asn Trp
            20                  25                  30

His Asn Gly Leu Ile Gly Thr Ser Leu Gln Val Lys Met Pro Lys Ser
        35                  40                  45

His Lys Ala Ile Gln Ala Asp Gly Trp Met Cys His Ala Ala Lys Trp
    50                  55                  60

Val Thr Thr Cys Asp Phe Arg Trp Tyr Gly Pro Lys Tyr Val Thr His
65                  70                  75                  80

Ser Ile Lys Ser Met Ile Pro Thr Val Asp Gln Cys Lys Glu Ser Ile
                85                  90                  95

Ala Gln Thr Lys Gln Gly Thr Trp Leu Asn Pro Gly Phe Pro Pro Gln
            100                 105                 110

Ser Cys Gly Tyr Ala Ser Val Thr Asp Ala Glu Ala Val Ile Val Lys
        115                 120                 125

Ala Thr Pro His Gln Val Leu Val Asp Glu Tyr Thr Gly Glu Trp Val
    130                 135                 140

Asp Ser Gln Phe Pro Thr Gly Lys Cys Asn Lys Asp Ile Cys Pro Thr
145                 150                 155                 160

Val His Asn Ser Thr Thr Trp His Ser Asp Tyr Lys Val Thr Gly Leu
                165                 170                 175

Cys Asp Ala Asn Leu Ile Ser Met Asp Ile Thr Phe Phe Ser Glu Asp
            180                 185                 190

Gly Lys Leu Thr Ser Leu Gly Lys Glu Gly Thr Gly Phe Arg Ser Asn
        195                 200                 205

Tyr Phe Ala Tyr Glu Asn Gly Asp Lys Ala Cys Arg Met Gln Tyr Cys
    210                 215                 220

Lys His Trp Gly Val Arg Leu Pro Ser Gly Val Trp Phe Glu Met Ala
225                 230                 235                 240

Asp Lys Asp Ile Tyr Asn Asp Ala Lys Phe Pro Asp Cys Pro Glu Gly
                245                 250                 255

Ser Ser Ile Ala Ala Pro Ser Gln Thr Ser Val Asp Val Ser Leu Ile
            260                 265                 270

Gln Asp Val Glu Arg Ile Leu Asp Tyr Ser Leu Cys Gln Glu Thr Trp
        275                 280                 285

Ser Lys Ile Arg Ala His Leu Pro Ile Ser Pro Val Asp Leu Ser Tyr
    290                 295                 300

Leu Ser Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Val Asp Ile Ala
                325                 330                 335

Gly Pro Ile Ile Pro Gln Met Arg Gly Val Ile Ser Gly Thr Thr Thr
            340                 345                 350

Glu Arg Glu Leu Trp Thr Asp Trp Pro Tyr Glu Asp Val Glu Ile
        355                 360                 365

Gly Pro Asn Gly Val Leu Lys Thr Ala Thr Gly Tyr Lys Phe Pro Leu
    370                 375                 380
```

Tyr Met Ile Gly His Gly Met Leu Asp Ser Asp Leu His Ile Ser Ser
385 390 395 400

Lys Ala Gln Val Phe Glu His Pro His Ile Gln Asp Ala Ala Ser Gln
405 410 415

Leu Pro Asp Asp Glu Ile Leu Phe Phe Gly Asp Thr Gly Leu Ser Lys
420 425 430

Asn Pro Ile Glu Leu Val Glu Gly Trp Phe Ser Gly Trp Lys Ser Thr
435 440 445

Ile Ala Ser Phe Phe Phe Ile Ile Gly Leu Val Ile Gly Leu Tyr Leu
450 455 460

Val Leu Arg Ile Gly Ile Ala Leu Cys Ile Lys Cys Arg Val Gln Glu
465 470 475 480

Lys Arg Pro Lys Ile Tyr Thr Asp Val Glu Met Asn Arg Leu Asp Arg
485 490 495

<210> SEQ ID NO 57
<211> LENGTH: 496
<212> TYPE: PRT
<213> ORGANISM: Artificial sequence
<220> FEATURE:
<223> OTHER INFORMATION: Glycoprotein Vesicular stomatitis Morreton virus Q22N T422L

<400> SEQUENCE: 57

Lys Phe Thr Ile Val Phe Pro His Asn Gln Lys Gly Asn Trp Lys Asn
1 5 10 15

Val Pro Ala Asn Tyr Asn Tyr Cys Pro Ser Ser Ser Asp Leu Asn Trp
20 25 30

His Asn Gly Leu Ile Gly Thr Ser Leu Gln Val Lys Met Pro Lys Ser
35 40 45

His Lys Ala Ile Gln Ala Asp Gly Trp Met Cys His Ala Ala Lys Trp
50 55 60

Val Thr Thr Cys Asp Phe Arg Trp Tyr Gly Pro Lys Tyr Val Thr His
65 70 75 80

Ser Ile Lys Ser Met Ile Pro Thr Val Asp Gln Cys Lys Glu Ser Ile
85 90 95

Ala Gln Thr Lys Gln Gly Thr Trp Leu Asn Pro Gly Phe Pro Pro Gln
100 105 110

Ser Cys Gly Tyr Ala Ser Val Thr Asp Ala Glu Ala Val Ile Val Lys
115 120 125

Ala Thr Pro His Gln Val Leu Val Asp Glu Tyr Thr Gly Glu Trp Val
130 135 140

Asp Ser Gln Phe Pro Thr Gly Lys Cys Asn Lys Asp Ile Cys Pro Thr
145 150 155 160

Val His Asn Ser Thr Thr Trp His Ser Asp Tyr Lys Val Thr Gly Leu
165 170 175

Cys Asp Ala Asn Leu Ile Ser Met Asp Ile Thr Phe Phe Ser Glu Asp
180 185 190

Gly Lys Leu Thr Ser Leu Gly Lys Glu Gly Thr Gly Phe Arg Ser Asn
195 200 205

Tyr Phe Ala Tyr Glu Asn Gly Asp Lys Ala Cys Arg Met Gln Tyr Cys
210 215 220

Lys His Trp Gly Val Arg Leu Pro Ser Gly Val Trp Phe Glu Met Ala
225 230 235 240

Asp Lys Asp Ile Tyr Asn Asp Ala Lys Phe Pro Asp Cys Pro Glu Gly
245 250 255

Ser Ser Ile Ala Ala Pro Ser Gln Thr Ser Val Asp Val Ser Leu Ile
260 265 270

Gln Asp Val Glu Arg Ile Leu Asp Tyr Ser Leu Cys Gln Glu Thr Trp
275 280 285

Ser Lys Ile Arg Ala His Leu Pro Ile Ser Pro Val Asp Leu Ser Tyr
290 295 300

Leu Ser Pro Lys Asn Pro Gly Thr Gly Pro Ala Phe Thr Ile Ile Asn
305 310 315 320

Gly Thr Leu Lys Tyr Phe Glu Thr Arg Tyr Ile Arg Val Asp Ile Ala
325 330 335

Gly Pro Ile Ile Pro Gln Met Arg Gly Val Ile Ser Gly Thr Thr Thr
340 345 350

Glu Arg Glu Leu Trp Thr Asp Trp Tyr Pro Tyr Glu Asp Val Glu Ile
355 360 365

Gly Pro Asn Gly Val Leu Lys Thr Ala Thr Gly Tyr Lys Phe Pro Leu
370 375 380

Tyr Met Ile Gly His Gly Met Leu Asp Ser Asp Leu His Ile Ser Ser
385 390 395 400

Lys Ala Gln Val Phe Glu His Pro His Ile Gln Asp Ala Ala Ser Gln
405 410 415

Leu Pro Asp Asp Glu Leu Leu Phe Phe Gly Asp Thr Gly Leu Ser Lys
420 425 430

Asn Pro Ile Glu Leu Val Glu Gly Trp Phe Ser Gly Trp Lys Ser Thr
435 440 445

Ile Ala Ser Phe Phe Phe Ile Ile Gly Leu Val Ile Gly Leu Tyr Leu
450 455 460

Val Leu Arg Ile Gly Ile Ala Leu Cys Ile Lys Cys Arg Val Gln Glu
465 470 475 480

Lys Arg Pro Lys Ile Tyr Thr Asp Val Glu Met Asn Arg Leu Asp Arg
485 490 495

<210> SEQ ID NO 58
<211> LENGTH: 496
<212> TYPE: PRT
<213> ORGANISM: Artificial sequence
<220> FEATURE:
<223> OTHER INFORMATION: Glycoprotein Vesicular stomatitis Morreton virus Q22N T422F

<400> SEQUENCE: 58

Lys Phe Thr Ile Val Phe Pro His Asn Gln Lys Gly Asn Trp Lys Asn
1 5 10 15

Val Pro Ala Asn Tyr Asn Tyr Cys Pro Ser Ser Ser Asp Leu Asn Trp
20 25 30

His Asn Gly Leu Ile Gly Thr Ser Leu Gln Val Lys Met Pro Lys Ser
35 40 45

His Lys Ala Ile Gln Ala Asp Gly Trp Met Cys His Ala Ala Lys Trp
50 55 60

Val Thr Thr Cys Asp Phe Arg Trp Tyr Gly Pro Lys Tyr Val Thr His
65 70 75 80

Ser Ile Lys Ser Met Ile Pro Thr Val Asp Gln Cys Lys Glu Ser Ile
85 90 95

```
Ala Gln Thr Lys Gln Gly Thr Trp Leu Asn Pro Gly Phe Pro Pro Gln
            100                 105                 110

Ser Cys Gly Tyr Ala Ser Val Thr Asp Ala Glu Ala Val Ile Val Lys
        115                 120                 125

Ala Thr Pro His Gln Val Leu Val Asp Glu Tyr Thr Gly Glu Trp Val
    130                 135                 140

Asp Ser Gln Phe Pro Thr Gly Lys Cys Asn Lys Asp Ile Cys Pro Thr
145                 150                 155                 160

Val His Asn Ser Thr Thr Trp His Ser Asp Tyr Lys Val Thr Gly Leu
                165                 170                 175

Cys Asp Ala Asn Leu Ile Ser Met Asp Ile Thr Phe Phe Ser Glu Asp
            180                 185                 190

Gly Lys Leu Thr Ser Leu Gly Lys Glu Gly Thr Gly Phe Arg Ser Asn
        195                 200                 205

Tyr Phe Ala Tyr Glu Asn Gly Asp Lys Ala Cys Arg Met Gln Tyr Cys
    210                 215                 220

Lys His Trp Gly Val Arg Leu Pro Ser Gly Val Trp Phe Glu Met Ala
225                 230                 235                 240

Asp Lys Asp Ile Tyr Asn Asp Ala Lys Phe Pro Asp Cys Pro Glu Gly
                245                 250                 255

Ser Ser Ile Ala Ala Pro Ser Gln Thr Ser Val Asp Val Ser Leu Ile
            260                 265                 270

Gln Asp Val Glu Arg Ile Leu Asp Tyr Ser Leu Cys Gln Glu Thr Trp
        275                 280                 285

Ser Lys Ile Arg Ala His Leu Pro Ile Ser Pro Val Asp Leu Ser Tyr
    290                 295                 300

Leu Ser Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Val Asp Ile Ala
                325                 330                 335

Gly Pro Ile Ile Pro Gln Met Arg Gly Val Ile Ser Gly Thr Thr Thr
            340                 345                 350

Glu Arg Glu Leu Trp Thr Asp Trp Tyr Pro Tyr Glu Asp Val Glu Ile
        355                 360                 365

Gly Pro Asn Gly Val Leu Lys Thr Ala Thr Gly Tyr Lys Phe Pro Leu
    370                 375                 380

Tyr Met Ile Gly His Gly Met Leu Asp Ser Asp Leu His Ile Ser Ser
385                 390                 395                 400

Lys Ala Gln Val Phe Glu His Pro His Ile Gln Asp Ala Ala Ser Gln
                405                 410                 415

Leu Pro Asp Asp Glu Phe Leu Phe Phe Gly Asp Thr Gly Leu Ser Lys
            420                 425                 430

Asn Pro Ile Glu Leu Val Glu Gly Trp Phe Ser Gly Trp Lys Ser Thr
        435                 440                 445

Ile Ala Ser Phe Phe Phe Ile Ile Gly Leu Val Ile Gly Leu Tyr Leu
    450                 455                 460

Val Leu Arg Ile Gly Ile Ala Leu Cys Ile Lys Cys Arg Val Gln Glu
465                 470                 475                 480

Lys Arg Pro Lys Ile Tyr Thr Asp Val Glu Met Asn Arg Leu Asp Arg
                485                 490                 495
```

<210> SEQ ID NO 59
<211> LENGTH: 496

<212> TYPE: PRT
<213> ORGANISM: Artificial sequence
<220> FEATURE:
<223> OTHER INFORMATION: Glycoprotein Vesicular stomatitis Morreton virus Q22N T422M

<400> SEQUENCE: 59

```
Lys Phe Thr Ile Val Phe Pro His Asn Gln Lys Gly Asn Trp Lys Asn
1               5                   10                  15

Val Pro Ala Asn Tyr Asn Tyr Cys Pro Ser Ser Ser Asp Leu Asn Trp
            20                  25                  30

His Asn Gly Leu Ile Gly Thr Ser Leu Gln Val Lys Met Pro Lys Ser
        35                  40                  45

His Lys Ala Ile Gln Ala Asp Gly Trp Met Cys His Ala Ala Lys Trp
    50                  55                  60

Val Thr Thr Cys Asp Phe Arg Trp Tyr Gly Pro Lys Tyr Val Thr His
65                  70                  75                  80

Ser Ile Lys Ser Met Ile Pro Thr Val Asp Gln Cys Lys Glu Ser Ile
                85                  90                  95

Ala Gln Thr Lys Gln Gly Thr Trp Leu Asn Pro Gly Phe Pro Pro Gln
            100                 105                 110

Ser Cys Gly Tyr Ala Ser Val Thr Asp Ala Glu Ala Val Ile Val Lys
        115                 120                 125

Ala Thr Pro His Gln Val Leu Val Asp Glu Tyr Thr Gly Glu Trp Val
    130                 135                 140

Asp Ser Gln Phe Pro Thr Gly Lys Cys Asn Lys Asp Ile Cys Pro Thr
145                 150                 155                 160

Val His Asn Ser Thr Thr Trp His Ser Asp Tyr Lys Val Thr Gly Leu
                165                 170                 175

Cys Asp Ala Asn Leu Ile Ser Met Asp Ile Thr Phe Phe Ser Glu Asp
            180                 185                 190

Gly Lys Leu Thr Ser Leu Gly Lys Glu Gly Thr Gly Phe Arg Ser Asn
        195                 200                 205

Tyr Phe Ala Tyr Glu Asn Gly Asp Lys Ala Cys Arg Met Gln Tyr Cys
    210                 215                 220

Lys His Trp Gly Val Arg Leu Pro Ser Gly Val Trp Phe Glu Met Ala
225                 230                 235                 240

Asp Lys Asp Ile Tyr Asn Asp Ala Lys Phe Pro Asp Cys Pro Glu Gly
                245                 250                 255

Ser Ser Ile Ala Ala Pro Ser Gln Thr Ser Val Asp Val Ser Leu Ile
            260                 265                 270

Gln Asp Val Glu Arg Ile Leu Asp Tyr Ser Leu Cys Gln Glu Thr Trp
        275                 280                 285

Ser Lys Ile Arg Ala His Leu Pro Ile Ser Pro Val Asp Leu Ser Tyr
    290                 295                 300

Leu Ser Pro Lys Asn Pro Gly Thr Gly Pro Ala Phe Thr Ile Ile Asn
305                 310                 315                 320

Gly Thr Leu Lys Tyr Phe Glu Thr Arg Tyr Ile Arg Val Asp Ile Ala
                325                 330                 335

Gly Pro Ile Ile Pro Gln Met Arg Gly Val Ile Ser Gly Thr Thr Thr
            340                 345                 350

Glu Arg Glu Leu Trp Thr Asp Trp Pro Tyr Glu Asp Val Glu Ile
        355                 360                 365

Gly Pro Asn Gly Val Leu Lys Thr Ala Thr Gly Tyr Lys Phe Pro Leu
    370                 375                 380
```

```
Tyr Met Ile Gly His Gly Met Leu Asp Ser Asp Leu His Ile Ser Ser
385                 390                 395                 400

Lys Ala Gln Val Phe Glu His Pro His Ile Gln Asp Ala Ala Ser Gln
                405                 410                 415

Leu Pro Asp Asp Glu Met Leu Phe Phe Gly Asp Thr Gly Leu Ser Lys
            420                 425                 430

Asn Pro Ile Glu Leu Val Glu Gly Trp Phe Ser Gly Trp Lys Ser Thr
        435                 440                 445

Ile Ala Ser Phe Phe Phe Ile Ile Gly Leu Val Ile Gly Leu Tyr Leu
    450                 455                 460

Val Leu Arg Ile Gly Ile Ala Leu Cys Ile Lys Cys Arg Val Gln Glu
465                 470                 475                 480

Lys Arg Pro Lys Ile Tyr Thr Asp Val Glu Met Asn Arg Leu Asp Arg
                485                 490                 495


<210> SEQ ID NO 60
<211> LENGTH: 496
<212> TYPE: PRT
<213> ORGANISM: Artificial sequence
<220> FEATURE:
<223> OTHER INFORMATION: Glycoprotein Vesicular stomatitis Morreton
      virus Q22N T422V

<400> SEQUENCE: 60

Lys Phe Thr Ile Val Phe Pro His Asn Gln Lys Gly Asn Trp Lys Asn
1               5                   10                  15

Val Pro Ala Asn Tyr Asn Tyr Cys Pro Ser Ser Ser Asp Leu Asn Trp
            20                  25                  30

His Asn Gly Leu Ile Gly Thr Ser Leu Gln Val Lys Met Pro Lys Ser
        35                  40                  45

His Lys Ala Ile Gln Ala Asp Gly Trp Met Cys His Ala Ala Lys Trp
    50                  55                  60

Val Thr Thr Cys Asp Phe Arg Trp Tyr Gly Pro Lys Tyr Val Thr His
65                  70                  75                  80

Ser Ile Lys Ser Met Ile Pro Thr Val Asp Gln Cys Lys Glu Ser Ile
                85                  90                  95

Ala Gln Thr Lys Gln Gly Thr Trp Leu Asn Pro Gly Phe Pro Pro Gln
            100                 105                 110

Ser Cys Gly Tyr Ala Ser Val Thr Asp Ala Glu Ala Val Ile Val Lys
        115                 120                 125

Ala Thr Pro His Gln Val Leu Val Asp Glu Tyr Thr Gly Glu Trp Val
    130                 135                 140

Asp Ser Gln Phe Pro Thr Gly Lys Cys Asn Lys Asp Ile Cys Pro Thr
145                 150                 155                 160

Val His Asn Ser Thr Thr Trp His Ser Asp Tyr Lys Val Thr Gly Leu
                165                 170                 175

Cys Asp Ala Asn Leu Ile Ser Met Asp Ile Thr Phe Phe Ser Glu Asp
            180                 185                 190

Gly Lys Leu Thr Ser Leu Gly Lys Glu Gly Thr Gly Phe Arg Ser Asn
        195                 200                 205

Tyr Phe Ala Tyr Glu Asn Gly Asp Lys Ala Cys Arg Met Gln Tyr Cys
    210                 215                 220

Lys His Trp Gly Val Arg Leu Pro Ser Gly Val Trp Phe Glu Met Ala
225                 230                 235                 240
```

Asp Lys Asp Ile Tyr Asn Asp Ala Lys Phe Pro Asp Cys Pro Glu Gly
245 250 255

Ser Ser Ile Ala Ala Pro Ser Gln Thr Ser Val Asp Val Ser Leu Ile
260 265 270

Gln Asp Val Glu Arg Ile Leu Asp Tyr Ser Leu Cys Gln Glu Thr Trp
275 280 285

Ser Lys Ile Arg Ala His Leu Pro Ile Ser Pro Val Asp Leu Ser Tyr
290 295 300

Leu Ser Pro Lys Asn Pro Gly Thr Gly Pro Ala Phe Thr Ile Ile Asn
305 310 315 320

Gly Thr Leu Lys Tyr Phe Glu Thr Arg Tyr Ile Arg Val Asp Ile Ala
325 330 335

Gly Pro Ile Ile Pro Gln Met Arg Gly Val Ile Ser Gly Thr Thr Thr
340 345 350

Glu Arg Glu Leu Trp Thr Asp Trp Tyr Pro Tyr Glu Asp Val Glu Ile
355 360 365

Gly Pro Asn Gly Val Leu Lys Thr Ala Thr Gly Tyr Lys Phe Pro Leu
370 375 380

Tyr Met Ile Gly His Gly Met Leu Asp Ser Asp Leu His Ile Ser Ser
385 390 395 400

Lys Ala Gln Val Phe Glu His Pro His Ile Gln Asp Ala Ala Ser Gln
405 410 415

Leu Pro Asp Asp Glu Val Leu Phe Phe Gly Asp Thr Gly Leu Ser Lys
420 425 430

Asn Pro Ile Glu Leu Val Glu Gly Trp Phe Ser Gly Trp Lys Ser Thr
435 440 445

Ile Ala Ser Phe Phe Phe Ile Ile Gly Leu Val Ile Gly Leu Tyr Leu
450 455 460

Val Leu Arg Ile Gly Ile Ala Leu Cys Ile Lys Cys Arg Val Gln Glu
465 470 475 480

Lys Arg Pro Lys Ile Tyr Thr Asp Val Glu Met Asn Arg Leu Asp Arg
485 490 495

<210> SEQ ID NO 61
<211> LENGTH: 494
<212> TYPE: PRT
<213> ORGANISM: Artificial sequence
<220> FEATURE:
<223> OTHER INFORMATION: Glycoprotein Vesicular stomatitis Alagoa virus
R22N

<400> SEQUENCE: 61

Lys Phe Thr Ile Val Phe Pro Gln Ser Gln Lys Gly Asp Trp Lys Asp
1 5 10 15

Val Pro Pro Asn Tyr Asn Tyr Cys Pro Ser Ser Ala Asp Gln Asn Trp
20 25 30

His Gly Asp Leu Leu Gly Val Asn Ile Arg Ala Lys Met Pro Lys Val
35 40 45

His Lys Ala Ile Lys Ala Asp Gly Trp Met Cys His Ala Ala Lys Trp
50 55 60

Val Thr Thr Cys Asp Tyr Arg Trp Tyr Gly Pro Gln Tyr Ile Thr His
65 70 75 80

Ser Ile His Ser Phe Ile Pro Thr Lys Ala Gln Cys Glu Glu Ser Ile
85 90 95

```
Lys Gln Thr Lys Glu Gly Val Trp Ile Asn Pro Gly Phe Pro Pro Lys
            100                 105                 110

Asn Cys Gly Tyr Ala Ser Val Ser Asp Ala Glu Ser Ile Ile Val Gln
        115                 120                 125

Ala Thr Ala His Ser Val Met Ile Asp Glu Tyr Ser Gly Asp Trp Leu
    130                 135                 140

Asp Ser Gln Phe Pro Thr Gly Arg Cys Thr Gly Ser Thr Cys Glu Thr
145                 150                 155                 160

Ile His Asn Ser Thr Leu Trp Tyr Ala Asp Tyr Gln Val Thr Gly Leu
                165                 170                 175

Cys Asp Ser Ala Leu Val Ser Thr Glu Val Thr Phe Tyr Ser Glu Asp
            180                 185                 190

Gly Leu Met Thr Ser Ile Gly Arg Gln Asn Thr Gly Tyr Arg Ser Asn
        195                 200                 205

Tyr Phe Pro Tyr Glu Lys Gly Ala Ala Ala Cys Arg Met Lys Tyr Cys
    210                 215                 220

Thr His Glu Gly Ile Arg Leu Pro Ser Gly Val Trp Phe Glu Met Val
225                 230                 235                 240

Asp Lys Glu Leu Leu Glu Ser Val Gln Met Pro Glu Cys Pro Ala Gly
                245                 250                 255

Leu Thr Ile Ser Ala Pro Thr Gln Thr Ser Val Asp Val Ser Leu Ile
            260                 265                 270

Leu Asp Val Glu Arg Met Leu Asp Tyr Ser Leu Cys Gln Glu Thr Trp
        275                 280                 285

Ser Lys Val His Ser Gly Leu Pro Ile Ser Pro Val Asp Leu Gly Tyr
    290                 295                 300

Ile Ala Pro Lys Asn Pro Gly Ala Gly Pro Ala Phe Thr Ile Val Asn
305                 310                 315                 320

Gly Thr Leu Lys Tyr Phe Asp Thr Arg Tyr Leu Arg Ile Asp Ile Glu
                325                 330                 335

Gly Pro Val Leu Lys Lys Met Thr Gly Lys Val Ser Gly Thr Pro Thr
            340                 345                 350

Lys Arg Glu Leu Trp Thr Glu Trp Phe Pro Tyr Asp Asp Val Glu Ile
        355                 360                 365

Gly Pro Asn Gly Val Leu Lys Thr Pro Glu Gly Tyr Lys Phe Pro Leu
    370                 375                 380

Tyr Met Ile Gly His Gly Leu Leu Asp Ser Asp Leu Gln Lys Thr Ser
385                 390                 395                 400

Gln Ala Glu Val Phe His His Pro Gln Ile Ala Glu Ala Val Gln Lys
                405                 410                 415

Leu Pro Asp Asp Glu Thr Leu Phe Phe Gly Asp Thr Gly Ile Ser Lys
            420                 425                 430

Asn Pro Val Glu Val Ile Glu Gly Trp Phe Ser Asn Trp Arg Ser Ser
        435                 440                 445

Val Met Ala Ile Val Phe Ala Ile Leu Leu Leu Val Ile Thr Val Leu
    450                 455                 460

Met Val Arg Leu Cys Val Ala Phe Arg His Phe Cys Cys Gln Lys Arg
465                 470                 475                 480

His Lys Ile Tyr Asn Asp Leu Glu Met Asn Gln Leu Arg Arg
                485                 490
```

<210> SEQ ID NO 62
<211> LENGTH: 494

<212> TYPE: PRT
<213> ORGANISM: Artificial sequence
<220> FEATURE:
<223> OTHER INFORMATION: Glycoprotein Vesicular stomatitis Alagoa virus
T422I

<400> SEQUENCE: 62

```
Lys Phe Thr Ile Val Phe Pro Gln Ser Gln Lys Gly Asp Trp Lys Asp
1               5                   10                  15

Val Pro Pro Asn Tyr Arg Tyr Cys Pro Ser Ser Ala Asp Gln Asn Trp
            20                  25                  30

His Gly Asp Leu Leu Gly Val Asn Ile Arg Ala Lys Met Pro Lys Val
        35                  40                  45

His Lys Ala Ile Lys Ala Asp Gly Trp Met Cys His Ala Ala Lys Trp
    50                  55                  60

Val Thr Thr Cys Asp Tyr Arg Trp Tyr Gly Pro Gln Tyr Ile Thr His
65                  70                  75                  80

Ser Ile His Ser Phe Ile Pro Thr Lys Ala Gln Cys Glu Glu Ser Ile
                85                  90                  95

Lys Gln Thr Lys Glu Gly Val Trp Ile Asn Pro Gly Phe Pro Pro Lys
            100                 105                 110

Asn Cys Gly Tyr Ala Ser Val Ser Asp Ala Glu Ser Ile Ile Val Gln
        115                 120                 125

Ala Thr Ala His Ser Val Met Ile Asp Glu Tyr Ser Gly Asp Trp Leu
    130                 135                 140

Asp Ser Gln Phe Pro Thr Gly Arg Cys Thr Gly Ser Thr Cys Glu Thr
145                 150                 155                 160

Ile His Asn Ser Thr Leu Trp Tyr Ala Asp Tyr Gln Val Thr Gly Leu
                165                 170                 175

Cys Asp Ser Ala Leu Val Ser Thr Glu Val Thr Phe Tyr Ser Glu Asp
            180                 185                 190

Gly Leu Met Thr Ser Ile Gly Arg Gln Asn Thr Gly Tyr Arg Ser Asn
        195                 200                 205

Tyr Phe Pro Tyr Glu Lys Gly Ala Ala Ala Cys Arg Met Lys Tyr Cys
    210                 215                 220

Thr His Glu Gly Ile Arg Leu Pro Ser Gly Val Trp Phe Glu Met Val
225                 230                 235                 240

Asp Lys Glu Leu Leu Glu Ser Val Gln Met Pro Glu Cys Pro Ala Gly
                245                 250                 255

Leu Thr Ile Ser Ala Pro Thr Gln Thr Ser Val Asp Val Ser Leu Ile
            260                 265                 270

Leu Asp Val Glu Arg Met Leu Asp Tyr Ser Leu Cys Gln Glu Thr Trp
        275                 280                 285

Ser Lys Val His Ser Gly Leu Pro Ile Ser Pro Val Asp Leu Gly Tyr
    290                 295                 300

Ile Ala Pro Lys Asn Pro Gly Ala Gly Pro Ala Phe Thr Ile Val Asn
305                 310                 315                 320

Gly Thr Leu Lys Tyr Phe Asp Thr Arg Tyr Leu Arg Ile Asp Ile Glu
                325                 330                 335

Gly Pro Val Leu Lys Lys Met Thr Gly Lys Val Ser Gly Thr Pro Thr
            340                 345                 350

Lys Arg Glu Leu Trp Thr Glu Trp Phe Pro Tyr Asp Asp Val Glu Ile
        355                 360                 365

Gly Pro Asn Gly Val Leu Lys Thr Pro Glu Gly Tyr Lys Phe Pro Leu
    370                 375                 380
```

Tyr Met Ile Gly His Gly Leu Leu Asp Ser Asp Leu Gln Lys Thr Ser
385 390 395 400

Gln Ala Glu Val Phe His His Pro Gln Ile Ala Glu Ala Val Gln Lys
405 410 415

Leu Pro Asp Asp Glu Ile Leu Phe Phe Gly Asp Thr Gly Ile Ser Lys
420 425 430

Asn Pro Val Glu Val Ile Glu Gly Trp Phe Ser Asn Trp Arg Ser Ser
435 440 445

Val Met Ala Ile Val Phe Ala Ile Leu Leu Leu Val Ile Thr Val Leu
450 455 460

Met Val Arg Leu Cys Val Ala Phe Arg His Phe Cys Cys Gln Lys Arg
465 470 475 480

His Lys Ile Tyr Asn Asp Leu Glu Met Asn Gln Leu Arg Arg
485 490

<210> SEQ ID NO 63
<211> LENGTH: 494
<212> TYPE: PRT
<213> ORGANISM: Artificial sequence
<220> FEATURE:
<223> OTHER INFORMATION: Glycoprotein Vesicular stomatitis Alagoa virus T422L

<400> SEQUENCE: 63

Lys Phe Thr Ile Val Phe Pro Gln Ser Gln Lys Gly Asp Trp Lys Asp
1 5 10 15

Val Pro Pro Asn Tyr Arg Tyr Cys Pro Ser Ser Ala Asp Gln Asn Trp
20 25 30

His Gly Asp Leu Leu Gly Val Asn Ile Arg Ala Lys Met Pro Lys Val
35 40 45

His Lys Ala Ile Lys Ala Asp Gly Trp Met Cys His Ala Ala Lys Trp
50 55 60

Val Thr Thr Cys Asp Tyr Arg Trp Tyr Gly Pro Gln Tyr Ile Thr His
65 70 75 80

Ser Ile His Ser Phe Ile Pro Thr Lys Ala Gln Cys Glu Glu Ser Ile
85 90 95

Lys Gln Thr Lys Glu Gly Val Trp Ile Asn Pro Gly Phe Pro Pro Lys
100 105 110

Asn Cys Gly Tyr Ala Ser Val Ser Asp Ala Glu Ser Ile Ile Val Gln
115 120 125

Ala Thr Ala His Ser Val Met Ile Asp Glu Tyr Ser Gly Asp Trp Leu
130 135 140

Asp Ser Gln Phe Pro Thr Gly Arg Cys Thr Gly Ser Thr Cys Glu Thr
145 150 155 160

Ile His Asn Ser Thr Leu Trp Tyr Ala Asp Tyr Gln Val Thr Gly Leu
165 170 175

Cys Asp Ser Ala Leu Val Ser Thr Glu Val Thr Phe Tyr Ser Glu Asp
180 185 190

Gly Leu Met Thr Ser Ile Gly Arg Gln Asn Thr Gly Tyr Arg Ser Asn
195 200 205

Tyr Phe Pro Tyr Glu Lys Gly Ala Ala Ala Cys Arg Met Lys Tyr Cys
210 215 220

Thr His Glu Gly Ile Arg Leu Pro Ser Gly Val Trp Phe Glu Met Val
225 230 235 240

```
Asp Lys Glu Leu Leu Glu Ser Val Gln Met Pro Glu Cys Pro Ala Gly
                245                 250                 255

Leu Thr Ile Ser Ala Pro Thr Gln Thr Ser Val Asp Val Ser Leu Ile
            260                 265                 270

Leu Asp Val Glu Arg Met Leu Asp Tyr Ser Leu Cys Gln Glu Thr Trp
        275                 280                 285

Ser Lys Val His Ser Gly Leu Pro Ile Ser Pro Val Asp Leu Gly Tyr
    290                 295                 300

Ile Ala Pro Lys Asn Pro Gly Ala Gly Pro Ala Phe Thr Ile Val Asn
305                 310                 315                 320

Gly Thr Leu Lys Tyr Phe Asp Thr Arg Tyr Leu Arg Ile Asp Ile Glu
                325                 330                 335

Gly Pro Val Leu Lys Lys Met Thr Gly Lys Val Ser Gly Thr Pro Thr
            340                 345                 350

Lys Arg Glu Leu Trp Thr Glu Trp Phe Pro Tyr Asp Asp Val Glu Ile
        355                 360                 365

Gly Pro Asn Gly Val Leu Lys Thr Pro Glu Gly Tyr Lys Phe Pro Leu
    370                 375                 380

Tyr Met Ile Gly His Gly Leu Leu Asp Ser Asp Leu Gln Lys Thr Ser
385                 390                 395                 400

Gln Ala Glu Val Phe His His Pro Gln Ile Ala Glu Ala Val Gln Lys
                405                 410                 415

Leu Pro Asp Asp Glu Leu Leu Phe Phe Gly Asp Thr Gly Ile Ser Lys
            420                 425                 430

Asn Pro Val Glu Val Ile Glu Gly Trp Phe Ser Asn Trp Arg Ser Ser
        435                 440                 445

Val Met Ala Ile Val Phe Ala Ile Leu Leu Leu Val Ile Thr Val Leu
    450                 455                 460

Met Val Arg Leu Cys Val Ala Phe Arg His Phe Cys Cys Gln Lys Arg
465                 470                 475                 480

His Lys Ile Tyr Asn Asp Leu Glu Met Asn Gln Leu Arg Arg
                485                 490


<210> SEQ ID NO 64
<211> LENGTH: 494
<212> TYPE: PRT
<213> ORGANISM: Artificial sequence
<220> FEATURE:
<223> OTHER INFORMATION: Glycoprotein Vesicular stomatitis Alagoa virus
      T422F

<400> SEQUENCE: 64

Lys Phe Thr Ile Val Phe Pro Gln Ser Gln Lys Gly Asp Trp Lys Asp
1               5                   10                  15

Val Pro Pro Asn Tyr Arg Tyr Cys Pro Ser Ser Ala Asp Gln Asn Trp
            20                  25                  30

His Gly Asp Leu Leu Gly Val Asn Ile Arg Ala Lys Met Pro Lys Val
        35                  40                  45

His Lys Ala Ile Lys Ala Asp Gly Trp Met Cys His Ala Ala Lys Trp
    50                  55                  60

Val Thr Thr Cys Asp Tyr Arg Trp Tyr Gly Pro Gln Tyr Ile Thr His
65                  70                  75                  80

Ser Ile His Ser Phe Ile Pro Thr Lys Ala Gln Cys Glu Glu Ser Ile
                85                  90                  95
```

```
Lys Gln Thr Lys Glu Gly Val Trp Ile Asn Pro Gly Phe Pro Pro Lys
            100                 105                 110

Asn Cys Gly Tyr Ala Ser Val Ser Asp Ala Glu Ser Ile Ile Val Gln
        115                 120                 125

Ala Thr Ala His Ser Val Met Ile Asp Glu Tyr Ser Gly Asp Trp Leu
    130                 135                 140

Asp Ser Gln Phe Pro Thr Gly Arg Cys Thr Gly Ser Thr Cys Glu Thr
145                 150                 155                 160

Ile His Asn Ser Thr Leu Trp Tyr Ala Asp Tyr Gln Val Thr Gly Leu
                165                 170                 175

Cys Asp Ser Ala Leu Val Ser Thr Glu Val Thr Phe Tyr Ser Glu Asp
            180                 185                 190

Gly Leu Met Thr Ser Ile Gly Arg Gln Asn Thr Gly Tyr Arg Ser Asn
        195                 200                 205

Tyr Phe Pro Tyr Glu Lys Gly Ala Ala Ala Cys Arg Met Lys Tyr Cys
    210                 215                 220

Thr His Glu Gly Ile Arg Leu Pro Ser Gly Val Trp Phe Glu Met Val
225                 230                 235                 240

Asp Lys Glu Leu Leu Glu Ser Val Gln Met Pro Glu Cys Pro Ala Gly
                245                 250                 255

Leu Thr Ile Ser Ala Pro Thr Gln Thr Ser Val Asp Val Ser Leu Ile
            260                 265                 270

Leu Asp Val Glu Arg Met Leu Asp Tyr Ser Leu Cys Gln Glu Thr Trp
        275                 280                 285

Ser Lys Val His Ser Gly Leu Pro Ile Ser Pro Val Asp Leu Gly Tyr
    290                 295                 300

Ile Ala Pro Lys Asn Pro Gly Ala Gly Pro Ala Phe Thr Ile Val Asn
305                 310                 315                 320

Gly Thr Leu Lys Tyr Phe Asp Thr Arg Tyr Leu Arg Ile Asp Ile Glu
                325                 330                 335

Gly Pro Val Leu Lys Lys Met Thr Gly Lys Val Ser Gly Thr Pro Thr
            340                 345                 350

Lys Arg Glu Leu Trp Thr Glu Trp Phe Pro Tyr Asp Asp Val Glu Ile
        355                 360                 365

Gly Pro Asn Gly Val Leu Lys Thr Pro Glu Gly Tyr Lys Phe Pro Leu
    370                 375                 380

Tyr Met Ile Gly His Gly Leu Leu Asp Ser Asp Leu Gln Lys Thr Ser
385                 390                 395                 400

Gln Ala Glu Val Phe His His Pro Gln Ile Ala Glu Ala Val Gln Lys
                405                 410                 415

Leu Pro Asp Asp Glu Phe Leu Phe Phe Gly Asp Thr Gly Ile Ser Lys
            420                 425                 430

Asn Pro Val Glu Val Ile Glu Gly Trp Phe Ser Asn Trp Arg Ser Ser
        435                 440                 445

Val Met Ala Ile Val Phe Ala Ile Leu Leu Leu Val Ile Thr Val Leu
    450                 455                 460

Met Val Arg Leu Cys Val Ala Phe Arg His Phe Cys Cys Gln Lys Arg
465                 470                 475                 480

His Lys Ile Tyr Asn Asp Leu Glu Met Asn Gln Leu Arg Arg
                485                 490
```

<210> SEQ ID NO 65
<211> LENGTH: 494

```
<212> TYPE: PRT
<213> ORGANISM: Artificial sequence
<220> FEATURE:
<223> OTHER INFORMATION: Glycoprotein Vesicular stomatitis Alagoa virus
      T422M

<400> SEQUENCE: 65

Lys Phe Thr Ile Val Phe Pro Gln Ser Gln Lys Gly Asp Trp Lys Asp
1               5                   10                  15

Val Pro Pro Asn Tyr Arg Tyr Cys Pro Ser Ser Ala Asp Gln Asn Trp
            20                  25                  30

His Gly Asp Leu Leu Gly Val Asn Ile Arg Ala Lys Met Pro Lys Val
        35                  40                  45

His Lys Ala Ile Lys Ala Asp Gly Trp Met Cys His Ala Ala Lys Trp
    50                  55                  60

Val Thr Thr Cys Asp Tyr Arg Trp Tyr Gly Pro Gln Tyr Ile Thr His
65                  70                  75                  80

Ser Ile His Ser Phe Ile Pro Thr Lys Ala Gln Cys Glu Glu Ser Ile
                85                  90                  95

Lys Gln Thr Lys Glu Gly Val Trp Ile Asn Pro Gly Phe Pro Pro Lys
            100                 105                 110

Asn Cys Gly Tyr Ala Ser Val Ser Asp Ala Glu Ser Ile Ile Val Gln
        115                 120                 125

Ala Thr Ala His Ser Val Met Ile Asp Glu Tyr Ser Gly Asp Trp Leu
    130                 135                 140

Asp Ser Gln Phe Pro Thr Gly Arg Cys Thr Gly Ser Thr Cys Glu Thr
145                 150                 155                 160

Ile His Asn Ser Thr Leu Trp Tyr Ala Asp Tyr Gln Val Thr Gly Leu
                165                 170                 175

Cys Asp Ser Ala Leu Val Ser Thr Glu Val Thr Phe Tyr Ser Glu Asp
            180                 185                 190

Gly Leu Met Thr Ser Ile Gly Arg Gln Asn Thr Gly Tyr Arg Ser Asn
        195                 200                 205

Tyr Phe Pro Tyr Glu Lys Gly Ala Ala Ala Cys Arg Met Lys Tyr Cys
    210                 215                 220

Thr His Glu Gly Ile Arg Leu Pro Ser Gly Val Trp Phe Glu Met Val
225                 230                 235                 240

Asp Lys Glu Leu Leu Glu Ser Val Gln Met Pro Glu Cys Pro Ala Gly
                245                 250                 255

Leu Thr Ile Ser Ala Pro Thr Gln Thr Ser Val Asp Val Ser Leu Ile
            260                 265                 270

Leu Asp Val Glu Arg Met Leu Asp Tyr Ser Leu Cys Gln Glu Thr Trp
        275                 280                 285

Ser Lys Val His Ser Gly Leu Pro Ile Ser Pro Val Asp Leu Gly Tyr
    290                 295                 300

Ile Ala Pro Lys Asn Pro Gly Ala Gly Pro Ala Phe Thr Ile Val Asn
305                 310                 315                 320

Gly Thr Leu Lys Tyr Phe Asp Thr Arg Tyr Leu Arg Ile Asp Ile Glu
                325                 330                 335

Gly Pro Val Leu Lys Lys Met Thr Gly Lys Val Ser Gly Thr Pro Thr
            340                 345                 350

Lys Arg Glu Leu Trp Thr Glu Trp Phe Pro Tyr Asp Asp Val Glu Ile
        355                 360                 365

Gly Pro Asn Gly Val Leu Lys Thr Pro Glu Gly Tyr Lys Phe Pro Leu
    370                 375                 380
```

```
Tyr Met Ile Gly His Gly Leu Leu Asp Ser Asp Leu Gln Lys Thr Ser
385                 390                 395                 400

Gln Ala Glu Val Phe His His Pro Gln Ile Ala Glu Ala Val Gln Lys
                405                 410                 415

Leu Pro Asp Asp Glu Met Leu Phe Phe Gly Asp Thr Gly Ile Ser Lys
            420                 425                 430

Asn Pro Val Glu Val Ile Glu Gly Trp Phe Ser Asn Trp Arg Ser Ser
        435                 440                 445

Val Met Ala Ile Val Phe Ala Ile Leu Leu Leu Val Ile Thr Val Leu
    450                 455                 460

Met Val Arg Leu Cys Val Ala Phe Arg His Phe Cys Cys Gln Lys Arg
465                 470                 475                 480

His Lys Ile Tyr Asn Asp Leu Glu Met Asn Gln Leu Arg Arg
                485                 490


<210> SEQ ID NO 66
<211> LENGTH: 494
<212> TYPE: PRT
<213> ORGANISM: Artificial sequence
<220> FEATURE:
<223> OTHER INFORMATION: Glycoprotein Vesicular stomatitis Alagoa virus
      T422V

<400> SEQUENCE: 66

Lys Phe Thr Ile Val Phe Pro Gln Ser Gln Lys Gly Asp Trp Lys Asp
1               5                   10                  15

Val Pro Pro Asn Tyr Arg Tyr Cys Pro Ser Ser Ala Asp Gln Asn Trp
            20                  25                  30

His Gly Asp Leu Leu Gly Val Asn Ile Arg Ala Lys Met Pro Lys Val
        35                  40                  45

His Lys Ala Ile Lys Ala Asp Gly Trp Met Cys His Ala Ala Lys Trp
    50                  55                  60

Val Thr Thr Cys Asp Tyr Arg Trp Tyr Gly Pro Gln Tyr Ile Thr His
65                  70                  75                  80

Ser Ile His Ser Phe Ile Pro Thr Lys Ala Gln Cys Glu Glu Ser Ile
                85                  90                  95

Lys Gln Thr Lys Glu Gly Val Trp Ile Asn Pro Gly Phe Pro Pro Lys
            100                 105                 110

Asn Cys Gly Tyr Ala Ser Val Ser Asp Ala Glu Ser Ile Ile Val Gln
        115                 120                 125

Ala Thr Ala His Ser Val Met Ile Asp Glu Tyr Ser Gly Asp Trp Leu
    130                 135                 140

Asp Ser Gln Phe Pro Thr Gly Arg Cys Thr Gly Ser Thr Cys Glu Thr
145                 150                 155                 160

Ile His Asn Ser Thr Leu Trp Tyr Ala Asp Tyr Gln Val Thr Gly Leu
                165                 170                 175

Cys Asp Ser Ala Leu Val Ser Thr Glu Val Thr Phe Tyr Ser Glu Asp
            180                 185                 190

Gly Leu Met Thr Ser Ile Gly Arg Gln Asn Thr Gly Tyr Arg Ser Asn
        195                 200                 205

Tyr Phe Pro Tyr Glu Lys Gly Ala Ala Ala Cys Arg Met Lys Tyr Cys
    210                 215                 220

Thr His Glu Gly Ile Arg Leu Pro Ser Gly Val Trp Phe Glu Met Val
225                 230                 235                 240
```

```
Asp Lys Glu Leu Leu Glu Ser Val Gln Met Pro Glu Cys Pro Ala Gly
                245                 250                 255

Leu Thr Ile Ser Ala Pro Thr Gln Thr Ser Val Asp Val Ser Leu Ile
            260                 265                 270

Leu Asp Val Glu Arg Met Leu Asp Tyr Ser Leu Cys Gln Glu Thr Trp
        275                 280                 285

Ser Lys Val His Ser Gly Leu Pro Ile Ser Pro Val Asp Leu Gly Tyr
    290                 295                 300

Ile Ala Pro Lys Asn Pro Gly Ala Gly Pro Ala Phe Thr Ile Val Asn
305                 310                 315                 320

Gly Thr Leu Lys Tyr Phe Asp Thr Arg Tyr Leu Arg Ile Asp Ile Glu
                325                 330                 335

Gly Pro Val Leu Lys Lys Met Thr Gly Lys Val Ser Gly Thr Pro Thr
            340                 345                 350

Lys Arg Glu Leu Trp Thr Glu Trp Phe Pro Tyr Asp Asp Val Glu Ile
        355                 360                 365

Gly Pro Asn Gly Val Leu Lys Thr Pro Glu Gly Tyr Lys Phe Pro Leu
    370                 375                 380

Tyr Met Ile Gly His Gly Leu Leu Asp Ser Asp Leu Gln Lys Thr Ser
385                 390                 395                 400

Gln Ala Glu Val Phe His His Pro Gln Ile Ala Glu Ala Val Gln Lys
                405                 410                 415

Leu Pro Asp Asp Glu Val Leu Phe Phe Gly Asp Thr Gly Ile Ser Lys
            420                 425                 430

Asn Pro Val Glu Val Ile Glu Gly Trp Phe Ser Asn Trp Arg Ser Ser
        435                 440                 445

Val Met Ala Ile Val Phe Ala Ile Leu Leu Leu Val Ile Thr Val Leu
    450                 455                 460

Met Val Arg Leu Cys Val Ala Phe Arg His Phe Cys Cys Gln Lys Arg
465                 470                 475                 480

His Lys Ile Tyr Asn Asp Leu Glu Met Asn Gln Leu Arg Arg
                485                 490


<210> SEQ ID NO 67
<211> LENGTH: 494
<212> TYPE: PRT
<213> ORGANISM: Artificial sequence
<220> FEATURE:
<223> OTHER INFORMATION: Glycoprotein Vesicular stomatitis Alagoa virus
      R22N T422I

<400> SEQUENCE: 67

Lys Phe Thr Ile Val Phe Pro Gln Ser Gln Lys Gly Asp Trp Lys Asp
1               5                   10                  15

Val Pro Pro Asn Tyr Asn Tyr Cys Pro Ser Ser Ala Asp Gln Asn Trp
            20                  25                  30

His Gly Asp Leu Leu Gly Val Asn Ile Arg Ala Lys Met Pro Lys Val
        35                  40                  45

His Lys Ala Ile Lys Ala Asp Gly Trp Met Cys His Ala Ala Lys Trp
    50                  55                  60

Val Thr Thr Cys Asp Tyr Arg Trp Tyr Gly Pro Gln Tyr Ile Thr His
65                  70                  75                  80

Ser Ile His Ser Phe Ile Pro Thr Lys Ala Gln Cys Glu Glu Ser Ile
                85                  90                  95
```

```
Lys Gln Thr Lys Glu Gly Val Trp Ile Asn Pro Gly Phe Pro Pro Lys
            100                 105                 110

Asn Cys Gly Tyr Ala Ser Val Ser Asp Ala Glu Ser Ile Ile Val Gln
        115                 120                 125

Ala Thr Ala His Ser Val Met Ile Asp Glu Tyr Ser Gly Asp Trp Leu
    130                 135                 140

Asp Ser Gln Phe Pro Thr Gly Arg Cys Thr Gly Ser Thr Cys Glu Thr
145                 150                 155                 160

Ile His Asn Ser Thr Leu Trp Tyr Ala Asp Tyr Gln Val Thr Gly Leu
                165                 170                 175

Cys Asp Ser Ala Leu Val Ser Thr Glu Val Thr Phe Tyr Ser Glu Asp
            180                 185                 190

Gly Leu Met Thr Ser Ile Gly Arg Gln Asn Thr Gly Tyr Arg Ser Asn
        195                 200                 205

Tyr Phe Pro Tyr Glu Lys Gly Ala Ala Ala Cys Arg Met Lys Tyr Cys
    210                 215                 220

Thr His Glu Gly Ile Arg Leu Pro Ser Gly Val Trp Phe Glu Met Val
225                 230                 235                 240

Asp Lys Glu Leu Leu Glu Ser Val Gln Met Pro Glu Cys Pro Ala Gly
                245                 250                 255

Leu Thr Ile Ser Ala Pro Thr Gln Thr Ser Val Asp Val Ser Leu Ile
            260                 265                 270

Leu Asp Val Glu Arg Met Leu Asp Tyr Ser Leu Cys Gln Glu Thr Trp
        275                 280                 285

Ser Lys Val His Ser Gly Leu Pro Ile Ser Pro Val Asp Leu Gly Tyr
    290                 295                 300

Ile Ala Pro Lys Asn Pro Gly Ala Gly Pro Ala Phe Thr Ile Val Asn
305                 310                 315                 320

Gly Thr Leu Lys Tyr Phe Asp Thr Arg Tyr Leu Arg Ile Asp Ile Glu
                325                 330                 335

Gly Pro Val Leu Lys Lys Met Thr Gly Lys Val Ser Gly Thr Pro Thr
            340                 345                 350

Lys Arg Glu Leu Trp Thr Glu Trp Phe Pro Tyr Asp Asp Val Glu Ile
        355                 360                 365

Gly Pro Asn Gly Val Leu Lys Thr Pro Glu Gly Tyr Lys Phe Pro Leu
    370                 375                 380

Tyr Met Ile Gly His Gly Leu Leu Asp Ser Asp Leu Gln Lys Thr Ser
385                 390                 395                 400

Gln Ala Glu Val Phe His His Pro Gln Ile Ala Glu Ala Val Gln Lys
                405                 410                 415

Leu Pro Asp Asp Glu Ile Leu Phe Phe Gly Asp Thr Gly Ile Ser Lys
            420                 425                 430

Asn Pro Val Glu Val Ile Glu Gly Trp Phe Ser Asn Trp Arg Ser Ser
        435                 440                 445

Val Met Ala Ile Val Phe Ala Ile Leu Leu Leu Val Ile Thr Val Leu
    450                 455                 460

Met Val Arg Leu Cys Val Ala Phe Arg His Phe Cys Cys Gln Lys Arg
465                 470                 475                 480

His Lys Ile Tyr Asn Asp Leu Glu Met Asn Gln Leu Arg Arg
                485                 490
```

<210> SEQ ID NO 68
<211> LENGTH: 494

<212> TYPE: PRT
<213> ORGANISM: Artificial sequence
<220> FEATURE:
<223> OTHER INFORMATION: Glycoprotein Vesicular stomatitis Alagoa virus R22N T422L

<400> SEQUENCE: 68

```
Lys Phe Thr Ile Val Phe Pro Gln Ser Gln Lys Gly Asp Trp Lys Asp
1               5                   10                  15

Val Pro Pro Asn Tyr Asn Tyr Cys Pro Ser Ser Ala Asp Gln Asn Trp
            20                  25                  30

His Gly Asp Leu Leu Gly Val Asn Ile Arg Ala Lys Met Pro Lys Val
        35                  40                  45

His Lys Ala Ile Lys Ala Asp Gly Trp Met Cys His Ala Ala Lys Trp
    50                  55                  60

Val Thr Thr Cys Asp Tyr Arg Trp Tyr Gly Pro Gln Tyr Ile Thr His
65                  70                  75                  80

Ser Ile His Ser Phe Ile Pro Thr Lys Ala Gln Cys Glu Glu Ser Ile
                85                  90                  95

Lys Gln Thr Lys Glu Gly Val Trp Ile Asn Pro Gly Phe Pro Pro Lys
            100                 105                 110

Asn Cys Gly Tyr Ala Ser Val Ser Asp Ala Glu Ser Ile Ile Val Gln
        115                 120                 125

Ala Thr Ala His Ser Val Met Ile Asp Glu Tyr Ser Gly Asp Trp Leu
    130                 135                 140

Asp Ser Gln Phe Pro Thr Gly Arg Cys Thr Gly Ser Thr Cys Glu Thr
145                 150                 155                 160

Ile His Asn Ser Thr Leu Trp Tyr Ala Asp Tyr Gln Val Thr Gly Leu
                165                 170                 175

Cys Asp Ser Ala Leu Val Ser Thr Glu Val Thr Phe Tyr Ser Glu Asp
            180                 185                 190

Gly Leu Met Thr Ser Ile Gly Arg Gln Asn Thr Gly Tyr Arg Ser Asn
        195                 200                 205

Tyr Phe Pro Tyr Glu Lys Gly Ala Ala Ala Cys Arg Met Lys Tyr Cys
    210                 215                 220

Thr His Glu Gly Ile Arg Leu Pro Ser Gly Val Trp Phe Glu Met Val
225                 230                 235                 240

Asp Lys Glu Leu Leu Glu Ser Val Gln Met Pro Glu Cys Pro Ala Gly
                245                 250                 255

Leu Thr Ile Ser Ala Pro Thr Gln Thr Ser Val Asp Val Ser Leu Ile
            260                 265                 270

Leu Asp Val Glu Arg Met Leu Asp Tyr Ser Leu Cys Gln Glu Thr Trp
        275                 280                 285

Ser Lys Val His Ser Gly Leu Pro Ile Ser Pro Val Asp Leu Gly Tyr
    290                 295                 300

Ile Ala Pro Lys Asn Pro Gly Ala Gly Pro Ala Phe Thr Ile Val Asn
305                 310                 315                 320

Gly Thr Leu Lys Tyr Phe Asp Thr Arg Tyr Leu Arg Ile Asp Ile Glu
                325                 330                 335

Gly Pro Val Leu Lys Lys Met Thr Gly Lys Val Ser Gly Thr Pro Thr
            340                 345                 350

Lys Arg Glu Leu Trp Thr Glu Trp Phe Pro Tyr Asp Asp Val Glu Ile
        355                 360                 365

Gly Pro Asn Gly Val Leu Lys Thr Pro Glu Gly Tyr Lys Phe Pro Leu
    370                 375                 380
```

```
Tyr Met Ile Gly His Gly Leu Leu Asp Ser Asp Leu Gln Lys Thr Ser
385                 390                 395                 400

Gln Ala Glu Val Phe His His Pro Gln Ile Ala Glu Ala Val Gln Lys
                405                 410                 415

Leu Pro Asp Asp Glu Leu Leu Phe Phe Gly Asp Thr Gly Ile Ser Lys
            420                 425                 430

Asn Pro Val Glu Val Ile Glu Gly Trp Phe Ser Asn Trp Arg Ser Ser
        435                 440                 445

Val Met Ala Ile Val Phe Ala Ile Leu Leu Leu Val Ile Thr Val Leu
    450                 455                 460

Met Val Arg Leu Cys Val Ala Phe Arg His Phe Cys Cys Gln Lys Arg
465                 470                 475                 480

His Lys Ile Tyr Asn Asp Leu Glu Met Asn Gln Leu Arg Arg
                485                 490


<210> SEQ ID NO 69
<211> LENGTH: 494
<212> TYPE: PRT
<213> ORGANISM: Artificial sequence
<220> FEATURE:
<223> OTHER INFORMATION: Glycoprotein Vesicular stomatitis Alagoa virus
      R22N T422F

<400> SEQUENCE: 69

Lys Phe Thr Ile Val Phe Pro Gln Ser Gln Lys Gly Asp Trp Lys Asp
1               5                   10                  15

Val Pro Pro Asn Tyr Asn Tyr Cys Pro Ser Ser Ala Asp Gln Asn Trp
            20                  25                  30

His Gly Asp Leu Leu Gly Val Asn Ile Arg Ala Lys Met Pro Lys Val
        35                  40                  45

His Lys Ala Ile Lys Ala Asp Gly Trp Met Cys His Ala Ala Lys Trp
    50                  55                  60

Val Thr Thr Cys Asp Tyr Arg Trp Tyr Gly Pro Gln Tyr Ile Thr His
65                  70                  75                  80

Ser Ile His Ser Phe Ile Pro Thr Lys Ala Gln Cys Glu Glu Ser Ile
                85                  90                  95

Lys Gln Thr Lys Glu Gly Val Trp Ile Asn Pro Gly Phe Pro Pro Lys
            100                 105                 110

Asn Cys Gly Tyr Ala Ser Val Ser Asp Ala Glu Ser Ile Ile Val Gln
        115                 120                 125

Ala Thr Ala His Ser Val Met Ile Asp Glu Tyr Ser Gly Asp Trp Leu
    130                 135                 140

Asp Ser Gln Phe Pro Thr Gly Arg Cys Thr Gly Ser Thr Cys Glu Thr
145                 150                 155                 160

Ile His Asn Ser Thr Leu Trp Tyr Ala Asp Tyr Gln Val Thr Gly Leu
                165                 170                 175

Cys Asp Ser Ala Leu Val Ser Thr Glu Val Thr Phe Tyr Ser Glu Asp
            180                 185                 190

Gly Leu Met Thr Ser Ile Gly Arg Gln Asn Thr Gly Tyr Arg Ser Asn
        195                 200                 205

Tyr Phe Pro Tyr Glu Lys Gly Ala Ala Ala Cys Arg Met Lys Tyr Cys
    210                 215                 220

Thr His Glu Gly Ile Arg Leu Pro Ser Gly Val Trp Phe Glu Met Val
225                 230                 235                 240
```

```
Asp Lys Glu Leu Leu Glu Ser Val Gln Met Pro Glu Cys Pro Ala Gly
                245                 250                 255

Leu Thr Ile Ser Ala Pro Thr Gln Thr Ser Val Asp Val Ser Leu Ile
            260                 265                 270

Leu Asp Val Glu Arg Met Leu Asp Tyr Ser Leu Cys Gln Glu Thr Trp
        275                 280                 285

Ser Lys Val His Ser Gly Leu Pro Ile Ser Pro Val Asp Leu Gly Tyr
    290                 295                 300

Ile Ala Pro Lys Asn Pro Gly Ala Gly Pro Ala Phe Thr Ile Val Asn
305                 310                 315                 320

Gly Thr Leu Lys Tyr Phe Asp Thr Arg Tyr Leu Arg Ile Asp Ile Glu
                325                 330                 335

Gly Pro Val Leu Lys Lys Met Thr Gly Lys Val Ser Gly Thr Pro Thr
            340                 345                 350

Lys Arg Glu Leu Trp Thr Glu Trp Phe Pro Tyr Asp Asp Val Glu Ile
        355                 360                 365

Gly Pro Asn Gly Val Leu Lys Thr Pro Glu Gly Tyr Lys Phe Pro Leu
    370                 375                 380

Tyr Met Ile Gly His Gly Leu Leu Asp Ser Asp Leu Gln Lys Thr Ser
385                 390                 395                 400

Gln Ala Glu Val Phe His His Pro Gln Ile Ala Glu Ala Val Gln Lys
                405                 410                 415

Leu Pro Asp Asp Glu Phe Leu Phe Phe Gly Asp Thr Gly Ile Ser Lys
            420                 425                 430

Asn Pro Val Glu Val Ile Glu Gly Trp Phe Ser Asn Trp Arg Ser Ser
        435                 440                 445

Val Met Ala Ile Val Phe Ala Ile Leu Leu Leu Val Ile Thr Val Leu
    450                 455                 460

Met Val Arg Leu Cys Val Ala Phe Arg His Phe Cys Cys Gln Lys Arg
465                 470                 475                 480

His Lys Ile Tyr Asn Asp Leu Glu Met Asn Gln Leu Arg Arg
                485                 490
```

<210> SEQ ID NO 70
<211> LENGTH: 494
<212> TYPE: PRT
<213> ORGANISM: Artificial sequence
<220> FEATURE:
<223> OTHER INFORMATION: Glycoprotein Vesicular stomatitis Alagoa virus R22N T422M

<400> SEQUENCE: 70

```
Lys Phe Thr Ile Val Phe Pro Gln Ser Gln Lys Gly Asp Trp Lys Asp
1               5                   10                  15

Val Pro Pro Asn Tyr Asn Tyr Cys Pro Ser Ser Ala Asp Gln Asn Trp
            20                  25                  30

His Gly Asp Leu Leu Gly Val Asn Ile Arg Ala Lys Met Pro Lys Val
        35                  40                  45

His Lys Ala Ile Lys Ala Asp Gly Trp Met Cys His Ala Ala Lys Trp
    50                  55                  60

Val Thr Thr Cys Asp Tyr Arg Trp Tyr Gly Pro Gln Tyr Ile Thr His
65                  70                  75                  80

Ser Ile His Ser Phe Ile Pro Thr Lys Ala Gln Cys Glu Glu Ser Ile
                85                  90                  95
```

```
Lys Gln Thr Lys Glu Gly Val Trp Ile Asn Pro Gly Phe Pro Pro Lys
            100                 105                 110

Asn Cys Gly Tyr Ala Ser Val Ser Asp Ala Glu Ser Ile Ile Val Gln
        115                 120                 125

Ala Thr Ala His Ser Val Met Ile Asp Glu Tyr Ser Gly Asp Trp Leu
    130                 135                 140

Asp Ser Gln Phe Pro Thr Gly Arg Cys Thr Gly Ser Thr Cys Glu Thr
145                 150                 155                 160

Ile His Asn Ser Thr Leu Trp Tyr Ala Asp Tyr Gln Val Thr Gly Leu
                165                 170                 175

Cys Asp Ser Ala Leu Val Ser Thr Glu Val Thr Phe Tyr Ser Glu Asp
            180                 185                 190

Gly Leu Met Thr Ser Ile Gly Arg Gln Asn Thr Gly Tyr Arg Ser Asn
        195                 200                 205

Tyr Phe Pro Tyr Glu Lys Gly Ala Ala Ala Cys Arg Met Lys Tyr Cys
    210                 215                 220

Thr His Glu Gly Ile Arg Leu Pro Ser Gly Val Trp Phe Glu Met Val
225                 230                 235                 240

Asp Lys Glu Leu Leu Glu Ser Val Gln Met Pro Glu Cys Pro Ala Gly
                245                 250                 255

Leu Thr Ile Ser Ala Pro Thr Gln Thr Ser Val Asp Val Ser Leu Ile
            260                 265                 270

Leu Asp Val Glu Arg Met Leu Asp Tyr Ser Leu Cys Gln Glu Thr Trp
        275                 280                 285

Ser Lys Val His Ser Gly Leu Pro Ile Ser Pro Val Asp Leu Gly Tyr
    290                 295                 300

Ile Ala Pro Lys Asn Pro Gly Ala Gly Pro Ala Phe Thr Ile Val Asn
305                 310                 315                 320

Gly Thr Leu Lys Tyr Phe Asp Thr Arg Tyr Leu Arg Ile Asp Ile Glu
                325                 330                 335

Gly Pro Val Leu Lys Lys Met Thr Gly Lys Val Ser Gly Thr Pro Thr
            340                 345                 350

Lys Arg Glu Leu Trp Thr Glu Trp Phe Pro Tyr Asp Asp Val Glu Ile
        355                 360                 365

Gly Pro Asn Gly Val Leu Lys Thr Pro Glu Gly Tyr Lys Phe Pro Leu
    370                 375                 380

Tyr Met Ile Gly His Gly Leu Leu Asp Ser Asp Leu Gln Lys Thr Ser
385                 390                 395                 400

Gln Ala Glu Val Phe His His Pro Gln Ile Ala Glu Ala Val Gln Lys
                405                 410                 415

Leu Pro Asp Asp Glu Met Leu Phe Phe Gly Asp Thr Gly Ile Ser Lys
            420                 425                 430

Asn Pro Val Glu Val Ile Glu Gly Trp Phe Ser Asn Trp Arg Ser Ser
        435                 440                 445

Val Met Ala Ile Val Phe Ala Ile Leu Leu Leu Val Ile Thr Val Leu
    450                 455                 460

Met Val Arg Leu Cys Val Ala Phe Arg His Phe Cys Cys Gln Lys Arg
465                 470                 475                 480

His Lys Ile Tyr Asn Asp Leu Glu Met Asn Gln Leu Arg Arg
                485                 490

<210> SEQ ID NO 71
<211> LENGTH: 494
```

<212> TYPE: PRT
<213> ORGANISM: Artificial sequence
<220> FEATURE:
<223> OTHER INFORMATION: Glycoprotein Vesicular stomatitis Alagoa virus
R22N T422V

<400> SEQUENCE: 71

```
Lys Phe Thr Ile Val Phe Pro Gln Ser Gln Lys Gly Asp Trp Lys Asp
1               5                   10                  15

Val Pro Pro Asn Tyr Asn Tyr Cys Pro Ser Ser Ala Asp Gln Asn Trp
            20                  25                  30

His Gly Asp Leu Leu Gly Val Asn Ile Arg Ala Lys Met Pro Lys Val
        35                  40                  45

His Lys Ala Ile Lys Ala Asp Gly Trp Met Cys His Ala Ala Lys Trp
    50                  55                  60

Val Thr Thr Cys Asp Tyr Arg Trp Tyr Gly Pro Gln Tyr Ile Thr His
65                  70                  75                  80

Ser Ile His Ser Phe Ile Pro Thr Lys Ala Gln Cys Glu Glu Ser Ile
                85                  90                  95

Lys Gln Thr Lys Glu Gly Val Trp Ile Asn Pro Gly Phe Pro Pro Lys
            100                 105                 110

Asn Cys Gly Tyr Ala Ser Val Ser Asp Ala Glu Ser Ile Ile Val Gln
        115                 120                 125

Ala Thr Ala His Ser Val Met Ile Asp Glu Tyr Ser Gly Asp Trp Leu
    130                 135                 140

Asp Ser Gln Phe Pro Thr Gly Arg Cys Thr Gly Ser Thr Cys Glu Thr
145                 150                 155                 160

Ile His Asn Ser Thr Leu Trp Tyr Ala Asp Tyr Gln Val Thr Gly Leu
                165                 170                 175

Cys Asp Ser Ala Leu Val Ser Thr Glu Val Thr Phe Tyr Ser Glu Asp
            180                 185                 190

Gly Leu Met Thr Ser Ile Gly Arg Gln Asn Thr Gly Tyr Arg Ser Asn
        195                 200                 205

Tyr Phe Pro Tyr Glu Lys Gly Ala Ala Ala Cys Arg Met Lys Tyr Cys
    210                 215                 220

Thr His Glu Gly Ile Arg Leu Pro Ser Gly Val Trp Phe Glu Met Val
225                 230                 235                 240

Asp Lys Glu Leu Leu Glu Ser Val Gln Met Pro Glu Cys Pro Ala Gly
                245                 250                 255

Leu Thr Ile Ser Ala Pro Thr Gln Thr Ser Val Asp Val Ser Leu Ile
            260                 265                 270

Leu Asp Val Glu Arg Met Leu Asp Tyr Ser Leu Cys Gln Glu Thr Trp
        275                 280                 285

Ser Lys Val His Ser Gly Leu Pro Ile Ser Pro Val Asp Leu Gly Tyr
    290                 295                 300

Ile Ala Pro Lys Asn Pro Gly Ala Gly Pro Ala Phe Thr Ile Val Asn
305                 310                 315                 320

Gly Thr Leu Lys Tyr Phe Asp Thr Arg Tyr Leu Arg Ile Asp Ile Glu
                325                 330                 335

Gly Pro Val Leu Lys Lys Met Thr Gly Lys Val Ser Gly Thr Pro Thr
            340                 345                 350

Lys Arg Glu Leu Trp Thr Glu Trp Phe Pro Tyr Asp Asp Val Glu Ile
        355                 360                 365

Gly Pro Asn Gly Val Leu Lys Thr Pro Glu Gly Tyr Lys Phe Pro Leu
    370                 375                 380
```

Tyr Met Ile Gly His Gly Leu Leu Asp Ser Asp Leu Gln Lys Thr Ser
385 390 395 400

Gln Ala Glu Val Phe His His Pro Gln Ile Ala Glu Ala Val Gln Lys
405 410 415

Leu Pro Asp Asp Glu Val Leu Phe Phe Gly Asp Thr Gly Ile Ser Lys
420 425 430

Asn Pro Val Glu Val Ile Glu Gly Trp Phe Ser Asn Trp Arg Ser Ser
435 440 445

Val Met Ala Ile Val Phe Ala Ile Leu Leu Leu Val Ile Thr Val Leu
450 455 460

Met Val Arg Leu Cys Val Ala Phe Arg His Phe Cys Cys Gln Lys Arg
465 470 475 480

His Lys Ile Tyr Asn Asp Leu Glu Met Asn Gln Leu Arg Arg
485 490

<210> SEQ ID NO 72
<211> LENGTH: 501
<212> TYPE: PRT
<213> ORGANISM: Artificial sequence
<220> FEATURE:
<223> OTHER INFORMATION: Glycoprotein Vesicular stomatitis New Jersey
virus V429I

<400> SEQUENCE: 72

Lys Ile Glu Ile Val Phe Pro Gln His Thr Thr Gly Asp Trp Lys Arg
1 5 10 15

Val Pro His Glu Tyr Asn Tyr Cys Pro Thr Ser Ala Asp Lys Asn Ser
20 25 30

His Gly Thr Gln Thr Gly Ile Pro Val Glu Leu Thr Met Pro Lys Gly
35 40 45

Leu Thr Thr His Gln Val Asp Gly Phe Met Cys His Ser Ala Leu Trp
50 55 60

Met Thr Thr Cys Asp Phe Arg Trp Tyr Gly Pro Lys Tyr Ile Thr His
65 70 75 80

Ser Ile His Asn Glu Glu Pro Thr Asp Tyr Gln Cys Leu Glu Ala Ile
85 90 95

Lys Ala Tyr Lys Asp Gly Val Ser Phe Asn Pro Gly Phe Pro Pro Gln
100 105 110

Ser Cys Gly Tyr Gly Thr Val Thr Asp Ala Glu Ala His Ile Val Thr
115 120 125

Val Thr Pro His Ser Val Lys Val Asp Glu Tyr Thr Gly Glu Trp Ile
130 135 140

Asp Pro His Phe Ile Gly Gly Arg Cys Lys Gly Gln Ile Cys Glu Thr
145 150 155 160

Val His Asn Ser Thr Lys Trp Phe Thr Ser Ser Asp Gly Glu Ser Val
165 170 175

Cys Ser Gln Leu Phe Thr Leu Val Gly Gly Thr Phe Phe Ser Asp Ser
180 185 190

Glu Glu Ile Thr Ser Met Gly Leu Pro Glu Thr Gly Ile Arg Ser Asn
195 200 205

Tyr Phe Pro Tyr Val Ser Thr Glu Gly Ile Cys Lys Met Pro Phe Cys
210 215 220

Arg Lys Pro Gly Tyr Lys Leu Lys Asn Asp Leu Trp Phe Gln Ile Thr
225 230 235 240

```
Asp Pro Asp Leu Asp Lys Thr Val Arg Asp Leu Pro His Ile Lys Asp
                245                 250                 255

Cys Asp Leu Ser Ser Ser Ile Val Thr Pro Gly Glu His Ala Thr Asp
            260                 265                 270

Ile Ser Leu Ile Ser Asp Val Glu Arg Ile Leu Asp Tyr Ala Leu Cys
        275                 280                 285

Gln Asn Thr Trp Ser Lys Ile Glu Ala Gly Glu Pro Ile Thr Pro Val
    290                 295                 300

Asp Leu Ser Tyr Leu Gly Pro Lys Asn Pro Gly Ala Gly Pro Val Phe
305                 310                 315                 320

Thr Ile Ile Asn Gly Ser Leu His Tyr Phe Met Ser Lys Tyr Leu Arg
                325                 330                 335

Val Glu Leu Glu Ser Pro Val Ile Pro Arg Met Glu Gly Lys Val Ala
            340                 345                 350

Gly Thr Arg Ile Val Arg Gln Leu Trp Asp Gln Trp Phe Pro Phe Gly
        355                 360                 365

Glu Val Glu Ile Gly Pro Asn Gly Val Leu Lys Thr Lys Gln Gly Tyr
    370                 375                 380

Lys Phe Pro Leu His Ile Ile Gly Thr Gly Glu Val Asp Asn Asp Ile
385                 390                 395                 400

Lys Met Glu Arg Ile Val Lys His Trp Glu His Pro His Ile Glu Ala
                405                 410                 415

Ala Gln Thr Phe Leu Lys Lys Asp Asp Thr Glu Glu Ile Leu Tyr Tyr
            420                 425                 430

Gly Asp Thr Gly Val Ser Lys Asn Pro Val Glu Leu Val Glu Gly Trp
        435                 440                 445

Phe Ser Gly Trp Arg Ser Ser Ile Met Gly Val Leu Ala Val Ile Ile
    450                 455                 460

Gly Phe Val Ile Leu Ile Phe Leu Ile Arg Leu Ile Gly Val Leu Ser
465                 470                 475                 480

Ser Leu Phe Arg Gln Lys Arg Arg Pro Ile Tyr Lys Ser Asp Val Glu
                485                 490                 495

Met Ala His Phe Arg
            500


<210> SEQ ID NO 73
<211> LENGTH: 501
<212> TYPE: PRT
<213> ORGANISM: Artificial sequence
<220> FEATURE:
<223> OTHER INFORMATION: Glycoprotein Vesicular stomatitis New Jersey
      virus V429L

<400> SEQUENCE: 73

Lys Ile Glu Ile Val Phe Pro Gln His Thr Thr Gly Asp Trp Lys Arg
1               5                   10                  15

Val Pro His Glu Tyr Asn Tyr Cys Pro Thr Ser Ala Asp Lys Asn Ser
            20                  25                  30

His Gly Thr Gln Thr Gly Ile Pro Val Glu Leu Thr Met Pro Lys Gly
        35                  40                  45

Leu Thr Thr His Gln Val Asp Gly Phe Met Cys His Ser Ala Leu Trp
    50                  55                  60

Met Thr Thr Cys Asp Phe Arg Trp Tyr Gly Pro Lys Tyr Ile Thr His
65                  70                  75                  80
```

```
Ser Ile His Asn Glu Glu Pro Thr Asp Tyr Gln Cys Leu Glu Ala Ile
                85                  90                  95

Lys Ala Tyr Lys Asp Gly Val Ser Phe Asn Pro Gly Phe Pro Pro Gln
            100                 105                 110

Ser Cys Gly Tyr Gly Thr Val Thr Asp Ala Glu Ala His Ile Val Thr
        115                 120                 125

Val Thr Pro His Ser Val Lys Val Asp Glu Tyr Thr Gly Glu Trp Ile
    130                 135                 140

Asp Pro His Phe Ile Gly Gly Arg Cys Lys Gly Gln Ile Cys Glu Thr
145                 150                 155                 160

Val His Asn Ser Thr Lys Trp Phe Thr Ser Ser Asp Gly Glu Ser Val
                165                 170                 175

Cys Ser Gln Leu Phe Thr Leu Val Gly Gly Thr Phe Phe Ser Asp Ser
            180                 185                 190

Glu Glu Ile Thr Ser Met Gly Leu Pro Glu Thr Gly Ile Arg Ser Asn
        195                 200                 205

Tyr Phe Pro Tyr Val Ser Thr Glu Gly Ile Cys Lys Met Pro Phe Cys
    210                 215                 220

Arg Lys Pro Gly Tyr Lys Leu Lys Asn Asp Leu Trp Phe Gln Ile Thr
225                 230                 235                 240

Asp Pro Asp Leu Asp Lys Thr Val Arg Asp Leu Pro His Ile Lys Asp
                245                 250                 255

Cys Asp Leu Ser Ser Ser Ile Val Thr Pro Gly Glu His Ala Thr Asp
            260                 265                 270

Ile Ser Leu Ile Ser Asp Val Glu Arg Ile Leu Asp Tyr Ala Leu Cys
        275                 280                 285

Gln Asn Thr Trp Ser Lys Ile Glu Ala Gly Glu Pro Ile Thr Pro Val
    290                 295                 300

Asp Leu Ser Tyr Leu Gly Pro Lys Asn Pro Gly Ala Gly Pro Val Phe
305                 310                 315                 320

Thr Ile Ile Asn Gly Ser Leu His Tyr Phe Met Ser Lys Tyr Leu Arg
                325                 330                 335

Val Glu Leu Glu Ser Pro Val Ile Pro Arg Met Glu Gly Lys Val Ala
            340                 345                 350

Gly Thr Arg Ile Val Arg Gln Leu Trp Asp Gln Trp Phe Pro Phe Gly
        355                 360                 365

Glu Val Glu Ile Gly Pro Asn Gly Val Leu Lys Thr Lys Gln Gly Tyr
    370                 375                 380

Lys Phe Pro Leu His Ile Ile Gly Thr Gly Glu Val Asp Asn Asp Ile
385                 390                 395                 400

Lys Met Glu Arg Ile Val Lys His Trp Glu His Pro His Ile Glu Ala
                405                 410                 415

Ala Gln Thr Phe Leu Lys Lys Asp Asp Thr Glu Glu Val Leu Tyr Tyr
            420                 425                 430

Gly Asp Thr Gly Val Ser Lys Asn Pro Val Glu Leu Val Glu Gly Trp
        435                 440                 445

Phe Ser Gly Trp Arg Ser Ser Ile Met Gly Val Leu Ala Val Ile Ile
    450                 455                 460

Gly Phe Val Ile Leu Ile Phe Leu Ile Arg Leu Ile Gly Val Leu Ser
465                 470                 475                 480

Ser Leu Phe Arg Gln Lys Arg Arg Pro Ile Tyr Lys Ser Asp Val Glu
                485                 490                 495
```

```
Met Ala His Phe Arg
            500


<210> SEQ ID NO 74
<211> LENGTH: 501
<212> TYPE: PRT
<213> ORGANISM: Artificial sequence
<220> FEATURE:
<223> OTHER INFORMATION: Glycoprotein Vesicular stomatitis New Jersey
      virus V429F

<400> SEQUENCE: 74

Lys Ile Glu Ile Val Phe Pro Gln His Thr Thr Gly Asp Trp Lys Arg
1               5                   10                  15

Val Pro His Glu Tyr Asn Tyr Cys Pro Thr Ser Ala Asp Lys Asn Ser
            20                  25                  30

His Gly Thr Gln Thr Gly Ile Pro Val Glu Leu Thr Met Pro Lys Gly
        35                  40                  45

Leu Thr Thr His Gln Val Asp Gly Phe Met Cys His Ser Ala Leu Trp
    50                  55                  60

Met Thr Thr Cys Asp Phe Arg Trp Tyr Gly Pro Lys Tyr Ile Thr His
65                  70                  75                  80

Ser Ile His Asn Glu Glu Pro Thr Asp Tyr Gln Cys Leu Glu Ala Ile
                85                  90                  95

Lys Ala Tyr Lys Asp Gly Val Ser Phe Asn Pro Gly Phe Pro Pro Gln
            100                 105                 110

Ser Cys Gly Tyr Gly Thr Val Thr Asp Ala Glu Ala His Ile Val Thr
        115                 120                 125

Val Thr Pro His Ser Val Lys Val Asp Glu Tyr Thr Gly Glu Trp Ile
    130                 135                 140

Asp Pro His Phe Ile Gly Gly Arg Cys Lys Gly Gln Ile Cys Glu Thr
145                 150                 155                 160

Val His Asn Ser Thr Lys Trp Phe Thr Ser Ser Asp Gly Glu Ser Val
                165                 170                 175

Cys Ser Gln Leu Phe Thr Leu Val Gly Gly Thr Phe Phe Ser Asp Ser
            180                 185                 190

Glu Glu Ile Thr Ser Met Gly Leu Pro Glu Thr Gly Ile Arg Ser Asn
        195                 200                 205

Tyr Phe Pro Tyr Val Ser Thr Glu Gly Ile Cys Lys Met Pro Phe Cys
    210                 215                 220

Arg Lys Pro Gly Tyr Lys Leu Lys Asn Asp Leu Trp Phe Gln Ile Thr
225                 230                 235                 240

Asp Pro Asp Leu Asp Lys Thr Val Arg Asp Leu Pro His Ile Lys Asp
                245                 250                 255

Cys Asp Leu Ser Ser Ser Ile Val Thr Pro Gly Glu His Ala Thr Asp
            260                 265                 270

Ile Ser Leu Ile Ser Asp Val Glu Arg Ile Leu Asp Tyr Ala Leu Cys
        275                 280                 285

Gln Asn Thr Trp Ser Lys Ile Glu Ala Gly Glu Pro Ile Thr Pro Val
    290                 295                 300

Asp Leu Ser Tyr Leu Gly Pro Lys Asn Pro Gly Ala Gly Pro Val Phe
305                 310                 315                 320

Thr Ile Ile Asn Gly Ser Leu His Tyr Phe Met Ser Lys Tyr Leu Arg
                325                 330                 335

Val Glu Leu Glu Ser Pro Val Ile Pro Arg Met Glu Gly Lys Val Ala
            340                 345                 350
```

```
Gly Thr Arg Ile Val Arg Gln Leu Trp Asp Gln Trp Phe Pro Phe Gly
        355                 360                 365

Glu Val Glu Ile Gly Pro Asn Gly Val Leu Lys Thr Lys Gln Gly Tyr
    370                 375                 380

Lys Phe Pro Leu His Ile Ile Gly Thr Gly Glu Val Asp Asn Asp Ile
385                 390                 395                 400

Lys Met Glu Arg Ile Val Lys His Trp Glu His Pro His Ile Glu Ala
                405                 410                 415

Ala Gln Thr Phe Leu Lys Lys Asp Asp Thr Glu Glu Phe Leu Tyr Tyr
            420                 425                 430

Gly Asp Thr Gly Val Ser Lys Asn Pro Val Glu Leu Val Glu Gly Trp
        435                 440                 445

Phe Ser Gly Trp Arg Ser Ser Ile Met Gly Val Leu Ala Val Ile Ile
    450                 455                 460

Gly Phe Val Ile Leu Ile Phe Leu Ile Arg Leu Ile Gly Val Leu Ser
465                 470                 475                 480

Ser Leu Phe Arg Gln Lys Arg Arg Pro Ile Tyr Lys Ser Asp Val Glu
                485                 490                 495

Met Ala His Phe Arg
            500


<210> SEQ ID NO 75
<211> LENGTH: 501
<212> TYPE: PRT
<213> ORGANISM: Artificial sequence
<220> FEATURE:
<223> OTHER INFORMATION: Glycoprotein Vesicular stomatitis New Jersey
      virus V429M

<400> SEQUENCE: 75

Lys Ile Glu Ile Val Phe Pro Gln His Thr Thr Gly Asp Trp Lys Arg
1               5                   10                  15

Val Pro His Glu Tyr Asn Tyr Cys Pro Thr Ser Ala Asp Lys Asn Ser
            20                  25                  30

His Gly Thr Gln Thr Gly Ile Pro Val Glu Leu Thr Met Pro Lys Gly
        35                  40                  45

Leu Thr Thr His Gln Val Asp Gly Phe Met Cys His Ser Ala Leu Trp
    50                  55                  60

Met Thr Thr Cys Asp Phe Arg Trp Tyr Gly Pro Lys Tyr Ile Thr His
65                  70                  75                  80

Ser Ile His Asn Glu Glu Pro Thr Asp Tyr Gln Cys Leu Glu Ala Ile
                85                  90                  95

Lys Ala Tyr Lys Asp Gly Val Ser Phe Asn Pro Gly Phe Pro Pro Gln
            100                 105                 110

Ser Cys Gly Tyr Gly Thr Val Thr Asp Ala Glu Ala His Ile Val Thr
        115                 120                 125

Val Thr Pro His Ser Val Lys Val Asp Glu Tyr Thr Gly Glu Trp Ile
    130                 135                 140

Asp Pro His Phe Ile Gly Gly Arg Cys Lys Gly Gln Ile Cys Glu Thr
145                 150                 155                 160

Val His Asn Ser Thr Lys Trp Phe Thr Ser Ser Asp Gly Glu Ser Val
                165                 170                 175

Cys Ser Gln Leu Phe Thr Leu Val Gly Gly Thr Phe Phe Ser Asp Ser
            180                 185                 190
```

Glu Glu Ile Thr Ser Met Gly Leu Pro Glu Thr Gly Ile Arg Ser Asn
195 200 205

Tyr Phe Pro Tyr Val Ser Thr Glu Gly Ile Cys Lys Met Pro Phe Cys
210 215 220

Arg Lys Pro Gly Tyr Lys Leu Lys Asn Asp Leu Trp Phe Gln Ile Thr
225 230 235 240

Asp Pro Asp Leu Asp Lys Thr Val Arg Asp Leu Pro His Ile Lys Asp
245 250 255

Cys Asp Leu Ser Ser Ser Ile Val Thr Pro Gly Glu His Ala Thr Asp
260 265 270

Ile Ser Leu Ile Ser Asp Val Glu Arg Ile Leu Asp Tyr Ala Leu Cys
275 280 285

Gln Asn Thr Trp Ser Lys Ile Glu Ala Gly Glu Pro Ile Thr Pro Val
290 295 300

Asp Leu Ser Tyr Leu Gly Pro Lys Asn Pro Gly Ala Gly Pro Val Phe
305 310 315 320

Thr Ile Ile Asn Gly Ser Leu His Tyr Phe Met Ser Lys Tyr Leu Arg
325 330 335

Val Glu Leu Glu Ser Pro Val Ile Pro Arg Met Glu Gly Lys Val Ala
340 345 350

Gly Thr Arg Ile Val Arg Gln Leu Trp Asp Gln Trp Phe Pro Phe Gly
355 360 365

Glu Val Glu Ile Gly Pro Asn Gly Val Leu Lys Thr Lys Gln Gly Tyr
370 375 380

Lys Phe Pro Leu His Ile Ile Gly Thr Gly Glu Val Asp Asn Asp Ile
385 390 395 400

Lys Met Glu Arg Ile Val Lys His Trp Glu His Pro His Ile Glu Ala
405 410 415

Ala Gln Thr Phe Leu Lys Lys Asp Asp Thr Glu Glu Met Leu Tyr Tyr
420 425 430

Gly Asp Thr Gly Val Ser Lys Asn Pro Val Glu Leu Val Glu Gly Trp
435 440 445

Phe Ser Gly Trp Arg Ser Ser Ile Met Gly Val Leu Ala Val Ile Ile
450 455 460

Gly Phe Val Ile Leu Ile Phe Leu Ile Arg Leu Ile Gly Val Leu Ser
465 470 475 480

Ser Leu Phe Arg Gln Lys Arg Arg Pro Ile Tyr Lys Ser Asp Val Glu
485 490 495

Met Ala His Phe Arg
500

<210> SEQ ID NO 76
<211> LENGTH: 502
<212> TYPE: PRT
<213> ORGANISM: Artificial sequence
<220> FEATURE:
<223> OTHER INFORMATION: Glycoprotein Vesicular stomatitis Carajas virus
V426I

<400> SEQUENCE: 76

Lys Ile Thr Ile Ser Phe Pro Gln Ser Leu Lys Gly Asp Trp Arg Pro
1 5 10 15

Val Pro Lys Gly Tyr Asn Tyr Cys Pro Thr Ser Ala Asp Lys Asn Leu
20 25 30

```
His Gly Asp Leu Ile Asp Ile Gly Leu Arg Leu Arg Ala Pro Lys Ser
        35                  40                  45

Phe Lys Gly Ile Ser Ala Asp Gly Trp Met Cys His Ala Ala Arg Trp
    50                  55                  60

Ile Thr Thr Cys Asp Phe Arg Trp Tyr Gly Pro Lys Tyr Ile Thr His
65                  70                  75                  80

Ser Ile His Ser Phe Arg Pro Ser Asn Asp Gln Cys Lys Glu Ala Ile
                85                  90                  95

Arg Leu Thr Asn Glu Gly Asn Trp Ile Asn Pro Gly Phe Pro Pro Gln
            100                 105                 110

Ser Cys Gly Tyr Ala Ser Val Thr Asp Ser Glu Ser Val Val Val Thr
        115                 120                 125

Val Thr Lys His Gln Val Leu Val Asp Glu Tyr Ser Gly Ser Trp Ile
    130                 135                 140

Asp Ser Gln Phe Pro Gly Gly Ser Cys Thr Ser Pro Ile Cys Asp Thr
145                 150                 155                 160

Val His Asn Ser Thr Leu Trp His Ala Asp His Thr Leu Asp Ser Ile
                165                 170                 175

Cys Asp Gln Glu Phe Val Ala Met Asp Ala Val Leu Phe Thr Glu Ser
            180                 185                 190

Gly Lys Phe Glu Glu Phe Gly Lys Pro Asn Ser Gly Ile Arg Ser Asn
        195                 200                 205

Tyr Phe Pro Tyr Glu Ser Leu Lys Asp Val Cys Gln Met Asp Phe Cys
    210                 215                 220

Lys Arg Lys Gly Phe Lys Leu Pro Ser Gly Val Trp Phe Glu Ile Glu
225                 230                 235                 240

Asp Ala Glu Lys Ser His Lys Ala Gln Val Glu Leu Lys Ile Lys Arg
                245                 250                 255

Cys Pro His Gly Ala Val Ile Ser Ala Pro Asn Gln Asn Ala Ala Asp
            260                 265                 270

Ile Asn Leu Ile Met Asp Val Glu Arg Ile Leu Asp Tyr Ser Leu Cys
        275                 280                 285

Gln Ala Thr Trp Ser Lys Ile Gln Asn Lys Glu Ala Leu Thr Pro Ile
    290                 295                 300

Asp Ile Ser Tyr Leu Gly Pro Lys Asn Pro Gly Pro Gly Pro Ala Phe
305                 310                 315                 320

Thr Ile Ile Asn Gly Thr Leu His Tyr Phe Asn Thr Arg Tyr Ile Arg
                325                 330                 335

Val Asp Ile Ala Gly Pro Val Thr Lys Glu Ile Thr Gly Phe Val Ser
            340                 345                 350

Gly Thr Ser Thr Ser Arg Val Leu Trp Asp Gln Trp Phe Pro Tyr Gly
        355                 360                 365

Glu Asn Ser Ile Gly Pro Asn Gly Leu Leu Lys Thr Ala Ser Gly Tyr
    370                 375                 380

Lys Tyr Pro Leu Phe Met Val Gly Thr Gly Val Leu Asp Ala Asp Ile
385                 390                 395                 400

His Lys Leu Gly Glu Ala Thr Val Ile Glu His Pro His Ala Lys Glu
                405                 410                 415

Ala Gln Lys Val Val Asp Asp Ser Glu Ile Ile Phe Phe Gly Asp Thr
            420                 425                 430

Gly Val Ser Lys Asn Pro Val Glu Val Val Glu Gly Trp Phe Ser Gly
        435                 440                 445
```

```
Trp Arg Ser Ser Leu Met Ser Ile Phe Gly Ile Ile Leu Leu Ile Val
    450                 455                 460

Cys Leu Val Leu Ile Val Arg Ile Leu Ile Ala Leu Lys Tyr Cys Cys
465                 470                 475                 480

Val Arg His Lys Lys Arg Thr Ile Tyr Lys Glu Asp Leu Glu Met Gly
                485                 490                 495

Arg Ile Pro Arg Arg Ala
            500


<210> SEQ ID NO 77
<211> LENGTH: 502
<212> TYPE: PRT
<213> ORGANISM: Artificial sequence
<220> FEATURE:
<223> OTHER INFORMATION: Glycoprotein Vesicular stomatitis Carajas virus
      V426L

<400> SEQUENCE: 77

Lys Ile Thr Ile Ser Phe Pro Gln Ser Leu Lys Gly Asp Trp Arg Pro
1               5                   10                  15

Val Pro Lys Gly Tyr Asn Tyr Cys Pro Thr Ser Ala Asp Lys Asn Leu
            20                  25                  30

His Gly Asp Leu Ile Asp Ile Gly Leu Arg Leu Arg Ala Pro Lys Ser
        35                  40                  45

Phe Lys Gly Ile Ser Ala Asp Gly Trp Met Cys His Ala Ala Arg Trp
    50                  55                  60

Ile Thr Thr Cys Asp Phe Arg Trp Tyr Gly Pro Lys Tyr Ile Thr His
65                  70                  75                  80

Ser Ile His Ser Phe Arg Pro Ser Asn Asp Gln Cys Lys Glu Ala Ile
                85                  90                  95

Arg Leu Thr Asn Glu Gly Asn Trp Ile Asn Pro Gly Phe Pro Pro Gln
            100                 105                 110

Ser Cys Gly Tyr Ala Ser Val Thr Asp Ser Glu Ser Val Val Thr
        115                 120                 125

Val Thr Lys His Gln Val Leu Val Asp Glu Tyr Ser Gly Ser Trp Ile
    130                 135                 140

Asp Ser Gln Phe Pro Gly Gly Ser Cys Thr Ser Pro Ile Cys Asp Thr
145                 150                 155                 160

Val His Asn Ser Thr Leu Trp His Ala Asp His Thr Leu Asp Ser Ile
                165                 170                 175

Cys Asp Gln Glu Phe Val Ala Met Asp Ala Val Leu Phe Thr Glu Ser
            180                 185                 190

Gly Lys Phe Glu Glu Phe Gly Lys Pro Asn Ser Gly Ile Arg Ser Asn
        195                 200                 205

Tyr Phe Pro Tyr Glu Ser Leu Lys Asp Val Cys Gln Met Asp Phe Cys
    210                 215                 220

Lys Arg Lys Gly Phe Lys Leu Pro Ser Gly Val Trp Phe Glu Ile Glu
225                 230                 235                 240

Asp Ala Glu Lys Ser His Lys Ala Gln Val Glu Leu Lys Ile Lys Arg
                245                 250                 255

Cys Pro His Gly Ala Val Ile Ser Ala Pro Asn Gln Asn Ala Ala Asp
            260                 265                 270

Ile Asn Leu Ile Met Asp Val Glu Arg Ile Leu Asp Tyr Ser Leu Cys
        275                 280                 285

Gln Ala Thr Trp Ser Lys Ile Gln Asn Lys Glu Ala Leu Thr Pro Ile
    290                 295                 300
```

Asp Ile Ser Tyr Leu Gly Pro Lys Asn Pro Gly Pro Gly Pro Ala Phe
305 310 315 320

Thr Ile Ile Asn Gly Thr Leu His Tyr Phe Asn Thr Arg Tyr Ile Arg
325 330 335

Val Asp Ile Ala Gly Pro Val Thr Lys Glu Ile Thr Gly Phe Val Ser
340 345 350

Gly Thr Ser Thr Ser Arg Val Leu Trp Asp Gln Trp Phe Pro Tyr Gly
355 360 365

Glu Asn Ser Ile Gly Pro Asn Gly Leu Leu Lys Thr Ala Ser Gly Tyr
370 375 380

Lys Tyr Pro Leu Phe Met Val Gly Thr Gly Val Leu Asp Ala Asp Ile
385 390 395 400

His Lys Leu Gly Glu Ala Thr Val Ile Glu His Pro His Ala Lys Glu
405 410 415

Ala Gln Lys Val Val Asp Asp Ser Glu Ile Leu Phe Phe Gly Asp Thr
420 425 430

Gly Val Ser Lys Asn Pro Val Glu Val Val Glu Gly Trp Phe Ser Gly
435 440 445

Trp Arg Ser Ser Leu Met Ser Ile Phe Gly Ile Ile Leu Leu Ile Val
450 455 460

Cys Leu Val Leu Ile Val Arg Ile Leu Ile Ala Leu Lys Tyr Cys Cys
465 470 475 480

Val Arg His Lys Lys Arg Thr Ile Tyr Lys Glu Asp Leu Glu Met Gly
485 490 495

Arg Ile Pro Arg Arg Ala
500

<210> SEQ ID NO 78
<211> LENGTH: 502
<212> TYPE: PRT
<213> ORGANISM: Artificial sequence
<220> FEATURE:
<223> OTHER INFORMATION: Glycoprotein Vesicular stomatitis Carajas virus V426F

<400> SEQUENCE: 78

Lys Ile Thr Ile Ser Phe Pro Gln Ser Leu Lys Gly Asp Trp Arg Pro
1 5 10 15

Val Pro Lys Gly Tyr Asn Tyr Cys Pro Thr Ser Ala Asp Lys Asn Leu
20 25 30

His Gly Asp Leu Ile Asp Ile Gly Leu Arg Leu Arg Ala Pro Lys Ser
35 40 45

Phe Lys Gly Ile Ser Ala Asp Gly Trp Met Cys His Ala Ala Arg Trp
50 55 60

Ile Thr Thr Cys Asp Phe Arg Trp Tyr Gly Pro Lys Tyr Ile Thr His
65 70 75 80

Ser Ile His Ser Phe Arg Pro Ser Asn Asp Gln Cys Lys Glu Ala Ile
85 90 95

Arg Leu Thr Asn Glu Gly Asn Trp Ile Asn Pro Gly Phe Pro Pro Gln
100 105 110

Ser Cys Gly Tyr Ala Ser Val Thr Asp Ser Glu Ser Val Val Val Thr
115 120 125

Val Thr Lys His Gln Val Leu Val Asp Glu Tyr Ser Gly Ser Trp Ile
130 135 140

Asp Ser Gln Phe Pro Gly Gly Ser Cys Thr Ser Pro Ile Cys Asp Thr
145 150 155 160

Val His Asn Ser Thr Leu Trp His Ala Asp His Thr Leu Asp Ser Ile
165 170 175

Cys Asp Gln Glu Phe Val Ala Met Asp Ala Val Leu Phe Thr Glu Ser
180 185 190

Gly Lys Phe Glu Glu Phe Gly Lys Pro Asn Ser Gly Ile Arg Ser Asn
195 200 205

Tyr Phe Pro Tyr Glu Ser Leu Lys Asp Val Cys Gln Met Asp Phe Cys
210 215 220

Lys Arg Lys Gly Phe Lys Leu Pro Ser Gly Val Trp Phe Glu Ile Glu
225 230 235 240

Asp Ala Glu Lys Ser His Lys Ala Gln Val Glu Leu Lys Ile Lys Arg
245 250 255

Cys Pro His Gly Ala Val Ile Ser Ala Pro Asn Gln Asn Ala Ala Asp
260 265 270

Ile Asn Leu Ile Met Asp Val Glu Arg Ile Leu Asp Tyr Ser Leu Cys
275 280 285

Gln Ala Thr Trp Ser Lys Ile Gln Asn Lys Glu Ala Leu Thr Pro Ile
290 295 300

Asp Ile Ser Tyr Leu Gly Pro Lys Asn Pro Gly Pro Gly Pro Ala Phe
305 310 315 320

Thr Ile Ile Asn Gly Thr Leu His Tyr Phe Asn Thr Arg Tyr Ile Arg
325 330 335

Val Asp Ile Ala Gly Pro Val Thr Lys Glu Ile Thr Gly Phe Val Ser
340 345 350

Gly Thr Ser Thr Ser Arg Val Leu Trp Asp Gln Trp Phe Pro Tyr Gly
355 360 365

Glu Asn Ser Ile Gly Pro Asn Gly Leu Leu Lys Thr Ala Ser Gly Tyr
370 375 380

Lys Tyr Pro Leu Phe Met Val Gly Thr Gly Val Leu Asp Ala Asp Ile
385 390 395 400

His Lys Leu Gly Glu Ala Thr Val Ile Glu His Pro His Ala Lys Glu
405 410 415

Ala Gln Lys Val Val Asp Asp Ser Glu Ile Val Phe Phe Gly Asp Thr
420 425 430

Gly Val Ser Lys Asn Pro Val Glu Val Val Glu Gly Trp Phe Ser Gly
435 440 445

Trp Arg Ser Ser Leu Met Ser Ile Phe Gly Ile Ile Leu Leu Ile Val
450 455 460

Cys Leu Val Leu Ile Val Arg Ile Leu Ile Ala Leu Lys Tyr Cys Cys
465 470 475 480

Val Arg His Lys Lys Arg Thr Ile Tyr Lys Glu Asp Leu Glu Met Gly
485 490 495

Arg Ile Pro Arg Arg Ala
500

<210> SEQ ID NO 79
<211> LENGTH: 502
<212> TYPE: PRT
<213> ORGANISM: Artificial sequence
<220> FEATURE:
<223> OTHER INFORMATION: Glycoprotein Vesicular stomatitis Carajas virus
V426M

<400> SEQUENCE: 79

```
Lys Ile Thr Ile Ser Phe Pro Gln Ser Leu Lys Gly Asp Trp Arg Pro
1               5                   10                  15

Val Pro Lys Gly Tyr Asn Tyr Cys Pro Thr Ser Ala Asp Lys Asn Leu
            20                  25                  30

His Gly Asp Leu Ile Asp Ile Gly Leu Arg Leu Arg Ala Pro Lys Ser
        35                  40                  45

Phe Lys Gly Ile Ser Ala Asp Gly Trp Met Cys His Ala Ala Arg Trp
    50                  55                  60

Ile Thr Thr Cys Asp Phe Arg Trp Tyr Gly Pro Lys Tyr Ile Thr His
65                  70                  75                  80

Ser Ile His Ser Phe Arg Pro Ser Asn Asp Gln Cys Lys Glu Ala Ile
                85                  90                  95

Arg Leu Thr Asn Glu Gly Asn Trp Ile Asn Pro Gly Phe Pro Pro Gln
            100                 105                 110

Ser Cys Gly Tyr Ala Ser Val Thr Asp Ser Glu Ser Val Val Val Thr
        115                 120                 125

Val Thr Lys His Gln Val Leu Val Asp Glu Tyr Ser Gly Ser Trp Ile
    130                 135                 140

Asp Ser Gln Phe Pro Gly Gly Ser Cys Thr Ser Pro Ile Cys Asp Thr
145                 150                 155                 160

Val His Asn Ser Thr Leu Trp His Ala Asp His Thr Leu Asp Ser Ile
                165                 170                 175

Cys Asp Gln Glu Phe Val Ala Met Asp Ala Val Leu Phe Thr Glu Ser
            180                 185                 190

Gly Lys Phe Glu Glu Phe Gly Lys Pro Asn Ser Gly Ile Arg Ser Asn
        195                 200                 205

Tyr Phe Pro Tyr Glu Ser Leu Lys Asp Val Cys Gln Met Asp Phe Cys
    210                 215                 220

Lys Arg Lys Gly Phe Lys Leu Pro Ser Gly Val Trp Phe Glu Ile Glu
225                 230                 235                 240

Asp Ala Glu Lys Ser His Lys Ala Gln Val Glu Leu Lys Ile Lys Arg
                245                 250                 255

Cys Pro His Gly Ala Val Ile Ser Ala Pro Asn Gln Asn Ala Ala Asp
            260                 265                 270

Ile Asn Leu Ile Met Asp Val Glu Arg Ile Leu Asp Tyr Ser Leu Cys
        275                 280                 285

Gln Ala Thr Trp Ser Lys Ile Gln Asn Lys Glu Ala Leu Thr Pro Ile
    290                 295                 300

Asp Ile Ser Tyr Leu Gly Pro Lys Asn Pro Gly Pro Gly Pro Ala Phe
305                 310                 315                 320

Thr Ile Ile Asn Gly Thr Leu His Tyr Phe Asn Thr Arg Tyr Ile Arg
                325                 330                 335

Val Asp Ile Ala Gly Pro Val Thr Lys Glu Ile Thr Gly Phe Val Ser
            340                 345                 350

Gly Thr Ser Thr Ser Arg Val Leu Trp Asp Gln Trp Phe Pro Tyr Gly
        355                 360                 365

Glu Asn Ser Ile Gly Pro Asn Gly Leu Leu Lys Thr Ala Ser Gly Tyr
    370                 375                 380

Lys Tyr Pro Leu Phe Met Val Gly Thr Gly Val Leu Asp Ala Asp Ile
385                 390                 395                 400

His Lys Leu Gly Glu Ala Thr Val Ile Glu His Pro His Ala Lys Glu
                405                 410                 415
```

```
Ala Gln Lys Val Val Asp Asp Ser Glu Ile Met Phe Phe Gly Asp Thr
            420                 425                 430

Gly Val Ser Lys Asn Pro Val Glu Val Val Glu Gly Trp Phe Ser Gly
        435                 440                 445

Trp Arg Ser Ser Leu Met Ser Ile Phe Gly Ile Ile Leu Leu Ile Val
    450                 455                 460

Cys Leu Val Leu Ile Val Arg Ile Leu Ile Ala Leu Lys Tyr Cys Cys
465                 470                 475                 480

Val Arg His Lys Lys Arg Thr Ile Tyr Lys Glu Asp Leu Glu Met Gly
                485                 490                 495

Arg Ile Pro Arg Arg Ala
            500


<210> SEQ ID NO 80
<211> LENGTH: 114
<212> TYPE: PRT
<213> ORGANISM: Artificial sequence
<220> FEATURE:
<223> OTHER INFORMATION: anti-GFP nanobody

<400> SEQUENCE: 80

Val Gln Leu Val Glu Ser Gly Gly Ala Leu Val Gln Pro Gly Gly Ser
1               5                   10                  15

Leu Arg Leu Ser Cys Ala Ala Ser Gly Phe Pro Val Asn Arg Tyr Ser
            20                  25                  30

Met Arg Trp Tyr Arg Gln Ala Pro Gly Lys Glu Arg Glu Trp Val Ala
        35                  40                  45

Gly Met Ser Ser Ala Gly Asp Arg Ser Ser Tyr Glu Asp Ser Val Lys
    50                  55                  60

Gly Arg Phe Thr Ile Ser Arg Asp Asp Ala Arg Asn Thr Val Tyr Leu
65                  70                  75                  80

Gln Met Asn Ser Leu Lys Pro Glu Asp Thr Ala Val Tyr Tyr Cys Asn
                85                  90                  95

Val Asn Val Gly Phe Glu Tyr Trp Gly Gln Gly Thr Gln Val Thr Val
            100                 105                 110

Ser Ser


<210> SEQ ID NO 81
<211> LENGTH: 10
<212> TYPE: PRT
<213> ORGANISM: Artificial sequence
<220> FEATURE:
<223> OTHER INFORMATION: Linker

<400> SEQUENCE: 81

Gly Gly Gly Gly Ser Gly Gly Gly Gly Ser
1               5                   10


<210> SEQ ID NO 82
<211> LENGTH: 637
<212> TYPE: PRT
<213> ORGANISM: Artificial sequence
<220> FEATURE:
<223> OTHER INFORMATION: Fusion polypeptide (signal peptide-QS-anti-GFP
      nanobody-linker-VSV Indiana G ectodomain H22N S422I)

<400> SEQUENCE: 82

Met Lys Cys Leu Leu Tyr Leu Ala Phe Leu Phe Ile Gly Val Asn Cys
1               5                   10                  15
```

```
Gln Ser Val Gln Leu Val Glu Ser Gly Gly Ala Leu Val Gln Pro Gly
            20                  25                  30

Gly Ser Leu Arg Leu Ser Cys Ala Ala Ser Gly Phe Pro Val Asn Arg
        35                  40                  45

Tyr Ser Met Arg Trp Tyr Arg Gln Ala Pro Gly Lys Glu Arg Glu Trp
    50                  55                  60

Val Ala Gly Met Ser Ser Ala Gly Asp Arg Ser Ser Tyr Glu Asp Ser
65                  70                  75                  80

Val Lys Gly Arg Phe Thr Ile Ser Arg Asp Asp Ala Arg Asn Thr Val
                85                  90                  95

Tyr Leu Gln Met Asn Ser Leu Lys Pro Glu Asp Thr Ala Val Tyr Tyr
            100                 105                 110

Cys Asn Val Asn Val Gly Phe Glu Tyr Trp Gly Gln Gly Thr Gln Val
        115                 120                 125

Thr Val Ser Ser Gly Gly Gly Gly Ser Gly Gly Gly Gly Ser Lys Phe
    130                 135                 140

Thr Ile Val Phe Pro His Asn Gln Lys Gly Asn Trp Lys Asn Val Pro
145                 150                 155                 160

Ser Asn Tyr Asn Tyr Cys Pro Ser Ser Ser Asp Leu Asn Trp His Asn
                165                 170                 175

Asp Leu Ile Gly Thr Ala Leu Gln Val Lys Met Pro Lys Ser His Lys
            180                 185                 190

Ala Ile Gln Ala Asp Gly Trp Met Cys His Ala Ser Lys Trp Val Thr
        195                 200                 205

Thr Cys Asp Phe Arg Trp Tyr Gly Pro Lys Tyr Ile Thr His Ser Ile
    210                 215                 220

Arg Ser Phe Thr Pro Ser Val Glu Gln Cys Lys Glu Ser Ile Glu Gln
225                 230                 235                 240

Thr Lys Gln Gly Thr Trp Leu Asn Pro Gly Phe Pro Pro Gln Ser Cys
                245                 250                 255

Gly Tyr Ala Thr Val Thr Asp Ala Glu Ala Val Ile Val Gln Val Thr
            260                 265                 270

Pro His His Val Leu Val Asp Glu Tyr Thr Gly Glu Trp Val Asp Ser
        275                 280                 285

Gln Phe Ile Asn Gly Lys Cys Ser Asn Tyr Ile Cys Pro Thr Val His
    290                 295                 300

Asn Ser Thr Thr Trp His Ser Asp Tyr Lys Val Lys Gly Leu Cys Asp
305                 310                 315                 320

Ser Asn Leu Ile Ser Met Asp Ile Thr Phe Phe Ser Glu Asp Gly Glu
                325                 330                 335

Leu Ser Ser Leu Gly Lys Glu Gly Thr Gly Phe Arg Ser Asn Tyr Phe
            340                 345                 350

Ala Tyr Glu Thr Gly Gly Lys Ala Cys Lys Met Gln Tyr Cys Lys His
        355                 360                 365

Trp Gly Val Arg Leu Pro Ser Gly Val Trp Phe Glu Met Ala Asp Lys
    370                 375                 380

Asp Leu Phe Ala Ala Ala Arg Phe Pro Glu Cys Pro Glu Gly Ser Ser
385                 390                 395                 400

Ile Ser Ala Pro Ser Gln Thr Ser Val Asp Val Ser Leu Ile Gln Asp
                405                 410                 415

Val Glu Arg Ile Leu Asp Tyr Ser Leu Cys Gln Glu Thr Trp Ser Lys
            420                 425                 430
```

```
Ile Arg Ala Gly Leu Pro Ile Ser Pro Val Asp Leu Ser Tyr Leu Ala
        435                 440                 445

Pro Lys Asn Pro Gly Thr Gly Pro Ala Phe Thr Ile Ile Asn Gly Thr
    450                 455                 460

Leu Lys Tyr Phe Glu Thr Arg Tyr Ile Arg Val Asp Ile Ala Ala Pro
465                 470                 475                 480

Ile Leu Ser Arg Met Val Gly Met Ile Ser Gly Thr Thr Thr Glu Arg
                485                 490                 495

Glu Leu Trp Asp Asp Trp Ala Pro Tyr Glu Asp Val Glu Ile Gly Pro
            500                 505                 510

Asn Gly Val Leu Arg Thr Ser Ser Gly Tyr Lys Phe Pro Leu Tyr Met
        515                 520                 525

Ile Gly His Gly Met Leu Asp Ser Asp Leu His Leu Ser Ser Lys Ala
    530                 535                 540

Gln Val Phe Glu His Pro His Ile Gln Asp Ala Ala Ser Gln Leu Pro
545                 550                 555                 560

Asp Asp Glu Ile Leu Phe Phe Gly Asp Thr Gly Leu Ser Lys Asn Pro
                565                 570                 575

Ile Glu Leu Val Glu Gly Trp Phe Ser Ser Trp Lys Ser Ser Ile Ala
            580                 585                 590

Ser Phe Phe Phe Ile Ile Gly Leu Ile Ile Gly Leu Phe Leu Val Leu
        595                 600                 605

Arg Val Gly Ile His Leu Cys Ile Lys Leu Lys His Thr Lys Lys Arg
    610                 615                 620

Gln Ile Tyr Thr Asp Ile Glu Met Asn Arg Leu Gly Lys
625                 630                 635
```

<210> SEQ ID NO 83
<211> LENGTH: 1536
<212> TYPE: DNA
<213> ORGANISM: Vesicular stomatitis Indiana virus

<400> SEQUENCE: 83

```
atgaagtgcc ttttgtactt agccttttta ttcattgggg tgaattgcaa gttcaccata      60

gtttttccac acaaccaaaa aggaaactgg aaaaatgttc cttctaatta ccattattgc     120

ccgtcaagct cagatttaaa ttggcataat gacttaatag gcacagcatt acaagtcaaa     180

atgcccaaga gtcacaaggc tattcaagca gacggttgga tgtgtcatgc ttccaaatgg     240

gtcactactt gtgatttccg ctggtatgga ccgaagtata taacacattc catccgatcc     300

ttcactccat ctgtagaaca atgcaaggaa agcattgaac aaacgaaaca aggaacttgg     360

ctgaatccag gcttccctcc tcaaagttgt ggatatgcaa ctgtgacgga tgccgaagca     420

gtgattgtcc aggtgactcc tcaccatgtg ctggttgatg aatacacagg agaatgggtt     480

gattcacagt tcatcaacgg aaaatgcagc aattacatat gccccactgt ccataactct     540

acaacctggc attctgacta taaggtcaaa gggctatgtg attctaacct catttccatg     600

gacatcacct tcttctcaga ggacggagag ctatcatccc tgggaaagga gggcacaggg     660

ttcagaagta actactttgc ttatgaaact ggaggcaagg cctgcaaaat gcaatactgc     720

aagcattggg gagtcagact cccatcaggt gtctggttcg agatggctga taaggatctc     780

tttgctgcag ccagattccc tgaatgccca gaagggtcaa gtatctctgc tccatctcag     840

acctcagtgg atgtaagtct aattcaggac gttgagagga tcttggatta ttccctctgc     900

caagaaacct ggagcaaaat cagagcgggt cttccaatct ctccagtgga tctcagctat     960
```

```
cttgctccta aaaacccagg aaccggtcct gctttcacca taatcaatgg taccctaaaa   1020
tactttgaga ccagatacat cagagtcgat attgctgctc caatcctctc aagaatggtc   1080
ggaatgatca gtggaactac cacagaaagg gaactgtggg atgactgggc accatatgaa   1140
gacgtggaaa ttggacccaa tggagttctg aggaccagtt caggatataa gtttccttta   1200
tacatgattg gacatggtat gttggactcc gatcttcatc ttagctcaaa ggctcaggtg   1260
ttcgaacatc ctcacattca agacgctgct tcgcaacttc ctgatgatga gagtttattt   1320
tttggtgata ctgggctatc caaaaatcca atcgagcttg tagaaggttg gttcagtagt   1380
tggaaaagct ctattgcctc ttttttcttt atcatagggt taatcattgg actattcttg   1440
gttctccgag ttggtatcca tctttgcatt aaattaaagc acaccaagaa aagacagatt   1500
tatacagaca tagagatgaa ccgacttgga aagtaa                             1536
```

<210> SEQ ID NO 84
<211> LENGTH: 1536
<212> TYPE: DNA
<213> ORGANISM: Artificial sequence
<220> FEATURE:
<223> OTHER INFORMATION: Glycoprotein Vesicular stomatitis Indiana virus c112a (H22N)

<400> SEQUENCE: 84

```
atgaagtgcc ttttgtactt agccttttta ttcattgggg tgaattgcaa gttcaccata     60
gtttttccac acaaccaaaa aggaaactgg aaaaatgttc cttctaatta caattattgc    120
ccgtcaagct cagatttaaa ttggcataat gacttaatag gcacagcatt acaagtcaaa    180
atgcccaaga gtcacaaggc tattcaagca gacggttgga tgtgtcatgc ttccaaatgg    240
gtcactactt gtgatttccg ctggtatgga ccgaagtata taacacattc catccgatcc    300
ttcactccat ctgtagaaca atgcaaggaa agcattgaac aaacgaaaca aggaacttgg    360
ctgaatccag gcttccctcc tcaaagttgt ggatatgcaa ctgtgacgga tgccgaagca    420
gtgattgtcc aggtgactcc tcaccatgtg ctggttgatg aatacacagg agaatgggtt    480
gattcacagt tcatcaacgg aaaatgcagc aattacatat gccccactgt ccataactct    540
acaacctggc attctgacta taaggtcaaa gggctatgtg attctaacct catttccatg    600
gacatcacct tcttctcaga ggacggagag ctatcatccc tgggaaagga gggcacaggg    660
ttcagaagta actactttgc ttatgaaact ggaggcaagg cctgcaaaat gcaatactgc    720
aagcattggg gagtcagact cccatcaggt gtctggttcg agatggctga taaggatctc    780
tttgctgcag ccagattccc tgaatgccca gaagggtcaa gtatctctgc tccatctcag    840
acctcagtgg atgtaagtct aattcaggac gttgagagga tcttggatta ttccctctgc    900
caagaaacct ggagcaaaat cagagcgggt cttccaatct ctccagtgga tctcagctat    960
cttgctccta aaaacccagg aaccggtcct gctttcacca taatcaatgg taccctaaaa   1020
tactttgaga ccagatacat cagagtcgat attgctgctc caatcctctc aagaatggtc   1080
ggaatgatca gtggaactac cacagaaagg gaactgtggg atgactgggc accatatgaa   1140
gacgtggaaa ttggacccaa tggagttctg aggaccagtt caggatataa gtttccttta   1200
tacatgattg gacatggtat gttggactcc gatcttcatc ttagctcaaa ggctcaggtg   1260
ttcgaacatc ctcacattca agacgctgct tcgcaacttc ctgatgatga gagtttattt   1320
tttggtgata ctgggctatc caaaaatcca atcgagcttg tagaaggttg gttcagtagt   1380
tggaaaagct ctattgcctc ttttttcttt atcatagggt taatcattgg actattcttg   1440
```

gttctccgag ttggtatcca tctttgcatt aaattaaagc acaccaagaa aagacagatt 1500
tatacagaca tagagatgaa ccgacttgga aagtaa 1536

<210> SEQ ID NO 85
<211> LENGTH: 1536
<212> TYPE: DNA
<213> ORGANISM: Artificial sequence
<220> FEATURE:
<223> OTHER INFORMATION: Glycoprotein Vesicular stomatitis Indiana virus g1313t (S422I)

<400> SEQUENCE: 85
atgaagtgcc ttttgtactt agccttttta ttcattgggg tgaattgcaa gttcaccata 60
gtttttccac acaaccaaaa aggaaactgg aaaaatgttc cttctaatta ccattattgc 120
ccgtcaagct cagatttaaa ttggcataat gacttaatag gcacagcatt acaagtcaaa 180
atgcccaaga gtcacaaggc tattcaagca gacggttgga tgtgtcatgc ttccaaatgg 240
gtcactactt gtgatttccg ctggtatgga ccgaagtata taacacattc catccgatcc 300
ttcactccat ctgtagaaca atgcaaggaa agcattgaac aaacgaaaca aggaacttgg 360
ctgaatccag gcttccctcc tcaaagttgt ggatatgcaa ctgtgacgga tgccgaagca 420
gtgattgtcc aggtgactcc tcaccatgtg ctggttgatg aatacacagg agaatgggtt 480
gattcacagt tcatcaacgg aaaatgcagc aattacatat gccccactgt ccataactct 540
acaacctggc attctgacta taaggtcaaa gggctatgtg attctaacct catttccatg 600
gacatcacct tcttctcaga ggacggagag ctatcatccc tgggaaagga gggcacaggg 660
ttcagaagta actactttgc ttatgaaact ggaggcaagg cctgcaaaat gcaatactgc 720
aagcattggg gagtcagact cccatcaggt gtctggttcg agatggctga taaggatctc 780
tttgctgcag ccagattccc tgaatgccca gaagggtcaa gtatctctgc tccatctcag 840
acctcagtgg atgtaagtct aattcaggac gttgagagga tcttggatta ttccctctgc 900
caagaaacct ggagcaaaat cagagcgggt cttccaatct ctccagtgga tctcagctat 960
cttgctccta aaaacccagg aaccggtcct gctttcacca taatcaatgg taccctaaaa 1020
tactttgaga ccagatacat cagagtcgat attgctgctc caatcctctc aagaatggtc 1080
ggaatgatca gtggaactac cacagaaagg gaactgtggg atgactgggc accatatgaa 1140
gacgtggaaa ttggacccaa tggagttctg aggaccagtt caggatataa gtttccttta 1200
tacatgattg gacatggtat gttggactcc gatcttcatc ttagctcaaa ggctcaggtg 1260
ttcgaacatc ctcacattca agacgctgct tcgcaacttc ctgatgatga gatttttattt 1320 tttggtgata ctgggctatc caaaaatcca atcgagcttg tagaaggttg gttcagtagt 1380
tggaaaagct ctattgcctc tttttcttt atcatagggt taatcattgg actattcttg 1440
gttctccgag ttggtatcca tctttgcatt aaattaaagc acaccaagaa aagacagatt 1500
tatacagaca tagagatgaa ccgacttgga aagtaa 1536

<210> SEQ ID NO 86
<211> LENGTH: 1536
<212> TYPE: DNA
<213> ORGANISM: Artificial sequence
<220> FEATURE:
<223> OTHER INFORMATION: Glycoprotein Vesicular stomatitis Indiana virus c112a g1313t (H22N S422I)

```
<400> SEQUENCE: 86

atgaagtgcc ttttgtactt agccttttta ttcattgggg tgaattgcaa gttcaccata     60

gtttttccac acaaccaaaa aggaaactgg aaaaatgttc cttctaatta caattattgc    120

ccgtcaagct cagatttaaa ttggcataat gacttaatag gcacagcatt acaagtcaaa    180

atgcccaaga gtcacaaggc tattcaagca gacggttgga tgtgtcatgc ttccaaatgg    240

gtcactactt gtgatttccg ctggtatgga ccgaagtata taacacattc catccgatcc    300

ttcactccat ctgtagaaca atgcaaggaa agcattgaac aaacgaaaca aggaacttgg    360

ctgaatccag gcttccctcc tcaaagttgt ggatatgcaa ctgtgacgga tgccgaagca    420

gtgattgtcc aggtgactcc tcaccatgtg ctggttgatg aatacacagg agaatgggtt    480

gattcacagt tcatcaacgg aaaatgcagc aattacatat gccccactgt ccataactct    540

acaacctggc attctgacta taaggtcaaa gggctatgtg attctaacct catttccatg    600

gacatcacct tcttctcaga ggacggagag ctatcatccc tgggaaagga gggcacaggg    660

ttcagaagta actactttgc ttatgaaact ggaggcaagg cctgcaaaat gcaatactgc    720

aagcattggg gagtcagact cccatcaggt gtctggttcg agatggctga taaggatctc    780

tttgctgcag ccagattccc tgaatgccca gaagggtcaa gtatctctgc tccatctcag    840

acctcagtgg atgtaagtct aattcaggac gttgagagga tcttggatta ttccctctgc    900

caagaaacct ggagcaaaat cagagcgggt cttccaatct ctccagtgga tctcagctat    960

cttgctccta aaaacccagg aaccggtcct gctttcacca taatcaatgg taccctaaaa   1020

tactttgaga ccagatacat cagagtcgat attgctgctc caatcctctc aagaatggtc   1080

ggaatgatca gtggaactac cacagaaagg gaactgtggg atgactgggc accatatgaa   1140

gacgtggaaa ttggacccaa tggagttctg aggaccagtt caggatataa gtttccttta   1200

tacatgattg gacatggtat gttggactcc gatcttcatc ttagctcaaa ggctcaggtg   1260

ttcgaacatc ctcacattca agacgctgct tcgcaacttc ctgatgatga gattttattt   1320

tttggtgata ctgggctatc caaaaatcca atcgagcttg tagaaggttg gttcagtagt   1380

tggaaaagct ctattgcctc ttttttcttt atcatagggt taatcattgg actattcttg   1440

gttctccgag ttggtatcca tctttgcatt aaattaaagc acaccaagaa aagacagatt   1500

tatacagaca tagagatgaa ccgacttgga aagtaa                             1536

<210> SEQ ID NO 87
<211> LENGTH: 15
<212> TYPE: DNA
<213> ORGANISM: Artificial Sequence
<220> FEATURE:
<223> OTHER INFORMATION: primer

<400> SEQUENCE: 87

tttttttttt ttcat                                                      15
```

MUTANT VSV ECTODOMAIN POLYPEPTIDE AND USES THEREOF

REFERENCE TO SEQUENCE LISTING SUBMITTED ELECTRONICALLY

This application contains a sequence listing, which is submitted electronically via EFS-Web as an ASCII formatted sequence listing with a file name "Sequence_Listing", creation date of Sep. 13, 2021, and having a size of about 346 KB. The sequence listing submitted via EFS-Web is part of the specification and is herein incorporated by reference in its entirety.

CROSS-REFERENCE TO RELATED APPLICATIONS

This application is a U.S. National Stage Application pursuant to 35 U.S.C. § 371 of International Patent Application PCT/EP2020/057144, filed on Mar. 16, 2020, and published as WO 2020/187850 on Sep. 24, 2020, which claims priority to European Patent Application 19305317.0, filed on Mar. 15, 2019, all of which are incorporated herein by reference in their entireties for all purposes.

TECHNICAL FIELD OF THE INVENTION

The present invention is in the field of viruses with improved properties, and more particularly of VSV viruses with improved properties, in particular for use in oncolytic cancer therapy, gene therapy, immunotherapy and selective delivery of a cargo to a chosen cell type, and relates to a mutant polypeptide comprising the amino acid sequence of the ectodomain of glycoprotein G of a Vesicular stomatitis virus (VSV) strain, wherein said ectodomain comprises the amino acid sequence as set forth in SEQ ID NO: 2 or a sequence having at least 50% of identity with the amino acid sequence as set forth in SEQ ID NO: 2, with at least one substitution of an amino acid residue selected from the group consisting of:

a) any amino acid residue located from position 421 to position 429 and any amino acid residue located from position 17 to position 25 of SEQ ID NO:2; or
b) any amino acid residue located from a position equivalent to position 421 to a position equivalent to position 429 of SEQ ID NO: 2 and any amino acid residue located from a position equivalent to position 17 to a position equivalent to position 25 of SEQ ID NO: 2, after optimal global alignment with SEQ ID NO:2.

BACKGROUND ART

Vesicular stomatitis virus (VSV) is an enveloped, negative strand RNA virus that belongs to the Vesiculovirus genus of the Rhabdovirus family. It is an arbovirus which can infect insects, cattle, horses, and pigs. In mammals, its ability to infect and kill tumor cells, while sparing normal cells makes it a promising oncolytic virus for the treatment of cancer (Barber. Oncogene 24, 7710-7719 (2005); Fernandez et al. J. Virol. 76, 895-904 (2002); Hastie et al. Virus Res. 176, 16-32 (2013)).

VSV genome consists of 11 kb single-stranded negative-sense RNA (FIG. 1A). It contains 5 genes encoding 5 structural proteins; one of them codes in particular for a transmembrane glycoprotein, the glycoprotein G (FIGS. 1A and 1B). Glycoprotein G plays a key role during the early stages of infection (Albertini et al. Viruses 4, 117-139 (2012)). First, by interacting with its cellular receptor (the LDL-R or members of the LDL-R family), it allows viral attachment. Then, after endocytosis of the virion, glycoprotein G undergoes a conformational change, induced by the acidification of the interior of the endosome, from a pre-fusion form to a post-fusion form. This structural transition catalyzes the fusion of the viral and endosomal membranes.

Glycoprotein G is the only protein responsible for VSV tropism. This tropism is wide due to the ubiquitous nature of LDL-R family members, allowing VSV to enter many cell types. This is why for example VSV glycoprotein G is used to pseudotype many retrovirals vectors. Nevertheless, despite this broad tropism, several cell types only have a low expression level or do not carry the VSV receptors (such as resting T cells, B cells, and CD341 cells) (Amirache. Blood 123, 1422-4 (2014))

Hence, there is a need for modified VSV viruses with an altered tropism. Such modified VSV viruses would infect cell types not carrying the natural VSV receptors.

In order to overcome this problem, the inventors sought to identify sites allowing the insertion of the sequence of a targeting moiety (such as a nanobody), specifically recognizing a given receptor, in the amino acid sequence of VSV glycoprotein G. In particular, this insertion should not interfere with the membrane fusion properties of glycoprotein G.

They analyzed several insertion sites and demonstrated that the amino-terminal site tolerated the insertion of a nanobody. The resulting first chimera (GNano described precisely in FIG. 2) was correctly folded and transported to the cell membrane. It had retained its fusion properties (which were nevertheless attenuated).

SUMMARY OF THE INVENTION

In the context of the invention, the inventors then built a recombinant VSV, in which the gene encoding the wild-type glycoprotein G was replaced by that encoding GNano (first chimera). The amplification of this initial recombinant VSV virus was however very difficult; and only very low infectious titers ~$1.8\cdot10^6$ pfu/ml were obtained after amplification in BSR cells after 24 hours. Such a low titer is not compatible with industrial production of a targeted VSV virus intended for therapy.

The inventors then performed several passages of this recombinant virus on BSR cells to select mutations improving its amplification. After 10 passages, the sequencing of the genomes of the viral population showed the progressive invasion of this population by a variant containing two mutations in the nucleotide sequence of the glycoprotein, resulting in the change of the histidine residue in position 22 into asparagine (H22N substitution) and of the serine 422 residue in position into isoleucine (S422I substitution). The titer of the recombinant virus obtained after this optimization was around ~$10^8$ pfu/ml.

Surprisingly, the inventors thus found that two mutations (H22N and S422I), in combination, allowed the recombinant virus (GNano H22N S422I, or improved chimera, see FIG. 2) to be produced at ~$10^8$ pfu/ml after amplification in BSR cells for 24 hours (see Example 1).

Moreover, the inventors also found that substitution S422I was able to rescue G fusion properties, which were completely abolished by substitution H407A. In this context, they demonstrated that S422I facilitates G folding and stabilizes G prefusion form by showing that it improves LDL-R CR domains recognition (the structural transition toward the postfusion state disrupts the CR domain binding site).

In the context of GNano H22N, they also demonstrated that substitutions S422F, S422M, S422L or S422V have a similar phenotype as S422I.

The inventors also verified that, in the presence of H22N substitution and/or S422I, S422F, S422M, S422L or S422V substitution, a recombinant VSV expressing a fusion polypeptide consisting of VSV Indiana G signal peptide, a dipeptide linker, an anti-GFP nanobody, a GGGGSGGGGS (SEQ ID NO:81) linker and VSV Indiana G ectodomain with one of substitutions S422I, S422F, S422M, S422L and S422V, was able to form syncytia when exposed to low pH, between 5.5 and 6.3, similarly to wild-type VSV Indiana. This also suggests that the presence of a hydrophobic residue in position 422 is key in the regulation of the pH-dependent structural transition, and facilitates G folding and stabilizes the prefusion form of a fusion polypeptide of G with a nanobody inserted N-terminal of the ectodomain (see Example 3). This is also confirmed by the crystal structure of VSV G ectodomain, solved by the inventors. Indeed, the inventors surprisingly showed that the C-terminal part (from residue 407 to residue 429, more particularly the region located from residue 421 to residue 429, even more particularly the region from residue 421 to residue 425) largely interacts with the fusion domain and therefore contributes to the stabilization of the pre-fusion complex. The crystal structure further revealed that compensatory substitution of S422 residue with a hydrophobic residue (such as I, F, M, L or V) stabilizes the beta-hairpin structure (and thus the pre-fusion state) through hydrophobic interactions (see Example 4).

In a first aspect, the present invention thus relates to a mutant polypeptide comprising, or consisting essentially of, or consisting of, the amino acid sequence of the ectodomain of glycoprotein G of a vesicular stomatitis virus (VSV) strain, wherein said ectodomain comprises, or consists essentially of, or consists of, the amino acid sequence as set forth in SEQ ID NO: 2 or a sequence having at least 50% of identity with the amino acid sequence as set forth in SEQ ID NO: 2, with at least one substitution of an amino acid residue selected from the group consisting of:

a) any amino acid residue located from position 421 to position 429 and any amino acid residue located from position 17 to position 25 of SEQ ID NO:2, preferably any amino acid residue located from position 421 to position 425 and any amino acid residue located from position 17 to position 25 of SEQ ID NO:2, more preferably any amino acid residue located in positions 422 and 22 of SEQ ID NO:2; or b) any amino acid residue located from a position equivalent to position 421 to a position equivalent to position 429 of SEQ ID NO: 2 and any amino acid residue located from a position equivalent to position 17 to a position equivalent to position 25 of SEQ ID NO: 2, after optimal global alignment with SEQ ID NO:2, preferably any amino acid residue located from a position equivalent to position 421 to a position equivalent to position 425 of SEQ ID NO: 2 and any amino acid residue located from a position equivalent to position 17 to a position equivalent to position 25 of SEQ ID NO: 2, after optimal global alignment with SEQ ID NO:2, more preferably any amino acid residue located in positions equivalent to positions 422 and 22 of SEQ ID NO: 2, after optimal global alignment with SEQ ID NO:2.

The present invention also relates to fusion polypeptide comprising, or consisting essentially of, or consisting of, the mutant polypeptide according to the invention, and an additional peptide, polypeptide or protein, wherein said additional peptide, polypeptide or protein is inserted:

a) in N-terminal of the mutant polypeptide, b) between any two consecutive amino acids located in regions corresponding to positions 192 to 202 of SEQ ID NO:2 or equivalent positions after optimal global alignment with SEQ ID NO:2, c) between any two consecutive amino acids located in regions corresponding to positions 240 to 257 of SEQ ID NO:2 or equivalent positions after optimal global alignment with SEQ ID NO:2, d) between any two consecutive amino acids located in regions corresponding to positions 347 to 353 of SEQ ID NO:2 or equivalent positions after optimal global alignment with SEQ ID NO:2, e) between any two consecutive amino acids located in regions corresponding to positions 364 to 366 of SEQ ID NO:2 or equivalent positions after optimal global alignment with SEQ ID NO:2, f) between any two consecutive amino acids located in regions corresponding to positions 376 to 379 of SEQ ID NO:2 or equivalent positions after optimal global alignment with SEQ ID NO:2, preferably said additional peptide, polypeptide or protein is inserted in N-terminal of the mutant polypeptide or between the amino acids at positions 351 and 352 of SEQ ID NO:2 or equivalent positions after optimal global alignment with SEQ ID NO:2.

The present invention also relates to a nucleic acid molecule encoding the mutant polypeptide or the fusion polypeptide according to the invention.

The present invention also relates to a vector comprising at least one nucleic acid according to the invention or expressing the mutant polypeptide or the fusion polypeptide according to the invention.

The present invention also relates to a host cell containing or expressing the mutant polypeptide or the fusion polypeptide according to the invention, or containing the nucleic acid molecule according to the invention, or containing the vector (in particular a VSV vector) according to the invention.

The present invention also relates to a composition comprising, or consisting essentially of, or consisting of, the mutant polypeptide or the fusion polypeptide according to the invention, the nucleic acid molecule according to the invention, the vector according to the invention, the host cell according to the invention, or any combination thereof.

The present invention also relates to therapeutic uses of the mutant polypeptide or the fusion polypeptide according to the invention, the nucleic acid molecule according to the invention, the vector according to the invention, the host cell according to the invention, the composition according to the invention, or any combination thereof.

The present invention also relates to the mutant polypeptide according to the invention or the fusion polypeptide according to the invention for use for targeting a lipid membrane in a subject to a specific target, for instance a cell, in particular a cell to be killed, such as a cancer cell, wherein said mutant polypeptide or fusion polypeptide is anchored in said lipid membrane.

The present invention also relates to an in vitro use of the mutant polypeptide according to the invention or the fusion polypeptide according to the invention for targeting a lipid membrane to a specific target, for instance a cell, in particular a cell to be killed, such as a cancer cell, wherein said mutant polypeptide or fusion polypeptide is anchored in said lipid membrane.

DESCRIPTION OF THE FIGURES

FIG. 3A. Optimal global alignment of the amino acid sequences of the ectodomain of glycoprotein G of VSV strains Indiana (SEQ ID NO:2) and Maraba (SEQ ID NO:4) using Emboss Needle software with default parameters. Positions 17-25 and 421-429 of SEQ ID NO: 2 and equivalent positions of SEQ ID NO:4 (also positions 17-25 and 421-429) are boxed. The preferred substitution positions (positions 22 and 422 of both SEQ ID NO:2 and SEQ ID NO: 4) are further boxed. The default parameters used are indicated. The obtained identity percentage ("Identity"), similarity percentage ("Similarity"), and similarity score ("Score") are indicated.

FIG. 3B. Optimal global alignment of the amino acid sequences of the ectodomain of glycoprotein G of VSV strains Indiana (SEQ ID NO:2) and Cocal (SEQ ID NO:6) using Emboss Needle software with default parameters. Positions 17-25 and 421-429 of SEQ ID NO: 2 and equivalent positions of SEQ ID NO:6 (also positions 17-25 and 421-429) are boxed. The preferred substitution positions (positions 22 and 422 of both SEQ ID NO:2 and SEQ ID NO: 6) are further boxed. The default parameters used are indicated. The obtained identity percentage ("Identity"), similarity percentage ("Similarity"), and similarity score ("Score") are indicated.

FIG. 3C. Optimal global alignment of the amino acid sequences of the ectodomain of glycoprotein G of VSV strains Indiana (SEQ ID NO:2) and Morreton (SEQ ID NO:8) using Emboss Needle software with default parameters. Positions 17-25 and 421-429 of SEQ ID NO: 2 and equivalent positions of SEQ ID NO:8 (also positions 17-25 and 421-429) are boxed. The preferred substitution positions (positions 22 and 422 of both SEQ ID NO:2 and SEQ ID NO: 8) are further boxed. The default parameters used are indicated. The obtained identity percentage ("Identity"), similarity percentage ("Similarity"), and similarity score ("Score") are indicated.

FIG. 3D. Optimal global alignment of the amino acid sequences of the ectodomain of glycoprotein G of VSV strains Indiana (SEQ ID NO:2) and Alagoa (SEQ ID NO: 10) using Emboss Needle software with default parameters. Positions 17-25 and 421-429 of SEQ ID NO: 2 and equivalent positions of SEQ ID NO: 10 (also positions 17-25 and 421-429) are boxed. The preferred substitution positions (positions 22 and 422 of both SEQ ID NO:2 and SEQ ID NO: 10) are further boxed. The default parameters used are indicated. The obtained identity percentage ("Identity"), similarity percentage ("Similarity"), and similarity score ("Score") are indicated.

FIG. 3E. Optimal global alignment of the amino acid sequences of the ectodomain of glycoprotein G of VSV strains Indiana (SEQ ID NO:2) and New Jersey (SEQ ID NO: 12) using Emboss Needle software with default parameters. Positions 17-25 and 421-429 of SEQ ID NO: 2 and equivalent positions of SEQ ID NO: 12 (positions 17-25 and 428-436) are boxed. The preferred substitution positions (positions 22 and 422 of SEQ ID NO:2 and positions 22 and 429 of SEQ ID NO: 12) are further boxed. The default parameters used are indicated. The obtained identity percentage ("Identity"), similarity percentage ("Similarity"), and similarity score ("Score") are indicated.

FIG. 3F. Optimal global alignment of the amino acid sequences of the ectodomains of glycoprotein G of VSV strains Indiana (SEQ ID NO:2) and Carajas (SEQ ID NO: 14) using Emboss Needle software with default parameters. Positions 17-25 and 421-429 of SEQ ID NO: 2 and equivalent positions of SEQ ID NO: 14 (positions 17-25 and 425-433) are boxed. The preferred substitution positions (positions 22 and 422 of SEQ ID NO:2 and positions 22 and 426 of SEQ ID NO: 14) are further boxed. The default parameters used are indicated. The obtained identity percentage ("Identity"), similarity percentage ("Similarity"), and similarity score ("Score") are indicated.

Bottom: Flow cytometry analysis of surface expression of mutant glycoproteins G-H407A and G.H407A/S422I. The surface G protein expression was detected with monoclonal antibody 8G5F11 (KeraFAST) and a goat anti-mouse IgG secondary antibody conjugated to Alexa Fluor 488. A total of 10,000 cells were counted by flow cytometry. In each frame, the black curve corresponds to the fluorescence of untransfected cells, the blue curve corresponds to the fluorescence of cells transfected by pCAGGS plasmids encoding WT G, and the red curve corresponds to the fluorescence of cells transfected by pCAGGS plasmids encoding the indicated mutant. In each frame, the surface expression of mutant G is expressed as a percentage of that of WT G.

Figure 7:
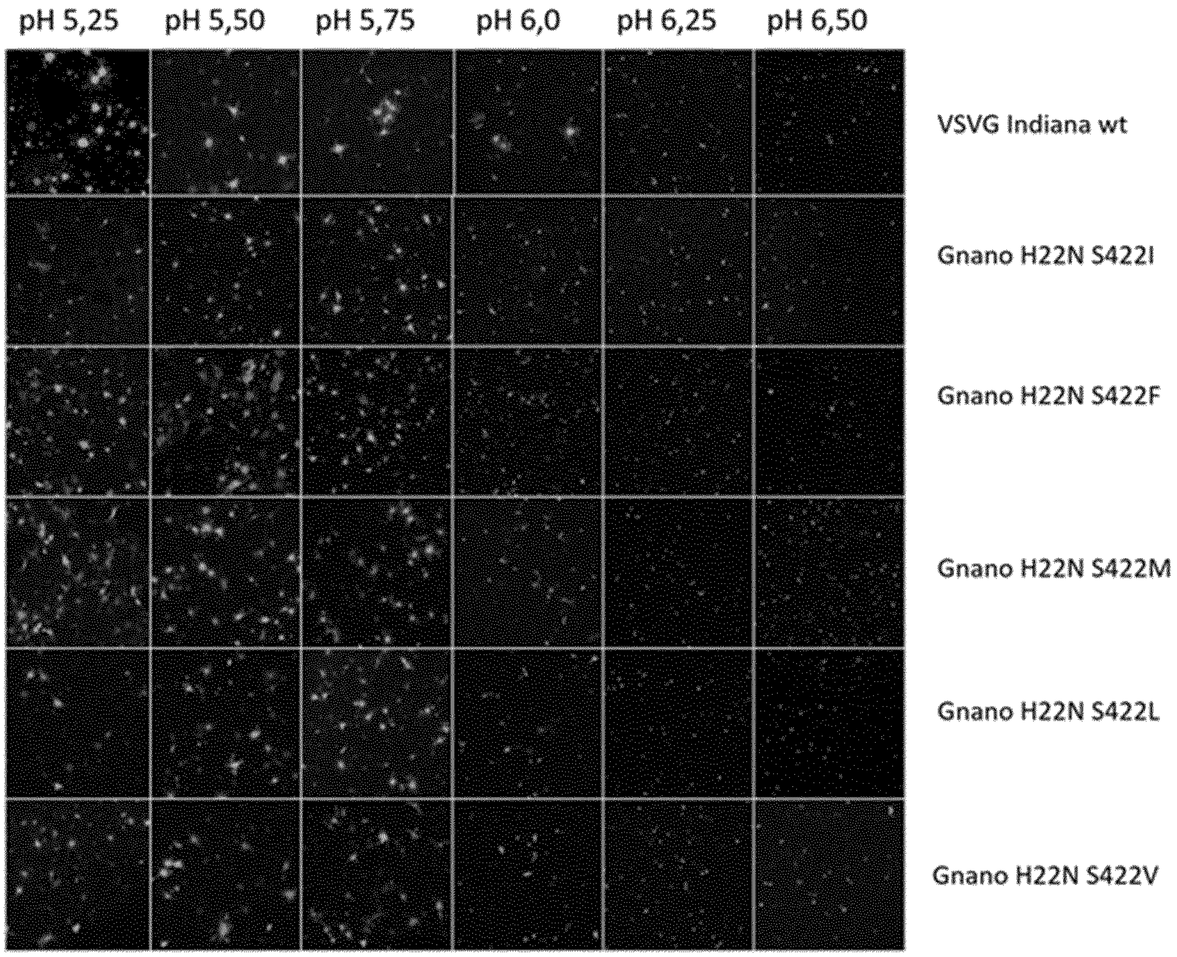

FIG. 7. Cell-cell fusion assays. Fusion activity of VSV G Indiana WT and VSV GNano after optimization (ie. Mutation of residue H22 to N and residue S422 to I, F, M, L, or V).

Figure 8:
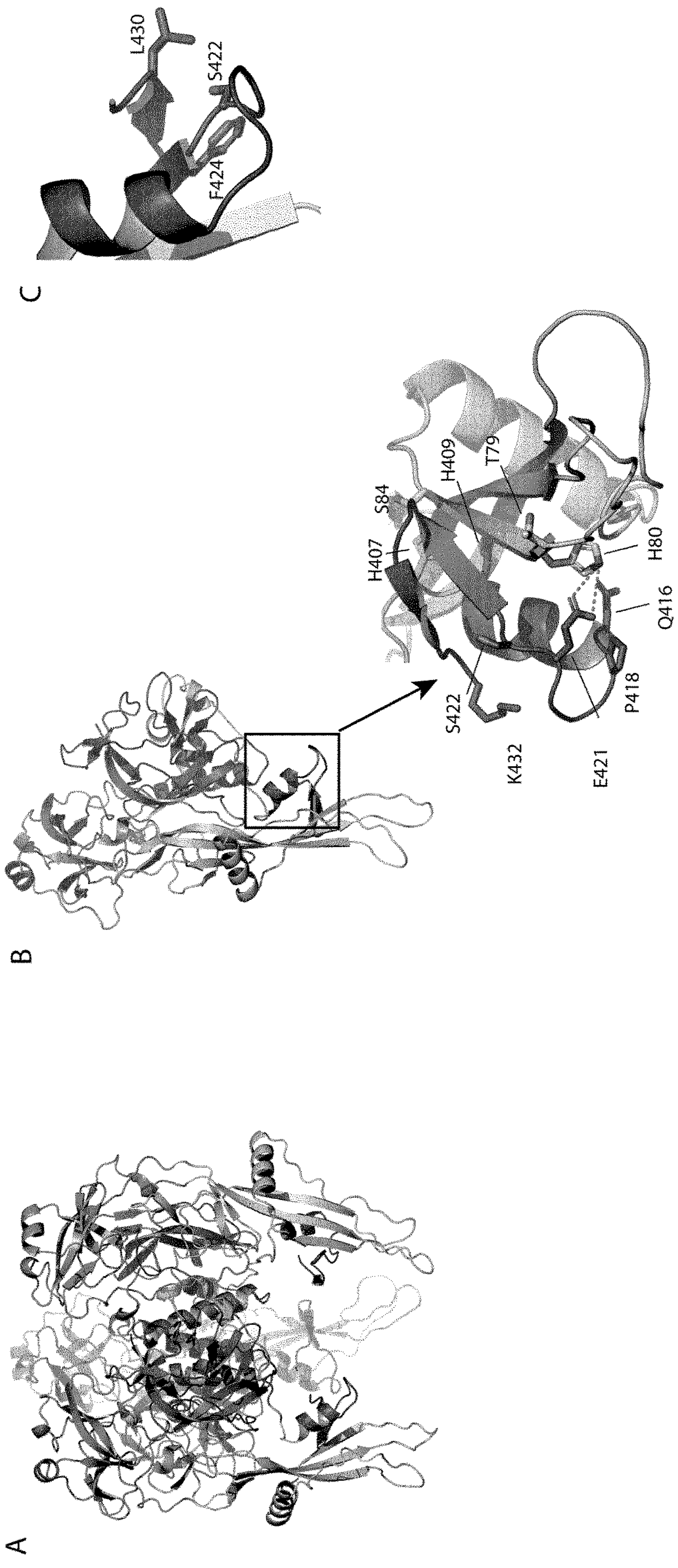

FIG. 8. Crystal structure of VSV G1-440 (residues 1 to 440 of VSV G Indiana WT) and environment of residue S422.

(A) Crystalline structure of the pre-fusion trimer of G1-440. The chain is traced up to residue 432. Residues 410 to 432 are in dark grey.

(B) Structure of segment 410-432. The two close-up detail the organization of segment 410-432 and its interactions with the fusion domain.

(C) Close-up view of residue S422 in G pre-fusion state.

DETAILED DESCRIPTION OF THE INVENTION

In the context of the present invention, the inventors surprisingly found that, while a recombinant VSV virus comprising a nanobody inserted between the signal peptide and the ectodomain of VSV Indiana glycoprotein G retained its fusion properties and infectivity, it was very difficult to amplify, not permitting an industrial use thereof. They further surprisingly found that insertion of at least one substitution in position 22 or position 422 of the ectodomain of VSV Indiana glycoprotein G, while retaining fusion properties and infectivity, permitted to dramatically increase the amplification of the recombinant virus, thus permitting an industrial use thereof (see Example 1). They also obtained results showing that the presence of a hydrophobic residue in position 422 is key in the regulation of the pH-dependent structural transition, and facilitates G folding and stabilizes the prefusion form of a fusion polypeptide of G with a nanobody inserted N-terminal of the ectodomain (see Examples 2, 3 and 4).

Mutant Polypeptide with Improved Production

The present invention thus firstly relates to a mutant polypeptide comprising, or consisting essentially of, or consisting of, the amino acid sequence of the ectodomain of glycoprotein G of a Vesicular stomatitis virus (VSV) strain, wherein said ectodomain comprises, or consists essentially of, or consists of, the amino acid sequence as set forth in SEQ ID NO: 2 or an amino acid sequence having at least 50% of identity with the amino acid sequence as set forth in SEQ ID NO: 2, with at least one substitution of an amino acid residue selected from the group consisting of:

a) any amino acid residue located from position 421 to position 429 and any amino acid residue located from position 17 to position 25 of SEQ ID NO:2, preferably any amino acid residue located from position 421 to position 425 and any amino acid residue located from position 17 to position 25 of SEQ ID NO:2, more preferably any amino acid residue located in positions 422 and 22 of SEQ ID NO:2; or b) any amino acid residue located from a position equivalent to position 421 to a position equivalent to position 429 of SEQ ID NO: 2 and any amino acid residue located from a position equivalent to position 17 to a position equivalent to position 25 of SEQ ID NO: 2, after optimal global alignment with SEQ ID NO:2, preferably any amino acid residue located from a position equivalent to position 421 to a position equivalent to position 425 of SEQ ID NO: 2 and any amino acid residue located from a position equivalent to position 17 to a position equivalent to position 25 of SEQ ID NO: 2, after optimal global alignment with SEQ ID NO:2, more preferably any amino acid residue located in positions equivalent to positions 422 and 22 of SEQ ID NO: 2, after optimal global alignment with SEQ ID NO:2.

In a preferred embodiment, the mutant polypeptide of the invention is an isolated and/or non-naturally occurring polypeptide.

Reference Sequences and Positions for Substitution

The mutant polypeptide is based on the amino acid sequence of the ectodomain of glycoprotein G of a Vesicular stomatitis virus (VSV) strain, which corresponds to the amino acid sequence of glycoprotein G without the signal peptide. In the present description, the reference VSV strain is the Indiana strain. The amino acid sequence of glycoprotein G of VSV Indiana strain is as set forth in SEQ ID NO:1. The amino acid sequence of the ectodomain of glycoprotein G of VSV Indiana strain is as set forth in SEQ ID NO:2, and corresponds to amino acids 17-511 of SEQ ID NO:1, amino acids 1-16 of SEQ ID NO: 1 corresponding to the signal peptide. In a preferred embodiment, the mutant polypeptide according to the invention is derived from the ectodomain of glycoprotein G of VSV Indiana strain and thus comprises, or consists essentially of, or consists of, the amino acid sequence as set forth in SEQ ID NO: 2, with at least one substitution of an amino acid residue selected from the group consisting of any amino acid residue located from position 421 to position 429 and any amino acid residue located from position 17 to position 25 of SEQ ID NO:2, preferably any amino acid residue located from position 421 to position 425 and any amino acid residue located from position 17 to position 25 of SEQ ID NO:2, more preferably any amino acid residue located in positions 422 and 22 of SEQ ID NO:2. However, the mutant polypeptide according to the invention may also be derived from the ectodomain of glycoprotein G of a VSV strain other than Indiana or may comprise further mutations, provided that it comprises, or consists essentially of, or consists of, an amino acid sequence having at least 50% of identity, preferably at least 55% of identity, at least 60% of identity, at least 65% of identity, more preferably at least 70% of identity, at least 75% of identity, at least 78% of identity, at least 79% of identity, at least 80% of identity, at least 81% of identity, at least 82% of identity, at least 83% of identity, at least 84% of identity, at least 85% of identity, at least 86% of identity, at least 87% of identity, at least 88% of identity, at least 89% of identity, at least 90% of identity, at least 91% of identity, at least 92% of identity, at least 93% of identity, at least 94% of identity, at least 95% of identity, at least 96% of identity, at least 97% of identity, at least 98% of identity, or even at least 99% of identity with the amino acid sequence as set forth in SEQ ID NO: 2, with at least one substitution of an amino acid residue selected from the group consisting of any amino acid residue located from a position equivalent to position 421 to a position equivalent to position 429 of SEQ ID NO: 2 and any amino acid residue located from a position equivalent to position 17 to a position equivalent to position 25 of SEQ ID NO: 2, after optimal global alignment with SEQ ID NO:2, preferably any amino acid residue located from a position equivalent to position 421 to a position equivalent to position 425 of SEQ ID NO: 2 and any amino acid residue located from a position equivalent to position 17 to a position equivalent to position 25 of SEQ ID NO: 2, after optimal global alignment with SEQ ID NO:2, more preferably any amino acid residue located in positions equivalent to positions 422 and 22 of SEQ ID NO: 2, after optimal global alignment with SEQ ID NO:2. In this case, an optimal global alignment of SEQ ID NO:2 and of the initial amino acid sequence (for instance amino acid sequence of the ectodomain of glycoprotein G of a VSV strain other than Indiana, provided that this sequence has at least 50% of identity or any other preferred minimal percentage of identity defined above with SEQ ID NO:2 after optimal global alignment) is made, and the initial amino acid sequence has at least one substitution of an amino acid residue selected from the group consisting of any amino acid residue located from a position equivalent to position 421 to a position equivalent to position 429 of SEQ ID NO: 2 and any amino acid residue located from a position equivalent to position 17 to a position equivalent to position 25 of SEQ ID NO: 2, after optimal global alignment with SEQ ID NO:2, preferably any amino acid residue located from a position equivalent to position 421 to a position equivalent to position 425 of SEQ ID NO: 2 and any amino acid residue located from a position equivalent to position 17 to a position equivalent to position 25 of SEQ ID NO: 2, after optimal global alignment with SEQ ID NO: 2, more preferably any amino acid residue located in positions equivalent to positions 422 and 22 of SEQ ID NO: 2, after optimal global alignment with SEQ ID NO:2.

The percent identities referred to in the context of the disclosure of the present invention are determined on the basis of an optimal global alignment of sequences to be compared, i.e., on an optimal alignment of the sequences taken in their entirety over their entire length using any algorithm well-known to a person skilled in the art, such as the algorithm of Needleman and Wunsch (1970). This sequence comparison may be performed using any software well-known to a person skilled in the art, for example the Emboss Needle software. The Emboss is at Needle software for example available www.ebi.ac.uk/Tools/psa/emboss-_needle/. This software reads two input sequences and writes their optimal global sequence alignment to file. It uses the Needleman-Wunsch alignment algorithm to find the optimum alignment (including gaps) of two sequences along their entire length. The algorithm uses a dynamic programming method to ensure the alignment is optimum, by exploring all possible alignments and choosing the best. A scoring matrix is read that contains values for every possible residue or nucleotide match. Needle finds the alignment with the maximum possible score where the score of an alignment is equal to the sum of the matches taken from the scoring matrix, minus penalties arising from opening and extending gaps in the aligned sequences. The substitution matrix and gap opening and extension penalties are user-specified. In the context of the invention, in order to obtain an optimal global alignment, the Emboss Needle software may be used with default parameters, i.e. using the "Gap open" parameter equal to 10.0, the "Gap extend" parameter equal to 0.5, the "End gap penalty" parameter to "false", the "End gap open" parameter to 10.0, and a "Blosum 62" matrix. When entering two amino acid sequences, the Emboss Needle software returns an optimal global alignment, as well as several values characterizing the alignment:

"Identity" is the percentage of identity, i.e. the percentage of identical matches between the two sequences over the reported aligned region (including any gaps in the length), "Similarity" is the percentage of similarity, i.e. the percentage of matches between the two sequences over the reported aligned region (including any gaps in the length), and "Score" is the total score of the alignment, corresponding to the best score obtained by the software for all tested global alignments (i.e. over the entire length of both sequences).

This score may be referred to as a "similarity score", since the higher is the value of the score between SEQ ID NO:2 and another initial sequence, the higher is the similarity between this initial sequence and SEQ ID NO:2, taking into account not only aligned identical amino acids, but also conservative substitutions that are not expected to significantly alter the function of the protein.

Once an optimal global alignment has been obtained between SEQ ID NO:2 and another initial sequence, the percentage of identity and position equivalent to specific position(s) of SEQ ID NO:2 are defined. In particular, a position equivalent to position N of SEQ ID NO: 2 is the position of the other initial sequence that is aligned with position N of SEQ ID NO: 2.

Examples of VSV strains other than Indiana also include 7 serotypes such as Maraba, Cocal, Morreton, Alagoa, New Jersey, and Carajas strains. The non-mutated (wild-type) amino acid sequences of the full-length glycoprotein G and of the ectodomain of glycoprotein G of these strains and Indiana strain are presented in Table 1 below:

TABLE 1 non-mutated (wild-type) amino acid sequences of the full-length glycoprotein G and of the ectodomain of glycoprotein G of Indiana, Maraba, Cocal, Morreton, Alagoa, New Jersey, and Carajas VSV strains. In the full-length amino acid sequences, the signal peptide is underlined. Positions of the signal peptide in the full-length amino acid sequences is further indicated.

| VSV strain | Full-length glycoprotein G amino acid sequence | Ectodomain of glycoprotein G amino acid sequence |
|---|---|---|
| Indiana | MKCLLYLAFLFIGVNCKFTIVFPHNQKGNWK<br>NVPSNYHYCPSSSDLNWHNDLIGTAIQVKMP<br>KSHKAIQADGWMCHASKWVTTCDFRWYGP<br>KYITQSIRSFTPSVEQCKESIEQTKQGTWLNP | KFTIVFPHNQKGNWKNVPSNYHYCPSSSDLN<br>WHNDLIGTAIQVKMPKSHKAIQADGWMCHA<br>SKWVTTCDFRWYGPKYITQSIRSFTPSVEQC<br>KESIEQTKQGTWLNPGFPPQSCGYATVTDAE |

TABLE 1-continued non-mutated (wild-type) amino acid sequences of the full-length glycoprotein G and of the ectodomain of glycoprotein G of Indiana, Maraba, Cocal, Morreton, Alagoa, New Jersey, and Carajas VSV strains. In the full-length amino acid sequences, the signal peptide is underlined. Positions of the signal peptide in the full-length amino acid sequences is further indicated.

| VSV strain | Full-length glycoprotein G amino acid sequence | Ectodomain of glycoprotein G amino acid sequence |
|---|---|---|
| | GFPPQSCGYATVTDAEAVIVQVTPHHVLVDE<br>YTGEWVDSQFINGKCSNYICPTVHNSTTWHS<br>DYKVKGLCDSNLISMDITFFSEDGELSSLGKE<br>GTGFRSNYFAYETGGKACKMQYCKHWGVR<br>LPSGVWFEMADKDLFAAARFPECPEGSSISAP<br>SQTSVDVSLIQDVERILDYSLCQETWSKIRAGL<br>PISPVDLSYLAPKNPGTGPAFTIINGTLKYFET<br>RYIRVDIAAPILSRMVGMISGTTTERELWDDW<br>APYEDVEIGPNGVLRTSSGYKFPLYMIGHGM<br>LDSDLHLSSKAQVFEHPHIQDAASQLPDDESL<br>FFGDTGLSKNPIELVEGWFSSWKSSIASFFFII<br>GLIIGLFLVLRVGIHLCIKLKHTKKRQIYTDIEM<br>NRLGK (SEQ ID NO: 1)<br>Positions of signal peptide: 1-16 | AVIVQVTPHHVLVDEYTGEWVDSQFINGKCS<br>NYICPTVHNSTTWHSDYKVKGLCDSNLISMDI<br>TFFSEDGELSSLGKEGTGFRSNYFAYETGGK<br>ACKMQYCKHWGVRLPSGVWFEMADKDLFA<br>AARFPECPEGSSISAPSQTSVDVSLIQDVERIL<br>DYSLCQETWSKIRAGLPISPVDLSYLAPKNPG<br>TGPAFTIINGTLKYFETRYIRVDIAAPILSRMV<br>GMISGTTTERELWDDWAPYEDVEIGPNGVLR<br>TSSGYKFPLYMIGHGMLDSDLHLSSKAQVFE<br>HPHIQDAASQLPDDESLFFGDTGLSKNPIELV<br>EGWFSSWKSSIASFFFIIGLIIGLFLVLRVGIHL<br>CIKLKHTKKRQIYTDIEMNRLGK<br>(SEQ ID NO: 2) |
| Maraba | MLRLFLFCFLALGAHSKFTIVFPHHQKGNWK<br>NVPSTYHYCPSSSDQNWHNDLTGVSLHVKIP<br>KSHKAIQADGWMCHAAKWVTTCDFRWYGP<br>KYITHSIHSMSPTLEQCKTSIEQTKQGVWINP<br>GFPPQSCGYATVTDAEVVVVQATPHHVLVD<br>EYTGEWIDSQLVGGKCSKEVCQTVHNSTVW<br>HADYKITGLCESNLASVDITFFSEDGQKTSLG<br>KPNTGFRSNHFAYESGEKACRMQYCTQWGI<br>RLPSGVWFELVDKDLFQAAKLPECPRGSSISA<br>PSQTSVDVSLIQDVERILDYSLCQETWSKIRAK<br>LPVSPVDLSYLAPKNPGSGPAFTIINGTLKYFE<br>TRYIRVDISNPIIPHMVGTMSGTTTERELWND<br>WYPYEDVEIGPNGVLKTPTGFKFPLYMIGHG<br>MLDSDLHKSSQAQVFEHPHAKDAASQLPDDE<br>TLFFGDTGLSKNPVELVEGWFSSWKSTLASF<br>FLIIGLGVALIFIIRIIVAIRYKYKGRKTQKIYND<br>VEMSRLGNK (SEQ ID NO: 3)<br>Positions of signal peptide: 1-16 | KFTIVFPHHQKGNWKNVPSTYHYCPSSSDQN<br>WHNDLTGVSLHVKIPKSHKAIQADGWMCHA<br>AKWVTTCDFRWYGPKYITHSIHSMSPTLEQC<br>KTSIEQTKQGVWINPGFPPQSCGYATVTDAE<br>VVVVQATPHHVLVDEYTGEWIDSQLVGGKC<br>SKEVCQTVHNSTVWHADYKITGLCESNLASV<br>DITFFSEDGQKTSLGKPNTGFRSNHFAYESGE<br>KACRMQYCTQWGIRLPSGVWFELVDKDLFQ<br>AAKLPECPRGSSISAPSQTSVDVSLIQDVERIL<br>DYSLCQETWSKIRAKLPVSPVDLSYLAPKNPG<br>SGPAFTIINGTLKYFETRYIRVDISNPIIPHMVG<br>TMSGTTTERELWNDWYPYEDVEIGPNGVLK<br>TPTGFKFPLYMIGHGMLDSDLHKSSQAQVFE<br>HPHAKDAASQLPDDETLFFGDTGLSKNPVEL<br>VEGWFSSWKSTLASFFLIIGLGVALIFIIRIIVAI<br>RYKYKGRKTQKIYNDVEMSRLGNK<br>(SEQ ID NO: 4) |
| Cocal | MNFLLLTFIVLPLCSHAKFSIVFPQSQKGNWK<br>NVPSSYHYCPSSSDQNWHNDLLGITMKVKMP<br>KTHKAIQADGWMCHAAKWITTCDFRWYGP<br>KYITHSIHSIQPTSEQCKESIKQTKQGTWMSP<br>GFPPQNCGYATVTDSVAVVVQATPHHVLVD<br>EYTGEWIDSQFPNGKCETEECETVHNSTVW<br>YSDYKVTGLCDATLVDTEITFFSEDGKKESIG<br>KPNTGYRSNYFAYEKGDKVCKMNYCKHAGV<br>RLPSGVWFEFVDQDVYAAAKLPECPVGATIS<br>APTQTSVDVSLILDVERILDYSLCQETWSKIRS<br>KQPVSPVDLSYLAPKNPGTGPAFTIINGTLKY<br>FETRYIRIDIDNPIISKMVGKISGSQTERELWTE<br>WFPYEGVEIGPNGILKTPTGYKFPLFMIGHG<br>MLDSDLHKTSQAEVFEHPHLAEAPKQLPEEE<br>TLFFGDTGISKNPVELIEGWFSSWKSTVVTFF<br>FAIGVFILLYVVARIVIAVRYRYQGSNNKRIYN<br>DIEMSRFRK (SEQ ID NO: 5)<br>Positions of signal peptide: 1-17 | KFSIVFPQSQKGNWKNVPSSYHYCPSSSDQN<br>WHNDLLGITMKVKMPKTHKAIQADGWMCH<br>AAKWITTCDFRWYGPKYITHSIHSIQPTSEQC<br>KESIKQTKQGTWMSPGFPPQNCGYATVTDS<br>VAVVVQATPHHVLVDEYTGEWIDSQFPNGK<br>CETEECETVHNSTVWYSDYKVTGLCDATLVD<br>TEITFFSEDGKKESIGKPNTGYRSNYFAYEKG<br>DKVCKMNYCKHAGVRLPSGVWFEFVDQDVY<br>AAAKLPECPVGATISAPTQTSVDVSLILDVERI<br>LDYSLCQETWSKIRSKQPVSPVDLSYLAPKNP<br>GTGPAFTIINGTLKYFETRYIRIDIDNPIISKMV<br>GKISGSQTERELWTEWFPYEGVEIGPNGILKT<br>PTGYKFPLFMIGHGMLDSDLHKTSQAEVFEH<br>PHLAEAPKQLPEEETLFFGDTGISKNPVELIE<br>GWFSSWKSTVVTFFFAIGVFILLYVVARIVIAV<br>RYRYQGSNNKRIYNDIEMSRFRK<br>(SEQ ID NO: 6) |
| Morreton | MLVLYLLLSLLALGAQCKFTIVFPHNQKGNW<br>KNVPANYQYCPSSSDLNWHNGLIGTSLQVKM<br>PKSHKAIQADGWMCHAAKWVTTCDFRWYG<br>PKYVTHSIKSMIPTVDQCKESIAQTKQGTWLN<br>PGFPPQSCGYASVTDAEAVIVKATPHQVLVD<br>EYTGEWVDSQFPTGKCNKDICPTVHNSTTW<br>HSDYKVTGLCDANLISMDITFFSEDGKLTSLG<br>KEGTGFRSNYFAYENGDKACRMQYCKHWG<br>VRLPSGVWFEMADKDIYNDAKFPDCPEGSSIA<br>APSQTSVDVSLIQDVERILDYSLCQETWSKIRA<br>HLPISPVDLSYLSPKNPGTGPAFTIINGTLKYF<br>ETRYIRVDIAGPIIPQMRGVISGTTTERELWTD<br>WYPYEDVEIGPNGVLKTATGYKFPLYMIGHG<br>MLDSDLHISSKAQVFEHPHIQDAASQLPDDET<br>LFFGDTGLSKNPIELVEGWFSGWKSTIASFFF | KFTIVFPHNQKGNWKNVPANYQYCPSSSDLN<br>WHNGLIGTSLQVKMPKSHKAIQADGWMCHA<br>AKWVTTCDFRWYGPKYVTHSIKSMIPTVDQC<br>KESIAQTKQGTWLNPGFPPQSCGYASVTDAE<br>AVIVKATPHQVLVDEYTGEWVDSQFPTGKC<br>NKDICPTVHNSTTWHSDYKVTGLCDANLISM<br>DITFFSEDGKLTSLGKEGTGFRSNYFAYENGD<br>KACRMQYCKHWGVRLPSGVWFEMADKDIYN<br>DAKFPDCPEGSSIAAPSQTSVDVSLIQDVERIL<br>DYSLCQETWSKIRAHLPISPVDLSYLSPKNPG<br>TGPAFTIINGTLKYFETRYIRVDIAGPIIPQMR<br>GVISGTTTERELWTDWYPYEDVEIGPNGVLK<br>TATGYKFPLYMIGHGMLDSDLHISSKAQVFEH<br>PHIQDAASQLPDDETLFFGDTGLSKNPIELVE<br>GWFSGWKSTIASFFFIIGLVIGLYLVLRIGIALC |

TABLE 1-continued non-mutated (wild-type) amino acid sequences of the full-length glycoprotein G and of the ectodomain of glycoprotein G of Indiana, Maraba, Cocal, Morreton, Alagoa, New Jersey, and Carajas VSV strains. In the full-length amino acid sequences, the signal peptide is underlined. Positions of the signal peptide in the full-length amino acid sequences is further indicated.

| VSV strain | Full-length glycoprotein G amino acid sequence | Ectodomain of glycoprotein G amino acid sequence |
| --- | --- | --- |
| | IIGLVIGLYLVLRIGIALCIKCRVQEKRPKIYTD<br>VEMNRLDR (SEQ ID NO: 7)<br>Positions of signal peptide: 1-17 | IKCRVQEKRPKIYTDVEMNRLDR<br>(SEQ ID NO: 8) |
| Alagoa | MTPAFILCMLLAGSSWAKFTIVFPQSQKGDW<br>KDVPPNYRYCPSSADQNWHGDLLGVNIRAK<br>MPKVHKAIKADGWMCHAAKWVTTCDYRWY<br>GPQYITHSIHSFIPTKAQCEESIKQTKEGVWIN<br>PGFPPKNCGYASVSDAESIIVQATAHSVMIDE<br>YSGDWLDSQFPTGRCTGSTCETIHNSTLWYA<br>DYQVTGLCDSALVSTEVTFYSEDGLMTSIGR<br>QNTGYRSNYFPYEKGAAACRMKYCTHEGIRL<br>PSGVWFEMVDKELLESVQMPECPAGLTISAP<br>TQTSVDVSLILDVERMLDYSLCQETWSKVHS<br>GLPISPVDLGYIAPKNPGAGPAFTIVNGTLKY<br>FDTRYLRIDIEGPVLKKMTGKVSGTPTKREL<br>WTEWFPYDDVEIGPNGVLKTPEGYKFPLYMI<br>GHGLLDSDLQKTSQAEVFHHPQIAEAVQKLP<br>DDETLFFGDTGISKNPVEVIEGWFSNWRSSV<br>MAIVFAILLLVITVLMVRLCVAFRHFCCQKRH<br>KIYNDLEMNQLRR (SEQ ID NO: 9)<br>Positions of signal peptide: 1-17 | KFTIVFPQSQKGDWKDVPPNYRYCPSSADQN<br>WHGDLLGVNIRAKMPKVHKAIKADGWMCHA<br>AKWVTTCDYRWYGPQYITHSIHSFIPTKAQC<br>EESIKQTKEGVWINPGFPPKNCGYASVSDAES<br>IIVQATAHSVMIDEYSGDWLDSQFPTGRCTGS<br>TCETIHNSTLWYADYQVTGLCDSALVSTEVT<br>FYSEDGLMTSIGRQNTGYRSNYFPYEKGAAA<br>CRMKYCTHEGIRLPSGVWFEMVDKELLESVQ<br>MPECPAGLTISAPTQTSVDVSLILDVERMLDY<br>SLCQETWSKVHSGLPISPVDLGYIAPKNPGAG<br>PAFTIVNGTLKYFDTRYLRIDIEGPVLKKMTG<br>KVSGTPTKRELWTEWFPYDDVEIGPNGVLKT<br>PEGYKFPLYMIGHGLLDSDLQKTSQAEVFHH<br>PQIAEAVQKLPDDETLFFGDTGISKNPVEVIE<br>GWFSNWRSSVMAIVFAILLLVITVLMVRLCVA<br>FRHFCCQKRHKIYNDLEMNQLRR<br>(SEQ ID NO: 10) |
| New Jersey | MLSYLIFALVVSPILGKIEIVFPQHTTGDWKRV<br>PHEYNYCPTSADKNSHGTQTGIPVELTMPKG<br>LTTHQVDGFMCHSALWMTTCDFRWYGPKYI<br>THSIHNEEPTDYQCLEAIKAYKDGVSFNPGFP<br>PQSCGYGTVTDAEAHIVTVTPHSVKVDEYTG<br>EWIDPHFIGGRCKGQICETVHNSTKWFTSSD<br>GESVCSQLFTLVGGTFFSDSEEITSMGLPETG<br>IRSNYFPYVSTEGICKMPFCRKPGYKLKNDLW<br>FQITDPDLDKTVRDLPHIKDCDLSSSIVTPGEH<br>ATDISLISDVERILDYALCQNTWSKIEAGEPITP<br>VDLSYLGPKNPGAGPVFTIINGSLHYFMSKYL<br>RVELESPVIPRMEGKVAGTRIVRQLWDQWFP<br>FGEVEIGPNGVLKTKQGYKFPLHIIGTGEVDN<br>DIKMERIVKHWEHPHIEAAQTFLKKDDTEEVL<br>YYGDTGVSKNPVELVEGWFSGWRSSIMGVL<br>AVIIGFVILIFLIRLIGVLSSLFRQKRRPIYKSDV<br>EMAHFR (SEQ ID NO: 11)<br>Positions of signal peptide: 1-16 | KIEIVFPQHTTGDWKRVPHEYNYCPTSADKN<br>SHGTQTGIPVELTMPKGLTTHQVDGFMCHS<br>ALWMTTCDFRWYGPKYITHSIHNEEPTDYQC<br>LEAIKAYKDGVSFNPGFPPQSCGYGTVTDAE<br>AHIVTVTPHSVKVDEYTGEWIDPHFIGGRCK<br>GQICETVHNSTKWFTSSDGESVCSQLFTLVG<br>GTFFSDSEEITSMGLPETGIRSNYFPYVSTEGI<br>CKMPFCRKPGYKLKNDLWFQITDPDLDKTVR<br>DLPHIKDCDLSSSIVTPGEHATDISLISDVERIL<br>DYALCQNTWSKIEAGEPITPVDLSYLGPKNP<br>GAGPVFTIINGSLHYFMSKYLRVELESPVIPRM<br>EGKVAGTRIVRQLWDQWFPFGEVEIGPNGV<br>LKTKQGYKFPLHIIGTGEVDNDIKMERIVKHW<br>EHPHIEAAQTFLKKDDTEEVLYYGDTGVSKN<br>PVELVEGWFSGWRSSIMGVLAVIIGFVILIFLIR<br>LIGVLSSLFRQKRRPIYKSDVEMAHFR<br>(SEQ ID NO: 12) |
| Carajas | MKMKMVIAGLILCIGILPAIGKITISFPQSLKGD<br>WRPVPKGYNYCPTSADKNLHGDLIDIGLRLR<br>APKSFKGISADGWMCHAARWITTCDFRWYG<br>PKYITHSIHSFRPSNDQCKEAIRLTNEGNWIN<br>PGFPPQSCGYASVTDSESVVVTVTKHQVLVD<br>EYSGSWIDSQFPGGSCTSPICDTVHNSTLWH<br>ADHTLDSICDQEFVAMDAVLFTESGKFEEFG<br>KPNSGIRSNYFPYESLKDVCQMDFCKRKGFKL<br>PSGVWFEIEDAEKSHKAQVELKIKRCPHGAVI<br>SAPNQNAADINLIMDVERILDYSLCQATWSKI<br>QNKEALTPIDISYLGPKNPGPGPAFTIINGTLH<br>YFNTRYIRVDIAGPVTKEITGFVSGTSTSRVL<br>WDQWFPYGENSIGPNGLLKTASGYKYPLFM<br>VGTGVLDADIHKLGEATVIEHPHAKEAQKVV<br>DDSEVIFFGDTGVSKNPVEVVEGWFSGWRSS<br>LMSIFGIILLIVCLVLIVRILIALKYCCVRHKKRTI<br>YKEDLEMGRIPRRA (SEQ ID NO: 13)<br>Positions of signal peptide: 1-21 | KITISFPQSLKGDWRPVPKGYNYCPTSADKNL<br>HGDLIDIGLRLRAPKSFKGISADGWMCHAAR<br>WITTCDFRWYGPKYITHSIHSFRPSNDQCKEA<br>IRLTNEGNWINPGFPPQSCGYASVTDSESVVV<br>TVTKHQVLVDEYSGSWIDSQFPGGSCTSPIC<br>DTVHNSTLWHADHTLDSICDQEFVAMDAVLF<br>TESGKFEEFGKPNSGIRSNYFPYESLKDVCQM<br>DFCKRKGFKLPSGVWFEIEDAEKSHKAQVEL<br>KIKRCPHGAVISAPNQNAADINLIMDVERILDY<br>SLCQATWSKIQNKEALTPIDISYLGPKNPGPG<br>PAFTIINGTLHYFNTRYIRVDIAGPVTKEITGF<br>VSGTSTSRVLWDQWFPYGENSIGPNGLLKTA<br>SGYKYPLFMVGTGVLDADIHKLGEATVIEHP<br>HAKEAQKVVDDSEVIFFGDTGVSKNPVEVVE<br>GWFSGWRSSLMSIFGIILLIVCLVLIVRILIALKY<br>CCVRHKKRTIYKEDLEMGRIPRRA<br>(SEQ ID NO: 14) |

An optimal global alignment of the non-mutated the amino acid sequences of the ectodomain of the glycoprotein G of VSV strain Indiana versus each of Maraba, Cocal, Morreton, Alagoa, New Jersey, and Carajas strains is presented in FIGS. 3A to 3F. Based on these optimal global alignments, the percentage of identity, the similarity score (obtained using the Emboss Needle software with default parameters as defined above), and the positions in the amino acid sequences of the ectodomain of the glycoprotein G of VSV strains Maraba, Cocal, Morreton, Alagoa, New Jersey, and Carajas equivalent to positions 17-25 and 421-429 of SEQ ID NO:2 (VSV Indiana glycoprotein G ectodomain) may be determined. They are listed in Table 2 below:

TABLE 2

Positions in the amino acid sequences of the ectodomain of the glycoprotein G of VSV strains Maraba, Cocal, Morreton, Alagoa, New Jersey, and Carajas equivalent to positions 17-25 and 421-429 of SEQ ID NO: 2 (VSV Indiana glycoprotein G ectodomain), % identity with SEQ ID NO: 2 after optimal global alignment and similarity score (as calculated by Emboss Needle, using default parameters: Gap open = 10.0, Gap extend = 0.5, End gap penalty = false, End gap open = 10.0, Blosum 62 matrix).

| VSV strain (sequence identifier) | Positions in SEQ ID NO: 2 | Equivalent positions | % identity | Similarity score |
|---|---|---|---|---|
| Indiana (SEQ ID NO: 2) | / | / | 100% | 2693 |
| Maraba (SEQ ID NO: 4) | 17-25<br>421-429 | 17-25<br>421-429 | 78.8 | 2227 |
| Cocal (SEQ ID NO: 6) | 17-25<br>421-429 | 17-25<br>421-429 | 73.1 | 2085 |
| Morreton (SEQ ID NO: 8) | 17-25<br>421-429 | 17-25<br>421-429 | 86.3 | 2385 |
| Alagoa (SEQ ID NO: 10) | 17-25<br>421-429 | 17-25<br>421-429 | 64.7 | 1916.5 |
| New Jersey (SEQ ID NO: 12) | 17-25<br>421-429 | 17-25<br>428-436 | 51.6 | 1404 |
| Carajas (SEQ ID NO: 14) | 17-25<br>421-429 | 17-25<br>425-433 | 56.4 | 1622 |

The alignments of FIGS. 3A to 3F also show that, in addition to identical amino acids between two amino acid sequences, some substitutions are conservative, ensuring the function of the ectodomain. The presence of such conservative substitutions is taken into account when calculating the similarity score of two sequences after optimal global alignment, in particular when using the Emboss Needle software with default parameters. Therefore, when an initial sequence different from SEQ ID NO:2 is used, in addition to an identity of at least 50% (or any other minimal identity percentage defined above) with SEQ ID NO:2, the initial sequence preferably has a similarity score after optimal global alignment (preferably using the Emboss Needle software with default parameters as defined above) of at least 1400, more preferably at least 1500, at least 1600, at least 1700, at least 1800, even more preferably at least 1900, at least 2000, at least 2100, at least 2200, or even at least 2300, knowing that the similarity score of SEQ ID NO:2 with itself is 2693.

Figure 4:
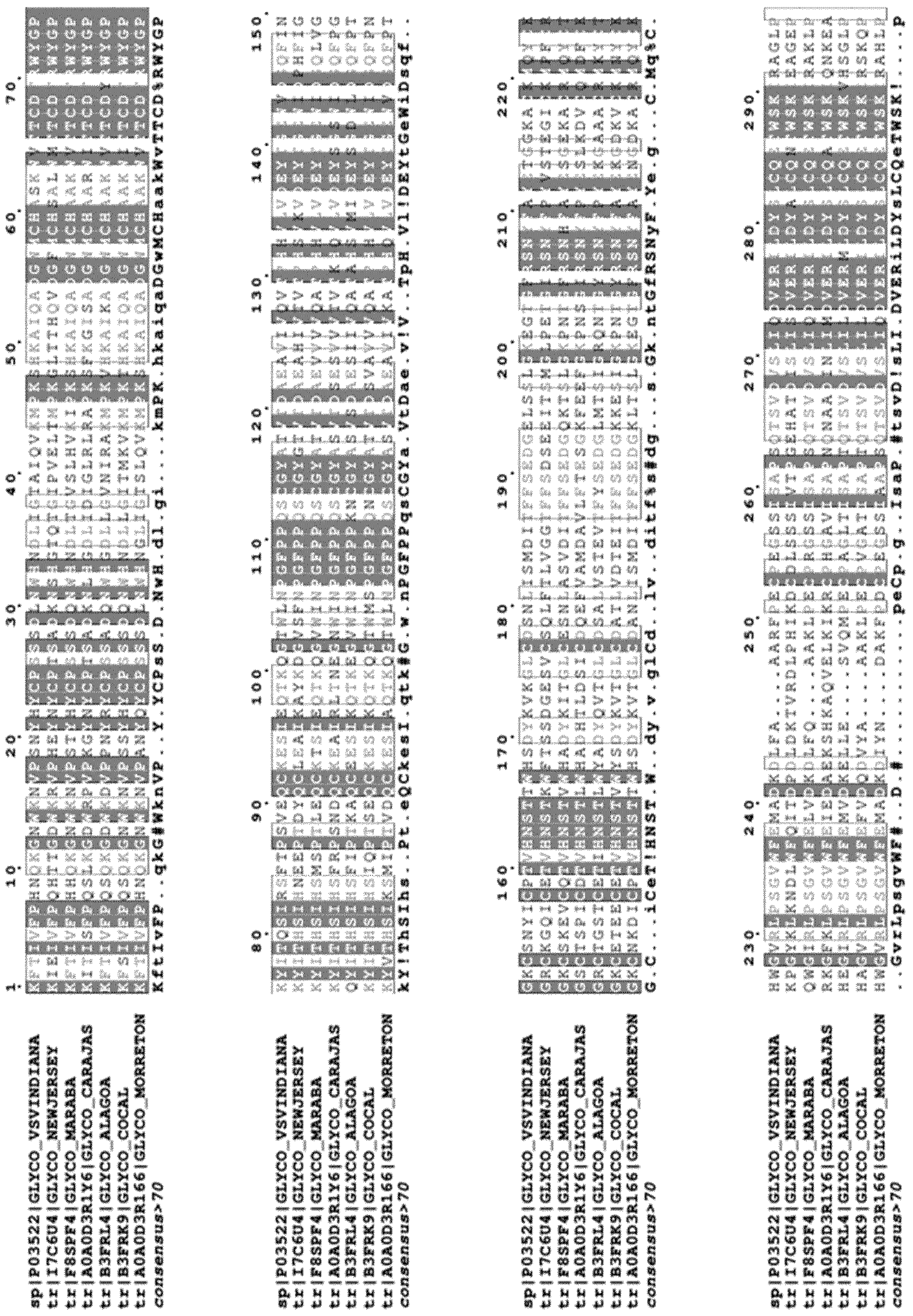
FIG. 4. Multiple sequence alignment of amino acid sequences of the ectodomains of glycoprotein G of VSV strains Indiana (SEQ ID NO:2), Maraba (SEQ ID NO:4), Cocal (SEQ ID NO: 6), Morreton (SEQ ID NO:8), Alagoa (SEQ ID NO: 10), New Jersey (SEQ ID NO: 12), and Carajas (SEQ ID NO: 14) generated using clustal omega (www.ebi.ac.uk/Tools/msa/clustalo/) and espript. Strictly Conserved amino acids (identical for all strains) are written in white on grey background. Boxed areas correspond to highly similar residues. The consensus sequence (similarity score >0.7) indicated at the bottom was generated using criteria from MultAlin: uppercase is identity, lowercase is consensus level >0.5, ! is anyone of IV, $ is anyone of LM, % is anyone of FY, #is anyone of NDQEBZ.
Figure 4:
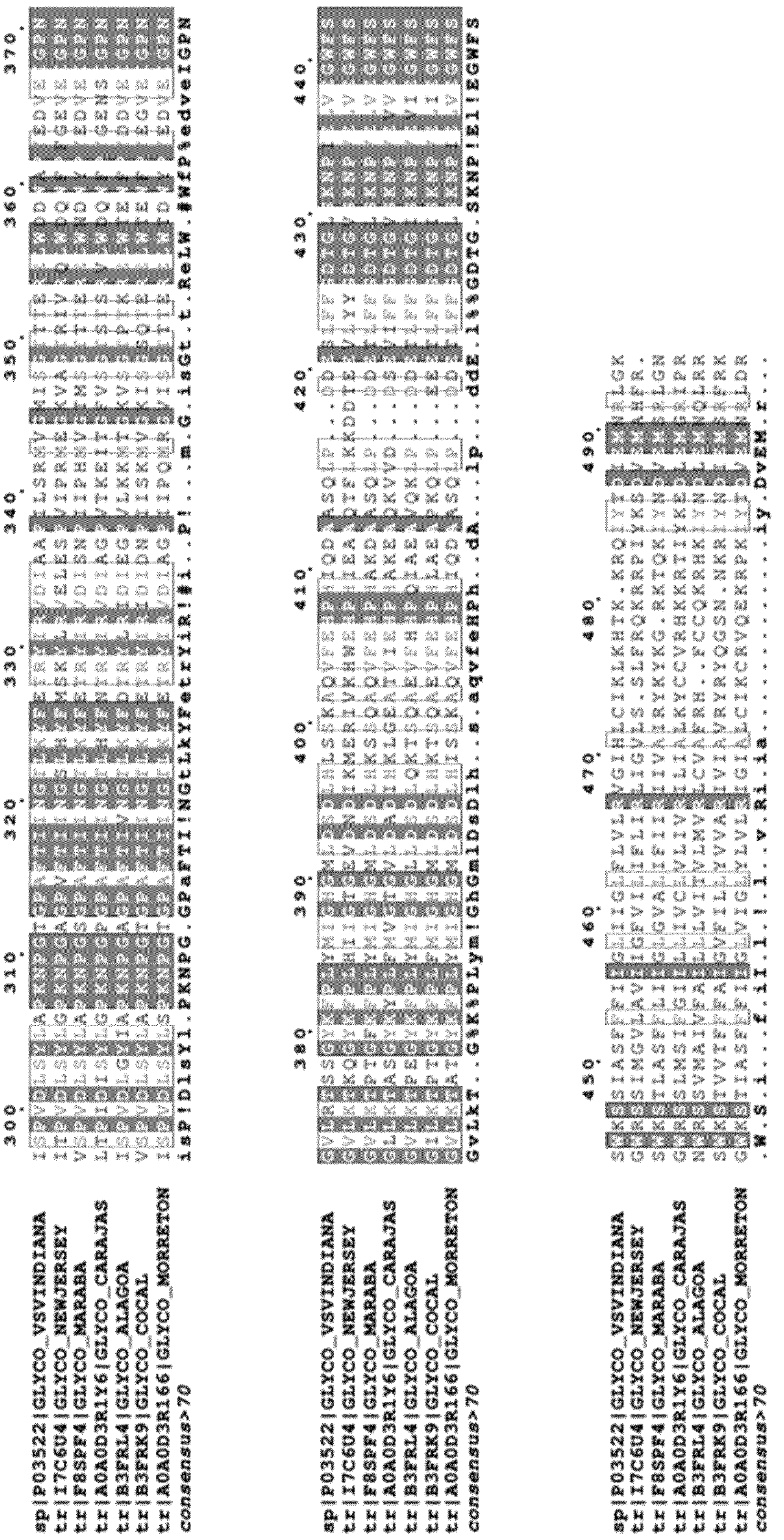

A multiple amino acid sequences alignment of the ectodomains of the glycoprotein G of VSV strains Indiana, Maraba, Cocal, Morreton, Alagoa, New Jersey, and Carajas is presented in FIG. 4. As appears from FIG. 4, all amino sequences of the ectodomain of glycoprotein G of VSV, no matter the specific strain, contain conserved amino acids and domains (i.e. amino acids or domains that are identical between SEQ ID NO:2 and the other aligned amino acid sequences).

In particular, positions 17-25 of SEQ ID NO:2 contain conserved amino acids in positions 17-18, 21 and 23-25. A consensus sequence of positions 17-25 of amino sequences of the ectodomain of glycoprotein G of VSV strains Indiana, Maraba, Cocal, Morreton, Alagoa, New Jersey, and Carajas may be defined as $VPX_1X_2YX_3YCP$ (SEQ ID NO: 15), wherein:

- $X_1$ is selected from serine(S), histidine (H), lysine (K), proline (P), and alanine (A),
- $X_2$ is selected from asparagine (N), glutamic acid (E), threonine (T), glycine (G), and serine(S), and
- $X_3$ is selected from histidine (H), asparagine (N), arginine (R), and glutamine (Q).

Similarly, positions 421-429 of SEQ ID NO:2 contain conserved amino acids in positions 421 and 426-429. A consensus sequence of positions 421-429 of amino sequences of the ectodomain of glycoprotein G of VSV strains Indiana, Maraba, Cocal, Morreton, Alagoa, New Jersey, and Carajas may be defined as $EX_4X_5X_6X_7GDTG$ (SEQ ID NO: 16), wherein:

- $X_4$ is selected from serine(S), valine (V), and threonine (T),
- $X_5$ is selected from leucine (L) and isoleucine (I),
- $X_6$ is selected from phenylalanine (F) and tyrosine (Y), and
- $X_7$ is selected from phenylalanine (F) and tyrosine (Y).

Therefore, in a preferred embodiment, the mutant polypeptide according to the invention comprises, or consists essentially of, or consists of:

a) the amino acid sequence as set forth in SEQ ID NO: 2 or a sequence having at least 50% of identity with the amino acid sequence as set forth in SEQ ID NO: 2 after optimal global alignment with SEQ ID NO:2, and b) two domains of sequence $VPX_1X_2YX_3YCP$ (SEQ ID NO: 15) and $EX_4X_5X_6X_7GDTG$ (SEQ ID NO: 16), wherein:

i) one of $X_4$ to $X_7$ (corresponding to positions 422-425 of SEQ ID NO:2), preferably $X_4$ (corresponding to position 422 of SEQ ID NO:2);

ii) one of $X_1$ to $X_3$ (corresponding to positions 19-20 and 22 of SEQ ID NO:2), preferably $X_3$ (corresponding to position 22 of SEQ ID NO:2); or iii) one of $X_1$ to $X_3$ (corresponding to positions 19-20 and 22 of SEQ ID NO:2) and one of $X_4$ to $X_7$ (corresponding to positions 422-425 of SEQ ID NO:2), preferably $X_3$ and $X_4$ (corresponding to positions 22 and 422 of SEQ ID NO:2), is(are) substituted.

Moreover, amino acids conserved in all amino sequences of the ectodomain of glycoprotein G of VSV strains Indiana, Maraba, Cocal, Morreton, Alagoa, New Jersey, and Carajas correspond to positions 1, 4, 6-7, 12, 14, 17-18, 21, 23-25, 27, 29, 31, 33, 46-4755-56, 58-60, 64, 66-69, 71-75, 77, 79, 81-82, 87, 91-92, 96, 102, 107-111, 114-116, 119, 121, 127, 130, 132, 134, 137-139, 141, 143, 145, 151, 153, 158, 160, 162-165, 167, 177, 199, 204, 206-208, 210, 212, 219, 221, 224, 228, 231, 236-237, 241, 253, 259, 262, 268, 271-272, 274-277, 279-281, 283-285, 287-290, 299, 301, 304, 307-311, 313-314, 316-318, 320-321, 323, 325-326, 330, 332, 338, 345, 349, 354, 356-357, 360, 362, 368-372, 374, 376, 379, 381, 383-384, 388, 390, 393, 395, 407-408, 413, 421, 426-429, 431-434, 436, 439-443, 445, 447, 456, 467, 487, and 489-490 of SEQ ID NO:2. In the following, these positions are referred to as "conserved positions".

Therefore, in some embodiments of the mutated polypeptide according to the invention, the amino acid sequence having at least 50% of identity with the amino acid sequence as set forth in SEQ ID NO: 2, after optimal global alignment with SEQ ID NO:2, has the same amino acids as SEQ ID NO: 2 in the above defined conserved positions.

An exception may be made for conserved positions 47 and 354, when it is desired to alter the ability of the ectodomain to bind to the low-density lipoprotein receptor (LDL-R) (see below section entitled "Further optional mutations"). In this case, the amino acid sequence having at least 50% of identity (or any other minimal % of identity disclosed above) with the amino acid sequence as set forth in SEQ ID NO: 2, after optimal global alignment with SEQ ID NO:2, may have the same amino acids as SEQ ID NO: 2 in the above defined conserved positions, except for possible additional substitution(s) in position 47 and/or 354 of SEQ ID NO:2.

Type of Amino Acid for Substitution

While the substitute amino acid(s) in the mutant polypeptide according to the invention may be selected from any amino acid different from the original amino acid, depending on the location(s) of the substitution(s), some particular types of amino acids are preferred.

In particular, when the mutant polypeptide according to the invention comprises a substitution in any amino acid residue located from position 421 to position 429 of SEQ ID NO: 2 or equivalent position after optimal global alignment with SEQ ID NO:2, the original amino acid is preferably substituted by a hydrophobic amino acid, preferably selected for the group consisting of glycine (G), alanine (A), valine (V), leucine (L), isoleucine (I), methionine (M), proline (P), phenylalanine (F) and tryptophan (W), more preferably isoleucine (I), leucine (L), methionine (M), valine (V) and phenylalanine (F), even more preferably isoleucine (I). Indeed, the present inventors have shown that the presence of a hydrophobic amino acid in any amino acid residue located from position 421 to position 429 of SEQ ID NO:2 or equivalent position after optimal global alignment with SEQ ID NO:2 results in the stabilization of the glycoprotein G prefusion conformation.

When the mutant polypeptide according to the invention comprises a substitution in any amino acid residue located from position 17 to position 25 of SEQ ID NO:2 or equivalent position after optimal global alignment with SEQ ID NO:2, the original amino acid is preferably substituted by a polar amino acid, preferably selected from the group consisting of asparagine (N), glutamine (Q), cysteine (C), tyrosine (Y), threonine (T), serine(S), more preferably asparagine (N). Indeed, it is believed that the presence of a polar amino acid in any amino acid residue located from position 17 to position 25 of SEQ ID NO: 2 or equivalent position after optimal global alignment with SEQ ID NO:2 results in the stabilization of the glycoprotein G prefusion conformation.

When the mutant polypeptide according to the invention comprises a substitution in any amino acid residue located from position 17 to position 25 of SEQ ID NO:2 or equivalent position after optimal global alignment with SEQ ID NO:2, and also a substitution in any amino acid residue located from position 421 to position 429 of SEQ ID NO:2 or equivalent position after optimal global alignment with SEQ ID NO:2:

a) the original amino acid located from position 17 to position 25 of SEQ ID NO:2 or equivalent position after optimal global alignment with SEQ ID NO:2 is preferably substituted by a polar amino acid, preferably selected from the group consisting of asparagine (N), glutamine (Q), cysteine (C), tyrosine (Y), threonine (T), serine (S), more preferably asparagine (N); and b) the original amino acid located from position 421 to position 429 of SEQ ID NO:2 or equivalent position after optimal global alignment with SEQ ID NO:2 is preferably substituted by a hydrophobic amino acid, preferably selected for the group consisting of glycine (G), alanine (A), valine (V), leucine (L), isoleucine (I), methionine (M), proline (P), phenylalanine (F) and tryptophan (W), more preferably isoleucine (I), leucine (L), methionine (M), valine (V) and phenylalanine (F), even more preferably isoleucine (I) (FIG. 7).

Preferred Mutant Polypeptides

Some preferred mutant polypeptides according to the invention are based on the amino acid sequence of the ectodomain of glycoprotein G of VSV Indiana strain, and may be selected from:

a) a mutant polypeptide comprising, or consisting essentially of, or consisting of, the amino acid sequence as set forth in SEQ ID NO: 17 corresponding to SEQ ID NO: 2 with a substitution of the histidine (H) amino acid residue in position 22 by an asparagine (N) amino acid residue;

b) a mutant polypeptide comprising, or consisting essentially of, or consisting of, the amino acid sequence as set forth in SEQ ID NO: 18 corresponding to SEQ ID NO: 2 with a substitution of the serine(S) amino acid residue in position 422 by an isoleucine (I) amino acid residue;

c) a mutant polypeptide comprising, or consisting essentially of, or consisting of, the amino acid sequence as set forth in SEQ ID NO: 19 corresponding to SEQ ID NO: 2 with a substitution of the serine(S) amino acid residue in position 422 by a leucine (L) amino acid residue;

d) a mutant polypeptide comprising, or consisting essentially of, or consisting of, the amino acid sequence as set forth in SEQ ID NO:20 corresponding to SEQ ID NO: 2 with a substitution of the serine(S) amino acid residue in position 422 by a phenylalanine (F) amino acid residue;

e) a mutant polypeptide comprising, or consisting essentially of, or consisting of, the amino acid sequence as set forth in SEQ ID NO:21 corresponding to SEQ ID NO: 2 with a substitution of the serine(S) amino acid residue in position 422 by a methionine (M) amino acid residue;

f) a mutant polypeptide comprising, or consisting essentially of, or consisting of, the amino acid sequence as set forth in SEQ ID NO:22 corresponding to SEQ ID NO: 2 with a substitution of the serine(S) amino acid residue in position 422 by a valine (V) amino acid residue;

g) a mutant polypeptide comprising, or consisting essentially of, or consisting of, the amino acid sequence as set forth in SEQ ID NO:23 corresponding to SEQ ID NO: 2 with a substitution of the histidine (H) amino acid residue in position 22 by an asparagine (N) amino acid residue and a substitution of the serine(S) amino acid residue in position 422 by an isoleucine (I) amino acid residue;

h) a mutant polypeptide comprising, or consisting essentially of, or consisting of, the amino acid sequence as set forth in SEQ ID NO:24 corresponding to SEQ ID NO: 2 with a substitution of the histidine (H) amino acid residue in position 22 by an asparagine (N) amino acid residue and a substitution of the serine(S) amino acid residue in position 422 by a leucine (L) amino acid residue;

i) a mutant polypeptide comprising, or consisting essentially of, or consisting of, the amino acid sequence as set forth in SEQ ID NO:25 corresponding to SEQ ID NO: 2 with a substitution of the histidine (H) amino acid residue in position 22 by an asparagine (N) amino acid residue and a substitution of the serine(S) amino acid residue in position 422 by a phenylalanine (F) amino acid residue;

j) a mutant polypeptide comprising, or consisting essentially of, or consisting of, the amino acid sequence as set forth in SEQ ID NO:26 corresponding to SEQ ID NO: 2 with a substitution of the histidine (H) amino acid residue in position 22 by an asparagine (N) amino acid residue and a substitution of the serine(S) amino acid residue in position 422 by a methionine (M) amino acid residue;

k) a mutant polypeptide comprising, or consisting essentially of, or consisting of, the amino acid sequence as set forth in SEQ ID NO:27 corresponding to SEQ ID NO: 2 with a substitution of the histidine (H) amino acid residue in position 22 by an asparagine (N) amino acid residue and a substitution of the serine(S) amino acid residue in position 422 by a valine (V) amino acid residue; and l) a mutant polypeptide comprising, or consisting essentially of, or consisting of, the amino acid sequence as defined in any one of a) to k) above, and further comprising a signal peptide in N-terminal, preferably the signal peptide corresponding to positions 1-16 of SEQ ID NO: 1.

Most preferred mutant polypeptides based on the amino acid sequence of the ectodomain of glycoprotein G of VSV Indiana strain are those comprising at least a substitution in position 422 (SEQ ID NO: 18 to 27 or a mutant polypeptide comprising one of these amino acid sequences and further comprising a signal peptide in N-terminal, preferably the signal peptide corresponding to positions 1-16 of SEQ ID NO:1).

The amino acid sequences SEQ ID NO: 17 to 27 of preferred mutant polypeptide derived from VSV Indiana glycoprotein G ectodomain are presented in Table 3 below.

TABLE 3

Amino acid sequences SEQ ID NO: 17 to 27 based on Indiana VSV strain glycoprotein G ectodonnain (SEQ ID NO: 2) and associated substitution compared to SEQ ID NO: 2. For each substitution, the initial amino acid in SEQ ID NO: 2 is indicated in one letter code and followed by its position in SEQ ID NO: 2 and the substitute amino acid in one letter code.

| Sequence identifier | Substitution(s) | Amino acid sequence |
|---|---|---|
| SEQ ID NO: 17 | H22N | KFTIVFPHNQKGNWKNVPSNYNYCPSSSDLNWHNDLIGTAIQVKMPKSH<br>KAIQADGWMCHASKWVTTCDFRWYGPKYITQSIRSFTPSVEQCKESIEQ<br>TKQGTWLNPGFPPQSCGYATVTDAEAVIVQVTPHHVLVDEYTGEWVDS<br>QFINGKCSNYICPTVHNSTTWHSDYKVKGLCDSNLISMDITFFSEDGELSS<br>LGKEGTGFRSNYFAYETGGKACKMQYCKHWGVRLPSGVWFEMADKDL<br>FAAARFPECPEGSSISAPSQTSVDVSLIQDVERILDYSLCQETWSKIRAGLP<br>ISPVDLSYLAPKNPGTGPAFTIINGTLKYFETRYIRVDIAAPILSRMVGMIS<br>GTTTERELWDDWAPYEDVEIGPNGVLRTSSGYKFPLYMIGHGMLDSDLH<br>LSSKAQVFEHPHIQDAASQLPDDESLFFGDTGLSKNPIELVEGWFSSWKS<br>SIASFFFIIGLIIGLFLVLRVGIHLCIKLKHTKKRQIYTDIEMNRLGK |
| SEQ ID NO: 18 | S422I | KFTIVFPHNQKGNWKNVPSNYHYCPSSSDLNWHNDLIGTAIQVKMPKSH<br>KAIQADGWMCHASKWVTTCDFRWYGPKYITQSIRSFTPSVEQCKESIEQ<br>TKQGTWLNPGFPPQSCGYATVTDAEAVIVQVTPHHVLVDEYTGEWVDS<br>QFINGKCSNYICPTVHNSTTWHSDYKVKGLCDSNLISMDITFFSEDGELSS<br>LGKEGTGFRSNYFAYETGGKACKMQYCKHWGVRLPSGVWFEMADKDL<br>FAAARFPECPEGSSISAPSQTSVDVSLIQDVERILDYSLCQETWSKIRAGLP<br>ISPVDLSYLAPKNPGTGPAFTIINGTLKYFETRYIRVDIAAPILSRMVGMIS<br>GTTTERELWDDWAPYEDVEIGPNGVLRTSSGYKFPLYMIGHGMLDSDLH<br>LSSKAQVFEHPHIQDAASQLPDDEILFFGDTGLSKNPIELVEGWFSSWKSS<br>IASFFFIIGLIIGLFLVLRVGIHLCIKLKHTKKRQIYTDIEMNRLGK |
| SEQ ID NO: 19 | S422L | KFTIVFPHNQKGNWKNVPSNYHYCPSSSDLNWHNDLIGTAIQVKMPKSH<br>KAIQADGWMCHASKWVTTCDFRWYGPKYITQSIRSFTPSVEQCKESIEQ<br>TKQGTWLNPGFPPQSCGYATVTDAEAVIVQVTPHHVLVDEYTGEWVDS<br>QFINGKCSNYICPTVHNSTTWHSDYKVKGLCDSNLISMDITFFSEDGELSS<br>LGKEGTGFRSNYFAYETGGKACKMQYCKHWGVRLPSGVWFEMADKDL<br>FAAARFPECPEGSSISAPSQTSVDVSLIQDVERILDYSLCQETWSKIRAGLP<br>ISPVDLSYLAPKNPGTGPAFTIINGTLKYFETRYIRVDIAAPILSRMVGMIS<br>GTTTERELWDDWAPYEDVEIGPNGVLRTSSGYKFPLYMIGHGMLDSDLH<br>LSSKAQVFEHPHIQDAASQLPDDELLFFGDTGLSKNPIELVEGWFSSWKS<br>SIASFFFIIGLIIGLFLVLRVGIHLCIKLKHTKKRQIYTDIEMNRLGK |
| SEQ ID NO: 20 | S422F | KFTIVFPHNQKGNWKNVPSNYHYCPSSSDLNWHNDLIGTAIQVKMPKSH<br>KAIQADGWMCHASKWVTTCDFRWYGPKYITQSIRSFTPSVEQCKESIEQ<br>TKQGTWLNPGFPPQSCGYATVTDAEAVIVQVTPHHVLVDEYTGEWVDS |

TABLE 3-continued

Amino acid sequences SEQ ID NO: 17 to 27 based on Indiana VSV strain glycoprotein G ectodonnain (SEQ ID NO: 2) and associated substitution compared to SEQ ID NO: 2. For each substitution, the initial amino acid in SEQ ID NO: 2 is indicated in one letter code and followed by its position in SEQ ID NO: 2 and the substitute amino acid in one letter code.

| Sequence identifier | Substitution(s) | Amino acid sequence |
|---|---|---|
| | | QFINGKCSNYICPTVHNSTTWHSDYKVKGLCDSNLISMDITFFSEDGELSS<br>LGKEGTGFRSNYFAYETGGKACKMQYCKHWGVRLPSGVWFEMADKDL<br>FAAARFPECPEGSSISAPSQTSVDVSLIQDVERILDYSLCQETWSKIRAGLP<br>ISPVDLSYLAPKNPGTGPAFTIINGTLKYFETRYIRVDIAAPILSRMVGMIS<br>GTTTERELWDDWAPYEDVEIGPNGVLRTSSGYKFPLYMIGHGMLDSDLH<br>LSSKAQVFEHPHIQDAASQLPDDEFLFGDTGLSKNPIELVEGWFSSWKSSI<br>ASFFFIIGLIIGLFLVLRVGIHLCIKLKHTKKRQIYTDIEMNRLGK |
| SEQ ID NO: 21 | S422M | KFTIVFPHNQKGNWKNVPSNYHYCPSSSDLNWHNDLIGTAIQVKMPKSH<br>KAIQADGWMCHASKWVTTCDFRWYGPKYITQSIRSFTPSVEQCKESIEQ<br>TKQGTWLNPGFPPQSCGYATVTDAEAVIVQVTPHHVLVDEYTGEWVDS<br>QFINGKCSNYICPTVHNSTTWHSDYKVKGLCDSNLISMDITFFSEDGELSS<br>LGKEGTGFRSNYFAYETGGKACKMQYCKHWGVRLPSGVWFEMADKDL<br>FAAARFPECPEGSSISAPSQTSVDVSLIQDVERILDYSLCQETWSKIRAGLP<br>ISPVDLSYLAPKNPGTGPAFTIINGTLKYFETRYIRVDIAAPILSRMVGMIS<br>GTTTERELWDDWAPYEDVEIGPNGVLRTSSGYKFPLYMIGHGMLDSDLH<br>LSSKAQVFEHPHIQDAASQLPDDEMLFFGDTGLSKNPIELVEGWFSSWKS<br>SIASFFFIIGLIIGLFLVLRVGIHLCIKLKHTKKRQIYTDIEMNRLGK |
| SEQ ID NO: 22 | S422V | KFTIVFPHNQKGNWKNVPSNYHYCPSSSDLNWHNDLIGTAIQVKMPKSH<br>KAIQADGWMCHASKWVTTCDFRWYGPKYITQSIRSFTPSVEQCKESIEQ<br>TKQGTWLNPGFPPQSCGYATVTDAEAVIVQVTPHHVLVDEYTGEWVDS<br>QFINGKCSNYICPTVHNSTTWHSDYKVKGLCDSNLISMDITFFSEDGELSS<br>LGKEGTGFRSNYFAYETGGKACKMQYCKHWGVRLPSGVWFEMADKDL<br>FAAARFPECPEGSSISAPSQTSVDVSLIQDVERILDYSLCQETWSKIRAGLP<br>ISPVDLSYLAPKNPGTGPAFTIINGTLKYFETRYIRVDIAAPILSRMVGMIS<br>GTTTERELWDDWAPYEDVEIGPNGVLRTSSGYKFPLYMIGHGMLDSDLH<br>LSSKAQVFEHPHIQDAASQLPDDEVLFFGDTGLSKNPIELVEGWFSSWKS<br>SIASFFFIIGLIIGLFLVLRVGIHLCIKLKHTKKRQIYTDIEMNRLGK |
| SEQ ID NO: 23 | H22N and S422I | KFTIVFPHNQKGNWKNVPSNYNYCPSSSDLNWHNDLIGTAIQVKMPKSH<br>KAIQADGWMCHASKWVTTCDFRWYGPKYITQSIRSFTPSVEQCKESIEQ<br>TKQGTWLNPGFPPQSCGYATVTDAEAVIVQVTPHHVLVDEYTGEWVDS<br>QFINGKCSNYICPTVHNSTTWHSDYKVKGLCDSNLISMDITFFSEDGELSS<br>LGKEGTGFRSNYFAYETGGKACKMQYCKHWGVRLPSGVWFEMADKDL<br>FAAARFPECPEGSSISAPSQTSVDVSLIQDVERILDYSLCQETWSKIRAGLP<br>ISPVDLSYLAPKNPGTGPAFTIINGTLKYFETRYIRVDIAAPILSRMVGMIS<br>GTTTERELWDDWAPYEDVEIGPNGVLRTSSGYKFPLYMIGHGMLDSDLH<br>LSSKAQVFEHPHIQDAASQLPDDEILFFGDTGLSKNPIELVEGWFSSWKSS<br>IASFFFIIGLIIGLFLVLRVGIHLCIKLKHTKKRQIYTDIEMNRLGK |
| SEQ ID NO: 24 | H22N and S422L | KFTIVFPHNQKGNWKNVPSNYNYCPSSSDLNWHNDLIGTAIQVKMPKSH<br>KAIQADGWMCHASKWVTTCDFRWYGPKYITQSIRSFTPSVEQCKESIEQ<br>TKQGTWLNPGFPPQSCGYATVTDAEAVIVQVTPHHVLVDEYTGEWVDS<br>QFINGKCSNYICPTVHNSTTWHSDYKVKGLCDSNLISMDITFFSEDGELSS<br>LGKEGTGFRSNYFAYETGGKACKMQYCKHWGVRLPSGVWFEMADKDL<br>FAAARFPECPEGSSISAPSQTSVDVSLIQDVERILDYSLCQETWSKIRAGLP<br>ISPVDLSYLAPKNPGTGPAFTIINGTLKYFETRYIRVDIAAPILSRMVGMIS<br>GTTTERELWDDWAPYEDVEIGPNGVLRTSSGYKFPLYMIGHGMLDSDLH<br>LSSKAQVFEHPHIQDAASQLPDDELLFFGDTGLSKNPIELVEGWFSSWKS<br>SIASFFFIIGLIIGLFLVLRVGIHLCIKLKHTKKRQIYTDIEMNRLGK |
| SEQ ID NO: 25 | H22N and S422F | KFTIVFPHNQKGNWKNVPSNYNYCPSSSDLNWHNDLIGTAIQVKMPKSH<br>KAIQADGWMCHASKWVTTCDFRWYGPKYITQSIRSFTPSVEQCKESIEQ<br>TKQGTWLNPGFPPQSCGYATVTDAEAVIVQVTPHHVLVDEYTGEWVDS<br>QFINGKCSNYICPTVHNSTTWHSDYKVKGLCDSNLISMDITFFSEDGELSS<br>LGKEGTGFRSNYFAYETGGKACKMQYCKHWGVRLPSGVWFEMADKDL<br>FAAARFPECPEGSSISAPSQTSVDVSLIQDVERILDYSLCQETWSKIRAGLP<br>ISPVDLSYLAPKNPGTGPAFTIINGTLKYFETRYIRVDIAAPILSRMVGMIS<br>GTTTERELWDDWAPYEDVEIGPNGVLRTSSGYKFPLYMIGHGMLDSDLH<br>LSSKAQVFEHPHIQDAASQLPDDEFLFGDTGLSKNPIELVEGWFSSWKSSI<br>ASFFFIIGLIIGLFLVLRVGIHLCIKLKHTKKRQIYTDIEMNRLGK |
| SEQ ID NO: 26 | H22N and S422M | KFTIVFPHNQKGNWKNVPSNYNYCPSSSDLNWHNDLIGTAIQVKMPKSH<br>KAIQADGWMCHASKWVTTCDFRWYGPKYITQSIRSFTPSVEQCKESIEQ<br>TKQGTWLNPGFPPQSCGYATVTDAEAVIVQVTPHHVLVDEYTGEWVDS<br>QFINGKCSNYICPTVHNSTTWHSDYKVKGLCDSNLISMDITFFSEDGELSS<br>LGKEGTGFRSNYFAYETGGKACKMQYCKHWGVRLPSGVWFEMADKDL<br>FAAARFPECPEGSSISAPSQTSVDVSLIQDVERILDYSLCQETWSKIRAGLP<br>ISPVDLSYLAPKNPGTGPAFTIINGTLKYFETRYIRVDIAAPILSRMVGMIS |

TABLE 3-continued

Amino acid sequences SEQ ID NO: 17 to 27 based on Indiana VSV strain glycoprotein G ectodonnain (SEQ ID NO: 2) and associated substitution compared to SEQ ID NO: 2. For each substitution, the initial amino acid in SEQ ID NO: 2 is indicated in one letter code and followed by its position in SEQ ID NO: 2 and the substitute amino acid in one letter code.

| Sequence identifier | Substitution(s) | Amino acid sequence |
|---|---|---|
| | | GTTTERELWDDWAPYEDVEIGPNGVLRTSSGYKFPLYMIGHGMLDSDLH<br>LSSKAQVFEHPHIQDAASQLPDDEMLFFGDTGLSKNPIELVEGWFSSWKS<br>SIASFFFIIGLIIGLFLVLRVGIHLCIKLKHTKKRQIYTDIEMNRLGK |
| SEQ ID NO: 27 | H22N and S422V | KFTIVFPHNQKGNWKNVPSNYNYCPSSSDLNWHNDLIGTAIQVKMPKSH<br>KAIQADGWMCHASKWVTTCDFRWYGPKYITQSIRSFTPSVEQCKESIEQ<br>TKQGTWLNPGFPPQSCGYATVTDAEAVIVQVTPHHVLVDEYTGEWVDS<br>QFINGKCSNYICPTVHNSTTWHSDYKVKGLCDSNLISMDITFFSEDGELSS<br>LGKEGTGFRSNYFAYETGGKACKMQYCKHWGVRLPSGVWFEMADKDL<br>FAAARFPECPEGSSISAPSQTSVDVSLIQDVERILDYSLCQETWSKIRAGLP<br>ISPVDLSYLAPKNPGTGPAFTIINGTLKYFETRYIRVDIAAPILSRMVGMIS<br>GTTTERELWDDWAPYEDVEIGPNGVLRTSSGYKFPLYMIGHGMLDSDLH<br>LSSKAQVFEHPHIQDAASQLPDDEVLFFGDTGLSKNPIELVEGWFSSWKS<br>SIASFFFIIGLIIGLFLVLRVGIHLCIKLKHTKKRQIYTDIEMNRLGK |

Other preferred mutant polypeptides according to the invention are based on the amino acid sequence of the ectodomain of glycoprotein G of VSV Maraba strain, and may be selected from:

a) a mutant polypeptide comprising, or consisting essentially of, or consisting of, the amino acid sequence as set forth in SEQ ID NO:28 corresponding to SEQ ID NO: 4 with a substitution of the histidine (H) amino acid residue in position 22 by an asparagine (N) amino acid residue;

b) a mutant polypeptide comprising, or consisting essentially of, or consisting of, the amino acid sequence as set forth in SEQ ID NO:29 corresponding to SEQ ID NO: 4 with a substitution of the threonine (T) amino acid residue in position 422 by an isoleucine (I) amino acid residue;

c) amino acid sequence as set forth in SEQ ID NO: 30 corresponding to SEQ ID NO: 4 with a substitution of the threonine (T) amino acid residue in position 422 by a leucine (L) amino acid residue;

d) a mutant polypeptide comprising, or consisting essentially of, or consisting of, the amino acid sequence as set forth in SEQ ID NO:31 corresponding to SEQ ID NO: 4 with a substitution of the threonine (T) amino acid residue in position 422 by a phenylalanine (F) amino acid residue;

e) a mutant polypeptide comprising, or consisting essentially of, or consisting of, the amino acid sequence as set forth in SEQ ID NO: 32 corresponding to SEQ ID NO: 4 with a substitution of the threonine (T) amino acid residue in position 422 by a methionine (M) amino acid residue;

f) a mutant polypeptide comprising, or consisting essentially of, or consisting of, the amino acid sequence as set forth in SEQ ID NO:33 corresponding to SEQ ID NO: 4 with a substitution of the threonine (T) amino acid residue in position 422 by a valine (V) amino acid residue;

g) a mutant polypeptide comprising, or consisting essentially of, or consisting of, the amino acid sequence as set forth in SEQ ID NO: 34 corresponding to SEQ ID NO: 4 with a substitution of the histidine (H) amino acid residue in position 22 by an asparagine (N) amino acid residue and a substitution of the threonine (T) amino acid residue in position 422 by an isoleucine (I) amino acid residue;

h) a mutant polypeptide comprising, or consisting essentially of, or consisting of, the amino acid sequence as set forth in SEQ ID NO:35 corresponding to SEQ ID NO: 4 with a substitution of the histidine (H) amino acid residue in position 22 by an asparagine (N) amino acid residue and a substitution of the threonine (T) amino acid residue in position 422 by a leucine (L) amino acid residue;

i) a mutant polypeptide comprising, or consisting essentially of, or consisting of, the amino acid sequence as set forth in SEQ ID NO:36 corresponding to SEQ ID NO: 4 with a substitution of the histidine (H) amino acid residue in position 22 by an asparagine (N) amino acid residue and a substitution of the threonine (T) amino acid residue in position 422 by a phenylalanine (F) amino acid residue;

j) a mutant polypeptide comprising, or consisting essentially of, or consisting of, the amino acid sequence as set forth in SEQ ID NO:37 corresponding to SEQ ID NO: 4 with a substitution of the histidine (H) amino acid residue in position 22 by an asparagine (N) amino acid residue and a substitution of the threonine (T) amino acid residue in position 422 by a methionine (M) amino acid residue; and k) a mutant polypeptide comprising, or consisting essentially of, or consisting of, the amino acid sequence as set forth in SEQ ID NO:38 corresponding to SEQ ID NO: 4 with a substitution of the histidine (H) amino acid residue in position 22 by an asparagine (N) amino acid residue and a substitution of the threonine (T) amino acid residue in position 422 by a valine (V) amino acid residue; and l) a mutant polypeptide comprising, or consisting essentially of, or consisting of, the amino acid sequence as defined in any one of a) to k) above, and further comprising a signal peptide in N-terminal, preferably the signal peptide corresponding to positions 1-16 of SEQ ID NO: 3.

Most preferred mutant polypeptides based on the amino acid sequence of the ectodomain of glycoprotein G of VSV Maraba strain are those comprising at least a substitution in position 422 (SEQ ID NO: 29 to 38 or a mutant polypeptide comprising one of these amino acid sequences and further comprising a signal peptide in N-terminal, preferably the signal peptide corresponding to positions 1-16 of SEQ ID NO:3).

The amino acid sequences SEQ ID NO:28 to 38 of preferred mutant polypeptide derived from VSV Maraba glycoprotein G ectodomain are presented in Table 4 below.

TABLE 4

Amino acid sequences SEQ ID NO: 28 to 38 based on Maraba VSV strain glycoprotein G ectodomain (SEQ ID NO: 4) and associated substitution compared to SEQ ID NO: 4. For each substitution, the initial amino acid in SEQ ID NO: 4 is indicated in one letter code and followed by its position in SEQ ID NO: 4 and the substitute amino acid in one letter code.

| Sequence identifier | Substitution(s) | Amino acid sequence |
|---|---|---|
| SEQ ID NO: 28 | H22N | KFTIVFPHHQKGNWKNVPSTYNYCPSSSDQNWHNDLTGVSLHVKIPKSH<br>KAIQADGWMCHAAKWVTTCDFRWYGPKYITHSIHSMSPTLEQCKTSIEQ<br>TKQGVWINPGFPPQSCGYATVTDAEVVVVQATPHHVLVDEYTGEWIDS<br>QLVGGKCSKEVCQTVHNSTVWHADYKITGLCESNLASVDITFFSEDGQK<br>TSLGKPNTGFRSNHFAYESGEKACRMQVCTQWGIRLPSGVWFELVDKD<br>LFQAAKLPECPRGSSISAPSQTSVDVSLIQDVERILDYSLCQETWSKIRAKL<br>PVSPVDLSYLAPKNPGSGPAFTIINGTLKYFETRYIRVDISNPIIPHMVGTM<br>SGTTTERELWNDWYPYEDVEIGPNGVLKTPTGFKFPLYMIGHGMLDSDL<br>HKSSQAQVFEHPHAKDAASQLPDDETLFFGDTGLSKNPVELVEGWFSS<br>WKSTLASFFLIIGLGVALIFIIRIIVAIRYKYKGRKTQKIYNDVEMSRLGNK |
| SEQ ID NO: 29 | T422I | KFTIVFPHHQKGNWKNVPSTYHYCPSSSDQNWHNDLTGVSLHVKIPKSH<br>KAIQADGWMCHAAKWVTTCDFRWYGPKYITHSIHSMSPTLEQCKTSIEQ<br>TKQGVWINPGFPPQSCGYATVTDAEVVVVQATPHHVLVDEYTGEWIDS<br>QLVGGKCSKEVCQTVHNSTVWHADYKITGLCESNLASVDITFFSEDGQK<br>TSLGKPNTGFRSNHFAYESGEKACRMQYCTQWGIRLPSGVWFELVDKD<br>LFQAAKLPECPRGSSISAPSQTSVDVSLIQDVERILDYSLCQETWSKIRAKL<br>PVSPVDLSYLAPKNPGSGPAFTIINGTLKYFETRYIRVDISNPIIPHMVGTM<br>SGTTTERELWNDWYPYEDVEIGPNGVLKTPTGFKFPLYMIGHGMLDSDL<br>HKSSQAQVFEHPHAKDAASQLPDDEILFFGDTGLSKNPVELVEGWFSSW<br>KSTLASFFLIIGLGVALIFIIRIIVAIRYKYKGRKTQKIYNDVEMSRLGNK |
| SEQ ID NO: 30 | T422L | KFTIVFPHHQKGNWKNVPSTYHYCPSSSDQNWHNDLTGVSLHVKIPKSH<br>KAIQADGWMCHAAKWVTTCDFRWYGPKYITHSIHSMSPTLEQCKTSIEQ<br>TKQGVWINPGFPPQSCGYATVTDAEVVVVQATPHHVLVDEYTGEWIDS<br>QLVGGKCSKEVCQTVHNSTVWHADYKITGLCESNLASVDITFFSEDGQK<br>TSLGKPNTGFRSNHFAYESGEKACRMQYCTQWGIRLPSGVWFELVDKD<br>LFQAAKLPECPRGSSISAPSQTSVDVSLIQDVERILDYSLCQETWSKIRAKL<br>PVSPVDLSYLAPKNPGSGPAFTIINGTLKYFETRYIRVDISNPIIPHMVGTM<br>SGTTTERELWNDWYPYEDVEIGPNGVLKTPTGFKFPLYMIGHGMLDSDL<br>HKSSQAQVFEHPHAKDAASQLPDDELLFFGDTGLSKNPVELVEGWFSSW<br>KSTLASFFLIIGLGVALIFIIRIIVAIRYKYKGRKTQKIYNDVEMSRLGNK |
| SEQ ID NO: 31 | T422F | KFTIVFPHHQKGNWKNVPSTYHYCPSSSDQNWHNDLTGVSLHVKIPKSH<br>KAIQADGWMCHAAKWVTTCDFRWYGPKYITHSIHSMSPTLEQCKTSIEQ<br>TKQGVWINPGFPPQSCGYATVTDAEVVVVQATPHHVLVDEYTGEWIDS<br>QLVGGKCSKEVCQTVHNSTVWHADYKITGLCESNLASVDITFFSEDGQK<br>TSLGKPNTGFRSNHFAYESGEKACRMQYCTQWGIRLPSGVWFELVDKD<br>LFQAAKLPECPRGSSISAPSQTSVDVSLIQDVERILDYSLCQETWSKIRAKL<br>PVSPVDLSYLAPKNPGSGPAFTIINGTLKYFETRYIRVDISNPIIPHMVGTM<br>SGTTTERELWNDWYPYEDVEIGPNGVLKTPTGFKFPLYMIGHGMLDSDL<br>HKSSQAQVFEHPHAKDAASQLPDDEFLFFGDTGLSKNPVELVEGWFSSW<br>KSTLASFFLIIGLGVALIFIIRIIVAIRYKYKGRKTQKIYNDVEMSRLGNK |
| SEQ ID NO: 32 | T422M | KFTIVFPHHQKGNWKNVPSTYHYCPSSSDQNWHNDLTGVSLHVKIPKSH<br>KAIQADGWMCHAAKWVTTCDFRWYGPKYITHSIHSMSPTLEQCKTSIEQ<br>TKQGVWINPGFPPQSCGYATVTDAEVVVVQATPHHVLVDEYTGEWIDS<br>QLVGGKCSKEVCQTVHNSTVWHADYKITGLCESNLASVDITFFSEDGQK<br>TSLGKPNTGFRSNHFAYESGEKACRMQYCTQWGIRLPSGVWFELVDKD<br>LFQAAKLPECPRGSSISAPSQTSVDVSLIQDVERILDYSLCQETWSKIRAKL<br>PVSPVDLSYLAPKNPGSGPAFTIINGTLKYFETRYIRVDISNPIIPHMVGTM<br>SGTTTERELWNDWYPYEDVEIGPNGVLKTPTGFKFPLYMIGHGMLDSDL<br>HKSSQAQVFEHPHAKDAASQLPDDEMLFFGDTGLSKNPVELVEGWFSS<br>WKSTLASFFLIIGLGVALIFIIRIIVAIRYKYKGRKTQKIYNDVEMSRLGNK |
| SEQ ID NO: 33 | T422V | KFTIVFPHHQKGNWKNVPSTYHYCPSSSDQNWHNDLTGVSLHVKIPKSH<br>KAIQADGWMCHAAKWVTTCDFRWYGPKYITHSIHSMSPTLEQCKTSIEQ<br>TKQGVWINPGFPPQSCGYATVTDAEVVVVQATPHHVLVDEYTGEWIDS<br>QLVGGKCSKEVCQTVHNSTVWHADYKITGLCESNLASVDITFFSEDGQK<br>TSLGKPNTGFRSNHFAYESGEKACRMQYCTQWGIRLPSGVWFELVDKD |

TABLE 4-continued

Amino acid sequences SEQ ID NO: 28 to 38 based on Maraba VSV strain glycoprotein G ectodomain (SEQ ID NO: 4) and associated substitution compared to SEQ ID NO: 4. For each substitution, the initial amino acid in SEQ ID NO: 4 is indicated in one letter code and followed by its position in SEQ ID NO: 4 and the substitute amino acid in one letter code.

| Sequence identifier | Substitution(s) | Amino acid sequence |
|---|---|---|
| | | LFQAAKLPECPRGSSISAPSQTSVDVSLIQDVERILDYSLCQETWSKIRAKL<br>PVSPVDLSYLAPKNPGSGPAFTIINGTLKYFETRYIRVDISNPIIPHMVGTM<br>SGTTTERELWNDWYPYEDVEIGPNGVLKTPTGFKFPLYMIGHGMLDSDL<br>HKSSQAQVFEHPHAKDAASQLPDDEVLFFGDTGLSKNPVELVEGWFSS<br>WKSTLASFFLIIGLGVALIFIIRIIVAIRYKYKGRKTQKIYNDVEMSRLGNK |
| SEQ ID NO: 34 | H22N and T422I | KFTIVFPHHQKGNWKNVPSTYNYCPSSSDQNWHNDLTGVSLHVKIPKSH<br>KAIQADGWMCHAAKWVTTCDFRWYGPKYITHSIHSMSPTLEQCKTSIEQ<br>TKQGVWINPGFPPQSCGYATVTDAEVVVVQATPHHVLVDEYTGEWIDS<br>QLVGGKCSKEVCQTVHNSTVWHADYKITGLCESNLASVDITFFSEDGQK<br>TSLGKPNTGFRSNHFAYESGEKACRMQVCTQWGIRLPSGVWFELVDKD<br>LFQAAKLPECPRGSSISAPSQTSVDVSLIQDVERILDYSLCQETWSKIRAKL<br>PVSPVDLSYLAPKNPGSGPAFTIINGTLKYFETRYIRVDISNPIIPHMVGTM<br>SGTTTERELWNDWYPYEDVEIGPNGVLKTPTGFKFPLYMIGHGMLDSDL<br>HKSSQAQVFEHPHAKDAASQLPDDEILFFGDTGLSKNPVELVEGWFSSW<br>KSTLASFFLIIGLGVALIFlIRIIVAIRYKYKGRKTQKIYNDVEMSRLGNK |
| SEQ ID NO: 35 | H22N and T422L | KFTIVFPHHQKGNWKNVPSTYNYCPSSSDQNWHNDLTGVSLHVKIPKSH<br>KAIQADGWMCHAAKWVTTCDFRWYGPKYITHSIHSMSPTLEQCKTSIEQ<br>TKQGVWINPGFPPQSCGYATVTDAEVVVVQATPHHVLVDEYTGEWIDS<br>QLVGGKCSKEVCQTVHNSTVWHADYKITGLCESNLASVDITFFSEDGQK<br>TSLGKPNTGFRSNHFAYESGEKACRMQVCTQWGIRLPSGVWFELVDKD<br>LFQAAKLPECPRGSSISAPSQTSVDVSLIQDVERILDYSLCQETWSKIRAKL<br>PVSPVDLSYLAPKNPGSGPAFTIINGTLKYFETRYIRVDISNPIIPHMVGTM<br>SGTTTERELWNDWYPYEDVEIGPNGVLKTPTGFKFPLYMIGHGMLDSDL<br>HKSSQAQVFEHPHAKDAASQLPDDELLFFGDTGLSKNPVELVEGWFSSW<br>KSTLASFFLIIGLGVALIFlIRIIVAIRYKYKGRKTQKIYNDVEMSRLGNK |
| SEQ ID NO: 36 | H22N and T422F | KFTIVFPHHQKGNWKNVPSTYNYCPSSSDQNWHNDLTGVSLHVKIPKSH<br>KAIQADGWMCHAAKWVTTCDFRWYGPKYITHSIHSMSPTLEQCKTSIEQ<br>TKQGVWINPGFPPQSCGYATVTDAEVVVVQATPHHVLVDEYTGEWIDS<br>QLVGGKCSKEVCQTVHNSTVWHADYKITGLCESNLASVDITFFSEDGQK<br>TSLGKPNTGFRSNHFAYESGEKACRMQYCTQWGIRLPSGVWFELVDKD<br>LFQAAKLPECPRGSSISAPSQTSVDVSLIQDVERILDYSLCQETWSKIRAKL<br>PVSPVDLSYLAPKNPGSGPAFTIINGTLKYFETRYIRVDISNPIIPHMVGTM<br>SGTTTERELWNDWYPYEDVEIGPNGVLKTPTGFKFPLYMIGHGMLDSDL<br>HKSSQAQVFEHPHAKDAASQLPDDEFLFFGDTGLSKNPVELVEGWFSSW<br>KSTLASFFLIIGLGVALIFIIRIIVAIRYKYKGRKTQKIYNDVEMSRLGNK |
| SEQ ID NO: 37 | H22N and T422M | KFTIVFPHHQKGNWKNVPSTYNYCPSSSDQNWHNDLTGVSLHVKIPKSH<br>KAIQADGWMCHAAKWVTTCDFRWYGPKYITHSIHSMSPTLEQCKTSIEQ<br>TKQGVWINPGFPPQSCGYATVTDAEVVVVQATPHHVLVDEYTGEWIDS<br>QLVGGKCSKEVCQTVHNSTVWHADYKITGLCESNLASVDITFFSEDGQK<br>TSLGKPNTGFRSNHFAYESGEKACRMQYCTQWGIRLPSGVWFELVDKD<br>LFQAAKLPECPRGSSISAPSQTSVDVSLIQDVERILDYSLCQETWSKIRAKL<br>PVSPVDLSYLAPKNPGSGPAFTIINGTLKYFETRYIRVDISNPIIPHMVGTM<br>SGTTTERELWNDWYPYEDVEIGPNGVLKTPTGFKFPLYMIGHGMLDSDL<br>HKSSQAQVFEHPHAKDAASQLPDDEMLFFGDTGLSKNPVELVEGWFSS<br>WKSTLASFFLIIGLGVALIFIIRIIVAIRYKYKGRKTQKIYNDVEMSRLGNK |
| SEQ ID NO: 38 | H22N and T422V | KFTIVFPHHQKGNWKNVPSTYNYCPSSSDQNWHNDLTGVSLHVKIPKSH<br>KAIQADGWMCHAAKWVTTCDFRWYGPKYITHSIHSMSPTLEQCKTSIEQ<br>TKQGVWINPGFPPQSCGYATVTDAEVVVVQATPHHVLVDEYTGEWIDS<br>QLVGGKCSKEVCQTVHNSTVWHADYKITGLCESNLASVDITFFSEDGQK<br>TSLGKPNTGFRSNHFAYESGEKACRMQYCTQWGIRLPSGVWFELVDKD<br>LFQAAKLPECPRGSSISAPSQTSVDVSLIQDVERILDYSLCQETWSKIRAKL<br>PVSPVDLSYLAPKNPGSGPAFTIINGTLKYFETRYIRVDISNPIIPHMVGTM<br>SGTTTERELWNDWYPYEDVEIGPNGVLKTPTGFKFPLYMIGHGMLDSDL<br>HKSSQAQVFEHPHAKDAASQLPDDEVLFFGDTGLSKNPVELVEGWFSS<br>WKSTLASFFLIIGLGVALIFIIRIIVAIRYKYKGRKTQKIYNDVEMSRLGNK |

Other preferred mutant polypeptides according to the invention are based on the amino acid sequence of the ectodomain of glycoprotein G of VSV Cocal strain, and may be selected from:

a) a mutant polypeptide comprising, or consisting essentially of, or consisting of, the amino acid sequence as set forth in SEQ ID NO:39 corresponding to SEQ ID NO: 6 with a substitution of the histidine (H) amino acid residue in position 22 by an asparagine (N) amino acid residue;

b) a mutant polypeptide comprising, or consisting essentially of, or consisting of, the amino acid sequence as set forth in SEQ ID NO:40 corresponding to SEQ ID NO: 6 with a substitution of the threonine (T) amino acid residue in position 422 by an isoleucine (I) amino acid residue;

c) a mutant polypeptide comprising, or consisting essentially of, or consisting of, the amino acid sequence as set forth in SEQ ID NO:41 corresponding to SEQ ID NO: 6 with a substitution of the threonine (T) amino acid residue in position 422 by a leucine (L) amino acid residue;

d) a mutant polypeptide comprising, or consisting essentially of, or consisting of, the amino acid sequence as set forth in SEQ ID NO:42 corresponding to SEQ ID NO: 6 with a substitution of the threonine (T) amino acid residue in position 422 by a phenylalanine (F) amino acid residue;

e) a mutant polypeptide comprising, or consisting essentially of, or consisting of, the amino acid sequence as set forth in SEQ ID NO:43 corresponding to SEQ ID NO: 6 with a substitution of the threonine (T) amino acid residue in position 422 by a methionine (M) amino acid residue;

f) a mutant polypeptide comprising, or consisting essentially of, or consisting of, the amino acid sequence as set forth in SEQ ID NO:44 corresponding to SEQ ID NO: 6 with a substitution of the threonine (T) amino acid residue in position 422 by a valine (V) amino acid residue;

g) a mutant polypeptide comprising, or consisting essentially of, or consisting of, the amino acid sequence as set forth in SEQ ID NO:45 corresponding to SEQ ID NO: 6 with a substitution of the histidine (H) amino acid residue in position 22 by an asparagine (N) amino acid residue and a substitution of the threonine (T) amino acid residue in position 422 by an isoleucine (I) amino acid residue;

h) a mutant polypeptide comprising, or consisting essentially of, or consisting of, the amino acid sequence as set forth in SEQ ID NO:46 corresponding to SEQ ID NO: 6 with a substitution of the histidine (H) amino acid residue in position 22 by an asparagine (N) amino acid residue and a substitution of the threonine (T) amino acid residue in position 422 by a leucine (L) amino acid residue;

i) a mutant polypeptide comprising, or consisting essentially of, or consisting of, the amino acid sequence as set forth in SEQ ID NO:47 corresponding to SEQ ID NO: 6 with a substitution of the histidine (H) amino acid residue in position 22 by an asparagine (N) amino acid residue and a substitution of the threonine (T) amino acid residue in position 422 by a phenylalanine (F) amino acid residue;

j) a mutant polypeptide comprising, or consisting essentially of, or consisting of, the amino acid sequence as set forth in SEQ ID NO:48 corresponding to SEQ ID NO: 6 with a substitution of the histidine (H) amino acid residue in position 22 by an asparagine (N) amino acid residue and a substitution of the threonine (T) amino acid residue in position 422 by a methionine (M) amino acid residue; and k) a mutant polypeptide comprising, or consisting essentially of, or consisting of, the amino acid sequence as set forth in SEQ ID NO:49 corresponding to SEQ ID NO: 6 with a substitution of the histidine (H) amino acid residue in position 22 by an asparagine (N) amino acid residue and a substitution of the threonine (T) amino acid residue in position 422 by a valine (V) amino acid residue; and l) a mutant polypeptide comprising, or consisting essentially of, or consisting of, the amino acid sequence as defined in any one of a) to k) above, and further comprising a signal peptide in N-terminal, preferably the signal peptide corresponding to positions 1-17 of SEQ ID NO:5.

Most preferred mutant polypeptides based on the amino acid sequence of the ectodomain of glycoprotein G of VSV Cocal strain are those comprising at least a substitution in position 422 (SEQ ID NO: 40 to 49 or a mutant polypeptide comprising one of these amino acid sequences and further comprising a signal peptide in N-terminal, preferably the signal peptide corresponding to positions 1-17 of SEQ ID NO:5).

The amino acid sequences SEQ ID NO:39 to 49 of preferred mutant polypeptide derived from VSV Cocal glycoprotein G ectodomain are presented in Table 5 below.

TABLE 5

Amino acid sequences SEQ ID NO: 39 to 49 based on Cocal VSV strain glycoprotein G ectodomain (SEQ ID NO: 6) and associated substitution compared to SEQ ID NO: 6. For each substitution, the initial amino acid in SEQ ID NO: 6 is indicated in one letter code and followed by its position in SEQ ID NO: 6 and the substitute amino acid in one letter code.

| Sequence identifier | Substitution(s) | Amino acid sequence |
|---|---|---|
| SEQ ID NO: 39 | H22N | KFSIVFPQSQKGNWKNVPSSYNYCPSSSDQNWHNDLLGITMKVKMPKTH<br>KAIQADGWMCHAAKWITTCDFRWYGPKYITHSIHSIQPTSEQCKESIKQT<br>KQGTWMSPGFPPQNCGYATVTDSVAVVVQATPHHVLVDEYTGEWIDS<br>QFPNGKCETEECETVHNSTVWYSDYKVTGLCDATLVDTEITFFSEDGKK<br>ESIGKPNTGYRSNYFAYEKGDKVCKMNYCKHAGVRLPSGVWFEFVDQD<br>VYAAAKLPECPVGATISAPTQTSVDVSLILDVERILDYSLCQETWSKIRSK<br>QPVSPVDLSYLAPKNPGTGPAFTIINGTLKYFETRYIRIDIDNPIISKMVGKI<br>SGSQTERELWTEWFPYEGVEIGPNGILKTPTGYKFPLFMIGHGMLDSDL<br>HKTSQAEVFEHPHLAEAPKQLPEEETLFFGDTGISKNPVELIEGWFSSWK<br>STVVTFFFAIGVFILLYVVARIVIAVRYRYQGSNNKRIYNDIEMSRFRK |
| SEQ ID NO: 40 | T422I | KFSIVFPQSQKGNWKNVPSSYHYCPSSSDQNWHNDLLGITMKVKMPKTH<br>KAIQADGWMCHAAKWITTCDFRWYGPKYITHSIHSIQPTSEQCKESIKQT<br>KQGTWMSPGFPPQNCGYATVTDSVAVVVQATPHHVLVDEYTGEWIDS<br>QFPNGKCETEECETVHNSTVWYSDYKVTGLCDATLVDTEITFFSEDGKK<br>ESIGKPNTGYRSNYFAYEKGDKVCKMNYCKHAGVRLPSGVWFEFVDQD<br>VYAAAKLPECPVGATISAPTQTSVDVSLILDVERILDYSLCQETWSKIRSK<br>QPVSPVDLSYLAPKNPGTGPAFTIINGTLKYFETRYIRIDIDNPIISKMVGKI |

TABLE 5-continued

Amino acid sequences SEQ ID NO: 39 to 49 based on Cocal VSV strain glycoprotein G ectodomain (SEQ ID NO: 6) and associated substitution compared to SEQ ID NO: 6. For each substitution, the initial amino acid in SEQ ID NO: 6 is indicated in one letter code and followed by its position in SEQ ID NO: 6 and the substitute amino acid in one letter code.

| Sequence identifier | Substitution(s) | Amino acid sequence |
|---|---|---|
| | | SGSQTERELWTEWFPYEGVEIGPNGILKTPTGYKFPLFMIGHGMLDSDL<br>HKTSQAEVFEHPHLAEAPKQLPEEEILFFGDTGISKNPVELIEGWFSSWKS<br>TVVTFFFAIGVFILLYVVARIVIAVRYRYQGSNNKRIYNDIEMSRFRK |
| SEQ ID NO: 41 | T422L | KFSIVFPQSQKGNWKNVPSSYHYCPSSSDQNWHNDLLGITMKVKMPKTH<br>KAIQADGWMCHAAKWITTCDFRWYGPKYITHSIHSIQPTSEQCKESIKQT<br>KQGTWMSPGFPPQNCGYATVTDSVAVVVQATPHHVLVDEYTGEWIDS<br>QFPNGKCETEECETVHNSTVWYSDYKVTGLCDATLVDTEITFFSEDGKK<br>ESIGKPNTGYRSNYFAYEKGDKVCKMNYCKHAGVRLPSGVWFEFVDQD<br>VYAAAKLPECPVGATISAPTQTSVDVSLILDVERILDYSLCQETWSKIRSK<br>QPVSPVDLSYLAPKNPGTGPAFTIINGTLKYFETRYIRIDIDNPIISKMVGKI<br>SGSQTERELWTEWFPYEGVEIGPNGILKTPTGYKFPLFMIGHGMLDSDL<br>HKTSQAEVFEHPHLAEAPKQLPEEELLFFGDTGISKNPVELIEGWFSSWK<br>STVVTFFFAIGVFILLYVVARIVIAVRYRYQGSNNKRIYNDIEMSRFRK |
| SEQ ID NO: 42 | T422F | KFSIVFPQSQKGNWKNVPSSYHYCPSSSDQNWHNDLLGITMKVKMPKTH<br>KAIQADGWMCHAAKWITTCDFRWYGPKYITHSIHSIQPTSEQCKESIKQT<br>KQGTWMSPGFPPQNCGYATVTDSVAVVVQATPHHVLVDEYTGEWIDS<br>QFPNGKCETEECETVHNSTVWYSDYKVTGLCDATLVDTEITFFSEDGKK<br>ESIGKPNTGYRSNYFAYEKGDKVCKMNYCKHAGVRLPSGVWFEFVDQD<br>VYAAAKLPECPVGATISAPTQTSVDVSLILDVERILDYSLCQETWSKIRSK<br>QPVSPVDLSYLAPKNPGTGPAFTIINGTLKYFETRYIRIDIDNPIISKMVGKI<br>SGSQTERELWTEWFPYEGVEIGPNGILKTPTGYKFPLFMIGHGMLDSDL<br>HKTSQAEVFEHPHLAEAPKQLPEEEFLFFGDTGISKNPVELIEGWFSSWK<br>STVVTFFFAIGVFILLYVVARIVIAVRYRYQGSNNKRIYNDIEMSRFRK |
| SEQ ID NO: 43 | T422M | KFSIVFPQSQKGNWKNVPSSYHYCPSSSDQNWHNDLLGITMKVKMPKTH<br>KAIQADGWMCHAAKWITTCDFRWYGPKYITHSIHSIQPTSEQCKESIKQT<br>KQGTWMSPGFPPQNCGYATVTDSVAVVVQATPHHVLVDEYTGEWIDS<br>QFPNGKCETEECETVHNSTVWYSDYKVTGLCDATLVDTEITFFSEDGKK<br>ESIGKPNTGYRSNYFAYEKGDKVCKMNYCKHAGVRLPSGVWFEFVDQD<br>VYAAAKLPECPVGATISAPTQTSVDVSLILDVERILDYSLCQETWSKIRSK<br>QPVSPVDLSYLAPKNPGTGAFTIINGTLKYFETRYIRIDIDNPIISKMVGKI<br>SGSQTERELWTEWFPYEGVEIGPNGILKTPTGYKFPLFMIGHGMLDSDL<br>HKTSQAEVFEHPHLAEAPKQLPEEEMLFFGDTGISKNPVELIEGWFSSWK<br>STVVTFFFAIGVFILLYVVARIVIAVRYRYQGSNNKRIYNDIMSRFRK |
| SEQ ID NO: 44 | T422V | KFSIVFPQSQKGNWKNVPSSYHYCPSSSDQNWHNDLLGITMKVKMPKTH<br>KAIQADGWMCHAAKWITTCDFRWYGPKYITHSIHSIQPTSEQCKESIKQT<br>KQGTWMSPGFPPQNCGYATVTDSVAVVVQATPHHVLVDEYTGEWIDS<br>QFPNGKCETEECETVHNSTVWYSDYKVTGLCDATLVDTEITFFSEDGKK<br>ESIGKPNTGYRSNYFAYEKGDKVCKMNYCKHAGVRLPSGVWFEFVDQD<br>VYAAAKLPECPVGATISAPTQTSVDVSLILDVERILDYSLCQETWSKIRSK<br>QPVSPVDLSYLAPKNPGTGPAFTIINGTLKYFETRYIRIDIDNPIISKMVGKI<br>SGSQTERELWTEWFPYEGVEIGPNGILKTPTGYKFPLFMIGHGMLDSDL<br>HKTSQAEVFEHPHLAEAPKQLPEEEVLFFGDTGISKNPVELIEGWFSSWK<br>STVVTFFFAIGVFILLYVVARIVIAVRYRYQGSNNKRIYNDIEMSRFRK |
| SEQ ID NO: 45 | H22N and T422I | KFSIVFPQSQKGNWKNVPSSYNYCPSSSDQNWHNDLLGITMKVKMPKTH<br>KAIQADGWMCHAAKWITTCDFRWYGPKYITHSIHSIQPTSEQCKESIKQT<br>KQGTWMSPGFPPQNCGYATVTDSVAVVVQATPHHVLVDEYTGEWIDS<br>QFPNGKCETEECETVHNSTVWYSDYKVTGLCDATLVDTEITFFSEDGKK<br>ESIGKPNTGYRSNYFAYEKGDKVCKMNYCKHAGVRLPSGVWFEFVDQD<br>VYAAAKLPECPVGATISAPTQTSVDVSLILDVERILDYSLCQETWSKIRSK<br>QPVSPVDLSYLAPKNPGTGPAFTIINGTLKYFETRYIRIDIDNPIISKMVGKI<br>SGSQTERELWTEWFPYEGVEIGPNGILKTPTGYKFPLFMIGHGMLDSDL<br>HKTSQAEVFEHPHLAEAPKQLPEEEILFFGDTGISKNPVELIEGWFSSWKS<br>TVVTFFFAIGVFILLYVVARIVIAVRYRYQGSNNKRIYNDIEMSRFRK |
| SEQ ID NO: 46 | H22N and T422L | KFSIVFPQSQKGNWKNVPSSYNYCPSSSDQNWHNDLLGITMKVKMPKTH<br>KAIQADGWMCHAAKWITTCDFRWYGPKYITHSIHSIQPTSEQCKESIKQT<br>KQGTWMSPGFPPQNCGYATVTDSVAVVVQATPHHVLVDEYTGEWIDS<br>QFPNGKCETEECETVHNSTVWYSDYKVTGLCDATLVDTEITFFSEDGKK<br>ESIGKPNTGYRSNYFAYEKGDKVCKMNYCKHAGVRLPSGVWFEFVDQD<br>VYAAAKLPECPVGATISAPTQTSVDVSLILDVERILDYSLCQETWSKIRSK<br>QPVSPVDLSYLAPKNPGTGPAFTIINGTLKYFETRYIRIDIDNPIISKMVGKI<br>SGSQTERELWTEWFPYEGVEIGPNGILKTPTGYKFPLFMIGHGMLDSDL<br>HKTSQAEVFEHPHLAEAPKQLPEEELLFFGDTGISKNPVELIEGWFSSWK<br>STVVTFFFAIGVFILLYVVARIVIAVRYRYQGSNNKRIYNDIEMSRFRK |

TABLE 5-continued

Amino acid sequences SEQ ID NO: 39 to 49 based on Cocal VSV strain glycoprotein G ectodomain (SEQ ID NO: 6) and associated substitution compared to SEQ ID NO: 6. For each substitution, the initial amino acid in SEQ ID NO: 6 is indicated in one letter code and followed by its position in SEQ ID NO: 6 and the substitute amino acid in one letter code.

| Sequence identifier | Substitution(s) | Amino acid sequence |
|---|---|---|
| SEQ ID NO: 47 | H22N and T422F | KFSIVFPQSQKGNWKNVPSSYNYCPSSSDQNWHNDLLGITMKVKMPKTH<br>KAIQADGWMCHAAKWITTCDFRWYGPKYITHSIHSIQPTSEQCKESIKQT<br>KQGTWMSPGFPPQNCGYATVTDSVAVVVQATPHHVLVDEYTGEWIDS<br>QFPNGKCETEECETVHNSTVWYSDYKVTGLCDATLVDTEITFFSEDGKK<br>ESIGKPNTGYRSNYFAYEKGDKVCKMNYCKHAGVRLPSGVWFEFVDQD<br>VYAAAKLPECPVGATISAPTQTSVDVSLILDVERILDYSLCQETWSKIRSK<br>QPVSPVDLSYLAPKNPGTGPAFTIINGTLKYFETRYIRIDIDNPIISKMVGKI<br>SGSQTERELWTEWFPYEGVEIGPNGILKTPTGYKFPLFMIGHGMLDSDL<br>HKTSQAEVFEHPHLAEAPKQLPEEEFLFFGDTGISKNPVELIEGWFSSWK<br>STVVTFFFAIGVFILLYVVARIVIAVRYRYQGSNNKRIYNDIEMSRFRK |
| SEQ ID NO: 48 | H22N and T422M | KFSIVFPQSQKGNWKNVPSSYNYCPSSSDQNWHNDLLGITMKVKMPKTH<br>KAIQADGWMCHAAKWITTCDFRWYGPKYITHSIHSIQPTSEQCKESIKQT<br>KQGTWMSPGFPPQNCGYATVTDSVAVVVQATPHHVLVDEYTGEWIDS<br>QFPNGKCETEECETVHNSTVWYSDYKVTGLCDATLVDTEITFFSEDGKK<br>ESIGKPNTGYRSNYFAYEKGDKVCKMNYCKHAGVRLPSGVWFEFVDQD<br>VYAAAKLPECPVGATISAPTQTSVDVSLILDVERILDYSLCQETWSKIRSK<br>QPVSPVDLSYLAPKNPGTGPAFTIINGTLKYFETRYIRIDIDNPIISKMVGKI<br>SGSQTERELWTEWFPYEGVEIGPNGILKTPTGYKFPLFMIGHGMLDSDL<br>HKTSQAEVFEHPHLAEAPKQLPEEEMLFFGDTGISKNPVELIEGWFSSWK<br>STVVTFFFAIGVFILLYVVARIVIAVRYRYQGSNNKRIYNDIEMSRFRK |
| SEQ ID NO: 49 | H22N and T422V | KFSIVFPQSQKGNWKNVPSSYNYCPSSSDQNWHNDLLGITMKVKMPKTH<br>KAIQADGWMCHAAKWITTCDFRWYGPKYITHSIHSIQPTSEQCKESIKQT<br>KQGTWMSPGFPPQNCGYATVTDSVAVVVQATPHHVLVDEYTGEWIDS<br>QFPNGKCETEECETVHNSTVWYSDYKVTGLCDATLVDTEITFFSEDGKK<br>ESIGKPNTGYRSNYFAYEKGDKVCKMNYCKHAGVRLPSGVWFEFVDQD<br>VYAAAKLPECPVGATISAPTQTSVDVSLILDVERILDYSLCQETWSKIRSK<br>QPVSPVDLSYLAPKNPGTGPAFTIINGTLKYFETRYIRIDIDNPIISKMVGKI<br>SGSQTERELWTEWFPYEGVEIGPNGILKTPTGYKFPLFMIGHGMLDSDL<br>HKTSQAEVFEHPHLAEAPKQLPEEEVLFFGDTGISKNPVELIEGWFSSWK<br>STVVTFFFAIGVFILLYVVARIVIAVRYRYQGSNNKRIYNDIEMSRFRK |

Other preferred mutant polypeptides according to the invention are based on the amino acid sequence of the ectodomain of glycoprotein G of VSV Morreton strain, and may be selected from:

a) a mutant polypeptide comprising, or consisting essentially of, or consisting of, the amino acid sequence as set forth in SEQ ID NO:50 corresponding to SEQ ID NO:8 with a substitution of the glutamine (Q) amino acid residue in position 22 by an asparagine (N) amino acid residue;
b) a mutant polypeptide comprising, or consisting essentially of, or consisting of, the amino acid sequence as set forth in SEQ ID NO:51 corresponding to SEQ ID NO:8 with a substitution of the threonine (T) amino acid residue in position 422 by an isoleucine (I) amino acid residue;
c) amino acid sequence as set forth in SEQ ID NO:52 corresponding to SEQ ID NO:8 with a substitution of the threonine (T) amino acid residue in position 422 by a leucine (L) amino acid residue;
d) a mutant polypeptide comprising, or consisting essentially of, or consisting of, the amino acid sequence as set forth in SEQ ID NO:53 corresponding to SEQ ID NO: 8 with a substitution of the threonine (T) amino acid residue in position 422 by a phenylalanine (F) amino acid residue;
e) a mutant polypeptide comprising, or consisting essentially of, or consisting of, the amino acid sequence as set forth in SEQ ID NO:54 corresponding to SEQ ID NO: 8 with a substitution of the threonine (T) amino acid residue in position 422 by a methionine (M) amino acid residue;
f) a mutant polypeptide comprising, or consisting essentially of, or consisting of, the amino acid sequence as set forth in SEQ ID NO:55 corresponding to SEQ ID NO:8 with a substitution of the threonine (T) amino acid residue in position 422 by a valine (V) amino acid residue;
g) a mutant polypeptide comprising, or consisting essentially of, or consisting of, the amino acid sequence as set forth in SEQ ID NO:56 corresponding to SEQ ID NO: 8 with a substitution of the glutamine (Q) amino acid residue in position 22 by an asparagine (N) amino acid residue and a substitution of the threonine (T) amino acid residue in position 422 by an isoleucine (I) amino acid residue;
h) a mutant polypeptide comprising, or consisting essentially of, or consisting of, the amino acid sequence as set forth in SEQ ID NO:57 corresponding to SEQ ID NO:8 with a substitution of the glutamine (Q) amino acid residue in position 22 by an asparagine (N) amino acid residue and a substitution of the threonine (T) amino acid residue in position 422 by a leucine (L) amino acid residue;
i) a mutant polypeptide comprising, or consisting essentially of, or consisting of, the amino acid sequence as set forth in SEQ ID NO:58 corresponding to SEQ ID NO:8 with a substitution of the glutamine (Q) amino acid residue in position 22 by an asparagine (N) amino acid residue and a substitution of the threonine (T) amino acid residue in position 422 by a phenylalanine (F) amino acid residue;

j) a mutant polypeptide comprising, or consisting essentially of, or consisting of, the amino acid sequence as set forth in SEQ ID NO:59 corresponding to SEQ ID NO: 8 with a substitution of the glutamine (Q) amino acid residue in position 22 by an asparagine (N) amino acid residue and a substitution of the threonine (T) amino acid residue in position 422 by a methionine (M) amino acid residue; and k) a mutant polypeptide comprising, or consisting essentially of, or consisting of, the amino acid sequence as set forth in SEQ ID NO:60 corresponding to SEQ ID NO: 8 with a substitution of the glutamine (Q) amino acid residue in position 22 by an asparagine (N) amino acid residue and a substitution of the threonine (T) amino acid residue in position 422 by a valine (V) amino acid residue; and l) a mutant polypeptide comprising, or consisting essentially of, or consisting of, the amino acid sequence as defined in any one of a) to k) above, and further comprising a signal peptide in N-terminal, preferably the signal peptide corresponding to positions 1-17 of SEQ ID NO:7.

Most preferred mutant polypeptides based on the amino acid sequence of the ectodomain of glycoprotein G of VSV Morreton strain are those comprising at least a substitution in position 422 (SEQ ID NO: 51 to 60 or a mutant polypeptide comprising one of these amino acid sequences and further comprising a signal peptide in N-terminal, preferably the signal peptide corresponding to positions 1-17 of SEQ ID NO:7).

The amino acid sequences SEQ ID NO:50 to 60 of preferred mutant polypeptide derived from VSV Morreton glycoprotein G ectodomain are presented in Table 6 below.

TABLE 6

Amino acid sequences SEQ ID NO: 50 to 60 based on Morreton VSV strain glycoprotein G ectodomain (SEQ ID NO: 8) and associated substitution compared to SEQ ID NO: 8. For each substitution, the initial amino acid in SEQ ID NO: 8 is indicated in one letter code and followed by its position in SEQ ID NO: 8 and the substitute amino acid in one letter code.

| Sequence identifier | Substitution(s) | Amino acid sequence |
|---|---|---|
| SEQ ID NO: 50 | Q22N | KFTIVFPHNQKGNWKNVPANYNYCPSSSDLNWHNGLIGTSLQVKMPKS<br>HKAIQADGWMCHAAKWVTTCDFRWYGPKYVTHSIKSMIPTVDQCKESI<br>AQTKQGTWLNPGFPPQSCGYASVTDAEAVIVKATPHQVLVDEYTGEWV<br>DSQFPTGKCNKDICPTVHNSTTWHSDYKVTGLCDANLISMDITFFSEDGK<br>LTSLGKEGTGFRSNYFAYENGDKACRMQYCKHWGVRLPSGVWFEMAD<br>KDIYNDAKFPDCPEGSSIAAPSQTSVDVSLIQDVERILDYSLCQETWSKIRA<br>HLPISPVDLSYLSPKNPGTGPAFTIINGTLKYFETRYIRVDIAGPIIPQMRG<br>VISGTTTERELWTDWYPYEDVEIGPNGVLKTATGYKFPLYMIGHGMLDS<br>DLHISSKAQVFEHPHIQDAASQLPDDETLFFGDTGLSKNPIELVEGWFSG<br>WKSTIASFFFIIGLVIGLYLVLRIGIALCIKCRVQEKRPKIYTDVEMNRLDR |
| SEQ ID NO: 51 | T422I | KFTIVFPHNQKGNWKNVPANYQYCPSSSDLNWHNGLIGTSLQVKMPKS<br>HKAIQADGWMCHAAKWVTTCDFRWYGPKYVTHSIKSMIPTVDQCKESI<br>AQTKQGTWLNPGFPPQSCGYASVTDAEAVIVKATPHQVLVDEYTGEWV<br>DSQFPTGKCNKDICPTVHNSTTWHSDYKVTGLCDANLISMDITFFSEDGK<br>LTSLGKEGTGFRSNYFAYENGDKACRMQYCKHWGVRLPSGVWFEMAD<br>KDIYNDAKFPDCPEGSSIAAPSQTSVDVSLIQDVERILDYSLCQETWSKIRA<br>HLPISPVDLSYLSPKNPGTGPAFTIINGTLKYFETRYIRVDIAGPIIPQMRG<br>VISGTTTERELWTDWYPYEDVEIGPNGVLKTATGYKFPLYMIGHGMLDS<br>DLHISSKAQVFEHPHIQDAASQLPDDEILFFGDTGLSKNPIELVEGWFSG<br>WKSTIASFFFIIGLVIGLYLVLRIGIALCIKCRVQEKRPKIYTDVEMNRLDR |
| SEQ ID NO: 52 | T422L | KFTIVFPHNQKGNWKNVPANYQYCPSSSDLNWHNGLIGTSLQVKMPKS<br>HKAIQADGWMCHAAKWVTTCDFRWYGPKYVTHSIKSMIPTVDQCKESI<br>AQTKQGTWLNPGFPPQSCGYASVTDAEAVIVKATPHQVLVDEYTGEWV<br>DSQFPTGKCNKDICPTVHNSTTWHSDYKVTGLCDANLISMDITFFSEDGK<br>LTSLGKEGTGFRSNYFAYENGDKACRMQYCKHWGVRLPSGVWFEMAD<br>KDIYNDAKFPDCPEGSSIAAPSQTSVDVSLIQDVERILDYSLCQETWSKIRA<br>HLPISPVDLSYLSPKNPGTGPAFTIINGTLKYFETRYIRVDIAGPIIPQMRG<br>VISGTTTERELWTDWYPYEDVEIGPNGVLKTATGYKFPLYMIGHGMLDS<br>DLHISSKAQVFEHPHIQDAASQLPDDELLFFGDTGLSKNPIELVEGWFSG<br>WKSTIASFFFIIGLVIGLYLVLRIGIALCIKCRVQEKRPKIYTDVEMNRLDR |
| SEQ ID NO: 53 | T422F | KFTIVFPHNQKGNWKNVPANYQYCPSSSDLNWHNGLIGTSLQVKMPKS<br>HKAIQADGWMCHAAKWVTTCDFRWYGPKYVTHSIKSMIPTVDQCKESI<br>AQTKQGTWLNPGFPPQSCGYASVTDAEAVIVKATPHQVLVDEYTGEWV<br>DSQFPTGKCNKDICPTVHNSTTWHSDYKVTGLCDANLISMDITFFSEDGK<br>LTSLGKEGTGFRSNYFAYENGDKACRMQYCKHWGVRLPSGVWFEMAD<br>KDIYNDAKFPDCPEGSSIAAPSQTSVDVSLIQDVERILDYSLCQETWSKIRA<br>HLPISPVDLSYLSPKNPGTGPAFTIINGTLKYFETRYIRVDIAGPIIPQMRG<br>VISGTTTERELWTDWYPYEDVEIGPNGVLKTATGYKFPLYMIGHGMLDS<br>DLHISSKAQVFEHPHIQDAASQLPDDEFLFFGDTGLSKNPIELVEGWFSG<br>WKSTIASFFFIIGLVIGLYLVLRIGIALCIKCRVQEKRPKIYTDVEMNRLDR |
| SEQ ID NO: 54 | T422M | KFTIVFPHNQKGNWKNVPANYQYCPSSSDLNWHNGLIGTSLQVKMPKS<br>HKAIQADGWMCHAAKWVTTCDFRWYGPKYVTHSIKSMIPTVDQCKESI |

TABLE 6-continued

Amino acid sequences SEQ ID NO: 50 to 60 based on Morreton VSV strain glycoprotein G ectodomain (SEQ ID NO: 8) and associated substitution compared to SEQ ID NO: 8. For each substitution, the initial amino acid in SEQ ID NO: 8 is indicated in one letter code and followed by its position in SEQ ID NO: 8 and the substitute amino acid in one letter code.

| Sequence identifier | Substitution(s) | Amino acid sequence |
|---|---|---|
| | | AQTKQGTWLNPGFPPQSCGYASVTDAEAVIVKATPHQVLVDEYTGEWV<br>DSQFPTGKCNKDICPTVHNSTTWHSDYKVTGLCDANLISMDITFFSEDGK<br>LTSLGKEGTGFRSNYFAYENGDKACRMQYCKHWGVRLPSGVWFEMAD<br>KDIYNDAKFPDCPEGSSIAAPSQTSVDVSLIQDVERILDYSLCQETWSKIRA<br>HLPISPVDLSYLSPKNPGTGPAFTIINGTLKYFETRYIRVDIAGPIIPQMRG<br>VISGTTTERELWTDWYPYEDVEIGPNGVLKTATGYKFPLYMIGHGMLDS<br>DLHISSKAQVFEHPHIQDAASQLPDDEMLFFGDTGLSKNPIELVEGWFSG<br>WKSTIASFFFIIGLVIGLYLVLRIGIALCIKCRVQEKRPKIYTDVEMNRLDR |
| SEQ ID NO: 55 | T422V | KFTIVFPHNQKGNWKNVPANYQYCPSSSDLNWHNGLIGTSLQVKMPKS<br>HKAIQADGWMCHAAKWVTTCDFRWYGPKYVTHSIKSMIPTVDQCKESI<br>AQTKQGTWLNPGFPPQSCGYASVTDAEAVIVKATPHQVLVDEYTGEWV<br>DSQFPTGKCNKDICPTVHNSTTWHSDYKVTGLCDANLISMDITFFSEDGK<br>LTSLGKEGTGFRSNYFAYENGDKACRMQYCKHWGVRLPSGVWFEMAD<br>KDIYNDAKFPDCPEGSSIAAPSQTSVDVSLIQDVERILDYSLCQETWSKIRA<br>HLPISPVDLSYLSPKNPGTGPAFTIINGTLKYFETRYIRVDIAGPIIPQMRG<br>VISGTTTERELWTDWYPYEDVEIGPNGVLKTATGYKFPLYMIGHGMLDS<br>DLHISSKAQVFEHPHIQDAASQLPDDEVLFFGDTGLSKNPIELVEGWFSG<br>WKSTIASFFFIIGLVIGLYLVLRIGIALCIKCRVQEKRPKIYTDVEMNRLDR |
| SEQ ID NO: 56 | Q22N and T422I | KFTIVFPHNQKGNWKNVPANYNYCPSSSDLNWHNGLIGTSLQVKMPKS<br>HKAIQADGWMCHAAKWVTTCDFRWYGPKYVTHSIKSMIPTVDQCKESI<br>AQTKQGTWLNPGFPPQSCGYASVTDAEAVIVKATPHQVLVDEYTGEWV<br>DSQFPTGKCNKDICPTVHNSTTWHSDYKVTGLCDANLISMDITFFSEDGK<br>LTSLGKEGTGFRSNYFAYENGDKACRMQYCKHWGVRLPSGVWFEMAD<br>KDIYNDAKFPDCPEGSSIAAPSQTSVDVSLIQDVERILDYSLCQETWSKIRA<br>HLPISPVDLSYLSPKNPGTGPAFTIINGTLKYFETRYIRVDIAGPIIPQMRG<br>VISGTTTERELWTDWYPYEDVEIGPNGVLKTATGYKFPLYMIGHGMLDS<br>DLHISSKAQVFEHPHIQDAASQLPDDEILFFGDTGLSKNPIELVEGWFSG<br>WKSTIASFFFIIGLVIGLYLVLRIGIALCIKCRVQEKRPKIYTDVEMNRLDR |
| SEQ ID NO: 57 | Q22N and T422L | KFTIVFPHNQKGNWKNVPANYNYCPSSSDLNWHNGLIGTSLQVKMPKS<br>HKAIQADGWMCHAAKWVTTCDFRWYGPKYVTHSIKSMIPTVDQCKESI<br>AQTKQGTWLNPGFPPQSCGYASVTDAEAVIVKATPHQVLVDEYTGEWV<br>DSQFPTGKCNKDICPTVHNSTTWHSDYKVTGLCDANLISMDITFFSEDGK<br>LTSLGKEGTGFRSNYFAYENGDKACRMQYCKHWGVRLPSGVWFEMAD<br>KDIYNDAKFPDCPEGSSIAAPSQTSVDVSLIQDVERILDYSLCQETWSKIRA<br>HLPISPVDLSYLSPKNPGTGPAFTIINGTLKYFETRYIRVDIAGPIIPQMRG<br>VISGTTTERELWTDWYPYEDVEIGPNGVLKTATGYKFPLYMIGHGMLDS<br>DLHISSKAQVFEHPHIQDAASQLPDDELLFFGDTGLSKNPIELVEGWFSG<br>WKSTIASFFFIIGLVIGLYLVLRIGIALCIKCRVQEKRPKIYTDVEMNRLDR |
| SEQ ID NO: 58 | Q22N and T422F | KFTIVFPHNQKGNWKNVPANYNYCPSSSDLNWHNGLIGTSLQVKMPKS<br>HKAIQADGWMCHAAKWVTTCDFRWYGPKYVTHSIKSMIPTVDQCKESI<br>AQTKQGTWLNPGFPPQSCGYASVTDAEAVIVKATPHQVLVDEYTGEWV<br>DSQFPTGKCNKDICPTVHNSTTWHSDYKVTGLCDANLISMDITFFSEDGK<br>LTSLGKEGTGFRSNYFAYENGDKACRMQYCKHWGVRLPSGVWFEMAD<br>KDIYNDAKFPDCPEGSSIAAPSQTSVDVSLIQDVERILDYSLCQETWSKIRA<br>HLPISPVDLSYLSPKNPGTGPAFTIINGTLKYFETRYIRVDIAGPIIPQMRG<br>VISGTTTERELWTDWYPYEDVEIGPNGVLKTATGYKFPLYMIGHGMLDS<br>DLHISSKAQVFEHPHIQDAASQLPDDEFLFFGDTGLSKNPIELVEGWFSG<br>WKSTIASFFFIIGLVIGLYLVLRIGIALCIKCRVQEKRPKIYTDVEMNRLDR |
| SEQ ID NO: 59 | Q22N and T422M | KFTIVFPHNQKGNWKNVPANYNYCPSSSDLNWHNGLIGTSLQVKMPKS<br>HKAIQADGWMCHAAKWVTTCDFRWYGPKYVTHSIKSMIPTVDQCKESI<br>AQTKQGTWLNPGFPPQSCGYASVTDAEAVIVKATPHQVLVDEYTGEWV<br>DSQFPTGKCNKDICPTVHNSTTWHSDYKVTGLCDANLISMDITFFSEDGK<br>LTSLGKEGTGFRSNYFAYENGDKACRMQYCKHWGVRLPSGVWFEMAD<br>KDIYNDAKFPDCPEGSSIAAPSQTSVDVSLIQDVERILDYSLCQETWSKIRA<br>HLPISPVDLSYLSPKNPGTGPAFTIINGTLKYFETRYIRVDIAGPIIPQMRG<br>VISGTTTERELWTDWYPYEDVEIGPNGVLKTATGYKFPLYMIGHGMLDS<br>DLHISSKAQVFEHPHIQDAASQLPDDEMLFFGDTGLSKNPIELVEGWFSG<br>WKSTIASFFFIIGLVIGLYLVLRIGIALCIKCRVQEKRPKIYTDVEMNRLDR |
| SEQ ID NO: 60 | Q22N and T422V | KFTIVFPHNQKGNWKNVPANYNYCPSSSDLNWHNGLIGTSLQVKMPKS<br>HKAIQADGWMCHAAKWVTTCDFRWYGPKYVTHSIKSMIPTVDQCKESI<br>AQTKQGTWLNPGFPPQSCGYASVTDAEAVIVKATPHQVLVDEYTGEWV<br>DSQFPTGKCNKDICPTVHNSTTWHSDYKVTGLCDANLISMDITFFSEDGK |

TABLE 6-continued

Amino acid sequences SEQ ID NO: 50 to 60 based on Morreton VSV strain glycoprotein G ectodomain (SEQ ID NO: 8) and associated substitution compared to SEQ ID NO: 8. For each substitution, the initial amino acid in SEQ ID NO: 8 is indicated in one letter code and followed by its position in SEQ ID NO: 8 and the substitute amino acid in one letter code.

| Sequence identifier | Substitution(s) | Amino acid sequence |
|---|---|---|
| | | LTSLGKEGTGFRSNYFAYENGDKACRMQYCKHWGVRLPSGVWFEMAD<br>KDIYNDAKFPDCPEGSSIAAPSQTSVDVSLIQDVERILDYSLCQETWSKIRA<br>HLPISPVDLSYLSPKNPGTGPAFTIINGTLKYFETRYIRVDIAGPIIPQMRG<br>VISGTTTERELWTDWYPYEDVEIGPNGVLKTATGYKFPLYMIGHGMLDS<br>DLHISSKAQVFEHPHIQDAASQLPDDEVLFFGDTGLSKNPIELVEGWFSG<br>WKSTIASFFFIIGLVIGLYLVLRIGIALCIKCRVQEKRPKIYTDVEMNRLDR |

Other preferred mutant polypeptides according to the invention are based on the amino acid sequence of the ectodomain of glycoprotein G of VSV Alagoa strain, and may be selected from:

a) a mutant polypeptide comprising, or consisting essentially of, or consisting of, the amino acid sequence as set forth in SEQ ID NO:61 corresponding to SEQ ID NO: 10 with a substitution of the arginine (R) amino acid residue in position 22 by an asparagine (N) amino acid residue;

b) a mutant polypeptide comprising, or consisting essentially of, or consisting of, the amino acid sequence as set forth in SEQ ID NO:62 corresponding to SEQ ID NO: 10 with a substitution of the threonine (T) amino acid residue in position 422 by an isoleucine (I) amino acid residue;

c) a mutant polypeptide comprising, or consisting essentially of, or consisting of, the amino acid sequence as set forth in SEQ ID NO:63 corresponding to SEQ ID NO: 10 with a substitution of the threonine (T) amino acid residue in position 422 by a leucine (L) amino acid residue;

d) a mutant polypeptide comprising, or consisting essentially of, or consisting of, the amino acid sequence as set forth in SEQ ID NO: 64 corresponding to SEQ ID NO: 10 with a substitution of the threonine (T) amino acid residue in position 422 by a phenylalanine (F) amino acid residue;

e) a mutant polypeptide comprising, or consisting essentially of, or consisting of, the amino acid sequence as set forth in SEQ ID NO: 65 corresponding to SEQ ID NO: 10 with a substitution of the threonine (T) amino acid residue in position 422 by a methionine (M) amino acid residue;

f) a mutant polypeptide comprising, or consisting essentially of, or consisting of, the amino acid sequence as set forth in SEQ ID NO:66 corresponding to SEQ ID NO: 10 with a substitution of the threonine (T) amino acid residue in position 422 by a valine (V) amino acid residue;

g) a mutant polypeptide comprising, or consisting essentially of, or consisting of, the amino acid sequence as set forth in SEQ ID NO: 67 corresponding to SEQ ID NO: 10 with a substitution of the arginine (R) amino acid residue in position 22 by an asparagine (N) amino acid residue and a substitution of the threonine (T) amino acid residue in position 422 by an isoleucine (I) amino acid residue;

h) a mutant polypeptide comprising, or consisting essentially of, or consisting of, the amino acid sequence as set forth in SEQ ID NO:68 corresponding to SEQ ID NO: 10 with a substitution of the arginine (R) amino acid residue in position 22 by an asparagine (N) amino acid residue and a substitution of the threonine (T) amino acid residue in position 422 by a leucine (L) amino acid residue;

i) a mutant polypeptide comprising, or consisting essentially of, or consisting of, the amino acid sequence as set forth in SEQ ID NO:69 corresponding to SEQ ID NO: 10 with a substitution of the arginine (R) amino acid residue in position 22 by an asparagine (N) amino acid residue and a substitution of the threonine (T) amino acid residue in position 422 by a phenylalanine (F) amino acid residue;

j) a mutant polypeptide comprising, or consisting essentially of, or consisting of, the amino acid sequence as set forth in SEQ ID NO:70 corresponding to SEQ ID NO: 10 with a substitution of the arginine (R) amino acid residue in position 22 by an asparagine (N) amino acid residue and a substitution of the threonine (T) amino acid residue in position 422 by a methionine (M) amino acid residue; and k) a mutant polypeptide comprising, or consisting essentially of, or consisting of, the amino acid sequence as set forth in SEQ ID NO:71 corresponding to SEQ ID NO: 10 with a substitution of the arginine (R) amino acid residue in position 22 by an asparagine (N) amino acid residue and a substitution of the threonine (T) amino acid residue in position 422 by a valine (V) amino acid residue; and l) a mutant polypeptide comprising, or consisting essentially of, or consisting of, the amino acid sequence as defined in any one of a) to k) above, and further comprising a signal peptide in N-terminal, preferably the signal peptide corresponding to positions 1-17 of SEQ ID NO:9.

Most preferred mutant polypeptides based on the amino acid sequence of the ectodomain of glycoprotein G of VSV Alagoa strain are those comprising at least a substitution in position 422 (SEQ ID NO: 62 to 71 or a mutant polypeptide comprising one of these amino acid sequences and further comprising a signal peptide in N-terminal, preferably the signal peptide corresponding to positions 1-17 of SEQ ID NO:9).

The amino acid sequences SEQ ID NO:61 to 71 of preferred mutant polypeptide derived from VSV Alagoa glycoprotein G ectodomain are presented in Table 7 below.

TABLE 7

Amino acid sequences SEQ ID NO: 61 to 71 based on Alagoa VSV strain glycoprotein G ectodomain (SEQ ID NO: 10) and associated substitution compared to SEQ ID NO: 10. For each substitution, the initial amino acid in SEQ ID NO: 10 is indicated in one letter code and followed by its position in SEQ ID NO: 10 and the substitute amino acid in one letter code.

| Sequence identifier | Substitution(s) | Amino acid sequence |
|---|---|---|
| SEQ ID NO: 61 | R22N | KFTIVFPQSQKGDWKDVPPNYNYCPSSADQNWHGDLLGVNIRAKMPKV<br>HKAIKADGWMCHAAKWVTTCDYRWYGPQYITHSIHSFIPTKAQCEESIK<br>QTKEGVWINPGFPPKNCGYASVSDAESIIVQATAHSVMIDEYSGDWLDSQ<br>FPTGRCTGSTCETIHNSTLWYADYQVTGLCDSALVSTEVTFYSEDGLMT<br>SIGRQNTGYRSNYFPYEKGAAACRMKYCTHEGIRLPSGVWFEMVDKELL<br>ESVQMPECPAGLTISAPTQTSVDVSLILDVERMLDYSLCQETWSKVHSGL<br>PISPVDLGYIAPKNPGAGPAFTIVNGTLKYFDTRYLRIDIEGPVLKKMTGK<br>VSGTPTKRELWTEWFPYDDVEIGPNGVLKTPEGYKFPLYMIGHGLLDSD<br>LQKTSQAEVFHHPQIAEAVQKLPDDETLFFGDTGISKNPVEVIEGWFSN<br>WRSSVMAIVFAILLLVITVLMVRLCVAFRHFCCQKRHKIYNDLEMNQLRR |
| SEQ ID NO: 62 | T422I | KFTIVFPQSQKGDWKDVPPNYRYCPSSADQNWHGDLLGVNIRAKMPKV<br>HKAIKADGWMCHAAKWVTTCDYRWYGPQYITHSIHSFIPTKAQCEESIK<br>QTKEGVWINPGFPPKNCGYASVSDAESIIVQATAHSVMIDEYSGDWLDSQ<br>FPTGRCTGSTCETIHNSTLWYADYQVTGLCDSALVSTEVTFYSEDGLMT<br>SIGRQNTGYRSNYFPYEKGAAACRMKYCTHEGIRLPSGVWFEMVDKELL<br>ESVQMPECPAGLTISAPTQTSVDVSLILDVERMLDYSLCQETWSKVHSGL<br>PISPVDLGYIAPKNPGAGPAFTIVNGTLKYFDTRYLRIDIEGPVLKKMTGK<br>VSGTPTKRELWTEWFPYDDVEIGPNGVLKTPEGYKFPLYMIGHGLLDSD<br>LQKTSQAEVFHHPQIAEAVQKLPDDEILFFGDTGISKNPVEVIEGWFSNW<br>RSSVMAIVFAILLLVITVLMVRLCVAFRHFCCQKRHKIYNDLEMNQLRR |
| SEQ ID NO: 63 | T422L | KFTIVFPQSQKGDWKDVPPNYRYCPSSADQNWHGDLLGVNIRAKMPKV<br>HKAIKADGWMCHAAKWVTTCDYRWYGPQYITHSIHSFIPTKAQCEESIK<br>QTKEGVWINPGFPPKNCGYASVSDAESIIVQATAHSVMIDEYSGDWLDSQ<br>FPTGRCTGSTCETIHNSTLWYADYQVTGLCDSALVSTEVTFYSEDGLMT<br>SIGRQNTGYRSNYFPYEKGAAACRMKYCTHEGIRLPSGVWFEMVDKELL<br>ESVQMPECPAGLTISAPTQTSVDVSLILDVERMLDYSLCQETWSKVHSGL<br>PISPVDLGYIAPKNPGAGPAFTIVNGTLKYFDTRYLRIDIEGPVLKKMTGK<br>VSGTPTKRELWTEWFPYDDVEIGPNGVLKTPEGYKFPLYMIGHGLLDSD<br>LQKTSQAEVFHHPQIAEAVQKLPDDELLFFGDTGISKNPVEVIEGWFSN<br>WRSSVMAIVFAILLLVITVLMVRLCVAFRHFCCQKRHKIYNDLEMNQLRR |
| SEQ ID NO: 64 | T422F | KFTIVFPQSQKGDWKDVPPNYRYCPSSADQNWHGDLLGVNIRAKMPKV<br>HKAIKADGWMCHAAKWVTTCDYRWYGPQYITHSIHSFIPTKAQCEESIK<br>QTKEGVWINPGFPPKNCGYASVSDAESIIVQATAHSVMIDEYSGDWLDSQ<br>FPTGRCTGSTCETIHNSTLWYADYQVTGLCDSALVSTEVTFYSEDGLMT<br>SIGRQNTGYRSNYFPYEKGAAACRMKYCTHEGIRLPSGVWFEMVDKELL<br>ESVQMPECPAGLTISAPTQTSVDVSLILDVERMLDYSLCQETWSKVHSGL<br>PISPVDLGYIAPKNPGAGPAFTIVNGTLKYFDTRYLRIDIEGPVLKKMTGK<br>VSGTPTKRELWTEWFPYDDVEIGPNGVLKTPEGYKFPLYMIGHGLLDSD<br>LQKTSQAEVFHHPQIAEAVQKLPDDEFLFFGDTGISKNPVEVIEGWFSN<br>WRSSVMAIVFAILLLVITVLMVRLCVAFRHFCCQKRHKIYNDLEMNQLRR |
| SEQ ID NO: 65 | T422M | KFTIVFPQSQKGDWKDVPPNYRYCPSSADQNWHGDLLGVNIRAKMPKV<br>HKAIKADGWMCHAAKWVTTCDYRWYGPQYITHSIHSFIPTKAQCEESIK<br>QTKEGVWINPGFPPKNCGYASVSDAESIIVQATAHSVMIDEYSGDWLDSQ<br>FPTGRCTGSTCETIHNSTLWYADYQVTGLCDSALVSTEVTFYSEDGLMT<br>SIGRQNTGYRSNYFPYEKGAAACRMKYCTHEGIRLPSGVWFEMVDKELL<br>ESVQMPECPAGLTISAPTQTSVDVSLILDVERMLDYSLCQETWSKVHSGL<br>PISPVDLGYIAPKNPGAGPAFTIVNGTLKYFDTRYLRIDIEGPVLKKMTGK<br>VSGTPTKRELWTEWFPYDDVEIGPNGVLKTPEGYKFPLYMIGHGLLDSD<br>LQKTSQAEVFHHPQIAEAVQKLPDDEMLFFGDTGISKNPVEVIEGWFSN<br>WRSSVMAIVFAILLLVITVLMVRLCVAFRHFCCQKRHKIYNDLEMNQLRR |
| SEQ ID NO: 66 | T422V | KFTIVFPQSQKGDWKDVPPNYRYCPSSADQNWHGDLLGVNIRAKMPKV<br>HKAIKADGWMCHAAKWVTTCDYRWYGPQYITHSIHSFIPTKAQCEESIK<br>QTKEGVWINPGFPPKNCGYASVSDAESIIVQATAHSVMIDEYSGDWLDSQ<br>FPTGRCTGSTCETIHNSTLWYADYQVTGLCDSALVSTEVTFYSEDGLMT<br>SIGRQNTGYRSNYFPYEKGAAACRMKYCTHEGIRLPSGVWFEMVDKELL<br>ESVQMPECPAGLTISAPTQTSVDVSLILDVERMLDYSLCQETWSKVHSGL<br>PISPVDLGYIAPKNPGAGPAFTIVNGTLKYFDTRYLRIDIEGPVLKKMTGK<br>VSGTPTKRELWTEWFPYDDVEIGPNGVLKTPEGYKFPLYMIGHGLLDSD<br>LQKTSQAEVFHHPQIAEAVQKLPDDEVLFFGDTGISKNPVEVIEGWFSN<br>WRSSVMAIVFAILLLVITVLMVRLCVAFRHFCCQKRHKIYNDLEMNQLRR |
| SEQ ID NO: 67 | R22N and T422I | KFTIVFPQSQKGDWKDVPPNYNYCPSSADQNWHGDLLGVNIRAKMPKV<br>HKAIKADGWMCHAAKWVTTCDYRWYGPQYITHSIHSFIPTKAQCEESIK<br>QTKEGVWINPGFPPKNCGYASVSDAESIIVQATAHSVMIDEYSGDWLDSQ<br>FPTGRCTGSTCETIHNSTLWYADYQVTGLCDSALVSTEVTFYSEDGLMT |

TABLE 7-continued

Amino acid sequences SEQ ID NO: 61 to 71 based on Alagoa VSV strain glycoprotein G ectodomain (SEQ ID NO: 10) and associated substitution compared to SEQ ID NO: 10. For each substitution, the initial amino acid in SEQ ID NO: 10 is indicated in one letter code and followed by its position in SEQ ID NO: 10 and the substitute amino acid in one letter code.

| Sequence identifier | Substitution(s) | Amino acid sequence |
|---|---|---|
| | | SIGRQNTGYRSNYFPYEKGAAACRMKYCTHEGIRLPSGVWFEMVDKELL<br>ESVQMPECPAGLTISAPTQTSVDVSLILDVERMLDYSLCQETWSKVHSGL<br>PISPVDLGYIAPKNPGAGPAFTIVNGTLKYFDTRYLRIDIEGPVLKKMTGK<br>VSGTPTKRELWTEWFPYDDVEIGPNGVLKTPEGYKFPLYMIGHGLLDSD<br>LQKTSQAEVFHHPQIAEAVQKLPDDEILFFGDTGISKNPVEVIEGWFSNW<br>RSSVMAIVFAILLLVITVLMVRLCVAFRHFCCQKRHKIYNDLEMNQLRR |
| SEQ ID NO: 68 | R22N and T422L | KFTIVFPQSQKGDWKDVPPNYNYCPSSADQNWHGDLLGVNIRAKMPKV<br>HKAIKADGWMCHAAKWVTTCDYRWYGPQYITHSIHSFIPTKAQCEESIK<br>QTKEGVWINPGFPPKNCGYASVSDAESIIVQATAHSVMIDEYSGDWLDSQ<br>FPTGRCTGSTCETIHNSTLWYADYQVTGLCDSALVSTEVTFYSEDGLMT<br>SIGRQNTGYRSNYFPYEKGAAACRMKYCTHEGIRLPSGVWFEMVDKELL<br>ESVQMPECPAGLTISAPTQTSVDVSLILDVERMLDYSLCQETWSKVHSGL<br>PISPVDLGYIAPKNPGAGPAFTIVNGTLKYFDTRYLRIDIEGPVLKKMTGK<br>VSGTPTKRELWTEWFPYDDVEIGPNGVLKTPEGYKFPLYMIGHGLLDSD<br>LQKTSQAEVFHHPQIAEAVQKLPDDELLFFGDTGISKNPVEVIEGWFSN<br>WRSSVMAIVFAILLLVITVLMVRLCVAFRHFCCQKRHKIYNDLEMNQLRR |
| SEQ ID NO: 69 | R22N and T422F | KFTIVFPQSQKGDWKDVPPNYNYCPSSADQNWHGDLLGVNIRAKMPKV<br>HKAIKADGWMCHAAKWVTTCDYRWYGPQYITHSIHSFIPTKAQCEESIK<br>QTKEGVWINPGFPPKNCGYASVSDAESIIVQATAHSVMIDEYSGDWLDSQ<br>FPTGRCTGSTCETIHNSTLWYADYQVTGLCDSALVSTEVTFYSEDGLMT<br>SIGRQNTGYRSNYFPYEKGAAACRMKYCTHEGIRLPSGVWFEMVDKELL<br>ESVQMPECPAGLTISAPTQTSVDVSLILDVERMLDYSLCQETWSKVHSGL<br>PISPVDLGYIAPKNPGAGPAFTIVNGTLKYFDTRYLRIDIEGPVLKKMTGK<br>VSGTPTKRELWTEWFPYDDVEIGPNGVLKTPEGYKFPLYMIGHGLLDSD<br>LQKTSQAEVFHHPQIAEAVQKLPDDEFLFFGDTGISKNPVEVIEGWFSN<br>WRSSVMAIVFAILLLVITVLMVRLCVAFRHFCCQKRHKIYNDLEMNQLRR |
| SEQ ID NO: 70 | R22N and T422M | KFTIVFPQSQKGDWKDVPPNYNYCPSSADQNWHGDLLGVNIRAKMPKV<br>HKAIKADGWMCHAAKWVTTCDYRWYGPQYITHSIHSFIPTKAQCEESIK<br>QTKEGVWINPGFPPKNCGYASVSDAESIIVQATAHSVMIDEYSGDWLDSQ<br>FPTGRCTGSTCETIHNSTLWYADYQVTGLCDSALVSTEVTFYSEDGLMT<br>SIGRQNTGYRSNYFPYEKGAAACRMKYCTHEGIRLPSGVWFEMVDKELL<br>ESVQMPECPAGLTISAPTQTSVDVSLILDVERMLDYSLCQETWSKVHSGL<br>PISPVDLGYIAPKNPGAGPAFTIVNGTLKYFDTRYLRIDIEGPVLKKMTGK<br>VSGTPTKRELWTEWFPYDDVEIGPNGVLKTPEGYKFPLYMIGHGLLDSD<br>LQKTSQAEVFHHPQIAEAVQKLPDDEMLFFGDTGISKNPVEVIEGWFSN<br>WRSSVMAIVFAILLLVITVLMVRLCVAFRHFCCQKRHKIYNDLEMNQLRR |
| SEQ ID NO: 71 | R22N and T422V | KFTIVFPQSQKGDWKDVPPNYNYCPSSADQNWHGDLLGVNIRAKMPKV<br>HKAIKADGWMCHAAKWVTTCDYRWYGPQYITHSIHSFIPTKAQCEESIK<br>QTKEGVWINPGFPPKNCGYASVSDAESIIVQATAHSVMIDEYSGDWLDSQ<br>FPTGRCTGSTCETIHNSTLWYADYQVTGLCDSALVSTEVTFYSEDGLMT<br>SIGRQNTGYRSNYFPYEKGAAACRMKYCTHEGIRLPSGVWFEMVDKELL<br>ESVQMPECPAGLTISAPTQTSVDVSLILDVERMLDYSLCQETWSKVHSGL<br>PISPVDLGYIAPKNPGAGPAFTIVNGTLKYFDTRYLRIDIEGPVLKKMTGK<br>VSGTPTKRELWTEWFPYDDVEIGPNGVLKTPEGYKFPLYMIGHGLLDSD<br>LQKTSQAEVFHHPQIAEAVQKLPDDEVLFFGDTGISKNPVEVIEGWFSN<br>WRSSVMAIVFAILLLVITVLMVRLCVAFRHFCCQKRHKIYNDLEMNQLRR |

Other preferred mutant polypeptides according to the invention are based on the amino acid sequence of the ectodomain of glycoprotein G of VSV New Jersey strain, and may be selected from:

a) a mutant polypeptide comprising, or consisting essentially of, or consisting of, the amino acid sequence as set forth in SEQ ID NO:72 corresponding to SEQ ID NO: 12 with a substitution of the valine (V) amino acid residue in position 429 by an isoleucine (I) amino acid residue;

b) a mutant polypeptide comprising, or consisting essentially of, or consisting of, the amino acid sequence as set forth in SEQ ID NO:73 corresponding to SEQ ID NO: 12 with a substitution of the valine (V) amino acid residue in position 429 by a leucine c) amino acid sequence as set forth in SEQ ID NO:74 corresponding to SEQ ID NO: 12 with a substitution of the valine (V) amino acid residue in position 429 by a phenylalanine (F) amino acid residue; and d) a mutant polypeptide comprising, or consisting essentially of, or consisting of, the amino acid sequence as set forth in SEQ ID NO:75 corresponding to SEQ ID NO: 12 with a substitution of the valine (V) amino acid residue in position 429 by a methionine (M) amino acid residue; and e) a mutant polypeptide comprising, or consisting essentially of, or consisting of, the amino acid sequence as defined in any one of a) to d) above, and further comprising a signal peptide in N-terminal, preferably the signal peptide corresponding to positions 1-16 of SEQ ID NO: 11.

The amino acid sequences SEQ ID NO:72 to 75 of preferred mutant polypeptide derived from VSV New Jersey glycoprotein G ectodomain are presented in Table 8 below.

TABLE 8

Amino acid sequences SEQ ID NO: 72 to 75 based on New Jersey VSV strain glycoprotein G ectodomain (SEQ ID NO: 12) and associated substitution compared to SEQ ID NO: 12. For each substitution, the initial amino acid in SEQ ID NO:12 is indicated in one letter code and followed by its position in SEQ ID NO: 12 and the substitute amino acid in one letter code.

| Sequence identifier | Substitution(s) | Amino acid sequence |
|---|---|---|
| SEQ ID NO: 72 | V429I | KIEIVFPQHTTGDWKRVPHEYNYCPTSADKNSHGTQTGIPVELTMPKGL<br>TTHQVDGFMCHSALWMTTCDFRWYGPKYITHSIHNEEPTDYQCLEAIKA<br>YKDGVSFNPGFPPQSCGYGTVTDAEAHIVTVTPHSVKVDEYTGEWIDPH<br>FIGGRCKGQICETVHNSTKWFTSSDGESVCSQLFTLVGGTFFSDSEEITS<br>MGLPETGIRSNYFPYVSTEGICKMPFCRKPGYKLKNDLWFQITDPDLDKT<br>VRDLPHIKDCDLSSSIVTPGEHATDISLISDVERILDYALCQNTWSKIEAGE<br>PITPVDLSYLGPKNPGAGPVFTIINGSLHYFMSKYLRVELESPVIPRMEGK<br>VAGTRIVRQLWDQWFPFGEVEIGPNGVLKTKQGYKFPLHIIGTGEVDND<br>IKMERIVKHWEHPHIEAAQTFLKKDDTEEILYYGDTGVSKNPVELVEGWF<br>SGWRSSIMGVLAVIIGFVILIFLIRLIGVLSSLFRQKRRPIYKSDVEMAHFR |
| SEQ ID NO: 73 | V429L | KIEIVFPQHTTGDWKRVPHEYNYCPTSADKNSHGTQTGIPVELTMPKGL<br>TTHQVDGFMCHSALWMTTCDFRWYGPKYITHSIHNEEPTDYQCLEAIKA<br>YKDGVSFNPGFPPQSCGYGTVTDAEAHIVTVTPHSVKVDEYTGEWIDPH<br>FIGGRCKGQICETVHNSTKWFTSSDGESVCSQLFTLVGGTFFSDSEEITS<br>MGLPETGIRSNYFPYVSTEGICKMPFCRKPGYKLKNDLWFQITDPDLDKT<br>VRDLPHIKDCDLSSSIVTPGEHATDISLISDVERILDYALCQNTWSKIEAGE<br>PITPVDLSYLGPKNPGAGPVFTIINGSLHYFMSKYLRVELESPVIPRMEGK<br>VAGTRIVRQLWDQWFPFGEVEIGPNGVLKTKQGYKFPLHIIGTGEVDND<br>IKMERIVKHWEHPHIEAAQTFLKKDDTEEVLYYGDTGVSKNPVELVEGW<br>FSGWRSSIMGVLAVIIGFVILIFLIRLIGVLSSLFRQKRRPIYKSDVEMAHFR |
| SEQ ID NO: 74 | V429F | KIEIVFPQHTTGDWKRVPHEYNYCPTSADKNSHGTQTGIPVELTMPKGL<br>TTHQVDGFMCHSALWMTTCDFRWYGPKYITHSIHNEEPTDYQCLEAIKA<br>YKDGVSFNPGFPPQSCGYGTVTDAEAHIVTVTPHSVKVDEYTGEWIDPH<br>FIGGRCKGQICETVHNSTKWFTSSDGESVCSQLFTLVGGTFFSDSEEITS<br>MGLPETGIRSNYFPYVSTEGICKMPFCRKPGYKLKNDLWFQITDPDLDKT<br>VRDLPHIKDCDLSSSIVTPGEHATDISLISDVERILDYALCQNTWSKIEAGE<br>PITPVDLSYLGPKNPGAGPVFTIINGSLHYFMSKYLRVELESPVIPRMEGK<br>VAGTRIVRQLWDQWFPFGEVEIGPNGVLKTKQGYKFPLHIIGTGEVDND<br>IKMERIVKHWEHPHIEAAQTFLKKDDTEEFLYYGDTGVSKNPVELVEGW<br>FSGWRSSIMGVLAVIIGFVILIFLIRLIGVLSSLFRQKRRPIYKSDVEMAHFR |
| SEQ ID NO: 75 | V429M | KIEIVFPQHTTGDWKRVPHEYNYCPTSADKNSHGTQTGIPVELTMPKGL<br>TTHQVDGFMCHSALWMTTCDFRWYGPKYITHSIHNEEPTDYQCLEAIKA<br>YKDGVSFNPGFPPQSCGYGTVTDAEAHIVTVTPHSVKVDEYTGEWIDPH<br>FIGGRCKGQICETVHNSTKWFTSSDGESVCSQLFTLVGGTFFSDSEEITS<br>MGLPETGIRSNYFPYVSTEGICKMPFCRKPGYKLKNDLWFQITDPDLDKT<br>VRDLPHIKDCDLSSSIVTPGEHATDISLISDVERILDYALCQNTWSKIEAGE<br>PITPVDLSYLGPKNPGAGPVFTIINGSLHYFMSKYLRVELESPVIPRMEGK<br>VAGTRIVRQLWDQWFPFGEVEIGPNGVLKTKQGYKFPLHIIGTGEVDND<br>IKMERIVKHWEHPHIEAAQTFLKKDDTEEMLYYGDTGVSKNPVELVEGW<br>FSGWRSSIMGVLAVIIGFVILIFLIRLIGVLSSLFRQKRRPIYKSDVEMAHFR |

Other preferred mutant polypeptides according to the invention are based on the amino acid sequence of the ectodomain of glycoprotein G of VSV Carajas strain, and may be selected from:

a) a mutant polypeptide comprising, or consisting essentially of, or consisting of, the amino acid sequence as set forth in SEQ ID NO:76 corresponding to SEQ ID NO: 14 with a substitution of the valine (V) amino acid residue in position 426 by an isoleucine (I) amino acid residue;

b) a mutant polypeptide comprising, or consisting essentially of, or consisting of, the amino acid sequence as set forth in SEQ ID NO:77 corresponding to SEQ ID NO: 14 with a substitution of the valine (V) amino acid residue in position 426 by a leucine c) amino acid sequence as set forth in SEQ ID NO:78 corresponding to SEQ ID NO: 14 with a substitution of the valine (V) amino acid residue in position 426 by a phenylalanine (F) amino acid residue;

d) a mutant polypeptide comprising, or consisting essentially of, or consisting of, the amino acid sequence as set forth in SEQ ID NO:79 corresponding to SEQ ID NO: 14 with a substitution of the valine (V) amino acid residue in position 426 by a methionine (M) amino acid residue; and e) a mutant polypeptide comprising, or consisting essentially of, or consisting of, the amino acid sequence as defined in any one of a) to d) above, and further comprising a signal peptide in N-terminal, preferably the signal peptide corresponding to positions 1-21 of SEQ ID NO: 13.

The amino acid sequences SEQ ID NO:76 to 79 of preferred mutant polypeptide derived from VSV Carajas glycoprotein G ectodomain are presented in Table 9 below.

TABLE 9

Amino acid sequences SEQ ID NO: 76 to 79 based on Carajas VSV strain glycoprotein G ectodomain (SEQ ID NO: 14) and associated substitution compared to SEQ ID NO: 14. For each substitution, the initial amino acid in SEQ ID NO: 14 is indicated in one letter code and followed by its position in SEQ ID NO: 14 and the substitute amino acid in one letter code.

| Sequence identifier | Substitution(s) | Amino acid sequence |
|---|---|---|
| SEQ ID NO: 76 | V426I | KITISFPQSLKGDWRPVPKGYNYCPTSADKNLHGDLIDIGLRLRAPKSFKG<br>ISADGWMCHAARWITTCDFRWYGPKYITHSIHSFRPSNDQCKEAIRLTNE<br>GNWINPGFPPQSCGYASVTDSESVVVTVTKHQVLVDEYSGSWIDSQFPG<br>GSCTSPICDTVHNSTLWHADHTLDSICDQEFVAMDAVLFTESGKFEEFGK<br>PNSGIRSNYFPYESLKDVCQMDFCKRKGFKLPSGVWFEIEDAEKSHKAQV<br>ELKIKRCPHGAVISAPNQNAADINLIMDVERILDYSLCQATWSKIQNKEAL<br>TPIDISYLGPKNPGPGPAFTIINGTLHYFNTRYIRVDIAGPVTKEITGFVSG<br>TSTSRVLWDQWFPYGENSIGPNGLLKTASGYKYPLFMVGTGVLDADIHK<br>LGEATVIEHPHAKEAQKVVDDSEIIFFGDTGVSKNPVEVVEGWFSGWRSS<br>LMSIFGIILLIVCLVLIVRILIALKYCCVRHKKRTIYKEDLEMGRIPRRA |
| SEQ ID NO: 77 | V426L | KITISFPQSLKGDWRPVPKGYNYCPTSADKNLHGDLIDIGLRLRAPKSFKG<br>ISADGWMCHAARWITTCDFRWYGPKYITHSIHSFRPSNDQCKEAIRLTNE<br>GNWINPGFPPQSCGYASVTDSESVVVTVTKHQVLVDEYSGSWIDSQFPG<br>GSCTSPICDTVHNSTLWHADHTLDSICDQEFVAMDAVLFTESGKFEEFGK<br>PNSGIRSNYFPYESLKDVCQMDFCKRKGFKLPSGVWFEIEDAEKSHKAQV<br>ELKIKRCPHGAVISAPNQNAADINLIMDVERILDYSLCQATWSKIQNKEAL<br>TPIDISYLGPKNPGPGPAFTIINGTLHYFNTRYIRVDIAGPVTKEITGFVSG<br>TSTSRVLWDQWFPYGENSIGPNGLLKTASGYKYPLFMVGTGVLDADIHK<br>LGEATVIEHPHAKEAQKVVDDSEILFFGDTGVSKNPVEVVEGWFSGWRS<br>SLMSIFGIILLIVCLVLIVRILIALKYCCVRHKKRTIYKEDLEMGRIPRRA |
| SEQ ID NO: 78 | V426F | KITISFPQSLKGDWRPVPKGYNYCPTSADKNLHGDLIDIGLRLRAPKSFKG<br>ISADGWMCHAARWITTCDFRWYGPKYITHSIHSFRPSNDQCKEAIRLTNE<br>GNWINPGFPPQSCGYASVTDSESVVVTVTKHQVLVDEYSGSWIDSQFPG<br>GSCTSPICDTVHNSTLWHADHTLDSICDQEFVAMDAVLFTESGKFEEFGK<br>PNSGIRSNYFPYESLKDVCQMDFCKRKGFKLPSGVWFEIEDAEKSHKAQV<br>ELKIKRCPHGAVISAPNQNAADINLIMDVERILDYSLCQATWSKIQNKEAL<br>TPIDISYLGPKNPGPGPAFTIINGTLHYFNTRYIRVDIAGPVTKEITGFVSG<br>TSTSRVLWDQWFPYGENSIGPNGLLKTASGYKYPLFMVGTGVLDADIHK<br>LGEATVIEHPHAKEAQKVVDDSEIVFFGDTGVSKNPVEVVEGWFSGWRS<br>SLMSIFGIILLIVCLVLIVRILIALKYCCVRHKKRTIYKEDLEMGRIPRRA |
| SEQ ID NO: 79 | V426M | KITISFPQSLKGDWRPVPKGYNYCPTSADKNLHGDLIDIGLRLRAPKSFKG<br>ISADGWMCHAARWITTCDFRWYGPKYITHSIHSFRPSNDQCKEAIRLTNE<br>GNWINPGFPPQSCGYASVTDSESVVVTVTKHQVLVDEYSGSWIDSQFPG<br>GSCTSPICDTVHNSTLWHADHTLDSICDQEFVAMDAVLFTESGKFEEFGK<br>PNSGIRSNYFPYESLKDVCQMDFCKRKGFKLPSGVWFEIEDAEKSHKAQV<br>ELKIKRCPHGAVISAPNQNAADINLIMDVERILDYSLCQATWSKIQNKEAL<br>TPIDISYLGPKNPGPGPAFTIINGTLHYFNTRYIRVDIAGPVTKEITGFVSG<br>TSTSRVLWDQWFPYGENSIGPNGLLKTASGYKYPLFMVGTGVLDADIHK<br>LGEATVIEHPHAKEAQKVVDDSEIMFFGDTGVSKNPVEVVEGWFSGWRS<br>SLMSIFGIILLIVCLVLIVRILIALKYCCVRHKKRTIYKEDLEMGRIPRRA |

Thus, the mutant polypeptide of the invention advantageously comprises, or consists essentially of, or consists of, an amino acid sequence selected from the group consisting of SEQ ID NO: 17-79, preferably selected from the group consisting of SEQ ID NO: 17-72 and SEQ ID NO: 74-79.

Further Optional Mutations

The mutant polypeptide according to the invention is derived from the amino acid sequence of the ectodomain of glycoprotein G of a VSV strain, and thus comprises, or consists essentially of, or consists of, an amino acid sequence as set forth in SEQ ID NO: 2 or an amino acid sequence having at least 50% of identity (or any other minimal % of identity disclosed above) with the amino acid sequence as set forth in SEQ ID NO: 2, with at least one substitution of an amino acid residue as defined above.

The mutant polypeptide according to the invention may further contain one or more (such as 1, 2, or more) additional substitutions at additional positions of SEQ ID NO:2, or equivalent positions after optimal global alignment with SEQ ID NO:2.

When it is desired not to alter the function of the ectodomain, the possible one or more additional substitutions will preferably be conservative, meaning that the substitute amino acid has a structure that is similar to that of the original amino acid and is therefore unlikely to change the biological activity of the polypeptide. Examples of such conservative substitutions are presented in Table 10 below:

TABLE 10

Examples of conservative substitutions.

| Original amino acid | Conservative substitution(s) |
|---|---|
| Ala (A) | Val, Gly, Pro |
| Arg (R) | Lys, His |
| Asn (N) | Gln |
| Asp (D) | Glu |
| Cys (C) | Ser |
| Gln (Q) | Asn |
| Glu (G) | Asp |
| Gly (G) | Ala |

TABLE 10-continued

| Examples of conservative substitutions. | |
|---|---|
| Original amino acid | Conservative substitution(s) |
| His (H) | Arg |
| Ile (I) | Leu |
| Leu (L) | Ile, Val, Met |
| Lys (K) | Arg |
| Met (M) | Leu |
| Phe (F) | Tyr |
| Pro (P) | Ala |
| Ser (S) | Thr, Cys |
| Thr (T) | Ser |
| Trp (W) | Tyr |
| Tyr (Y) | Phe, Trp |
| Val (V) | Leu, Ala |

In addition, as explained above, the alignment presented in FIG. 4 shows that positions 1, 4, 6-7, 12, 14, 17-18, 21, 23-25, 27, 29, 31, 33, 46-47, 55-56, 58-60, 64, 66-69, 71-75, 77, 79, 81-82, 87, 91-92, 96, 102, 107-111, 114-116, 119, 121, 127, 130, 132, 134, 137-139, 141, 143, 145, 151, 153, 158, 160, 162-165, 167, 177, 199, 204, 206-208, 210, 212, 219, 221, 224, 228, 231, 236-237, 241, 253, 259, 262, 268, 271-272, 274-277, 279-281, 283-285, 287-290, 299, 301, 304, 307-311, 313-314, 316-318, 320-321, 323, 325-326, 330, 332, 338, 345, 349, 354, 356-357, 360, 362, 368-372, 374, 376, 379, 381, 383-384, 388, 390, 393, 395, 407-408, 413, 421, 426-429, 431-434, 436, 439-443, 445, 447, 456, 467, 487, and 489-490 of SEQ ID NO:2 are conserved in the amino acid sequences of the ectodomain of glycoprotein G of VSV strains Indiana, Maraba, Cocal, Morreton, Alagoa, New Jersey, and Carajas. Conserved amino acid positions are often associated with conserved function, and the mutant polypeptide according to the invention comprising an amino acid sequence having at least 50% of identity (or any other minimal % of identity disclosed above) with the amino acid sequence as set forth in SEQ ID NO: 2, after optimal global alignment with SEQ ID NO:2, preferably has the same amino acids as SEQ ID NO: 2 in one or more of the above defined conserved positions, such as in all the above defined conserved positions when it is desired not to alter the function of the ectodomain.

However, in some cases, it may be desired to alter the function of the ectodomain, for instance in order to alter the ability of the ectodomain to bind to the low-density lipoprotein receptor (LDL-R), as described in the application filed under number PCT/EP2018/075824 and in Nikolic et al. Nat Commun. 2018 Mar. 12; 9 (1): 1029. This permits to alter the tropism of a VSV expressing an ectodomain unable to interact with LDL membrane receptor.

Therefore, in an embodiment of the present invention, the mutant polypeptide according to the invention further comprises at least one substitution of an amino acid residue selected from the group consisting of amino acid residues located at positions 8, 47, 209 and 354 of SEQ ID NO:2 or amino acid residues located at positions equivalent to positions 8, 47, 209 and 354 of SEQ ID NO:2 after optimal global alignment with SEQ ID NO:2. For substitution in position 8 or equivalent position after optimal global alignment with SEQ ID NO:2, the original amino acid is preferably substituted by any amino acid except histidine (H), glutamine (Q) or tyrosine (Y), more preferably the original amino acid is substituted by alanine (A).

For substitution in position 47 of SEQ ID NO:2 or equivalent position after optimal global alignment with SEQ ID NO:2, the original amino acid is preferably substituted by any amino acid except lysine (K) or arginine (R), more preferably the original amino acid is substituted by alanine (A) or glutamine (Q).

For substitution in position 209 or equivalent position after optimal global alignment with SEQ ID NO:2, the original amino acid is preferably substituted by any amino acid except tyrosine (Y) or histidine (H), more preferably the original amino acid is substituted by alanine (A).

For substitution in position 354 or equivalent position after optimal global alignment with SEQ ID NO:2, the original amino acid is preferably substituted by any amino acid except lysine (K) or arginine (R), more preferably the original amino acid is substituted by alanine (A) or glutamine (Q).

Positions 47 and 354 of SEQ ID NO:2 or equivalent positions after optimal global alignment with SEQ ID NO:2 are preferred for obtaining an ectodomain unable to interact with LDL membrane receptor. When it is desired that the mutant polypeptide according to the invention is unable to interact with LDL membrane receptor; the mutant polypeptide further thus preferably comprises a substitution at position 47 of SEQ ID NO:2 or equivalent position after optimal global alignment with SEQ ID NO:2, a substitution at position 354 of SEQ ID NO:2 or equivalent position after optimal global alignment with SEQ ID NO:2, or two substitutions at positions 47 and 354 of SEQ ID NO:2 or equivalent positions after optimal global alignment with SEQ ID NO:2. More preferably, the substitutions at position (s) 47 and/or 354 are those defined as preferred above.

Fusion Polypeptide

The present invention also relates to a fusion polypeptide comprising, or consisting essentially of, or consisting of, the mutant polypeptide of the invention, and an additional peptide, polypeptide or protein, wherein said additional peptide, polypeptide or protein is inserted:

a) in N-terminal of the mutant polypeptide,
b) between any two consecutive amino acids located in regions corresponding to positions 192 to 202 of SEQ ID NO:2 or equivalent positions after optimal global alignment with SEQ ID NO:2,
c) between any two consecutive amino acids located in regions corresponding to positions 240 to 257 of SEQ ID NO:2 or equivalent positions after optimal global alignment with SEQ ID NO:2,
d) between any two consecutive amino acids located in regions corresponding to positions 347 to 353 of SEQ ID NO:2 or equivalent positions after optimal global alignment with SEQ ID NO:2,
e) between any two consecutive amino acids located in regions corresponding to positions 364 to 366 of SEQ ID NO:2 or equivalent positions after optimal global alignment with SEQ ID NO:2,
f) between any two consecutive amino acids located in regions corresponding to positions 376 to 379 of SEQ ID NO:2 or equivalent positions after optimal global alignment with SEQ ID NO:2, preferably said additional peptide, polypeptide or protein is inserted in N-terminal of the mutant polypeptide or between the amino acids at positions 351 and 352 of SEQ ID NO:2 or equivalent positions after optimal global alignment with SEQ ID NO:2.

The additional peptide, polypeptide or protein may have various functions, but may notably be used in order to target a recombinant VSV virus to specific target cells. In this case, any additional peptide, polypeptide or protein that is able to specifically bind to an antigen expressed at the extracellular surface of the target cells may be used. In particular, the additional peptide, polypeptide or protein may comprise at least part of a ligand of a cellular receptor.

When the target cell expresses at its surface one of the components of a (receptor-ligand) couple (for instance: EGF-EGFR, TNFa-TNFaR, PD1-PDL1 or PDL2, etc.s (which will happen often, since molecules expressed at the cell surface generally have a cognate receptor or ligand), then at least part (provided that it is still able to bind its cognate receptor or ligand) of the second component of the (receptor-ligand) couple (i.e. the natural receptor or ligand of the targeted cell surface antigen) may be used.

Alternatively, an antibody, a functional antibody fragment.

By "antibody" or "immunoglobulin" is meant a molecule comprising at least one binding domain for a given antigen and a constant domain comprising an Fc fragment capable of binding to Fc receptors (FcR). In most mammals, like humans and mice, an antibody consists of four polypeptide chains: two heavy chains and two light chains bound together by a variable number of disulfide bridges providing flexibility to the molecule. Each light chain consists of a constant domain (CL) and a variable domain (VL); the heavy chains consisting of a variable domain (VH) and three or four constant domains (CH1 to CH3 or CH1 to CH4) according to the isotype of the antibody. In a few rare mammals, such as camels and llamas, the antibodies consist of only two heavy chains, each heavy chain comprising a variable domain (VH) and a constant region.

The variable domains are involved in antigen recognition, while the constant domains are involved in the biological, pharmacokinetic and effector properties of the antibody.

By "functional antibody fragment" is meant an antibody fragment retaining the antigen-binding domain and thus having the same antigen specificity as the original antibody. In most mammals, such functional antibody fragments comprise the fragments Fv, ScFv, Fab, $F(ab')_2$, Fab', and scFv-Fc. In the case of camels and llamas, in which the antibodies consist of only two heavy chains, each heavy chain comprising a variable domain (referred to as VHH) and a constant region, such functional antibody corresponds to the VHH fragment, also known as nanobody.

In the context of the invention, the additional peptide, polypeptide or protein will preferably be a peptide or relatively short polypeptide (preferably less than 200 amino acids), in order not to alter the function of the mutated polypeptide according to the invention. As a result, when antibodies or functional antibody fragments are the selected type of additional peptide, polypeptide or protein, functional antibody fragments will preferably be used. While any suitable functional antibody fragment may be used in the context of the invention, a nanobody (or VHH fragment) will preferably be used, because of its small size, globular shape and robustness.

Depending on the targeted cell, the antigen targeted at the cell surface will vary. For instance, when a recombinant VSV virus expressing the mutant polypeptide according to the invention is used as on oncolytic virus, the mutated polypeptide according to the invention may be fused as described above with an antibody or functional antibody fragment (in particular a nanobody) targeting the G ectodomain to a cancer cell antigen. For instance, an anti-HER2 or anti-MUC18 or anti-EGFR or anti-CD20 or anti-CD52 antibody or functional antibody fragment (in particular a nanobody) may be used. In another context, an antibody or functional antibody fragment (in particular a nanobody) targeting an inhibitory immune checkpoint (such as PD1 or its ligands PD-L1 and PD-L2, or CTLA4) may be used, when it is desired to target immune cells expressing such inhibitory immune checkpoints. Also, an antibody or functional antibody fragment (in particular a nanobody) targeting an inhibitory immune checkpoint (such as PD1 or its ligands PD-L1 and PD-L2, or CTLA4) may be used, when it is desired to target immune cells expressing such inhibitory immune checkpoints. Likewise, an antibody or functional antibody fragment (in particular a nanobody) targeting the B-lymphocyte antigen CD19 may be used, when it is desired to target B cells. An exemplary nanobody directed to GFP has the amino acid sequence SEQ ID NO:80

```
(VQLVESGGALVQPGGSLRLSCAASGFPVNRYSMRWYRQAPGK
EREWVAGMSSAGDRSSYEDSVKGRFTISRDDARNTVYLQMNSL
KPEDTAVYYCNVNVGFEYWGQGTQVTVSS).
```

When the additional peptide, polypeptide or protein (preferably a functional antibody fragment such as a nanobody) is inserted in N-terminal of the mutant polypeptide according to the invention, it may be fused directly to the N-terminal extremity of the mutant polypeptide, or separated from the N-terminal extremity of the mutant polypeptide by a linker peptide, preferably it is separated from the N-terminal extremity of the mutant polypeptide by a first linker peptide.

Typically, linkers are 1 to 30 amino acids long peptides composed of amino acid residues such as glycine (G), serine(S), threonine (T), asparagine (N), glutamine (Q), alanine (A) proline (P), and/or phenylalanine (F). Preferred linkers in the context of this invention comprise 2 to 15 amino acids, with a preference for 2, 3, 4, 5, 6, 7, 8, 9, 10, 11 or 12 amino acids.

The first linker peptide between the additional peptide, polypeptide or protein (preferably a functional antibody fragment such as a nanobody) and the mutated polypeptide according to the invention is 2 to 15 amino acids long, preferably 4 to 12 or 6 to 10 amino acids long, and notably 8 amino acids long. Alternatively or in combination, its amino acid sequence is preferably constituted of amino acids selected from glycine (G), serine(S), threonine (T), asparagine (N), glutamine (Q), alanine (A), proline (P), and phenylalanine (F), more preferably selected from glycine (G), serine(S), threonine (T), and alanine (A), or from glycine (G), serine(S), threonine (T), or from glycine (G), serine (S), and alanine (A), even more preferably from glycine (G) and serine(S). In a preferred embodiment, the first linker peptide is constituted of 6 to 10 amino acids selected from glycine (G) and serine(S), and may notably be of amino acid sequence GGGGSGGGGS (SEQ ID NO: 81).

When the additional peptide, polypeptide or protein (preferably a functional antibody fragment such as a nanobody) is inserted in N-terminal of the mutant polypeptide according to the invention, the fusion polypeptide may further comprise, in N-terminal of the additional peptide, polypeptide or protein (preferably a functional antibody fragment such as a nanobody), a signal peptide in order to address the fusion polypeptide to the virus envelope (when the fusion polypeptide is expressed by a virus) or to the cell membrane (when the fusion polypeptide is expressed by a host cell).

In this case, the fusion polypeptide according to the invention comprises, or consists essentially of, or consists of, from N- to C-terminal: a signal peptide, optionally a second linker peptide, an additional peptide, polypeptide or protein (preferably a functional antibody fragment such as a nanobody), optionally a first linker peptide, and the mutated polypeptide according to the invention. In this fusion polypeptide, the first linker peptide, when present, is as described above. The second linker peptide (between the signal peptide and the additional peptide, polypeptide or protein (preferably a functional antibody fragment such as a nanobody)), when present, is 2 to 15 amino acids long, preferably 2 to 6 amino acids long, 2 to 4 amino acids long, and notably 2 or 3 amino acids long. Alternatively or in combination, its amino acid sequence is preferably constituted of amino acids selected from glycine (G), serine(S), threonine (T), asparagine (N), glutamine (Q), alanine (A), proline (P), phenylalanine (F), more preferably selected from serine(S), threonine (T), asparagine (N), glutamine (Q), and phenylalanine (F), and in particular from serine(S), threonine (T), asparagine (N), and glutamine (Q), or from glutamine (Q) and serine(S), or glutamine (Q) and phenylalanine (F). In a preferred embodiment, the second linker peptide is constituted of 2 to 4 amino acids selected from serine(S), threonine (T), asparagine (N), glutamine (Q), and phenylalanine (F), and in particular from serine(S), threonine (T), asparagine (N), and glutamine (Q), or from glutamine (Q) and serine(S), or glutamine (Q) and phenylalanine (F), and may notably be of amino acid sequence QF or QS.

In a preferred embodiment, the fusion polypeptide according to the invention comprises a first linker peptide or a second linker peptide, and more preferably both a first linker peptide and a second linker peptide.

When the fusion polypeptide according to the invention comprises both a first linker peptide and a second linker peptide:

- the first linker peptide (between the additional peptide, polypeptide or protein (preferably a functional antibody fragment such as a nanobody) and the mutated polypeptide according to the invention) is preferably constituted of 6 to 10 amino acids selected from glycine (G) and serine(S), and may notably be of amino acid sequence GGGGSGGGGS (SEQ ID NO:81); and
- the second linker peptide (between the signal peptide and the additional peptide, polypeptide or protein (preferably a functional antibody fragment such as a nanobody)) is preferably constituted of 2 to 4 amino acids selected from serine (S), threonine (T), asparagine (N), glutamine (Q), and phenylalanine (F), and in particular from serine(S), threonine (T), asparagine (N), and glutamine (Q), or from glutamine (Q) and serine(S), or glutamine (Q) and phenylalanine (F), and may notably be of amino acid sequence QF or QS.

In a preferred embodiment, when the fusion polypeptide according to the invention comprises both a first linker peptide and a second linker peptide, the first linker peptide (between the additional peptide, polypeptide or protein (preferably a functional antibody fragment such as a nanobody) and the mutated polypeptide according to the invention) has the amino acid sequence GGGGSGGGGS (SEQ ID NO:81)., and the second linker peptide (between the signal peptide and the additional peptide, polypeptide or protein (preferably a functional antibody fragment such as a nanobody)) has the amino acid sequence QF or QS.

An exemplary preferred fusion polypeptide has the sequence SEQ ID NO:82

```
(MKCLLYLAFLFIGVNCQSVQLVESGGALVQPGGSLRLSCAAS
GFPVNRYSMRWYRQAPGKEREWVAGMSSAGDRSSYEDSVKGRF
TISRDDARNTVYLQMNSLKPEDTAVYYCNVNVGFEYWGQGTQV
TVSSGGGGSGGGGSKFTIVFPHNQKGNWKNVPSNYNYCPSSSD
LNWHNDLIGTALQVKMPKSHKAIQADGWMCHASKWVTTCDFRW
YGPKYITHSIRSFTPSVEQCKESIEQTKQGTWLNPGFPPQSCG
YATVTDAEAVIVQVTPHHVLVDEYTGEWVDSQFINGKCSNYIC
PTVHNSTTWHSDYKVKGLCDSNLISMDITFFSEDGELSSLGKE
GTGFRSNYFAYETGGKACKMQYCKHWGVRLPSGVWFEMADKDL
FAAARFPECPEGSSISAPSQTSVDVSLIQDVERILDYSLCQET
WSKIRAGLPISPVDLSYLAPKNPGTGPAFTIINGTLKYFETRY
IRVDIAAPILSRMVGMISGTTTERELWDDWAPYEDVEIGPNGV
LRTSSGYKFPLYMIGHGMLDSDLHLSSKAQVFEHPHIQDAASQ
LPDDEILFFGDTGLSKNPIELVEGWFSSWKSSIASFFFIIGLI
IGLFLVLRVGIHLCIKLKHTKKRQIYTDIEMNRLGK).
```

Nucleic Acid Molecule

The present invention also relates to a nucleic acid molecule encoding the mutant polypeptide or the fusion polypeptide according to the invention.

All the different nucleic sequences encoding a particular amino acid sequence, because of degeneration of the genetic code, are within the scope of the invention.

In particular, the sequence of a nucleic acid according to the invention may be optimized to promote the expression thereof in a host cell or any other production host. Indeed, there are in general several three-nucleotide combinations encoding the same amino acid (except for methionine and tryptophan), called synonymous codons. However, some of these combinations are in general used preferentially by a cell or a given organism (this is referred to as genetic code usage bias). This preference depends notably on the producing organism from which the cell is derived. Consequently, when a protein derived from one or more organisms is produced in a heterologous organism or a cell of such a heterologous organism, it may be useful to modify the nucleic sequence encoding the protein to use mainly the preferred codons of the heterologous organism. Data are available in the literature concerning the use of codons preferred by different species and a person skilled in the art knows how to optimize the expression of a given protein in a heterologous organism or a cell of a heterologous organism.

Preferred nucleic acid molecules include those based on the natural nucleotide sequence encoding the ectodomain of glycoprotein G of VSV Indiana strain (SEQ ID NO:83), mutated at one or more nucleotides in order to generate a substitution as defined above. Preferred nucleic acid molecules include those having a nucleotide sequence selected from SEQ ID NO: 83 to SEQ ID NO:86, which are more precisely defined in Table 11 below.

TABLE 11

Preferred nucleotide sequences encoding wild-type (SEQ ID NO: 83) or mutated (SEQ ID NO: 84: c112a nucleotide substitution encoding H22N mutant of amino acid sequence SEQ ID NO: 17; SEQ ID NO: 85: g1313t nucleotide substitution encoding S422I mutant of amino acid sequence SEQ ID NO: 18; and SEQ ID NO: 86: c112a g1313t nucleotide substitutions encoding H22N S422I mutant of amino acid sequence SEQ ID NO: 23) VSV Indiana glycoprotein G ectodomain.

| Sequence identifier | VSV strain | Mutation | Nucleotide sequence |
|---|---|---|---|
| SEQ ID NO: 83 | Indiana | None | ATGAAGTGCCTTTTGTACTTAGCCTTTTTATTCATTGGGGTGA<br>ATTGCAAGTTCACCATAGTTTTTCCACACAACCAAAAAGGAAAC<br>TGGAAAAATGTTCCTTCTAATTACCATTATTGCCCGTCAAGCTC<br>AGATTTAAATTGGCATAATGACTTAATAGGCACAGCATTACAA<br>GTCAAAATGCCCAAGAGTCACAAGGCTATTCAAGCAGACGGTT<br>GGATGTGTCATGCTTCCAAATGGGTCACTACTTGTGATTTCCG<br>CTGGTATGGACCGAAGTATATAACACATTCCATCCGATCCTTCA<br>CTCCATCTGTAGAACAATGCAAGGAAAGCATTGAACAAACGAA<br>ACAAGGAACTTGGCTGAATCCAGGCTTCCCTCCTCAAAGTTGT<br>GGATATGCAACTGTGACGGATGCCGAAGCAGTGATTGTCCAG<br>GTGACTCCTCACCATGTGCTGGTTGATGAATACACAGGAGAAT<br>GGGTTGATTCACAGTTCATCAACGGAAAATGCAGCAATTACAT<br>ATGCCCCACTGTCCATAACTCTACAACCTGGCATTCTGACTATA<br>AGGTCAAAGGGCTATGTGATTCTAACCTCATTTCCATGGACAT<br>CACCTTCTTCTCAGAGGACGGAGAGCTATCATCCCTGGGAAAG<br>GAGGGCACAGGGTTCAGAAGTAACTACTTTGCTTATGAAACTG<br>GAGGCAAGGCCTGCAAAATGCAATACTGCAAGCATTGGGGAG<br>TCAGACTCCCATCAGGTGTCTGGTTCGAGATGGCTGATAAGGA<br>TCTCTTTGCTGCAGCCAGATTCCCTGAATGCCCAGAAGGGTCA<br>AGTATCTCTGCTCCATCTCAGACCTCAGTGGATGTAAGTCTAA<br>TTCAGGACGTTGAGAGGATCTTGGATTATTCCCTCTGCCAAGA<br>AACCTGGAGCAAAATCAGAGCGGGTCTTCCAATCTCTCCAGTG<br>GATCTCAGCTATCTTGCTCCTAAAAACCCAGGAACCGGTCCTG<br>CTTTCACCATAATCAATGGTACCCTAAAATACTTTGAGACCAGA<br>TACATCAGAGTCGATATTGCTGCTCCAATCCTCTCAAGAATGG<br>TCGGAATGATCAGTGGAACTACCACAGAAAGGGAACTGTGGG<br>ATGACTGGGCACCATATGAAGACGTGGAAATTGGACCCAATGG<br>AGTTCTGAGGACCAGTTCAGGATATAAGTTTCCTTTATACATG<br>ATTGGACATGGTATGTTGGACTCCGATCTTCATCTTAGCTCAA<br>AGGCTCAGGTGTTCGAACATCCTCACATTCAAGACGCTGCTTC<br>GCAACTTCCTGATGATGAGAGTTTATTTTTTGGTGATACTGGG<br>CTATCCAAAAATCCAATCGAGCTTGTAGAAGGTTGGTTCAGTA<br>GTTGGAAAAGCTCTATTGCCTCTTTTTTCTTTATCATAGGGTTA<br>ATCATTGGACTATTCTTGGTTCTCCGAGTTGGTATCCATCTTT<br>GCATTAAATTAAAGCACACCAAGAAAAGACAGATTTATACAGAC<br>ATAGAGATGAACCGACTTGGAAAGTAA |
| SEQ ID NO: 84 | Indiana | c112a (H22N) | ATGAAGTGCCTTTTGTACTTAGCCTTTTTATTCATTGGGGTGA<br>ATTGCAAGTTCACCATAGTTTTTCCACACAACCAAAAAGGAAAC<br>TGGAAAAATGTTCCTTCTAATTACaATTATTGCCCGTCAAGCTC<br>AGATTTAAATTGGCATAATGACTTAATAGGCACAGCATTACAA<br>GTCAAAATGCCCAAGAGTCACAAGGCTATTCAAGCAGACGGTT<br>GGATGTGTCATGCTTCCAAATGGGTCACTACTTGTGATTTCCG<br>CTGGTATGGACCGAAGTATATAACACATTCCATCCGATCCTTCA<br>CTCCATCTGTAGAACAATGCAAGGAAAGCATTGAACAAACGAA<br>ACAAGGAACTTGGCTGAATCCAGGCTTCCCTCCTCAAAGTTGT<br>GGATATGCAACTGTGACGGATGCCGAAGCAGTGATTGTCCAG<br>GTGACTCCTCACCATGTGCTGGTTGATGAATACACAGGAGAAT<br>GGGTTGATTCACAGTTCATCAACGGAAAATGCAGCAATTACAT<br>ATGCCCCACTGTCCATAACTCTACAACCTGGCATTCTGACTATA<br>AGGTCAAAGGGCTATGTGATTCTAACCTCATTTCCATGGACAT<br>CACCTTCTTCTCAGAGGACGGAGAGCTATCATCCCTGGGAAAG<br>GAGGGCACAGGGTTCAGAAGTAACTACTTTGCTTATGAAACTG<br>GAGGCAAGGCCTGCAAAATGCAATACTGCAAGCATTGGGGAG<br>TCAGACTCCCATCAGGTGTCTGGTTCGAGATGGCTGATAAGGA<br>TCTCTTTGCTGCAGCCAGATTCCCTGAATGCCCAGAAGGGTCA<br>AGTATCTCTGCTCCATCTCAGACCTCAGTGGATGTAAGTCTAA<br>TTCAGGACGTTGAGAGGATCTTGGATTATTCCCTCTGCCAAGA<br>AACCTGGAGCAAAATCAGAGCGGGTCTTCCAATCTCTCCAGTG<br>GATCTCAGCTATCTTGCTCCTAAAAACCCAGGAACCGGTCCTG<br>CTTTCACCATAATCAATGGTACCCTAAAATACTTTGAGACCAGA<br>TACATCAGAGTCGATATTGCTGCTCCAATCCTCTCAAGAATGG<br>TCGGAATGATCAGTGGAACTACCACAGAAAGGGAACTGTGGG<br>ATGACTGGGCACCATATGAAGACGTGGAAATTGGACCCAATGG<br>AGTTCTGAGGACCAGTTCAGGATATAAGTTTCCTTTATACATG<br>ATTGGACATGGTATGTTGGACTCCGATCTTCATCTTAGCTCAA<br>AGGCTCAGGTGTTCGAACATCCTCACATTCAAGACGCTGCTTC<br>GCAACTTCCTGATGATGAGAGTTTATTTTTTGGTGATACTGGG<br>CTATCCAAAAATCCAATCGAGCTTGTAGAAGGTTGGTTCAGTA |

TABLE 11-continued

Preferred nucleotide sequences encoding wild-type (SEQ ID NO: 83) or mutated (SEQ ID NO: 84: c112a nucleotide substitution encoding H22N mutant of amino acid sequence SEQ ID NO: 17; SEQ ID NO: 85: g1313t nucleotide substitution encoding S422I mutant of amino acid sequence SEQ ID NO: 18; and SEQ ID NO: 86: c112a g1313t nucleotide substitutions encoding H22N S422I mutant of amino acid sequence SEQ ID NO: 23) VSV Indiana glycoprotein G ectodomain.

| Sequence identifier | VSV strain | Mutation | Nucleotide sequence |
|---|---|---|---|
| | | | GTTGGAAAAGCTCTATTGCCTCTTTTTTCTTTATCATAGGGTTA<br>ATCATTGGACTATTCTTGGTTCTCCGAGTTGGTATCCATCTTT<br>GCATTAAATTAAAGCACACCAAGAAAAGACAGATTTATACAGAC<br>ATAGAGATGAACCGACTTGGAAAGTAA |
| SEQ ID NO: 85 | Indiana | g1313t (S422I) | ATGAAGTGCCTTTTGTACTTAGCCTTTTTATTCATTGGGGTGA<br>ATTGCAAGTTCACCATAGTTTTTCCACACAACCAAAAAGGAAAC<br>TGGAAAAATGTTCCTTCTAATTACCATTATTGCCCGTCAAGCTC<br>AGATTTAAATTGGCATAATGACTTAATAGGCACAGCATTACAA<br>GTCAAAATGCCCAAGAGTCACAAGGCTATTCAAGCAGACGGTT<br>GGATGTGTCATGCTTCCAAATGGGTCACTACTTGTGATTTCCG<br>CTGGTATGGACCGAAGTATATAACACATTCCATCCGATCCTTCA<br>CTCCATCTGTAGAACAATGCAAGGAAAGCATTGAACAAACGAA<br>ACAAGGAACTTGGCTGAATCCAGGCTTCCCTCCTCAAAGTTGT<br>GGATATGCAACTGTGACGGATGCCGAAGCAGTGATTGTCCAG<br>GTGACTCCTCACCATGTGCTGGTTGATGAATACACAGGAGAAT<br>GGGTTGATTCACAGTTCATCAACGGAAAATGCAGCAATTACAT<br>ATGCCCCACTGTCCATAACTCTACAACCTGGCATTCTGACTATA<br>AGGTCAAAGGGCTATGTGATTCTAACCTCATTTCCATGGACAT<br>CACCTTCTTCTCAGAGGACGGAGAGCTATCATCCCTGGGAAAG<br>GAGGGCACAGGGTTCAGAAGTAACTACTTTGCTTATGAAACTG<br>GAGGCAAGGCCTGCAAAATGCAATACTGCAAGCATTGGGGAG<br>TCAGACTCCCATCAGGTGTCTGGTTCGAGATGGCTGATAAGGA<br>TCTCTTTGCTGCAGCCAGATTCCCTGAATGCCCAGAAGGGTCA<br>AGTATCTCTGCTCCATCTCAGACCTCAGTGGATGTAAGTCTAA<br>TTCAGGACGTTGAGAGGATCTTGGATTATTCCCTCTGCCAAGA<br>AACCTGGAGCAAAATCAGAGCGGGTCTTCCAATCTCTCCAGTG<br>GATCTCAGCTATCTTGCTCCTAAAAACCCAGGAACCGGTCCTG<br>CTTTCACCATAATCAATGGTACCCTAAAATACTTTGAGACCAGA<br>TACATCAGAGTCGATATTGCTGCTCCAATCCTCTCAAGAATGG<br>TCGGAATGATCAGTGGAACTACCACAGAAAGGGAACTGTGGG<br>ATGACTGGGCACCATATGAAGACGTGGAAATTGGACCCAATGG<br>AGTTCTGAGGACCAGTTCAGGATATAAGTTTCCTTTATACATG<br>ATTGGACATGGTATGTTGGACTCCGATCTTCATCTTAGCTCAA<br>AGGCTCAGGTGTTCGAACATCCTCACATTCAAGACGCTGCTTC<br>GCAACTTCCTGATGATGAGAtTTTATTTTTTGGTGATACTGGG<br>CTATCCAAAAATCCAATCGAGCTTGTAGAAGGTTGGTTCAGTA<br>GTTGGAAAAGCTCTATTGCCTCTTTTTTCTTTATCATAGGGTTA<br>ATCATTGGACTATTCTTGGTTCTCCGAGTTGGTATCCATCTTT<br>GCATTAAATTAAAGCACACCAAGAAAAGACAGATTTATACAGAC<br>ATAGAGATGAACCGACTTGGAAAGTAA |
| SEQ ID NO: 86 | Indiana | c112a g1313t (H22N S4221) | ATGAAGTGCCTTTTGTACTTAGCCTTTTTATTCATTGGGGTGA<br>ATTGCAAGTTCACCATAGTTTTTCCACACAACCAAAAAGGAAAC<br>TGGAAAAATGTTCCTTCTAATTACaATTATTGCCCGTCAAGCTC<br>AGATTTAAATTGGCATAATGACTTAATAGGCACAGCATTACAA<br>GTCAAAATGCCCAAGAGTCACAAGGCTATTCAAGCAGACGGTT<br>GGATGTGTCATGCTTCCAAATGGGTCACTACTTGTGATTTCCG<br>CTGGTATGGACCGAAGTATATAACACATTCCATCCGATCCTTCA<br>CTCCATCTGTAGAACAATGCAAGGAAAGCATTGAACAAACGAA<br>ACAAGGAACTTGGCTGAATCCAGGCTTCCCTCCTCAAAGTTGT<br>GGATATGCAACTGTGACGGATGCCGAAGCAGTGATTGTCCAG<br>GTGACTCCTCACCATGTGCTGGTTGATGAATACACAGGAGAAT<br>GGGTTGATTCACAGTTCATCAACGGAAAATGCAGCAATTACAT<br>ATGCCCCACTGTCCATAACTCTACAACCTGGCATTCTGACTATA<br>AGGTCAAAGGGCTATGTGATTCTAACCTCATTTCCATGGACAT<br>CACCTTCTTCTCAGAGGACGGAGAGCTATCATCCCTGGGAAAG<br>GAGGGCACAGGGTTCAGAAGTAACTACTTTGCTTATGAAACTG<br>GAGGCAAGGCCTGCAAAATGCAATACTGCAAGCATTGGGGAG<br>TCAGACTCCCATCAGGTGTCTGGTTCGAGATGGCTGATAAGGA<br>TCTCTTTGCTGCAGCCAGATTCCCTGAATGCCCAGAAGGGTCA<br>AGTATCTCTGCTCCATCTCAGACCTCAGTGGATGTAAGTCTAA<br>TTCAGGACGTTGAGAGGATCTTGGATTATTCCCTCTGCCAAGA<br>AACCTGGAGCAAAATCAGAGCGGGTCTTCCAATCTCTCCAGTG<br>GATCTCAGCTATCTTGCTCCTAAAAACCCAGGAACCGGTCCTG<br>CTTTCACCATAATCAATGGTACCCTAAAATACTTTGAGACCAGA<br>TACATCAGAGTCGATATTGCTGCTCCAATCCTCTCAAGAATGG<br>TCGGAATGATCAGTGGAACTACCACAGAAAGGGAACTGTGGG<br>ATGACTGGGCACCATATGAAGACGTGGAAATTGGACCCAATGG |

TABLE 11-continued

Preferred nucleotide sequences encoding wild-type (SEQ ID NO: 83) or mutated (SEQ ID NO: 84: c112a nucleotide substitution encoding H22N mutant of amino acid sequence SEQ ID NO: 17; SEQ ID NO: 85: g1313t nucleotide substitution encoding S422I mutant of amino acid sequence SEQ ID NO: 18; and SEQ ID NO: 86: c112a g1313t nucleotide substitutions encoding H22N S422I mutant of amino acid sequence SEQ ID NO: 23) VSV Indiana glycoprotein G ectodomain.

| Sequence identifier | VSV strain | Mutation | Nucleotide sequence |
|---|---|---|---|
| | | | AGTTCTGAGGACCAGTTCAGGATATAAGTTTCCTTTATACATG ATTGGACATGGTATGTTGGACTCCGATCTTCATCTTAGCTCAA AGGCTCAGGTGTTCGAACATCCTCACATTCAAGACGCTGCTTC GCAACTTCCTGATGATGAGAtTTTATTTTTTGGTGATACTGGG CTATCCAAAAATCCAATCGAGCTTGTAGAAGGTTGGTTCAGTA GTTGGAAAAGCTCTATTGCCTCTTTTTTCTTTATCATAGGGTTA ATCATTGGACTATTCTTGGTTCTCCGAGTTGGTATCCATCTTT GCATTAAATTAAAGCACACCAAGAAAAGACAGATTTATACAGAC ATAGAGATGAACCGACTTGGAAAGTAA |

The nucleic acid molecule according to the invention may further contain any modification aimed to improve cloning and/or expression of the encoded mutated polypeptide or fusion polypeptide according to the invention, as well as its folding and stability.

Vector

The present invention also relates to a vector comprising at least one nucleic acid according to the invention or expressing the mutant polypeptide or the fusion polypeptide according to the invention.

Such a vector comprises the elements necessary for the expression of said nucleic sequence, and notably a promoter, a transcription initiation codon, termination sequences, and suitable transcription regulatory sequences. These elements vary according to the host used for the expression and are easily selected by persons skilled in the art based on their general knowledge.

In the context of the invention, the term "vector" has to be understood broadly as including plasmid and viral vectors. Vectors which are appropriate in the context of the present invention, include, without limitation, bacteriophage, plasmid or cosmid vectors for expression in prokaryotic host cells such as bacteria (e.g. *E. coli*, BCG or *Listeria*); vectors for expression in yeast (e.g. *Saccharomyces cerevisiae, Schizosaccharomyces pombe, Pichia pastoris*); baculovirus vectors for expression in insect cell systems (e.g. Sf9 cells); as well as plasmid and viral vectors for expression in higher eukaryotic cells or subjects. Typically, such vectors are commercially available (e.g. in Invitrogen, Stratagene, Amersham Biosciences, Promega, etc.) or available from depositary institutions such as the American Type Culture Collection (ATCC, Rockville, Md.) or have been the subject of numerous publications describing their sequence, organization and methods of producing, allowing the skilled person to apply them.

A "plasmid vector" as used herein refers to a replicable DNA construct. Usually plasmid vectors contain selectable marker genes that allow host cells carrying the plasmid vector to be selected for or against in the presence of a corresponding selective drug. A variety of positive and negative selectable marker genes are known in the art. By way of illustration, an antibiotic resistance gene can be used as a positive selectable marker gene that allows a host cell to be selected in the presence of the corresponding antibiotic. Suitable plasmid vectors are commercially available.

The term "viral vector" as used herein refers to a nucleic acid vector that includes at least one element of a virus genome and may be packaged into a viral particle or to a viral particle. The terms "virus", "virions", "viral particles" and "viral vector particle" are used interchangeably to refer to viral particles that are formed when the nucleic acid vector is transduced into an appropriate cell or cell line according to suitable conditions allowing the generation of viral particles. In the context of the present invention, the term "viral vector" has to be understood broadly as including nucleic acid vector (e.g. DNA viral vector) as well as viral particles generated thereof. The term "infectious" refers to the ability of a viral vector to infect and enter into a host cell or subject.

The viral vector may preferably be a Vesicular stomatitis virus (VSV) vector comprising at least one nucleic acid according to the invention or expressing the mutant polypeptide or the fusion polypeptide according to the invention.

VSV is an enveloped, negative-strand RNA virus that belongs to the Vesiculovirus genus of the Rhabdovirus family. VSV negative-strand RNA genome encodes five structural proteins and comprises, from 3' to 5': a leader region, the genes for the nucleoprotein (N), the phosphoprotein (P), the matrix protein (M), the glycoprotein (G), the polymerase protein (L), and the trailer region. A mutated VSV vector according to the invention may thus be obtained by replacing the natural wild-type sequence encoding the natural wild-type glycoprotein G by a nucleic acid sequence according to the invention, encoding a mutant polypeptide or a fusion polypeptide according to the invention. Standard techniques for generating mutated VSV vectors may be used for this purpose. In particular, reverse genetic for the recovery of recombinant viruses may be used.

With respect to other regions of the VSV genome (leader, genes encoding the nucleoprotein (N), the phosphoprotein (P), the matrix protein (M), the glycoprotein (G), the polymerase protein (L), and trailer region), the mutated VSV vector may contain any suitable natural or artificial sequence. In particular, sequences of the complete genome of various Indiana strain isolates (Rodriguez et al. J Gen Virol. 2002 October; 83 (Pt 10): 2475-83) and of New Jersey strain isolates (Velazquez-Salinas et al. Genome Announc. 2017 Sep. 14; 5 (37)) are known in the art. In addition, various VSV strains are available at the American Type Culture Collection (ATCC) under references VR-1238, VR-1239, VR-159, and VR-1415 to VR-1421.

In an embodiment, the vector and preferably the VSV vector according to the invention may preferably be oncolytic, meaning that it preferentially infects and kills cancer cells. All strains of VSV previously listed (Indiana, Maraba, Cocal, Morreton, Alagoa, New Jersey, and Carajas) are potentially oncolytic and may thus be used.

Alternatively or in combination, the vector and preferably the VSV vector according to the invention may also be used for gene therapy, immunotherapy and selective delivery of a cargo to a chosen cell type.

When used for gene therapy, the vector and preferably the VSV vector according to the invention further encodes a gene of therapeutic interest, in order to restore the activity of this gene in cells that are deficient for this activity.

When used for immunotherapy, the vector and preferably the VSV vector according to the invention further encodes at least one antigen of interest and/or molecules involved in regulation of immune responses, such as cytokines, adjuvants, immune checkpoint modulators, antibodies targeting cytokines.

When intended for delivery of a cargo to a chosen cell type such as unstimulated T cells, B cells, and hematopoietic cells, the recombinant mutated glycoprotein can be inserted at the surface of VLP containing a therapeutic molecule a marker or any drug.

According to a preferred embodiment, the viral vector according to the invention (in particular the VSV vector) is in the form of infectious viral particles. Typically, such viral particles are produced by a process comprising the steps of (i) introducing the viral vector of the invention into a suitable producer cell, (ii) culturing said producer cell under suitable conditions allowing the production of said infectious viral particle, (iii) recovering the produced viral particles from the culture of said producer cell, and (iv) optionally purifying said recovered viral particle.

Host Cell

The present invention also relates to a host cell containing or expressing the mutant polypeptide or the fusion polypeptide according to the invention, or containing the nucleic acid molecule according to the invention, or containing the vector (in particular a VSV vector) according to the invention.

When the host cell contains the vector (in particular a VSV vector) according to the invention, the host cell is preferably an eukaryotic cell suitable for VSV replication, such as BSR cells (a clone of BHK-21: Baby Hamster Kidney cells; ATCC CCL-10), BHK-21 cells (ATCC CCL-10), or Vero cells (ATCC CCL-81).

Composition

The present invention also relates to a composition comprising, or consisting essentially of, or consisting of, the mutant polypeptide or the fusion polypeptide according to the invention, the nucleic acid molecule according to the invention, the vector according to the invention, the host cell according to the invention, or any combination thereof. Preferably, the composition is a pharmaceutical composition which comprises a therapeutically effective amount of the active agent(s) (the mutant polypeptide or the fusion polypeptide according to the invention, the nucleic acid molecule according to the invention, the vector according to the invention, the host cell according to the invention, or any combination thereof), and one or more pharmaceutically acceptable vehicle(s). As used herein, a “pharmaceutically acceptable vehicle” is intended to include any and all carriers, solvents, diluents, excipients, adjuvants, dispersion media, coatings, antibacterial and antifungal agents, and absorption delaying agents, and the like, compatible with administration in a subject and in particular in a human.

As used herein a “therapeutically effective amount” is a dose sufficient for the intended use.

The composition preferably comprises a vector according to the invention, and more particularly a VSV vector according to the invention.

Therapeutic/In Vivo Uses

The present invention also relates to a vector according to the invention (in particular a VSV vector according to the invention, preferably an oncolytic VSV vector according to the invention) or a (pharmaceutical) composition according to the invention (in particular a composition comprising a vector according to the invention, and more particularly a composition comprising VSV vector according to the invention, preferably an oncolytic VSV vector according to the invention), for use as a drug.

The present invention also relates to a vector according to the invention (in particular a VSV vector according to the invention, preferably an oncolytic VSV vector according to the invention) or a (pharmaceutical) composition according to the invention (in particular a composition comprising a vector according to the invention, and more particularly a composition comprising VSV vector according to the invention, preferably an oncolytic VSV vector according to the invention), for use for treating cancer.

The present invention also relates to the use of a vector according to the invention (in particular a VSV vector according to the invention, preferably an oncolytic VSV vector according to the invention) or of a (pharmaceutical) composition according to the invention (in particular a composition comprising a vector according to the invention, and more particularly a composition comprising VSV vector according to the invention, preferably an oncolytic VSV vector according to the invention), for the manufacture of a drug for treating cancer.

The present invention also relates to the use of a vector according to the invention (in particular a VSV vector according to the invention, preferably an oncolytic VSV vector according to the invention) or of a (pharmaceutical) composition according to the invention (in particular a composition comprising a vector according to the invention, and more particularly a composition comprising VSV vector according to the invention, preferably an oncolytic VSV vector according to the invention), for treating cancer.

The present invention also relates to a method for treating cancer in a subject in need thereof, comprising administering to said subject a therapeutically effective amount of a vector according to the invention (in particular a VSV vector according to the invention, preferably an oncolytic VSV vector according to the invention) or of a (pharmaceutical) composition according to the invention (in particular a composition comprising a vector according to the invention, and more particularly a composition comprising VSV vector according to the invention, preferably an oncolytic VSV vector according to the invention).

Since the VSV virus is an oncolytic virus, it may be used in the treatment of various types of cancers, including prostate cancers, breast cancers, pancreatic cancers and melanoma (Bishnoi. Viruses 10, (2018)).

The present invention also relates to a vector according to the invention (in particular a VSV vector according to the invention) or a (pharmaceutical) composition according to the invention (in particular a composition comprising a vector according to the invention, and more particularly a composition comprising VSV vector according to the invention), for use in gene therapy or immunotherapy (in particular as a vaccine).

The present invention also relates to the use of a vector according to the invention (in particular a VSV vector according to the invention) or of a (pharmaceutical) composition according to the invention (in particular a composition comprising a vector according to the invention, and more particularly a composition comprising VSV vector according to the invention), for the manufacture of a drug for gene therapy or immunotherapy (in particular as a vaccine).

The present invention also relates to the use of a vector according to the invention (in particular a VSV vector according to the invention) or of a (pharmaceutical) composition according to the invention (in particular a composition comprising a vector according to the invention, and more particularly a composition comprising VSV vector according to the invention), for gene therapy or immunotherapy (in particular as a vaccine).

The present invention also relates to a method of gene therapy or immunotherapy in a subject in need thereof, comprising administering to said subject a therapeutically effective amount of a vector according to the invention (in particular a VSV vector according to the invention) or of a (pharmaceutical) composition according to the invention (in particular a composition comprising a vector according to the invention, and more particularly a composition comprising VSV vector according to the invention).

Vectors according to the invention (and in particular VSV vectors according to the invention) used in gene therapy or immunotherapy are preferably as disclosed above in "Vector" section.

Gene therapy may be used each time it is necessary to correct deficient gene activity in deficient cells.

Immunotherapy may be used for the treatment of various types of diseases, including cancers, infectious diseases, and inflammatory diseases (in particular autoimmune diseases).

The present invention also relates to a vector according to the invention (in particular a VSV vector according to the invention) or a (pharmaceutical) composition according to the invention (in particular a composition comprising a vector according to the invention, and more particularly a composition comprising VSV vector according to the invention), for use for selective delivery in vivo of a cargo to a chosen cell type.

The present invention also relates to the use of a vector according to the invention (in particular a VSV vector according to the invention) or of a (pharmaceutical) composition according to the invention (in particular a composition comprising a vector according to the invention, and more particularly a composition comprising VSV vector according to the invention), for the manufacture of a drug for selective delivery in vivo of a cargo to a chosen cell type.

The present invention also relates to the use of a vector according to the invention (in particular a VSV vector according to the invention) or of a (pharmaceutical) composition according to the invention (in particular a composition comprising a vector according to the invention, and more particularly a composition comprising VSV vector according to the invention), for selective delivery in vivo of a cargo to a chosen cell type.

The present invention also relates to a method for selective delivery in vivo of a cargo to a chosen cell type in a subject in need thereof, comprising administering to said subject a therapeutically effective amount of a vector according to the invention (in particular a VSV vector according to the invention) or of a (pharmaceutical) composition according to the invention (in particular a composition comprising a vector according to the invention, and more particularly a composition comprising VSV vector according to the invention). Vectors according to the invention (and in particular VSV vectors according to the invention) used for selective delivery in vivo of a cargo to a chosen cell type are preferably as disclosed above in "Vector" section.

The present invention also relates to the mutant polypeptide according to the invention or the fusion polypeptide according to the invention or the vector according to the invention or the host cell according to the invention or of a composition according to the invention (in particular a composition comprising a vector according to the invention, and more particularly a composition comprising VSV vector according to the invention) or of a combination thereof, for use for targeting a lipid membrane in a subject to a specific target, for instance a cell, in particular a cell to be killed (such as a cancer cell) or unstimulated T cells, B cells, and hematopoietic cells, wherein said mutant polypeptide or fusion polypeptide is anchored in said lipid membrane.

In Vitro Uses

The present invention also relates to the in vitro use of the mutant polypeptide according to the invention or the fusion polypeptide according to the invention or the vector according to the invention (in particular a VSV vector according to the invention) or the host cell according to the invention, or of a composition according to the invention (in particular a composition comprising a vector according to the invention, and more particularly a composition comprising VSV vector according to the invention) or of a combination thereof, for selective delivery of a cargo to a chosen cell type, such as unstimulated T cells, B cells, and hematopoietic cells.

Vectors according to the invention (and in particular VSV vectors according to the invention) used for selective in vitro delivery of a cargo to a chosen cell type are preferably as disclosed above in "Vector" section.

The present invention also relates to an in vitro use of the mutant polypeptide according to the invention or the fusion polypeptide according to the invention or the vector according to the invention or the host cell according to the invention or of a composition according to the invention (in particular a composition comprising a vector according to the invention, and more particularly a composition comprising VSV vector according to the invention) or of a combination thereof, for targeting a lipid membrane to a specific target, for instance a cell, in particular a cell to be killed (such as a cancer cell) or unstimulated T cells, B cells, and hematopoietic cells, wherein said mutant polypeptide or fusion polypeptide is anchored in said lipid membrane.

The following examples merely intend to illustrate the present invention.

EXAMPLES

Example 1: Selection of Mutations H22N and S422I in Indiana VSV G for Production of Recombinant VSV Virus Expressing an Anti-GFP Targeted G Protein

Materials and Methods

Construction of GNano (First Chimera)

GNano constructions were created starting from the cloned VSV G gene (Indiana strain) in the pCAGGS plasmid. pCAGGS plasmids containing the desired coding GNano sequence with the nanobody inserted at various position were generated using Gibson assembly method. The empty vector pCAGGS was linearized using EcoRI restriction enzyme. Then 3 PCR products with overlapping parts were generated. The product I is the fragment of G before the insertion site of the nanobody. The product II is the nanobody gene. The product III is the fragment of G after the insertion site. PCR products and linearized vector were combined and joint by incubation with Gibson Assembly® Master Mix (NEB).

Obtention and Amplification of Recombinant VSV Virus in BSR Cells

Recombinant VSV were obtained as described in Schnell et al. J. virol. 1996. A Plasmid pVSVFL(+)-GNano expressing the 11,161-nucleotide (nt) positive-strand full-length VSV RNA sequence with the mutant GNano in place of the wt VSV G was generated using two unique restriction sites present on pVSVFL(+), MluI In the 5' noncoding sequence of the G gene and NheI present in a sequence introduced between the G gene and the L gene. BSR cells were infected with vaccinia virus at a moi of 10. After one hour plasmids pBS-N, pBS-P, pBS-L and pcDNA3.1-G, respectively, encoding N, P, L and G proteins plus the pVSVFL(+)-GNano plasmid were transfected into the cells using lipofectamine 2000 (Invitrogen) in the presence of 10 μg/ml AraC (Sigma). Plasmids and amounts were as follows: 5 μg of pVSVFL(+)_GNano, 2.5 μg of pBS-N, 2 μg of pBS-P, 1 μg of pCDNA3.1-G and 0.5 μg of pBS-L. After 48 h of incubation at 37° C. in 5% CO2, supernatants from transfected cells were collected and debris were pelleted from the cell lysates by centrifugation. Supernatants were filtered through 0.2 μm to remove vaccinia virus, and 2.5 ml of this filtrate was added to approximately 106 BSR cells in a 3.5-cm-diameter plate. After 24 h, the supernatant containing the recombinant VSV was clarified by centrifugation and stored for further use at-80.

Titer in pfu/ml of the obtained recombinant VSV supernatants were determined by plaque assay in 6 well plates on BSR cells by counting the plaques in each wheel 24 h after infection using crystal violet coloration.

Then, the harvested recombinant virus was amplified by infecting 3 $10^6$ BSR cells at moi 0.1 on a 6 cm-diameter cell plate. This new supernatant was tittered by plaque assay and stored for further use at −80.

To obtain higher titers, 3 $10^6$ BSR cells in a 6-cm-diameter plate were infected with 10 000 pfu in order to favor apparition of mutation susceptible to increase the growth rate of the recombinant virus. Ten subsequent passages of the viral supernatant on BSR cells were made. Titer was again estimated using plaque assay.

Titration by Plaque Assay

The day before, 106 BSR cells were seed in 6 wheel plate to ensure a ~90% confluent monolayer the day after. Then cells were infected with 200 μL of tenfold serial dilutions for 1 h at room temperature. After the infection, cells are overlaid with immobilizing medium added directly to the inoculums containing 0.8% agarose in the wheel.

After addition of the overlay, plates are incubated at 37° C. in 5% CO2 for 24 h. To determine viral titer plaques are counted in wells containing from 5 to 100 plaques. The viral titer is determined as follow: pfu/ml=(average number of plaque)/(dilution×volume of dilution added to the plate).

Sequencing of the G Gene in the Viral Population

3 $10^6$ BSR cells on a 6 cm-diameter plate were infected at MOI 3 and total RNA extracts was done using TRIzol (Invitrogen). Then RT-PCR using the primer TTTTTTTTTTTTCAT (SEQ ID NO: 87) specific of all viral mRNAs and was performed on total RNA extracts. Then VSVG gene was amplified by PCR and the PCR product obtained was sent to sequencing to identify compensatory mutations.

Results

Figure 1:
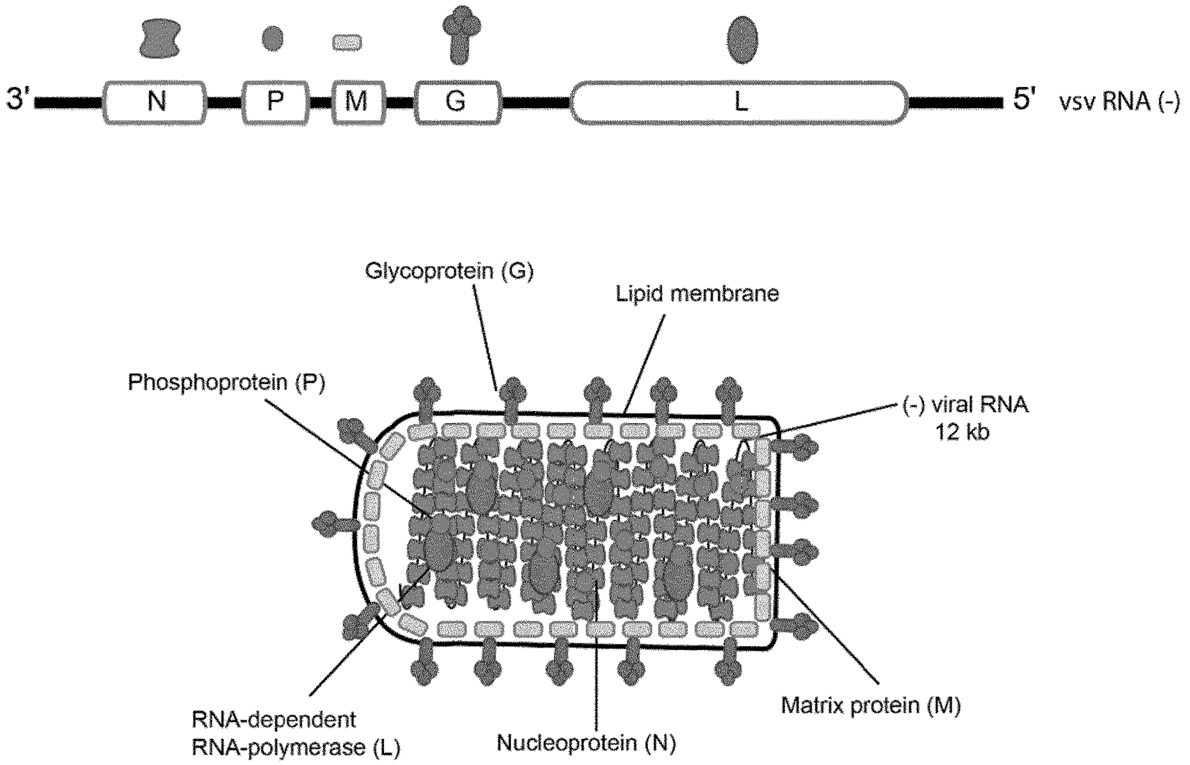
FIG. 1. A. VSV genome is a single RNA molecule of negative polarity; it encodes 5 structural proteins N (nucleoprotein), P (phosphoprotein), M (matrix protein), G (glycoprotein) and L (Large RNA-dependent RNA polymerase). B. VSV is an enveloped virus, glycoprotein G is the only protein external to the virus. It is involved in the steps of virus entry (receptor interaction and membrane fusion).
Figure 2:
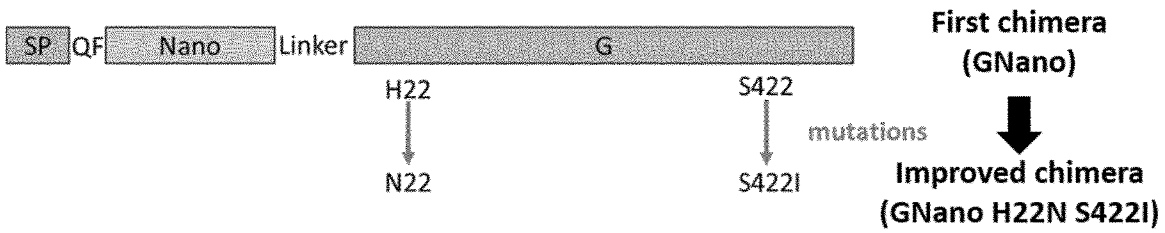
FIG. 2. Schematic representation of first chimera (GNano) and improved chimera (GNano H22N S422I). The mutations that have been selected are indicated. (SP: signal peptide of VSV glycoprotein G, Nano: nanobody, G: glycoprotein G of VSV). The additional inserts (dipeptide QF and the linker which has the sequence GGGGSGGGGS (SEQ ID NO: 81)) are also indicated.

A recombinant VSV virus, in which the gene encoding the wild-type glycoprotein G was replaced by that encoding GNano (first chimera, consisting of the signal peptide of VSV Indiana G protein, a two amino acids QF linker, an anti-GFP nanobody of sequence SEQ ID NO: 80, a 10 amino acids linker GGGGSGGGGS (SEQ ID NO:81) and wild-type VSV Indiana G protein ectodomain (SEQ ID NO:2), see top of FIG. 2) was constructed. The amplification of this initial recombinant VSV virus was however very difficult; and only very low infectious titers-8.104 pfu/ml were obtained after amplification in BSR cells after 24 hours. Such a low titer is not compatible with industrial production of a targeted VSV virus intended for therapy.

Several passages of this recombinant virus on BSR cells were then performed in order to select mutations improving its amplification. After 10 passages, the sequencing of the genomes of the viral population showed the progressive invasion of this population by a variant containing two mutations in the nucleotide sequence of the glycoprotein resulting in the change of:

- the histidine residue in position 22 into asparagine (H22N substitution), and
- the serine 422 residue in position into isoleucine (S422I substitution).

The titer of the recombinant virus obtained after this optimization was around ~108 pfu/ml.

The resulting improved chimera (Mutated GNano, see bottom of FIG. 2) thus shows high amplification in BSR cells after 24 hours, compatible with industrial production of a targeted VSV virus intended for therapy.

The titers obtained in BSR cells at 24 hours after infection are presented in Table 12 below:

TABLE 12

Recombinant VSV titers in BSR cells at 24 hours after infection.

| Recombinant VSV virus | Titer in BSR cells at 24 hours after infection (pfu/ml) |
|---|---|
| First chimera (see top of FIG. 2) | 1.8 $10^6$ |
| Mutated chimera (H22N and S4221) | $9.10^7$ |

It is worth noting that a third mutation subsequently appeared in about 50% of cases in the sequence encoding the dipeptide linker consisting of glutamine and phenylalanine (QF) and located between the signal peptide of VSV glycoprotein G and the inserted nanobody. This mutation led to the replacement of phenylalanine to serine (QF->QS; data not shown).

Importantly, this third mutation had no effect on the kinetics and on the viral titer (data not shown). Indeed, the titer of the recombinant viruses having the 3 mutations was still ~$10^8$ pfu/ml. Therefore, this third mutation did not affect the improved amplification of the recombinant virus in BSR cells.

Conclusions

The insertion of mutations H22N and S422I in the ectodomain of VSV Indiana glycoprotein G surprisingly resulted in a dramatic increase in the ability to amplify a recombinant VSV virus comprising a GFP targeted glycoprotein G (by insertion of an anti-GFP nanobody).

Example 2: The Mutation S422I in Indiana VSV G was Also Selected in Another Context which Explains its Role In an attempt to identify the histidines which play the role of pH sensitive molecular switch, we replaced the histidines of G ectodomain by an alanine.

Figure 5:
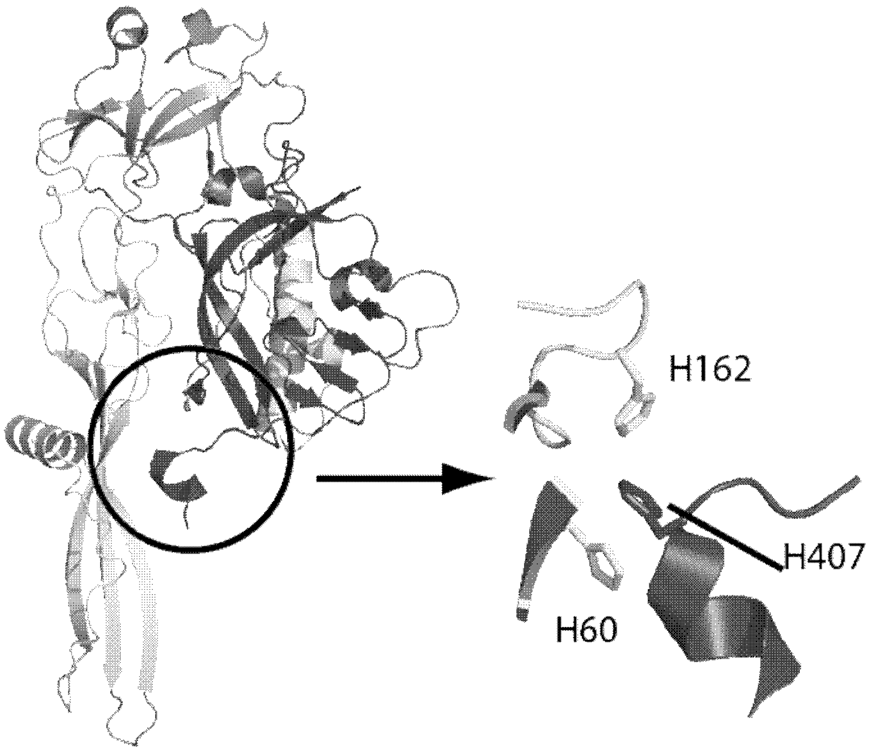
FIG. 5. Histidine cluster in the prefusion protomer of VSV Indiana G. The mutation of Histidine 407 into an alanine abolishes G fusion properties.

Particularly, in VSV Indiana G, in the prefusion form of the protomer, there is a cluster of four histidines (H60, H162, H407) (FIG. 5). We made the hypothesis that protonation of these histidines create a cluster of positive charge which induces a local repulsive force which initiates the structural transition.

Materials and Methods

Plasmids and Cloning.

Point mutations were created starting from the cloned VSV G gene (Indiana Mudd-Summer strain) in the pCAGGS plasmid. Briefly, forward and reverse primers containing the desired mutation were combined separately with one of the primers flanking the G gene to generate two PCR products. These two G gene fragments overlap in the region containing the mutation and were assembled into the pCAGGS linearized vector (by EcoRI) using Gibson assembly reaction kit (New England Biolabs).

Cells and Antibodies.

BSR, clones of BHK-21 (baby hamster kidney; ATCC CCL-10), and HEK-293T (human embryonic kidney expressing simian virus 40 T antigen [SV40T]; ATCC CRL-3216) cells were grown in Dulbecco's modified Eagle's medium (DMEM) supplemented with 8% fetal calf serum (FCS). Mouse monoclonal antibody directed against G ectodomain was supplied by KeraFAST (8G5F11);

Transfection.

For fusion assays and indirect immunofluorescence, BSR cells, grown in six-well plate at 70% confluence, were transfected by the phosphate calcium method (5 μg of the appropriate plasmid per well). For pseudotyped virus production, HEK-293 cells were grown in 10-cm dishes; they were transfected by 6 μg of the appropriate plasmid with polyethylenimine (PEI; Sigma-Aldrich).

Cell Surface Expression.

Figure 6:
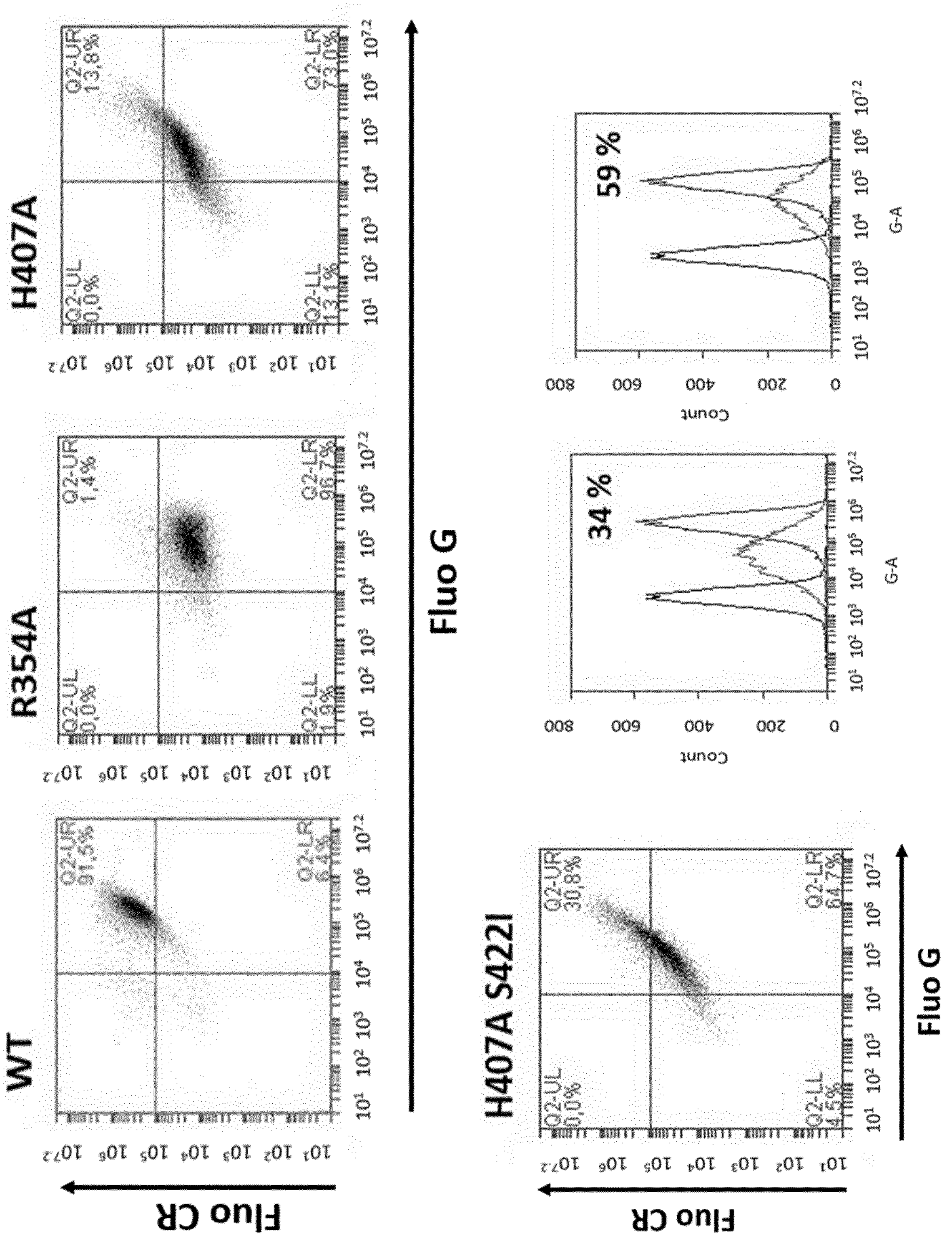
FIG. 6. Top: Flow cytometry analysis of the expression of WT and mutant glycoproteins at the surface of HEK293T cells and of the binding of fluorescent GST-CR2 (CR2 with an amino-terminal GST fusion). After 24 h of transfection, cell surface expression of WT and mutant G was assessed using monoclonal anti-G antibody 8G5F11 directly on living cells at 4° C. during 1 h. Cells were then incubated simultaneously with anti-mouse Alexa Fluor 488 and the indicated GST-CR$2_{ATTO550}$. Cells transfected with a G construct that was still able to bind GST-CR proteins exhibited red fluorescence due the ATTO550 dye. Mutant R354A is a mutant unable to bind CR domains.

In order to quantify the expression of G protein on the cell surface, HEK-293 cells plated on six-well dishes at 70% confluence were transfected as described above. At 24 h after transfection, cells were collected by scraping into 1 mM EDTA-PBS, followed by centrifugation at 600 g for 5 min. Cells were incubated with a 1:2,000 dilution of mouse monoclonal anti-G ectodomain antibody (8G5F11; KeraFAST) in PBS on ice for 1 h. Cells were washed twice in PBS, fixed at 4° C. in paraformaldehyde, incubated with a 1:100 dilution of goat anti-mouse Alexa Fluor 488 (Invitrogen) on ice for 1 h, and rinsed in PBS. After resuspension in 500 ml of 0.5 mM EDTA-PBS, the fluorescence of 10,000 cells from each population was determined by flow cytometry using a BD Accuri C6 fluorescence-activated cell sorter (FACS). The mean fluorescence intensity (MFI) of the transfected cells expressing G was quantified by flow cytometry. The relative cell surface expression of transfected cells was determined as follows: (MFI for the mutant)/(MFI for the WT). For each mutant, the percentage given in the bottom of FIG. 6 is the average of three independent experiments.

Results

Mutation H407A completely abolishes G fusion properties. This mutation is lethal for the virus. Therefore, the recombinant viruses (VSV G H407A) cannot be generated spontaneously. We have employed a complementation strategy to support its growth. Briefly, the recovery of the recombinant VSV was supported by expression of functional WT VSV G protein in trans from a transfected plasmid. To generate virus particles containing only the fusion-defective VSV G expressed from the viral genome, viruses present in the supernatant were amplified in cells that lack the trans-complementing VSV G plasmid. Sequence analysis of independent clones revealed two distinct compensatory mutations: one of them resulted in the replacement of serine 422 by an isoleucine (leading to the double mutant VSV G H407A S422I).

Conclusions

The comparison of the characteristics of VSV G H407A with those of VSV G H407A/S422I revealed that, in the context of mutation H407A, S422I improves the efficiency of VSV G transport efficiency and G recognition by a soluble form of LDL-R CR2 domain (FIG. 6). This strongly suggests that the mutation S422I (or similar substitutions, such as S422F, S422M, S422L or S422V, or equivalent substitutions in equivalent positions of G ectodomain of other VSV strains) facilitates G folding and stabilizes the prefusion form (as the structural transition disrupts the CR domain binding site) in the context of mutation H407A.

Example 3: Cell-Cell Fusion Assays. Comparison of the Fusion Properties of VSV Indiana WTG Glycoprotein with VSV Indiana GNano Optimized Glycoprotein

Materials and Methods

Cell-Cell Fusion Assay.

BSR cells plated on glass coverslips at 70% confluence were cotransfected with pCAGGS plasmids encoding wild-type (WT) G or mutant G, and P-GFP plasmid encoding the phosphoprotein of Rabies virus fused to GFP (cytoplasmic marker). Twenty-four hours after transfection, cells were incubated with fusion buffer (DMEM+10 mM MES) at various pH values (from 5.0 to 6.5) for 10 min at 37. Cells were then washed once and incubated with DMEM+10 mM HEPES-NaOH buffered at pH 7.4, 1% BSA at 37° C. for 1 h. Cells were fixed with 4% paraformaldehyde in 1×PBS for 15 min. Cells nuclei were stained with DAPI, and syncytium formation was analyzed with Zeiss Axio vert 200 fluorescence microscope with a 20× lens.

Results

Fusion properties of VSV G Indiana WT and VSV GNano after optimization (ie. Mutation of residue H22 to N and residue S422 to I, F, M, L, or V) were analysed in cell-cell fusion assay. For this, BSR cells were transfected with pCAGGS plasmids expressing VSV G (either WT or mutant) and P-GFP (a protein exclusively cytoplasmic allowing an easy observation of syncytia). At 24 h post-transfection, the cells were exposed for 10 min to DMEM adjusted to the indicated pH, which was then replaced by DMEM at pH 7.4. The cells were then kept at 37° C. for 1 h before fixation.

Cells expressing wild-type G protein formed massive syncytia when exposed to low pH, between 5.5 and 6.3 (FIG. 7). Cells expressing GNano after optimization were all able to form syncytia when exposed at low pH (FIG. 7).

Conclusions

The results are consistent with the fact that the presence of a hydrophobic residue in position 422 is key in the regulation of the pH-dependent structural transition. This strongly suggests that the mutation S422I (or S422F, S422M, S422L or S422V, or equivalent substitutions in equivalent positions of G ectodomain of other VSV strains) facilitates G folding and stabilizes the prefusion form of GNano.

Example 4: VSV G C-Terminal Part Contributes to the Locking of the Ectodomain in its Pre-Fusion State Results The structure of WT Indiana VSV G ectodomain (G1-440 comprising residues 1 to 440) was determined at 2.1 Å resolution. The ectodomain was crystallized in its trimeric pre-fusion conformation and its structure was determined at 2.1 Å resolution (FIG. 8). The polypeptidic chain could be traced up to residue 432. The C-terminal part of G1-440 is made of an alpha-helix (residues 409 to 416) followed by a kinked region ending with a beta-turn between Pro 418 and Glu 421 and a short beta-hairpin structure (residues 422 to 432). The hairpin structure interacts with strand 79-84 of VSV G fusion domain beta-sheet through hydrogen bonds between the main chain of both segments and between the lateral chain of residues H80 and E421.

Conclusions

This X-ray structure of VSV G ectodomain reveals that the C-terminal part (from residue 407 to residue 425) largely interacts with the fusion domain and therefore contributes to the stabilization of the pre-fusion complex. Particularly relevant for the present invention, is the fact that, in this pre-fusion structure, residue S422 is pointing toward F424 and L430. Therefore, the compensatory mutation S422I stabilizes the beta-hairpin structure (and thus the pre-fusion state) through hydrophobic interactions between 1422 and residues F424 and L430. This also explained why the replacement of S422 by other hydrophobic residues (L, M, V or F) has the same effect (i.e. stabilizes the pre-fusion conformation).

BIBLIOGRAPHIC REFERENCES

Albertini et al. Viruses 4, 117-139 (2012).
Amirache. Blood 123, 1422-4 (2014).
Barber. Oncogene 24, 7710-7719 (2005).
Bishnoi et al. Viruses 10, 90 (2018).
Fernandez et al. J. Virol. 76, 895-904 (2002).
Hastie et al. Virus Res. 176, 16-32 (2013).
Needleman et Wunsch. J. Mol. Biol. 48,443-453, 1970.
Nikolic et al. Nat Commun. 2018 Mar. 12; 9 (1): 1029.
Rodriguez et al. J Gen Virol. 2002 October; 83 (Pt 10): 2475-83.
Schnell et al. J. virol. 1996 70:2318-2323.
Velazquez-Salinas et al. Genome Announc. 2017 Sep. 14; 5 (37).

The invention claimed is:

1. A mutant polypeptide comprising the amino acid sequence of the ectodomain of glycoprotein G of a Vesicular stomatitis virus (VSV) strain, wherein said ectodomain comprises the amino acid sequence of SEQ ID NO:2 or an amino acid sequence having at least 90% identity with the amino acid sequence of SEQ ID NO:2, with at least one substitution of an amino acid residue selected from the group consisting of:

a) the amino acid residue located at position 422 of SEQ ID NO:2;

b) the amino acid residue located at position 22 of SEQ ID NO:2;

c) any amino acid residue located at position equivalent to position 422 of SEQ ID NO:2 after optimal global alignment with SEQ ID NO:2 and d) any amino acid residue located at a position equivalent to position 22 of SEQ ID NO:2, after optimal global alignment with SEQ ID NO:2.

2. The mutant polypeptide according to claim 1, wherein:
a) any amino acid residue located at position 422 of SEQ ID NO:2 or equivalent position after optimal global alignment with SEQ ID NO:2 is substituted by a hydrophobic amino acid; and/or
b) any amino acid residue located at position 22 of SEQ ID NO:2 or equivalent position after optimal global alignment with SEQ ID NO: 2 is substituted by a polar amino acid.

3. The mutant polypeptide according to claim 2, wherein:
a) the hydrophobic amino acid is selected for the group consisting of glycine (G), alanine (A), valine (V), leucine (L), isoleucine (I), methionine (M), proline (P), phenylalanine (F), and tryptophan (W); and/or
b) the polar amino acid is selected from the group consisting of asparagine (N), glutamine (Q), cysteine (C), tyrosine (Y), threonine (T), and serine(S).

4. The mutant polypeptide according to claim 1, which further comprises a substitution at position 47 of SEQ ID NO:2 or equivalent position after optimal global alignment with SEQ ID NO:2, or a substitution at position 354 of SEQ ID NO:2 or equivalent position after optimal global alignment with SEQ ID NO: 2, or two substitutions at positions 47 and 354 of SEQ ID NO:2 or equivalent positions after optimal global alignment with SEQ ID NO:2.

5. The mutant polypeptide according to claim 1, comprising an amino acid sequence selected from the group consisting of SEQ ID NOs 17-78 and 79.

6. The mutant polypeptide according to claim 1, which further comprises at least one substitution of an amino acid residue selected from the group consisting of amino acid residues located at positions 8, 47, 209 and 354 of SEQ ID NO:2 or amino acid residues located at positions equivalent to positions 8, 47, 209, and 354 of SEQ ID NO:2 after optimal global alignment with SEQ ID NO:2.

7. A fusion polypeptide comprising the mutant polypeptide according to claim 1, and an additional peptide, polypeptide, or protein, wherein the additional peptide, polypeptide, or protein is inserted in the N-terminus of the mutant polypeptide, or between any two consecutive amino acids located in regions corresponding to positions 192 to 202, 240 to 257, 347 to 353, 364 to 366, or 376 to 379 of SEQ ID NO:2 or equivalent positions after optimal global alignment with SEQ ID NO:2.

8. The fusion polypeptide according to claim 7, wherein the additional peptide, polypeptide, or protein is inserted in the N-terminal of the mutant polypeptide or between the amino acids at positions 351 and 352 of SEQ ID NO: 2 or equivalent positions after optimal global alignment with SEQ ID NO:2.

9. The fusion polypeptide according to claim 7, wherein the additional peptide, polypeptide, or protein is at least a part of a ligand of a cellular receptor.

10. The fusion polypeptide according to claim 9, wherein the at least a part of a ligand of a cellular receptor is an antibody or a functional antibody fragment or a nanobody.

11. A host cell containing or expressing at least one selected from:
the mutant polypeptide according to claim 1,
a fusion polypeptide comprising the mutant polypeptide according to claim 1 and an additional peptide,
a nucleic acid encoding the mutant polypeptide according to claim 1,
a nucleic acid encoding a fusion polypeptide comprising the mutant polypeptide according to claim 1 and an additional peptide,
a vector comprising at least one nucleic acid selected from the group consisting of a nucleic acid encoding the mutant polypeptide according to claim 1 and a nucleic acid encoding a fusion polypeptide comprising the mutant polypeptide according to claim 1 and an additional peptide,
a vector expressing at least one selected from the group consisting of the mutant polypeptide according to claim 1 and a fusion polypeptide comprising the mutant polypeptide according to claim 1 and an additional peptide, and
any combination thereof.

12. A composition comprising at least one selected from the group consisting of:
the mutant polypeptide according to claim 1,
a fusion polypeptide comprising the mutant polypeptide according to claim 1 and an additional peptide,
a nucleic acid encoding the mutant polypeptide according to claim 1,
a nucleic acid encoding a fusion polypeptide comprising the mutant polypeptide according to claim 1 and an additional peptide,
a vector comprising at least one nucleic acid selected from the group consisting of a nucleic acid encoding the mutant polypeptide according to claim 1 and a nucleic acid encoding a fusion polypeptide comprising the mutant polypeptide according to claim 1 and an additional peptide,
a vector expressing at least one selected from the group consisting of the mutant polypeptide according to claim 1 and a fusion polypeptide comprising the mutant polypeptide according to claim 1 and an additional peptide,
and
any combination thereof.

13. A method for treating a disease, comprising administering, to a subject in need thereof, the composition according to claim 12.

14. The method according to claim 13, for treating cancer, for gene therapy, or for immunotherapy.

15. The method according to claim 13, for selective delivery in vivo of a cargo to a chosen cell type or for targeting a lipid membrane in a subject to a specific target, wherein the mutant polypeptide or fusion polypeptide is anchored to the cargo or anchored in the lipid membrane.

16. An in vitro method of using the composition according to claim 12, for selective delivery in vitro of a cargo to a chosen cell type or for targeting a lipid membrane to a specific target, wherein the mutant polypeptide or fusion polypeptide is anchored to the cargo or anchored in the lipid membrane.

17. A nucleic acid molecule encoding the mutant polypeptide according to claim 1 or a fusion polypeptide comprising the mutant polypeptide according to claim 1 and an additional peptide.

18. A vector comprising at least one nucleic acid selected from the group consisting of a nucleic acid encoding the mutant polypeptide according to claim 1 and a nucleic acid encoding a fusion polypeptide comprising the mutant polypeptide according to claim 1 and an additional peptide, or a vector expressing at least one selected from the group consisting of the mutant polypeptide according to claim 1 and a fusion polypeptide comprising the mutant polypeptide according to claim 1 and an additional peptide.

19. The vector according to claim 18, which is a viral vector.

* * * * *